US010960067B2

(12) United States Patent
Laver et al.

(10) Patent No.: US 10,960,067 B2
(45) Date of Patent: Mar. 30, 2021

(54) **MENINGOCOCCAL INFECTION AND MODIFIED *NEISSERIA LACTAMICA***

(71) Applicant: University of Southampton, Southampton (GB)

(72) Inventors: Jay Robert Laver, Southampton (GB); Robert Charles Read, Southampton (GB)

(*) Notice: Subject to any disclaimer, the term of this patent is extended or adjusted under 35 U.S.C. 154(b) by 0 days.

(21) Appl. No.: 16/062,867

(22) PCT Filed: Dec. 15, 2016

(86) PCT No.: PCT/GB2016/053944

§ 371 (c)(1),
(2) Date: Jun. 15, 2018

(87) PCT Pub. No.: WO2017/103593

PCT Pub. Date: Jun. 22, 2017

(65) Prior Publication Data

US 2019/0307874 A1 Oct. 10, 2019

(30) Foreign Application Priority Data

Dec. 15, 2015 (GB) ...................................... 1522153

(51) Int. Cl.

| | |
|---|---|
| ***A61K 39/00*** | (2006.01) |
| ***A61K 39/02*** | (2006.01) |
| ***A61K 39/095*** | (2006.01) |
| ***C12N 15/74*** | (2006.01) |

(52) U.S. Cl.

CPC ............ *A61K 39/095* (2013.01); *C12N 15/74* (2013.01); *A61K 2039/523* (2013.01); *A61K 2039/543* (2013.01)

(58) Field of Classification Search

CPC ....... A61K 39/00; A61K 39/02; A61K 39/095
USPC ...... 424/9.1, 9.2, 184.1, 200.1, 234.1, 249.1
See application file for complete search history.

(56) References Cited

FOREIGN PATENT DOCUMENTS

| | | | |
|---|---|---|---|
| WO | WO 2000/050074 | 8/2000 | |
| WO | WO 2001/064922 | 9/2001 | |
| WO | WO 2003/051379 | 6/2003 | |
| WO | WO 2011/077143 | 6/2011 | |
| WO | WO-2011077143 A1 * | 6/2011 | ............. C12N 15/74 |
| WO | WO 2013/033398 | 3/2013 | |

OTHER PUBLICATIONS

Laver, et al. "Neisserial molecular adaptations to the nasopharyngeal niche." In *Advances in Microbial Physiology*, vol. 66, pp. 32-355. Academic Press, 2015.

New England Biolabs, Inc., I Schildkraut. "*Neisseria laciarnica* Hollis et al., pEGsph50-2 [NEB808] (ATCC® 69045™)", ATCC, last accessed Feb. 13, 2017, available at: https://www.atcc.org/Products/A11/69045.aspx.

O'Dwyer, et al. "Expression of heterologous antigens in commensal *Neisseria* spp.: preservation of conformational epitopes with vaccine potential." *Infection and Immunity* 72, No. 11 (2004): 6511-6518.

Search Report under Section 17(5) for GB1522153.4, dated Sep. 16, 2016 by the Intellectual Property Office of the United Kingdom (4 pages).

* cited by examiner

*Primary Examiner* — Rodney P Swartz

(74) *Attorney, Agent, or Firm* — Klarquist Sparkman, LLP

(57) ABSTRACT

The invention relates to a modified *Neisseria lactamica*, wherein the modified *Neisseria lactamica* is transformed with recombinant DNA encoding a heterologous protein; a method of prophylactic treatment for pathogenic infection of a subject comprising nasopharyngeal inoculation of a modified *Neisseria lactamica*; a method of reducing or preventing meningococcal colonisation of a subject; a method of modifying the microbiome of a subject; a wild-type *Neisseria lactamica* for use for the prophylactic treatment of meningococcal infection of a subject or reducing colonisation of a subject, wherein the prophylactic treatment comprises nasopharyngeal inoculation of the wild-type *Neisseria lactamica*; associated nucleic acid for mutagenesis of *Neisseria lactamica*; methods of mutagenesis; outer membrane vesicle (OMV) vaccines; and associated compositions and methods thereof.

15 Claims, 49 Drawing Sheets

Figure 1:
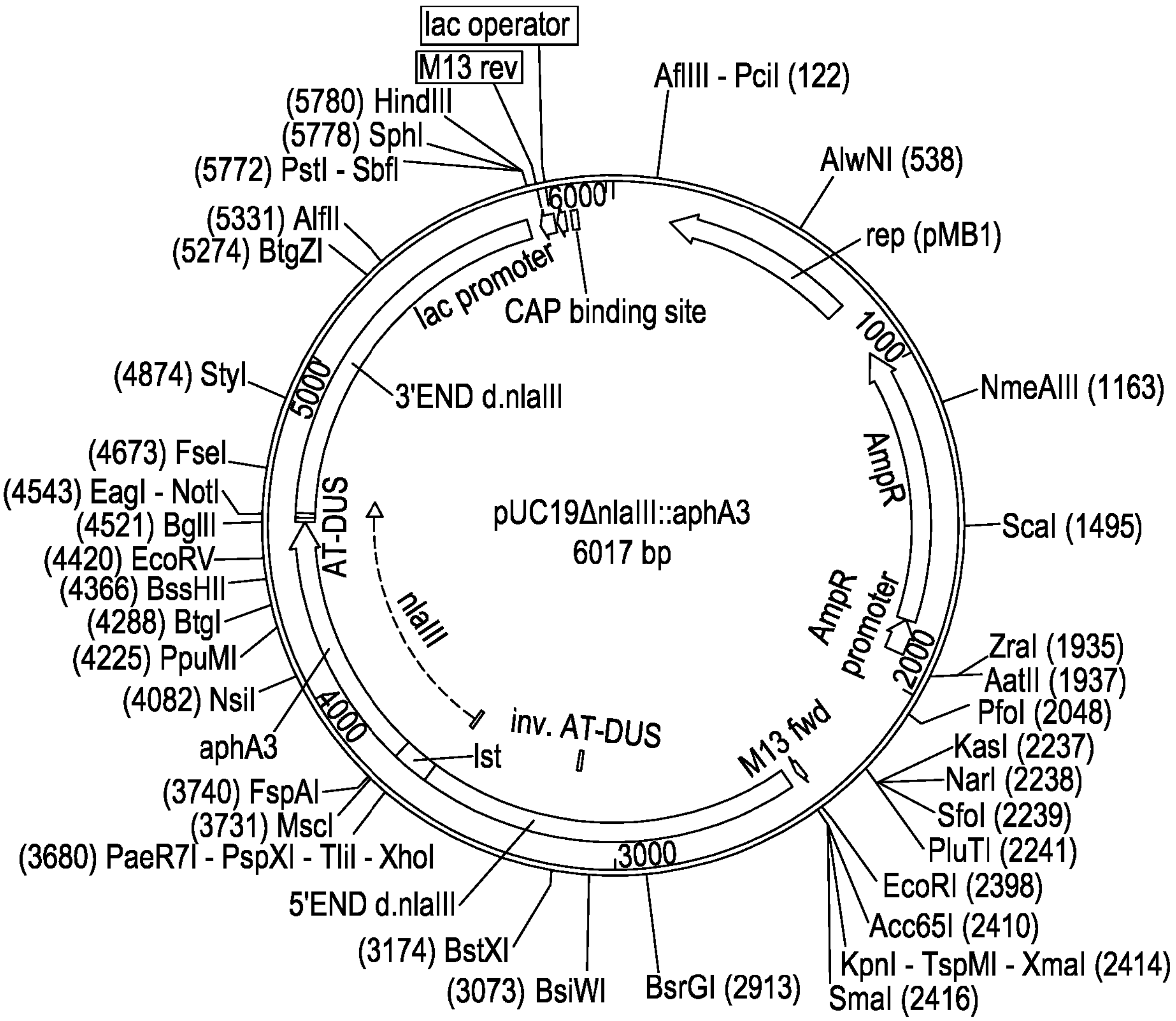

Specification includes a Sequence Listing.

5' -

ATGGTTTCGAAAGGGGAAGAACTGTTTACAGGCGTGGTACCAATCCTCGTGGAACTGGATGGCGATGTCAACGGCCATAAATTC

TCTGTCCGCGGCGAAGGTGAAGGCGATGCAACCAATGGCAAATTGACGTTGAAATTCATTTGCACCACCGGCAAACTGCCCGTTC

CGTGGCCGACGCTGGTCACAACCTTCGGATATGGCGTCGCCTGCTTCTCGCGCTACCCGGATCACATGAAACAACACGACTTCTT

CAAATCCGCAATGCCGGAAGGTTATGTTCAGGAACGTACTATTTCGTTCAAGGATGACGGCACCTACAAAACCCGCGCCGAAGTC

AAATTTGAAGGCGATACCTTAGTTAACCGTATTGAATTGAAAGGCATTGACTTTAAAGAAGACGGCAACATCCTGGGCCACAAAT

TAGAATACAACTTCAACTCGCATAACGTCTATATCACAGCCGATAAGCAGAAAAATGGCATAAAAGCCAACTTCAAAATTCGCCA

CAACGTTGAGGATGGTAGCGTTCAGTTGGCTGACCACTATCAACAAAACACTCCCATCGGCGACGGTCCGGTACTGTTGCCCGAC

AACCATTACCTTTCCCACCAGTCCGCCCTGTCCAAAGATCCGAATGAAAAACGCGACCACATGGTTCTGCTGGAGTTCGTCACTGC

AGCGGGCATCACGCACGGAATGGACGAACTCTATAAATAGGCGGCCGCgccgtctgaattaaaggaaatCATATGGCCAAAATGCGCA TTAGTCCGGAACTGAAAAAATTGATTGAAAAGTACCGCTGTGTCAAAGATACTGAGGGTATGTCGCCCGCCAAAGTCTACAAGCT GGTCGGCGAAAATGAAAACCTGTACTTGAAAATGACAGATAGTCGCTACAAAGGCACCACCTACGACGTAGAGCGCGAGAAAG ATATGATGTTATGGCTGGAAGGTAAACTGCCTGTTCCGAAAGTTCTGCATTTCGAACGCCACGACGGTTGGAGCAACCTGCTGAT GTCGGAAGCAGATGGCGTATTGTGTAGCGAAGAATACGAAGACGAACAATCGCCGGAGAAAATCATCGAATTGTACGCGGAAT GCATCCGCTTGTTTCACAGCATCGACATCAGTGATTGCCCTTACACCAACTCCTTAGATAGCCGCCTGGCTGAACTTGATTATTTGT TGAATAACGACTTGGCTGATGTAGACTGCGAAAACTGGGAGGAAGATACACCCTTCAAGGACCCGCGCGAGCTCTACGACTTTC TGAAAACTGAAAAACCGGAAGAAGAGCTGGTTTTCTCCCACGGCGATCTGGGCGACTCGAATATTTTCGTAAAAGATGGCAAAG TTTCCGGCTTTATCGACTTGGGCCGCAGCGGGCGCGCAGATAAATGGTACGACATTGCGTTCTGCGTCCGCAGCATCCGTGAAG ATATCGGTGAAGAACAATACGTCGAGCTCTTTTTCGACTTGCTGGGTATTAAACCGGATTGGGAAAAAATCAAATATTATATCCT

GTTGGATGAATTATTCTAG - 3'

Figure 2 (SEQ ID NO: 3)

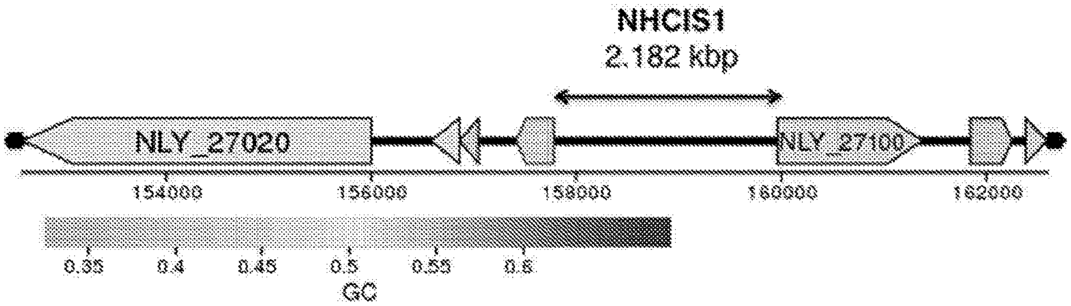

5′ NHCIS1: (SEQ ID NO: 4)

5′CTGATACCGAGCTTTTCCCATGGTTTATCGCGACTGATAGTGTTTTCGGCGAGGTAGTCGGCACGTGTTTGAGACCACCAGCGA
GTGATTGTGCTTTCAGCTACAATAATTTTGCTGCTTGCTCTATGTTTAAAAATCTATCCATATTGGATAGTTTAGATTAGACTTAAG
TGGATTTCAAGTGAGCTGTTTAACCCTTAGCTAGCAAGGGTTTTGGTGGCGTAAGGTTACTGAACTTAAGCATATCGGCGGCCAA
AGTACCGCTGCCATTGCCAATCTCGCCGGGGAAATGAAAAGGCTCGCTAAAAAATCAAAAATGTTACTGAAAGGACTTTGGTCAT
TTTTATCCTCTACAATATCTACATTTAAAAATAAATCGGTCATTGTTTAAACCTTACTGTAAAACTGTACAACTGCTAAACTGTAAAC
ACAGAAAGAGGCAATACTAACAGCACAAAACAACAGATATCCAAACTCCATAAAGTGCATTATTCTGACTTTTTTCGTTGCCTGAT
GTATTTATGCTATTTGTGCTGTTCTTATATATGTGTTGCTGGTTACGTTGCGTTTTTTCGGAAAATTCAACCGGTAGGGGACCGATA
CGCAGTTTCATCTCTTTGCTTAGGGAGAGTAGGGGGGTAGATTACGACCTTAGTTTTGGTATCCGTAATATCATCATTTTTTCGTCT
AGGGAGTATATCGACTTCAGAAAACAGGTATTAGATACTGCCTTTTCTTACGAGAGTGATGGCAAGATAGTTCTCTTCAAGTCAAT
CAAACAGGAAAGTATTTCTTTTCTGTCTGAAGATTTGAAAAAGGACTGAATGTTTCACAAGGTTAAAACTGGGGAAAAAGATGGA
TATGGTTCAGATGAAATGCTGAGCGCACCCCGTATCTATTTGGAAATGATGTCGCGGAAAACGGAAGTCCCCTACTCCAGTATTC
TTTAAATTCTAAGCAGAAAACTTCTTCGTCGGTCTTTTTTTTGTTGTTTGGTTTGCATGGAGTAAAACTGTGCAAC3′

3′NHCIS1: (SEQ ID NO: 5)

5′TGCTGAAGTAGAAAACCAGCAAGAAGGTAAAAAGAAAGAAGCAGTTTTTTGGATTTTAGATGTTACCGCAATTGGTTTCCT
TTCCTAAAATTTGTTTAAATTATTTGCAATATTAATATAAACTGGATATTAATGATGAGGATTCAAAAAGGCATACTGAATATAATT
TGTACAAAATATTTGCAGTATTTAAAAATGTTGGTTCGTATATGAAAAGTTAAAAATGCCAAAATGTACAGTTGCTAAACTGTAAA
ACTGCTAAAGCAACAAAACATAAAAAGGAATGCAGGGATGCGATCACTACATCTTTTTATTCCGTAAGCATTTATGACTTTACGGT
CAACTGCTACTCTATGTTTCCAGCTTTTCAGCTCCCTATTTTCGAATATTGGACGAGGCATTTTCATCAGTGTCGTAATGCCGACCG
AAACCCTCACAAACCATATTGGTTCTTGTGGCAGCAACACCTATCCGTTTGTTCAAGCGGCCACAAGAGTAACATGATTGGCTGGT
GGCATTGGCTTTAATCTCTTCGATATGAACTCCATTTTTAGCTGCACCTTCTTTCAGCGTATGCAACAGTGGGGATGGGGCAACTA
TCTTCTGGTGGAGTTTGTTGACTTCAATCTGTATGCACTGTAGGTTGAGCAGATTCAGTTTTTTGATACAGATTATCCGGCTTTGTT
CGGCAATTCTGTTGGCGAACGTATAGTAGAGCTGTCGTCTTGCCGCTTTCAATTTGCGGTAGGTATTTTACCATTCCATGCGTAGC
CGCTCGGTACGTTTGAGCCAAATGTTATCTTCGCCATTTGTACCAATTTGTTTTTACATTAGGCTGTGTTTTAGTAATCTATTGATTT
CAATTATTTGCAAGGGAAAAGACAATTATTTTCCGGTTAGGAATAAACCTATCCTATTGAATATATTGAAGCCAAGTACGCTTATC
AACACTATATTAAAACACAGCCTTTTTTAATATAGTAGACACAATCTTTCCTTATTTATGAAGGTGATAGCTTCTTTCAG3′

Figure 10

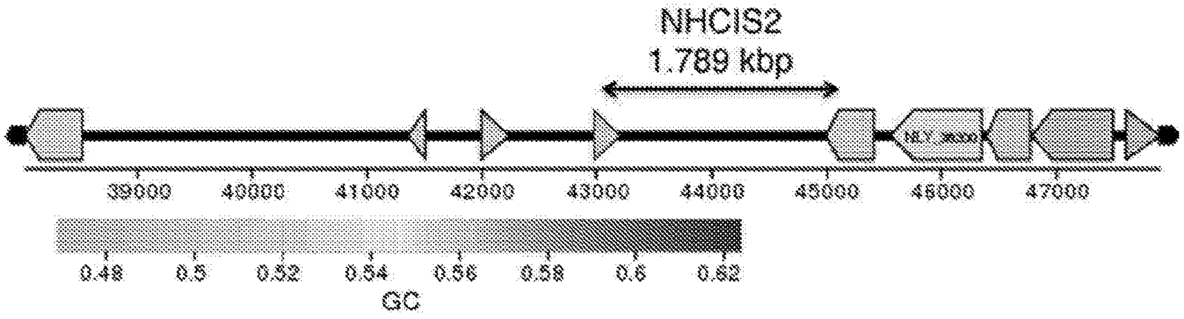

5′ NHCIS2: (SEQ ID NO: 6)

5′*CGGGCCGGAAGACGATTATATGAATGACGATCATCTGGCTTTTTTCCGCGAATTGCTGGTAAAAATGCAAGACGAACTCAT*
*CGAAAATGCTTCCGCTACGACAGGGCATCTCCAAGAACATGAATCAGCCCCCGATCCTGCCGACCGTGCCACACAGGAAGAAGAG*
*TACGCATTGGAACTCCGTACCCGCGATCGGGAACGAAAACTTCTCAGTAAAATACAGGCGACCATCCGCAATATTGACAGGGGCG*
*ATTATGGATTCTGCGCCGATACGGGAGAACCTATCGGGCTGAAGCGGCTGTTGGCGCGCCCGACCGCCACTTTGTCCGTAGAGGC*
*GCAAGAGCGTCGTGAGAGAATGAAAAAACAGTTTGCCGACTAA*TAGCGGCAAACGAAAATGCCGTCTGAAGCCCCGAGTTTCA
GACGGCATATTCACAAAGGCGCACCAGCCAGAGGAGAAGAGGAAGGGATTTTTGGAGGCGGCGCAGCATTTGGCGGAAATAA
AAAACCTTATCTGACAGGGATATGACGAATTTCCCCAAAAAATCCCGCTGAAAGTGTTGACCGCCTCCGTCTTCGGGCGTATAGTT
CGGTTCTTCGCTGCCGACGAAGCGGCGGAATGAAACGGACAAGTATATCACGGTTTGCAGGATGTTTGACGCATCGGCCGTACA
TACCGACAGTTTCAAACGCTCTTTAACAAAACAGATTACCGATAAGTGTGAGTGCCTCGGGCCTCACACTGTTTGAAAGACAGAC
AAGATAATGTTTTGAACATTGTCCTGTCGGTTTCTTTGAAGCAGACCAGAAGTTAAAAAGTTAGAGATTGAACATAAGAGTTTGA
TCCTGGCTCAGATTGAACGCTGGCGGCATGCTTTACACATGCAAGTCGGACGGCAGCGGGGTAGTGCTTGCACTACTGCCGGCG
AGTGGCGAACGGGTGAGTAACATATCGGAACGTACCGGGCAGTGGGGGATAACTGATCGAAAGATCAGCTAATACCGCATATTT
TCTGAGGAAGAAAGCAGGGG3′

3′ NHCIS2: (SEQ ID NO: 7)

5′ACCATTTGGCCTTGCGCTATCCGAGCGGCCGATATCTGATTAGCTTGTTGGCGGGGTAAGGGCCCACCAAGGCGACGATC
AGTAGCGGGTCTGAGAGGACGATCCGCCACACTGGGACTGAGACACGGCCCAGACTCCTACGGGAGGCAGCAGTGGGGAATTT
TGGACAATGGGCGCAAGCCTGATCCAGCCATGCCGCGTGTCTGAAGAAGGCCTTCGGGTTGTAAAGGACTTTTGTCGGGGAAGA
AAAGGCTGTTGCTAATATCAGCGGCTGATGACGGTACCCGAAGAATAAGCACCGGCTAACTACGTGCCAGCAGCCGCGGTAATA
CGTAGGGTGCGAGCGTTAATCGGAATTACTGGGCGTAAAGCGGGCGCAGACGGTTACTTAAGCAGGATGTGAAATCCCCGGGC
TCAACCCGGGAATTGCGTTCTGAACTGGGTGGCTAGAGTGTGTCAGAGGGAGGTAGAATTCCACGTGTAGCAGTGAAATGCGTA
GAGATGTGGAGGAATACCGATGGCGAAGGCAGCCTCCTGGGATAACACTGACGTTCATGTCCGAAAGCGTGGGTAGCAAACAG
GATTAGATACCCTGGTAGTCCACGCCCTAAACGATGTCGATTAGCTGTTGGGCAGCCTGACTGCTTGGTAGCGAAGCTAACGCGT
GAAATCGACCGCCTGGGGAGTACGGTCGCAAGATTAAAACTCAAAGGAATTGACGGGGACCCGCACAAGCGGTGGATGATGTG
GATTAATTCGATGCAACGCGAAGAACCTTACCCGGTTTTGACATGTACGGAATCCTCCGGAGACGGAGGAGTGCCTTCGGGAGC
CGTAACACAGGTGCTGCATGGCTGTCGTCAGCTCGTGTCGTGAGATGTTGGGTTAAGTCCCGCAACGAGCGCAACCCTTGTCATT
AGTTGCCATCATTCAGTTGGGCACTCTAATGAGACTGCCGGTGACAAGCCGGAGGAAGGTGGGGATGAC3′

Figure 11

Heterologous Antigen Expression Cassette 1 – HAEC1:(Z)-(Z')

(SEQ ID NO: 8)

gccgtctgaaGTCGACTATtcggcaACTGTCGGAATATCTGCtaaaatTCCGCATTTTCCGCACCGGGTTTCCGCACCGGGACACTCG DUS SalI -35 *lst* -10 *lst* 5' UTR GGGCGTATGTTCAATTTGTCGGAATGGAGTTTAAAGGAATCTCGAGNNNNNNNNNNGCGGCCGCAAGTTTGTTTTTTCGGGC

*lst* 5' UTR (contd) RBS XhoI LINKER NotI -35

GGGAACATTTATAGTTTCAAACAAGGAATCGACGAAAACGTCGTCGGTAAATGCAAAGCTAAGCGGCTCGGAAAGCCCGGTTCG

*porB* -10 *porB* 5' UTR

CTTAAATTTCTTAACCAAAAAAGGAATACACATATGNNNNNNNNNNAAGCTTTCTGCAAAGATTGGTATCAACAAAAAGCCT

*porB* 5' UTR (contd) RBS NdeI LINKER HindIII *porB* TERMINATOR

GTCGTCAGACAGGCTTTTTTTCTGTTTTCTGTTTTTAGatgccgtctgaa

*porB* TERMINATOR contd. AT-DUS

Figure 12

Heterologous Antigen Expression Cassette 2 – HAEC2:(Z)-(Z')

(SEQ ID NO: 9)

gccgtctgaaGTCGACAGTTTGTTTTTTCGGGCGGGAACATTTATAGTTTCAAACAAGGAATCGACGAAAACGTCGTCGGTAAATGC DUS Sall -35 *porB* -10 *porB* 5' UTR AAAGCTAAGCGGCTCGGAAAGCCCGGTTCGCTTAAATTTCTTAACCAAAAAAGGAATCTCGAGNNNNNNNNNNNGCGGCCGC

*porB* 5' UTR (contd) RBS XhoI LINKER NotI

ATATtcggcaACTGTCGGAATATCTGCtaaaatTCCGCATTTTCCGCACCGGGTTTCCGCACCGGGACACTCGGGGCGTATGTTCA -35 *lst* -10 *lst* 5' UTR ATTTGTCGGAATGGAGTTTAAAGGAATACACATATGNNNNNNNNNNAAGCTT TCTGCAAAGATTGGTATCAACAAAAAGCCT

*lst* 5' UTR (contd) RBS NdeI LINKER HindIII *porB* TERMINATOR

GTCGTCAGACAGGCTTTTTTTCTGTTTTCTGTTTTTAGatgccgtctgaa

*porB* TERMINATOR contd. AT-DUS

Figure 13 anti-PorA 1,7 (SM300) – alexafluor488

NHCIS1::X (where X represents one of the *lst* promoter-derived constructs detailed below):

*lst:lacZ* (SEQ ID NO: 10)

GTCGACtcggcaactgtcggaatatctgctaaaattccgcattttccgcaccgggtttccgcaccgggacactcggggcgtatgttcaatttg
tcggaatggagtttaaaggaatacaCAT

*lst*(50): *lacZ* (SEQ ID NO: 11)

GTCGACTCATTTTTAAAATAAAGGTTGCGGCATTTATCAGATATTTGTTCTGAAAAtcggcaactgtcggaatatctg
ctaaaattccgcattttccgcaccgggtttccgcaccgggacactcggggcgtatgttcaatttgtcggaatggagtttaaaggaatacaCAT

*lst*(100): *lacZ* (SEQ ID NO: 12)

GTCGACAAACACAACGTTTTTGAAAAAATAAGCTATTGTTTTATATCAAAATATAATCATTTTTAAAATAAAG
GTTGCGGCATTTATCAGATATTTGTTCTGAAAAtcggcaactgtcggaatatctgctaaaattccgcattttccgcaccgggtttc
cgcaccgggacactcggggcgtatgttcaatttgtcggaatggagtttaaaggaatacaCAT

*lst*(150): *lacZ* (SEQ ID NO: 13)

GTCGACGGCAGCAGCGCATCGGCTCGCACGAGGTCTGCGCTTGAATTGTGTTGTAGAAACACAACGTTTTT
GAAAAAATAAGCTATTGTTTTATATCAAAATATAATCATTTTTAAAATAAAGGTTGCGGCATTTATCAGATAT
TTGTTCTGAAAAtcggcaactgtcggaatatctgctaaaattccgcattttccgcaccgggtttccgcaccgggacactcggggcgtatgtt
caatttgtcggaatggagtttaaaggaatacaCAT

*lst*(200): *lacZ* (SEQ ID NO: 14)

GTCGACGTGCCGCGTGTGTTTTTTTATGGCGTTTTAAAAAGCCGAGACTGCATCCGGGCAGCAGCGCATCG
GCTCGCACGAGGTCTGCGCTTGAATTGTGTTGTAGAAACACAACGTTTTTGAAAAAATAAGCTATTGTTTTAT
ATCAAAATATAATCATTTTTAAAATAAAGGTTGCGGCATTTATCAGATATTTGTTCTGAAAAtcggcaactgtcgga
atatctgctaaaattccgcattttccgcaccgggtttccgcaccgggacactcggggcgtatgttcaatttgtcggaatggagtttaaaggaata
caCAT

*lst*(250): *lacZ* (SEQ ID NO: 15)

GTCGACGAGCTAAGGCGAGGCAACGCCGTACTTGTTTTTGTTAATCCACTATAAAGTGCCGCGTGTGTTTTT
TTATGGCGTTTTAAAAAGCCGAGACTGCATCCGGGCAGCAGCGCATCGGCTCGCACGAGGTCTGCGCTTGA
ATTGTGTTGTAGAAACACAACGTTTTTGAAAAAATAAGCTATTGTTTTATATCAAAATATAATCATTTTTAAAA
TAAAGGTTGCGGCATTTATCAGATATTTGTTCTGAAAAtcggcaactgtcggaatatctgctaaaattccgcattttccgcacc
gggtttccgcaccgggacactcggggcgtatgttcaatttgtcggaatggagtttaaaggaatacaCAT

*lst*(400):*lacZ* (SEQ ID NO: 16)

GTCGACATTCGGCTTGATTTCGATACACCCGACACACGCAGGAAATTATAGTGGATTAATAAAAATCAGGAC
AAGGCGACGAAGCCGAAGACAGTACAGATAGTACGAAACCGATTCACTTGGTGCTTCAGCACCTTAGAGAA
TCGTTCTCTTTGAGCTAAGGCGAGGCAACGCCGTACTTGTTTTTGTTAATCCACTATAAAGTGCCGCGTGTGT
TTTTTTATGGCGTTTTAAAAAGCCGAGACTGCATCCGGGCAGCAGCGCATCGGCTCGCACGAGGTCTGCGCT
TGAATTGTGTTGTAGAAACACAACGTTTTTGAAAAAATAAGCTATTGTTTTATATCAAAATATAATCATTTTTA
AAATAAAGGTTGCGGCATTTATCAGATATTTGTTCTGAAAAtcggcaactgtcggaatatctgctaaaattccgcattttccg
caccgggtttccgcaccgggacactcggggcgtatgttcaatttgtcggaatggagtttaaaggaatacaCAT

Figure 21

Figure 23 (SEQ ID NO: 17)

*lst*(200+5): *lacZ*

GTCGACGTGCCGCGTGTGTTTTTTTATGGCGTTTTAAAAAGCCGAGACTGCATCCGGGCAGCAGCGCATCG

SalI

GCTCGCACGAGGTCTGCGCTTGAATTGTGTTGTAGAAACACAACGTTTTTGAAAAAATAAGCTATTGTTTTAT

*porA* enhancer sequence

ATCAAAATATAATCATTTTTAAAATAAAGGTTGCGGCATTTATCAGATATTTGTTCTGAAAATGCATtcggcaac

NsiI -35 tgtcggaatatctgctaaaattccgcattttccgcaccgggtttccgcaccgggacactcggggcgtatgttcaatttgtcggaatggagtttaa

*porB* -10 *porB* 5' UTR aggaatacaCATATG

NdeI

START codon...

Figure 25

Heterologous Antigen Expression Cassette 3 – HAEC3:(Z)-(Z')

(SEQ ID NO: 18)

GTCGACGAGCTAAGGCGAGGCAACGCCGTACTTGTTTTTGTTAATCCACTATAAAGTGCCGCGTGTGTTTTTTTATGGCGTTTTAA

SalI

AAAGCCGAGACTGCATCCGGGCAGCAGCGCATCGGCTCGCACGAGGTTCTGCGCTTGAATTGTGTTGTAGAAACACAACGTTTTT

*porA* enhancer sequence (250 bp)

GAAAAAATAAGCTATTGTTTTATATCAAAATATAATCATTTTTAAAATAAAGGTTGCGGCATTTATCAGATATTTGTTCTGAAAAAT

GGTTtttcgggcgggaacattTATAATTGAAGACGTATCGGGTGTTTGCCCGATGTTTTTAGGTTTTTATCAAATTTACAAAAGGAACTC -35 *porB* -10 *porA* 5' UTR RBS GAGNNNNNNNNNNGCGGCCGCAAGTTTGTTTACTGTCGGAATATCTGCTATAGTTTCAAACAAGGAATCGACGAAAACGTC XhoI LINKER NotI -35 *lst* -10

GTCGGTAAATGCAAAGCTAAGCGGCTCGGAAAGCCCGGTTCGCTTAAATTTCTTAACCAAAAAAGGAATACACATATGNNNNN

*porB* 5' UTR RBS NdeI

NNNNNAAGCTTTCTGCAAGATTGGTATCAACAAAAAGCCTGTCGTCAGACAGGCTTTTTTTCTGTTTTCTGTTTTTAGatgccgtctg

LINKER HindIII *porB* TERMINATOR AT-DUS aa

Figure 26

Heterologous Antigen Expression Cassette 4 – HAEC4:(Z)-(Z')

(SEQ ID NO: 19)

GTCGACGTGCCGCGTGTGTTTTTTTATGGCGTTTTAAAAAGCCGAGACTGCATCCGGGCAGCAGCGCATCGGCTCGCACGAGGTT

SalI porA enhancer sequence (200 bp)

CTGCGCTTGAATTGTGTTGTAGAAACACAACGTTTTTGAAAAAATAAGCTATTGTTTTATATCAAAATATAATCATTTTTAAAATAA

AGGTTGCGGCATTTATCAGATATTTGTTCTGAAAAATGGTTtttcgggcgggaacattTATAATTGAAGACGTATCGGGTGTTTGCCCG -35 porB -10

ATGTTTTTAGGTTTTTATCAAATTTACAAAAGGAACTCGAGNNNNNNNNNNNGCGGCCGCATATtcggcaACTGTCGGAATATCT porA 5' UTR RBS XhoI LINKER NotI -35 lst GCtaaaatTCCGCATTTTCCGCACCGGGTTTCCGCACCGGGACACTCGGGGCGTATGTTCAATTTGTCGGAATGGAGTTTAAAGGA -10 lst 5' UTR RBS ATACACATATGNNNNNNNNNNNAAGCTTTCTGCAAAGATTGGTATCAACAAAAAGCCTGTCGTCAGACAGGCTTTTTTTCTGTT NdeI LINKER HindIII porB TERMINATOR TTCTGTTTTTAGatgccgtctgaa

AT-DUS

**>Coding sequence of synth.*lacZ* (CAI: 0.687) (SEQ ID NO: 20)**

ATGCTGTTGGCAAACTACTACCAAGACCCGGAAATTACCCGCATCAACGCACTCCCGCAtCATTCCTACTTCA
TCCCATTCGACAAgAAAGACAAAGTTGACCAATTTTCGCGCGAgAAcTCCAGCTTCTTCACATCCCTGAACG
GCATGTGGCAgTTCGCtTACTACCCTTCTATGCAAGACcTGCCGGAATCTCCCGAtGAgATtGCGTTCACTAAA
CAgATaAACGTACCGAGCAACTGGCAaAACCATGGCTTcGACGCGCAcCAgTACACCAACATcAACTACCCGT
TtCCATTtGACCCtCCgTTCGTACCCCTGGAAAATCCGTGTGGTGTCTACCAgAAACAaGTTAACCTGAAgAAA
AACATCAACAAACGTTAccTcCTGGTtCTGGAgGGcGTgGACagcTGCagcTACATCTAcGTgAAtCACCAGTTcG
TtGGTTACGGCAGCATTTCCCATtcCACgAACGAGTTcGAcATCACTGAcTACTTGCATGACGGcGAgAATACg
CTCACtGTCTTCGTAtTGAAGTGGTGCGCgGGCtcCTAtCTGGAgGAcCAAGACAAgTTCCGCATGTCCGGTAT
CTTtCGGGACGTcTACTTGcTcGAgCGCGAACAcCATTACCTGCAGGATCTCAACATCCGCACtGTcCTGAGCG
AgGACCTcagcCTcGGCCAaATcTGCCTTGAcCTGAACTTCGCCGGTGAcGCCGGCGACGTgGGTGTcagTCTcT
TCGACACCGAtGGCCAGATCGTgCAgGCCGGTTCCGCCATtACTACgGACAAgCAgCGTATGCAgATTCGtCTG
GAcAAcATcCCgTTGACTAAAAGtCGTttgTGGAAcGCCGAgAAtCCGGCATTGTAcACgcTtGTTCTGAATACC
AAAGAgGAgATTATcACgCAAAAAATtGGCTTtCGtAAAGTTGAAGTGAAgAATGGCGTGcTGTTGCTGAAcA
ACCAaCCGATCAAgTTtAAGGGtGTTAAtCGCCATGActcCGACCCTAAAACGGGGTACGCTATTTCCGTCGCC
CAAGCCGTCACGGACCTGTCACTGATGAAAAAACACAATATCAACGCGATTCGCACTGCACATTATCCGAAT
TCCCCCTGGTTCTGCGAACTGTGTGACAAATATGGGTTTTACGTGATCAGTGAAAGCGACATTGAATCACAC
GGTGCAGCCTTCCAGGCTATCTCCCATCCGGAACCGTCAATTTTCCTTAACGTGGAAAACCCCAACGAAGAA
CCGCGGATCCGCCAACAAACAATCGACAACTTTTGCTACTTCGCTCGTGAACCGTTGTATCGTGCGGCACTG
CTGGAACGTACCAAAGCCAACATTGAACGTGACAAAAACCGCTCTTCCATTTTGATTTGGTCTTTGGGCAAC
GAGAGCGGCTACGGCGAAAACTTCGAATACTGCGCAAAATGGGTTAAAGAACGCGATCCTGATCGTTTGGT
CCACTACGAATCAAGCATCTATCAGCATAGCGCATACCAAAATAACACCGGTCATTTGGATCTATACAGTGAA
ATGTACTCCGATACGGAAGCCATTGATGCCTACTTTGCAGACCACAGCCAGACCAAAAAACCGTTCCTGCTA
TGTGAATACAGCCACGCCATGGGCAATTCCAACGGTGACATGGAAGATTACTTTCAAACCTTTAACAAATAC
TCCGGCTGTTGCGGCGGTTTCATCTGGGAATGGTGTGACCACGCACAATATATCACCCCGACGAAATTGGGC
TACGGTGGCGACTTTGGAGAGAAAATCCATGATGGCAATTTCTGTGTCGATGGGTTGGTTAGCCCTGAACG
CGTACCCCACTCGAATCTGTTGGAGGTTAAGAACGTTAACCGCCCGGTCCGCGCTAACCTGAGGGGTGAAC
AAATAGAATTGTACAACTACTTCGATTTCACCAACTTAAAAGACATCTTGTGCGTAAAATACGAATGGGTCAA
AAATGGTCAAATTACTGGCACCGGTACACTGGCGGTCGACTGCGAACCCCACCACTCCCAGATTTTGCCTAT
cCAaCTGCCGAAGGAGCGTGAgGGTcTcTTgTGGcTtAAtCTGTACTATTGtGCCagcCGTCAGACcGACCTGCT
CCCTGCgGGCCACCACTTtGGCTTtGACCAgATcATCCTGTCAAAAGAGTAtACCCCCGCGATTGGCAGCGAC
AAgGACGAcTGtCCaCCtCTGGAGATCACtGAgACCGTCCGCCAGATTGTGGTcCGTAAtAACCGTTACTACTT
CGAgTTCAAtAAATTGACTGGtATTATCGATGAGATcAAgGTGAACGGtAAAGCCTTTATtCAcAAACCGCTCG
CCTGGAAcATCTGGCGtGCCCCCACCGAcAAcGAtCGTTTGATcCGCTCACAGTGGCAgAACGCGGGCTACG
AcCAgATGTACTCTAAAGTcTAtGACATCTGtGCACACCGCCAgGGCAAtGGcGTCGTTGTCTCGGTAAAGTCG
GCGCTCGTCGCAGACGCCAAATCGAAgATtATGACGCTGGAgACCCAATACTTGCTCagcGAgAACGGCAAA
CTGGACATCCAgACCAACGCaGTGTTTCAtGAACAcCTCCCGTTtTTaCCACGCTTTGGCCTcCGtTTCTTtCTG
GATGAgCAAAAgACCCCGTTCACTTAtCTGGGCTAcGGCGCCGGCGAgTCTTACATCGACAAgCAcCAAGCCA
CgAAATTGGGCATcTAcTCCACCACCGCCGGCGAgAACCATGTcGGtTAccTgAAACCGCAGGAAAATGGTTC
CCAcTACGGcTGTTTcTAcGTGCAgAAtGAcATGATtCGCGTAGAAAGCGGCCAACCcTTCTCCTTTAAttTaagc
CCGTACACCCAgGAAGAgTTGACCCAAAAgAAaCACTCCTACGAgCTCGTCTGcagcGGATAcGACGTCctcTG
CATTGAtTAcAAAATGTCTGGcATTGGCTCCAACAGCTGTGGCCCCAACcTGAAACCTCAgTACCGCCTCATC
GAgAACAAtATtAAcTTtGAcATTTCCATTCGCCTCTAG Figure 37 SEQ ID NO: 20

Points represent Mean ± SD, where no error bars are visible they fall within the points 1-way ANOVA of AUC w Tukey's multiple comparisons test, ns n = 4.

Bars represent Mean ± SD. *p ≤ 0.05; *p ≤ 0.001; **p ≤ 0.0001; RM 2-way ANOVA w Tukey's multiple comparisons test, n = 4

Table 1. E-test results: MIC vs. (GM)-*N. lactamica* strains

| | WT | 4NB1 | 4OA2 | 4NOA1 | 4YB2 |
|---|---|---|---|---|---|
| RIF | 0.38 | 0.38 | 0.38 | 0.38 | 0.75 |
| Cip | 0.003 | 0.003 | 0.002 | 0.003 | 0.008 |
| Ceftri | <.002 | 0.003 | <.002 | 0.003 | <.002 |

Table 2. MIC breakpoints for pathogenic *Neisseria* species

| | Breakpoint MIC (mg/L) | | | Reference |
|---|---|---|---|---|
| Antibiotic | R > | I | S ≤ | |
| RIF | 1 | - | 1 | Taha *et al. Antimicrob Agents Chemother.* 2010 Sep;54(9):3651-8. |
| Cip | 0.06 | 0.06 | 0.03 | BSAC Standardized Disc Susceptibility Testing Method v .12 (2013) |
| Ceftri | 0.12 | - | 0.12 | BSAC Standardized Disc Susceptibility Testing Method v .12 (2013) |

Figure 42

RM 1-way ANOVA with Tukey's Multiple Comparisons test, ns n = 6.

SEQUENCE LISTING

```
<160> NUMBER OF SEQ ID NOS: 35

<210> SEQ ID NO 1
<211> LENGTH: 10
<212> TYPE: DNA
<213> ORGANISM: Neisseria meningitidis

<400> SEQUENCE: 1

gccgtctgaa                                                              10


<210> SEQ ID NO 2
<211> LENGTH: 12
<212> TYPE: DNA
<213> ORGANISM: Neisseria meningitidis

<400> SEQUENCE: 2

atgccgtctg aa                                                           12


<210> SEQ ID NO 3
<211> LENGTH: 1547
<212> TYPE: DNA
<213> ORGANISM: Artificial Sequence
<220> FEATURE:
<223> OTHER INFORMATION: Modified gene sequences

<400> SEQUENCE: 3

atggtttcga aaggggaaga actgtttaca ggcgtggtac caatcctcgt ggaactggat      60

ggcgatgtca acggccataa attctctgtc cgcggcgaag gtgaaggcga tgcaaccaat     120

ggcaaattga cgttgaaatt catttgcacc accggcaaac tgcccgttcc gtggccgacg     180

ctggtcacaa ccttcggata tggcgtcgcc tgcttctcgc gctacccgga tcacatgaaa     240

caacacgact tcttcaaatc cgcaatgccg gaaggttatg ttcaggaacg tactatttcg     300

ttcaaggatg acggcaccta caaaacccgc gccgaagtca aatttgaagg cgataccttta    360

gttaaccgta ttgaattgaa aggcattgac tttaaagaag acggcaacat cctgggccac     420

aaattagaat acaacttcaa ctcgcataac gtctatatca cagccgataa gcagaaaaat     480

ggcataaaag ccaacttcaa aattcgccac aacgttgagg atggtagcgt tcagttggct     540

gaccactatc aacaaaacac tcccatcggc gacggtccgg tactgttgcc cgacaaccat     600

tacctttccc accagtccgc cctgtccaaa gatccgaatg aaaaacgcga ccacatggtt     660

ctgctggagt tcgtcactgc agcgggcatc acgcacggaa tggacgaact ctataaatag     720

gcggccgcgc cgtctgaatt aaaggaaatc atatggccaa aatgcgcatt agtccggaac     780

tgaaaaaatt gattgaaaag taccgctgtg tcaaagatac tgagggtatg tcgcccgcca     840

aagtctacaa gctggtcggc gaaaatgaaa acctgtactt gaaaatgaca gatagtcgct     900

acaaaggcac cacctacgac gtagagcgcg agaaagatat gatgttatgg ctggaaggta     960

aactgcctgt tccgaaagtt ctgcatttcg aacgccacga cggttggagc aacctgctga    1020

tgtcggaagc agatggcgta ttgtgtagcg aagaatacga agacgaacaa tcgccggaga    1080

aaatcatcga attgtacgcg gaatgcatcc gcttgtttca cagcatcgac atcagtgatt    1140
```

-continued

```
gcccttacac caactcctta gatagccgcc tggctgaact tgattatttg ttgaataacg   1200

acttggctga tgtagactgc gaaaactggg aggaagatac acccttcaag gacccgcgcg   1260

agctctacga ctttctgaaa actgaaaaac cggaagaaga gctggttttc tcccacggcg   1320

atctgggcga ctcgaatatt ttcgtaaaag atggcaaagt ttccggcttt atcgacttgg   1380

gccgcagcgg gcgcgcagat aaatggtacg acattgcgtt ctgcgtccgc agcatccgtg   1440

aagatatcgg tgaagaacaa tacgtcgagc tctttttcga cttgctgggt attaaaccgg   1500

attgggaaaa aatcaaatat tatatcctgt tggatgaatt attctag                 1547
```

<210> SEQ ID NO 4
<211> LENGTH: 1021
<212> TYPE: DNA
<213> ORGANISM: Neisseria lactamica

<400> SEQUENCE: 4

```
ctgataccga gcttttccca tggtttatcg cgactgatag tgttttcggc gaggtagtcg     60

gcacgtgttt gagaccacca gcgagtgatt gtgctttcag ctacaataat tttgctgctt    120

gctctatgtt taaaaatcta tccatattgg atagtttaga ttagacttaa gtggatttca    180

agtgagctgt ttaaccctta gctagcaagg gttttggtgg cgtaaggtta ctgaacttaa    240

gcatatcggc ggccaaagta ccgctgccat tgccaatctc gccggggaaa tgaaaaggct    300

cgctaaaaaa tcaaaaatgt tactgaaagg actttggtca tttttatcct ctacaatatc    360

tacatttaaa aataaatcgg tcattgttta aaccttactg taaaactgta caactgctaa    420

actgtaaaca cagaaagagg caatactaac agcacaaaac aacagatatc caaactccat    480

aaagtgcatt attctgactt ttttcgttgc ctgatgtatt tatgctattt gtgctgttct    540

tatatatgtg ttgctggtta cgttgcgttt tttcggaaaa ttcaaccggt aggggaccga    600

tacgcagttt catctctttg cttagggaga gtagggggt agattacgac cttagttttg    660

gtatccgtaa tatcatcatt ttttcgtcta gggagtatat cgacttcaga aaacaggtat    720

tagatactgc cttttcttac gagagtgatg gcaagatagt tctcttcaag tcaatcaaac    780

aggaaagtat ttcttttctg tctgaagatt tgaaaaagga ctgaatgttt cacaaggtta    840

aaactgggga aaaagatgga tatggttcag atgaaatgct gagcgcaccc cgtatctatt    900

tggaaatgat gtcgcggaaa acggaagtcc cctactccag tattctttaa attctaagca    960

gaaaacttct tcgtcggtct tttttttgtt gtttggtttg catggagtaa aactgtgcaa   1020

c                                                                   1021
```

<210> SEQ ID NO 5
<211> LENGTH: 1026
<212> TYPE: DNA
<213> ORGANISM: Neisseria lactamica

<400> SEQUENCE: 5

```
tgctgaagta gaaaaccagc aagaaggtaa aaagaaagaa gcagtttttt ggattttaga     60

tgttaccgca attggtttcc tttcctaaaa tttgtttaaa ttatttgcaa tattaatata    120

aactggatat taatgatgag gattcaaaaa ggcatactga atataatttg tacaaaatat    180

ttgcagtatt taaaaatgtt ggttcgtata tgaaaagtta aaaatgccaa aatgtacagt    240

tgctaaactg taaaactgct aaagcaacaa aacataaaaa ggaatgcagg gatgcgatca    300

ctacatcttt ttattccgta agcatttatg actttacggt caactgctac tctatgtttc    360
```

-continued

```
cagcttttca gctccctatt ttcgaatatt ggacgaggca ttttcatcag tgtcgtaatg    420

ccgaccgaaa ccctcacaaa ccatattggt tcttgtggca gcaacaccta tccgtttgtt    480

caagcggcca caagagtaac atgattggct ggtggcattg gctttaatct cttcgatatg    540

aactccattt ttagctgcac cttctttcag cgtatgcaac agtggggatg gggcaactat    600

cttctggtgg agtttgttga cttcaatctg tatgcactgt aggttgagca gattcagttt    660

tttgatacag attatccggc tttgttcggc aattctgttg gcgaacgtat agtagagctg    720

tcgtcttgcc gctttcaatt tgcggtaggt attttaccat tccatgcgta gccgctcggt    780

acgtttgagc caaatgttat cttcgccatt tgtaccaatt tgtttttaca ttaggctgtg    840

ttttagtaat ctattgattt caattatttg caagggaaaa gacaattatt ttccggttag    900

gaataaacct atcctattga atatattgaa gccaagtacg cttatcaaca ctatattaaa    960

acacagcctt ttttaatata gtagacacaa tctttcctta tttatgaagg tgatagcttc   1020

tttcag                                                              1026
```

<210> SEQ ID NO 6
<211> LENGTH: 1029
<212> TYPE: DNA
<213> ORGANISM: Neisseria lactamica

<400> SEQUENCE: 6

```
cgggccggaa gacgattata tgaatgacga tcatctggct tttttccgcg aattgctggt     60

aaaaatgcaa gacgaactca tcgaaaatgc ttccgctacg acagggcatc tccaagaaca    120

tgaatcagcc cccgatcctg ccgaccgtgc cacacaggaa gaagagtacg cattggaact    180

ccgtacccgc gatcgggaac gaaaacttct cagtaaaata caggcgacca tccgcaatat    240

tgacaggggc gattatggat tctgcgccga tacgggagaa cctatcgggc tgaagcggct    300

gttggcgcgc ccgaccgcca ctttgtccgt agaggcgcaa gagcgtcgtg agagaatgaa    360

aaaacagttt gccgactaat agcggcaaac gaaaatgccg tctgaagccc cgagtttcag    420

acggcatatt cacaaaggcg caccagccag aggagaagag gaagggattt ttggaggcgg    480

cgcagcattt ggcggaaata aaaaacctta tctgacaggg atatgacgaa tttccccaaa    540

aaatcccgct gaaagtgttg accgcctccg tcttcgggcg tatagttcgg ttcttcgctg    600

ccgacgaagc ggcggaatga aacggacaag tatatcacgg tttgcaggat gtttgacgca    660

tcggccgtac ataccgacag tttcaaacgc tctttaacaa aacagattac cgataagtgt    720

gagtgcctcg ggcctcacac tgtttgaaag acagacaaga taatgttttg aacattgtcc    780

tgtcggtttc tttgaagcag accagaagtt aaaaagttag agattgaaca taagagtttg    840

atcctggctc agattgaacg ctggcggcat gctttacaca tgcaagtcgg acggcagcgg    900

ggtagtgctt gcactactgc cggcgagtgg cgaacgggtg agtaacatat cggaacgtac    960

cgggcagtgg gggataactg atcgaaagat cagctaatac cgcatatttt ctgaggaaga   1020

aagcagggg                                                           1029
```

<210> SEQ ID NO 7
<211> LENGTH: 987
<212> TYPE: DNA
<213> ORGANISM: Neisseria lactamica

<400> SEQUENCE: 7

```
accatttggc cttgcgctat ccgagcggcc gatatctgat tagcttgttg gcggggtaag     60

ggcccaccaa ggcgacgatc agtagcgggt ctgagaggac gatccgccac actgggactg    120
```

```
agacacggcc cagactccta cgggaggcag cagtggggaa ttttggacaa tgggcgcaag    180

cctgatccag ccatgccgcg tgtctgaaga aggccttcgg gttgtaaagg acttttgtcg    240

gggaagaaaa ggctgttgct aatatcagcg gctgatgacg gtacccgaag aataagcacc    300

ggctaactac gtgccagcag ccgcggtaat acgtagggtg cgagcgttaa tcggaattac    360

tgggcgtaaa gcgggcgcag acggttactt aagcaggatg tgaaatcccc gggctcaacc    420

cgggaattgc gttctgaact gggtggctag agtgtgtcag agggaggtag aattccacgt    480

gtagcagtga aatgcgtaga gatgtggagg aataccgatg gcgaaggcag cctcctggga    540

taacactgac gttcatgtcc gaaagcgtgg gtagcaaaca ggattagata ccctggtagt    600

ccacgcccta aacgatgtcg attagctgtt gggcagcctg actgcttggt agcgaagcta    660

acgcgtgaaa tcgaccgcct ggggagtacg gtcgcaagat taaaactcaa aggaattgac    720

ggggacccgc acaagcggtg gatgatgtgg attaattcga tgcaacgcga agaaccttac    780

ccggttttga catgtacgga atcctccgga gacggaggag tgccttcggg agccgtaaca    840

caggtgctgc atggctgtcg tcagctcgtg tcgtgagatg ttgggttaag tcccgcaacg    900

agcgcaaccc ttgtcattag ttgccatcat tcagttgggc actctaatga gactgccggt    960

gacaagccgg aggaaggtgg ggatgac                                        987
```

<210> SEQ ID NO 8
<211> LENGTH: 386
<212> TYPE: DNA
<213> ORGANISM: Artificial Sequence
<220> FEATURE:
<223> OTHER INFORMATION: Expression cassette
<220> FEATURE:
<221> NAME/KEY: misc_feature
<222> LOCATION: (135)..(144)
<223> OTHER INFORMATION: n is a, c, g, or t
<220> FEATURE:
<221> NAME/KEY: misc_feature
<222> LOCATION: (291)..(300)
<223> OTHER INFORMATION: n is a, c, g, or t

<400> SEQUENCE: 8

```
gccgtctgaa gtcgactatt cggcaactgt cggaatatct gctaaaattc cgcattttcc     60

gcaccgggtt tccgcaccgg gacactcggg gcgtatgttc aatttgtcgg aatggagttt    120

aaaggaatct cgagnnnnnn nnnngcggcc gcaagtttgt tttttcgggc gggaacattt    180

atagtttcaa acaaggaatc gacgaaaacg tcgtcggtaa atgcaaagct aagcggctcg    240

gaaagcccgg ttcgcttaaa tttcttaacc aaaaaaggaa tacacatatg nnnnnnnnnn    300

aagctttctg caaagattgg tatcaacaaa aagcctgtcg tcagacaggc tttttttctg    360

ttttctgttt ttagatgccg tctgaa                                         386
```

<210> SEQ ID NO 9
<211> LENGTH: 386
<212> TYPE: DNA
<213> ORGANISM: Artificial Sequence
<220> FEATURE:
<223> OTHER INFORMATION: Expression cassette
<220> FEATURE:
<221> NAME/KEY: misc_feature
<222> LOCATION: (151)..(160)
<223> OTHER INFORMATION: n is a, c, g, or t
<220> FEATURE:
<221> NAME/KEY: misc_feature
<222> LOCATION: (291)..(300)
<223> OTHER INFORMATION: n is a, c, g, or t

```
<400> SEQUENCE: 9

gccgtctgaa gtcgacagtt tgttttttcg ggcgggaaca tttatagttt caaacaagga     60

atcgacgaaa acgtcgtcgg taaatgcaaa gctaagcggc tcggaaagcc cggttcgctt    120

aaatttctta accaaaaaag gaatctcgag nnnnnnnnnn gcggccgcat attcggcaac    180

tgtcggaata tctgctaaaa ttccgcattt tccgcaccgg gtttccgcac cgggacactc    240

ggggcgtatg ttcaatttgt cggaatggag tttaaaggaa tacacatatg nnnnnnnnnn    300

aagctttctg caaagattgg tatcaacaaa aagcctgtcg tcagacaggc ttttttctg     360

ttttctgttt ttagatgccg tctgaa                                         386


<210> SEQ ID NO 10
<211> LENGTH: 121
<212> TYPE: DNA
<213> ORGANISM: Artificial Sequence
<220> FEATURE:
<223> OTHER INFORMATION: Modified promoter

<400> SEQUENCE: 10

gtcgactcgg caactgtcgg aatatctgct aaaattccgc attttccgca ccgggtttcc     60

gcaccgggac actcggggcg tatgttcaat ttgtcggaat ggagtttaaa ggaatacaca    120

t                                                                    121


<210> SEQ ID NO 11
<211> LENGTH: 171
<212> TYPE: DNA
<213> ORGANISM: Artificial Sequence
<220> FEATURE:
<223> OTHER INFORMATION: Modified promoter

<400> SEQUENCE: 11

gtcgactcat ttttaaaata aaggttgcgg catttatcag atatttgttc tgaaaatcgg     60

caactgtcgg aatatctgct aaaattccgc attttccgca ccgggtttcc gcaccgggac    120

actcggggcg tatgttcaat ttgtcggaat ggagtttaaa ggaatacaca t             171


<210> SEQ ID NO 12
<211> LENGTH: 221
<212> TYPE: DNA
<213> ORGANISM: Artificial Sequence
<220> FEATURE:
<223> OTHER INFORMATION: Modified promoter

<400> SEQUENCE: 12

gtcgacaaac acaacgtttt tgaaaaaata agctattgtt ttatatcaaa atataatcat     60

ttttaaaata aaggttgcgg catttatcag atatttgttc tgaaaatcgg caactgtcgg    120

aatatctgct aaaattccgc attttccgca ccgggtttcc gcaccgggac actcggggcg    180

tatgttcaat ttgtcggaat ggagtttaaa ggaatacaca t                        221


<210> SEQ ID NO 13
<211> LENGTH: 271
<212> TYPE: DNA
<213> ORGANISM: Artificial Sequence
<220> FEATURE:
<223> OTHER INFORMATION: Modified promoter

<400> SEQUENCE: 13

gtcgacggca gcagcgcatc ggctcgcacg aggtctgcgc ttgaattgtg ttgtagaaac     60

acaacgtttt tgaaaaaata agctattgtt ttatatcaaa atataatcat ttttaaaata    120
```

```
aaggttgcgg catttatcag atatttgttc tgaaaatcgg caactgtcgg aatatctgct    180

aaaattccgc attttccgca ccgggtttcc gcaccgggac actcggggcg tatgttcaat    240

ttgtcggaat ggagtttaaa ggaatacaca t                                   271


<210> SEQ ID NO 14
<211> LENGTH: 321
<212> TYPE: DNA
<213> ORGANISM: Artificial Sequence
<220> FEATURE:
<223> OTHER INFORMATION: Modified promoter

<400> SEQUENCE: 14

gtcgacgtgc cgcgtgtgtt tttttatggc gttttaaaaa gccgagactg catccgggca     60

gcagcgcatc ggctcgcacg aggtctgcgc ttgaattgtg ttgtagaaac acaacgtttt    120

tgaaaaaata agctattgtt ttatatcaaa atataatcat ttttaaaata aaggttgcgg    180

catttatcag atatttgttc tgaaaatcgg caactgtcgg aatatctgct aaaattccgc    240

attttccgca ccgggtttcc gcaccgggac actcggggcg tatgttcaat ttgtcggaat    300

ggagtttaaa ggaatacaca t                                              321


<210> SEQ ID NO 15
<211> LENGTH: 370
<212> TYPE: DNA
<213> ORGANISM: Artificial Sequence
<220> FEATURE:
<223> OTHER INFORMATION: Modified promoter

<400> SEQUENCE: 15

gtcgacgagc taaggcgagg caacgccgta cttgtttttg ttaatccact ataaagtgcc     60

gcgtgtgttt ttttatggcg ttttaaaaag ccgagactgc atccgggcag cagcgcatcg    120

gctcgcacga ggtctgcgct tgaattgtgt tgtagaaaca caacgttttt gaaaaaataa    180

gctattgttt tatatcaaaa tataatcatt tttaaaataa aggttgcggc atttatcaga    240

tatttgttct gaaaatcggc aactgtcgga atatctgcta aaattccgca ttttccgcac    300

cgggtttccg caccgggaca ctcggggcgt atgttcaatt tgtcggaatg gagtttaaag    360

gaatacacat                                                           370


<210> SEQ ID NO 16
<211> LENGTH: 518
<212> TYPE: DNA
<213> ORGANISM: Artificial Sequence
<220> FEATURE:
<223> OTHER INFORMATION: Modified promoter

<400> SEQUENCE: 16

gtcgacattc ggcttgattt cgatacaccc gacacacgca ggaaattata gtggattaat     60

aaaaatcagg acaaggcgac gaagccgaag acagtacaga tagtacgaaa ccgattcact    120

tggtgcttca gcaccttaga gaatcgttct ctttgagcta aggcgaggca acgccgtact    180

tgtttttgtt aatccactat aaagtgccgc gtgtgttttt ttatggcgtt ttaaaaagcc    240

gagactgcat ccgggcagca gcgcatcggc tcgcacgagg tctgcgcttg aattgtgttg    300

tagaaacaca acgtttttga aaaaataagc tattgtttta tatcaaaata taatcatttt    360

taaaataaag gttgcggcat ttatcagata tttgttctga aaatcggcaa ctgtcggaat    420

atctgctaaa attccgcatt ttccgcaccg ggtttccgca ccgggacact cggggcgtat    480
```

gttcaatttg tcggaatgga gtttaaagga atacacat 518

<210> SEQ ID NO 17
<211> LENGTH: 329
<212> TYPE: DNA
<213> ORGANISM: Artificial Sequence
<220> FEATURE:
<223> OTHER INFORMATION: Modified promoter

<400> SEQUENCE: 17
gtcgacgtgc cgcgtgtgtt tttttatggc gttttaaaaa gccgagactg catccgggca 60
gcagcgcatc ggctcgcacg aggtctgcgc ttgaattgtg ttgtagaaac acaacgtttt 120
tgaaaaaata agctattgtt ttatatcaaa atataatcat ttttaaaata aaggttgcgg 180
catttatcag atatttgttc tgaaaatgca ttcggcaact gtcggaatat ctgctaaaat 240
tccgcatttt ccgcaccggg tttccgcacc gggacactcg gggcgtatgt tcaatttgtc 300
ggaatggagt ttaaaggaat acacatatg 329

<210> SEQ ID NO 18
<211> LENGTH: 602
<212> TYPE: DNA
<213> ORGANISM: Artificial Sequence
<220> FEATURE:
<223> OTHER INFORMATION: Expression construct
<220> FEATURE:
<221> NAME/KEY: misc_feature
<222> LOCATION: (351)..(360)
<223> OTHER INFORMATION: n is a, c, g, or t
<220> FEATURE:
<221> NAME/KEY: misc_feature
<222> LOCATION: (507)..(516)
<223> OTHER INFORMATION: n is a, c, g, or t

<400> SEQUENCE: 18
gacgtcgagc taaggcgagg caacgccgta cttgtttttg ttaatccact ataaagtgcc 60
gcgtgtgttt ttttatggcg ttttaaaaag ccgagactgc atccgggcag cagcgcatcg 120
gctcgcacga ggtctgcgct tgaattgtgt tgtagaaaca caacgttttt gaaaaaataa 180
gctattgttt tatatcaaaa tataatcatt tttaaaataa aggttgcggc atttatcaga 240
tatttgttct gaaaaatggt ttttcgggcg ggaacattta taattgaaga cgtatcgggt 300
gtttgcccga tgtttttagg tttttatcaa atttacaaaa ggaactcgag nnnnnnnnnn 360
gcggccgcaa gtttgtttac tgtcggaata tctgctatag tttcaaacaa ggaatcgacg 420
aaaacgtcgt cggtaaatgc aaagctaagc ggctcggaaa gcccggttcg cttaaatttc 480
ttaaccaaaa aaggaataca catatgnnnn nnnnnnaagc tttctgcaaa gattggtatc 540
aacaaaaagc ctgtcgtcag acaggctttt tttctgtttt ctgtttttag atgccgtctg 600
aa 602

<210> SEQ ID NO 19
<211> LENGTH: 537
<212> TYPE: DNA
<213> ORGANISM: Artificial Sequence
<220> FEATURE:
<223> OTHER INFORMATION: Expression construct
<220> FEATURE:
<221> NAME/KEY: misc_feature
<222> LOCATION: (302)..(311)
<223> OTHER INFORMATION: n is a, c, g, or t
<220> FEATURE:
<221> NAME/KEY: misc_feature
<222> LOCATION: (442)..(451)
<223> OTHER INFORMATION: n is a, c, g, or t

<400> SEQUENCE: 19
gtcgacgtgc cgcgtgtgtt tttttatggc gttttaaaaa gccgagactg catccgggca 60
gcagcgcatc ggctcgcacg aggtctgcgc ttgaattgtg ttgtagaaac acaacgtttt 120
tgaaaaaata agctattgtt ttatatcaaa atataatcat ttttaaaata aaggttgcgg 180
catttatcag atatttgttc tgaaaaatgg tttttcgggc gggaacattt ataattgaag 240
acgtatcggg tgtttgcccg atgtttttag gtttttatca aatttacaaa aggaactcga 300
gnnnnnnnnn ngcggccgca tattcggcaa ctgtcggaat atctgctaaa attccgcatt 360
ttccgcaccg ggtttccgca ccgggacact cggggcgtat gttcaatttg tcggaatgga 420
gtttaaagga atacacatat gnnnnnnnnn naagctttct gcaaagattg gtatcaacaa 480
aaagcctgtc gtcagacagg ctttttttct gttttctgtt tttagatgcc gtctgaa 537

<210> SEQ ID NO 20
<211> LENGTH: 3039
<212> TYPE: DNA
<213> ORGANISM: Artificial Sequence
<220> FEATURE:
<223> OTHER INFORMATION: Modified lacZ

<400> SEQUENCE: 20
atgctgttgg caaactacta ccaagacccg gaaattaccc gcatcaacgc actcccgcat 60
cattcctact tcatcccatt cgacaagaaa gacaaagttg accaattttc gcgcgagaac 120
tccagcttct tcacatccct gaacggcatg tggcagttcg cttactaccc ttctatgcaa 180
gacctgccgg aatctcccga tgagattgcg ttcactaaac agataaacgt accgagcaac 240
tggcaaaacc atggcttcga cgcgcaccag tacaccaaca tcaactaccc gtttccattt 300
gaccctccgt tcgtacccct ggaaaatccg tgtggtgtct accagaaaca agttaacctg 360
aagaaaaaca tcaacaaacg ttacctcctg gttctggagg gcgtggacag ctgcagctac 420
atctacgtga atcaccagtt cgttggttac ggcagcattt cccattccac gaacgagttc 480
gacatcactg actacttgca tgacggcgag aatacgctca ctgtcttcgt attgaagtgg 540
tgcgcgggct cctatctgga ggaccaagac aagttccgca tgtccggtat ctttcgggac 600
gtctacttgc tcgagcgcga acaccattac ctgcaggatc tcaacatccg cactgtcctg 660
agcgaggacc tcagcctcgg ccaaatctgc cttgacctga acttcgccgg tgacgccggc 720
gacgtgggtg tcagtctctt cgacaccgat ggccagatcg tgcaggccgg ttccgccatt 780
actacggaca agcagcgtat gcagattcgt ctggacaaca tcccgttgac taaaagtcgt 840
ttgtggaacg ccgagaatcc ggcattgtac acgcttgttc tgaataccaa agaggagatt 900
atcacgcaaa aaattggctt tcgtaaagtt gaagtgaaga atggcgtgct gttgctgaac 960
aaccaaccga tcaagtttaa gggtgttaat cgccatgact ccgaccctaa aacggggtac 1020
gctatttccg tcgcccaagc cgtcacggac ctgtcactga tgaaaaaaca caatatcaac 1080
gcgattcgca ctgcacatta tccgaattcc ccctggttct gcgaactgtg tgacaaatat 1140
gggttttacg tgatcagtga aagcgacatt gaatcacacg gtgcagcctt ccaggctatc 1200
tcccatccgg aaccgtcaat tttccttaac gtggaaaacc ccaacgaaga accgcggatc 1260
cgccaacaaa caatcgacaa cttttgctac ttcgctcgtg aaccgttgta tcgtgcggca 1320
ctgctggaac gtaccaaagc caacattgaa cgtgacaaaa accgctcttc cattttgatt 1380
tggtctttgg gcaacgagag cggctacggc gaaaacttcg aatactgcgc aaaatgggtt 1440

-continued

```
aaagaacgcg atcctgatcg tttggtccac tacgaatcaa gcatctatca gcatagcgca   1500
taccaaaata acaccggtca tttggatcta tacagtgaaa tgtactccga tacggaagcc   1560
attgatgcct actttgcaga ccacagccag accaaaaaac cgttcctgct atgtgaatac   1620
agccacgcca tgggcaattc caacggtgac atggaagatt actttcaaac ctttaacaaa   1680
tactccggct gttgcggcgg tttcatctgg gaatggtgtg accacgcaca atatatcacc   1740
ccgacgaaat tgggctacgg tggcgacttt ggagagaaaa tccatgatgg caatttctgt   1800
gtcgatgggt tggttagccc tgaacgcgta ccccactcga atctgttgga ggttaagaac   1860
gttaaccgcc cggtccgcgc taacctgagg ggtgaacaaa tagaattgta caactacttc   1920
gatttcacca acttaaaaga catcttgtgc gtaaaatacg aatgggtcaa aaatggtcaa   1980
attactggca ccggtacact ggcggtcgac tgcgaacccc accactccca gattttgcct   2040
atccaactgc cgaaggagcg tgagggtctc ttgtggctta atctgtacta ttgtgccagc   2100
cgtcagaccg acctgctccc tgcgggccac cactttggct ttgaccagat catcctgtca   2160
aaagagtata cccccgcgat tggcagcgac aaggacgact gtccacctct ggagatcact   2220
gagaccgtcc gccagattgt ggtccgtaat aaccgttact acttcgagtt caataaattg   2280
actggtatta tcgatgagat caaggtgaac ggtaaagcct ttattcacaa accgctcgcc   2340
tggaacatct ggcgtgcccc caccgacaac gatcgtttga tccgctcaca gtggcagaac   2400
gcgggctacg accagatgta ctctaaagtc tatgacatct gtgcacaccg ccagggcaat   2460
ggcgtcgttg tctcggtaaa gtcggcgctc gtcgcagacg ccaaatcgaa gattatgacg   2520
ctggagaccc aatacttgct cagcgagaac ggcaaactgg acatccagac caacgcagtg   2580
tttcatgaac acctcccgtt tttaccacgc tttggcctcc gtttctttct ggatgagcaa   2640
aagaccccgt tcacttatct gggctacggc gccggcgagt cttacatcga caagcaccaa   2700
gccacgaaat tgggcatcta ctccaccacc gccggcgaga accatgtcgg ttacctgaaa   2760
ccgcaggaaa atggttccca ctacggctgt ttctacgtgc agaatgacat gattcgcgta   2820
gaaagcggcc aacccttctc ctttaattta agcccgtaca cccaggaaga gttgacccaa   2880
aagaaacact cctacgagct cgtctgcagc ggatacgacg tcctctgcat tgattacaaa   2940
atgtctggca ttggctccaa cagctgtggc cccaacctga aacctcagta ccgcctcatc   3000
gagaacaata ttaactttga catttccatt cgcctctag                         3039
```

<210> SEQ ID NO 21
<211> LENGTH: 7170
<212> TYPE: DNA
<213> ORGANISM: Artificial Sequence
<220> FEATURE:
<223> OTHER INFORMATION: Vector

<400> SEQUENCE: 21

```
tcttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
```

```
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aagaacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccatatg cggtgtgaaa taccgcacag atgcgtaagg   2220
agaaaatacc gcatcaggcg ccattcgcca ttcaggctgc gcaactgttg ggaagggcga   2280
tcggtgcggg cctcttcgct attacgccag ctggcgaaag ggggatgtgc tgcaaggcga   2340
ttaagttggg taacgccagg gttttcccag tcacgacgtt gtaaaacgac ggccagtgaa   2400
ttcgagctcg gtacccgggg atcctctaga gtcgccttac aagcagaatg tcggcggttc   2460
gactccgtca tcacccacca agtttccttt cattgttgca aacaatggat gcgcggtggt   2520
agctcagttg gttagagtac cggcctgtca cgccgggggt cgcgggttcg agccccgtcc   2580
gccgcgccaa gtttcaaaat actgactctg tcggtatttt ttatgttcgg gtgattagct   2640
cagttggtag agcgtctgcc ttacaagcag aatgtcggcg gttcgactcc gtcatcaccc   2700
accaagtttc ctttcattgt tgcaaacaat ggatgcgcgg tggtagctca gttggttaga   2760
gtaccggcct gtcacgccgg gggtcgcggg ttcgagcccc gtccgccgcg ccaaaagtta   2820
```

-continued

```
aaaaatacca acctccggtt ggtatttttt ttgtttgtac gctttaaaaa atgtttgttt   2880
ccggattttt ccattcccat ccggttttgc gctgtacaag gtgttttagc gcgggctttg   2940
gcgtatgttg caaaatgttc cgatattgca tcgtttgcca tattgccgga ggataacggc   3000
ggtgtgcctt gcattggcgt atggcaattg cggaatctat gggcgtgtca tccgaacggg   3060
aacggttttc ggcgtacggt acgacggaat tgtaatccat aaactgcctg tccccgccgc   3120
gccggcattc gttcagacgg catcggccca ataaaaatcc ccctttccag atgtctggcg   3180
gaagggcttt ccaagctgta aaactgccca aagccataaa attacacaat aaaacgcccg   3240
taaaccgggc agccggttcg cagaaagcca aaaataaagc cggatccgag gagggtaaaa   3300
caggatgttc cgcaccggac gaccgccttt atggcaaaat ccgaaggctg tattgtaacc   3360
atcgggcgat ttgggcggtt tgtccccgat tccgacgata cggtgcgtcc aatagtggtg   3420
actatatttt ttaaaaaagt gttttgagta tgaaaatcac aaaaacagaa ctatttttaa   3480
gattagccaa accaaatgaa caaggtattt cccgttgggt tagtacaagt gaatttgccg   3540
gggaatataa agatttgaaa ttaggtaatg gggaagctg gtgtcggaaa gattctccat    3600
tggcgagaga atattcggca actgtcggaa tatctgctaa aattccgcat tttccgcacc   3660
gggtttccgc accgggacac tcgaggcgta tgttcaattt gtcggaatgg agtttaaagg   3720
aaatcatatg gtttcgaaag gggaagaact gtttacaggc gtggtaccaa tcctcgtgga   3780
actggatggc gatgtcaacg gccataaatt ctctgtccgc ggcgaaggtg aaggcgatgc   3840
aaccaatggc aaattgacgt tgaaattcat ttgcaccacc ggcaaactgc ccgttccgtg   3900
gccgacgctg gtcacaacct tcggatatgg cgtcgcctgc ttctcgcgct acccggatca   3960
catgaaacaa cacgacttct tcaaatccgc aatgccggaa ggttatgttc aggaacgtac   4020
tatttcgttc aaggatgacg gcacctacaa aacccgcgcc gaagtcaaat ttgaaggcga   4080
taccttagtt aaccgtattg aattgaaagg cattgacttt aaagaagacg gcaacatcct   4140
gggccacaaa ttagaataca acttcaactc gcataacgtc tatatcacag ccgataagca   4200
gaaaaatggc ataaaagcca acttcaaaat tcgccacaac gttgaggatg gtagcgttca   4260
gttggctgac cactatcaac aaaacactcc catcggcgac ggtccggtac tgttgcccga   4320
caaccattac ctttcccacc agtccgccct gtccaaagat ccgaatgaaa aacgcgacca   4380
catggttctg ctggagttcg tcactgcagc gggcatcacg cacggaatgg acgaactcta   4440
taaataggcg gccgcgccgt ctgaattaaa ggaaatcata tggccaaaat gcgcattagt   4500
ccggaactga aaaaattgat tgaaaagtac cgctgtgtca aagatactga gggtatgtcg   4560
cccgccaaag tctacaagct ggtcggcgaa aatgaaaacc tgtacttgaa aatgacagat   4620
agtcgctaca aaggcaccac ctacgacgta gagcgcgaga aagatatgat gttatggctg   4680
gaaggtaaac tgcctgttcc gaaagttctg catttcgaac gccacgacgg ttggagcaac   4740
ctgctgatgt cggaagcaga tggcgtattg tgtagcgaag aatacgaaga cgaacaatcg   4800
ccggagaaaa tcatcgaatt gtacgcggaa tgcatccgct tgtttcacag catcgacatc   4860
agtgattgcc cttacaccaa ctccttagat agccgcctgg ctgaacttga ttatttgttg   4920
aataacgact tggctgatgt agactgcgaa aactgggagg aagatacacc cttcaaggac   4980
ccgcgcgagc tctacgactt tctgaaaact gaaaaaccgg aagaagagct ggttttctcc   5040
cacggcgatc tgggcgactc gaatattttc gtaaaagatg gcaaagtttc cggctttatc   5100
gacttgggcc gcagcgggcg cgcagataaa tggtacgaca ttgcgttctg cgtccgcagc   5160
atccgtgaag atatcggtga agaacaatac gtcgagctct tttcgactt gctgggtatt    5220
```

-continued

```
aaaccggatt gggaaaaaat caaatattat atcctgttgg atgaattatt ctagtatcta   5280
gagatgcaat ccgccttaat ggctttaatc aagaaaagca ttttaaacaa tatatccgaa   5340
aagatatcaa agacgcgctt aaaacaagaa attgtgtgat gttgggggtt aatggaaaat   5400
ctgaaaatac caagattgaa atcgatcata aagacggtag gaaaaacaat catcgtgtca   5460
gtgacattaa aacgcaaaaa ttagaagatt tccaaccgct ttgcaaagca gccaatgatg   5520
tcaaacgcca aatctgcaaa gcctgtaaag agacgaacaa gcggtggagc gctaaaaata   5580
tttcgggcaa tccctatgcg ttttatatgg gcgatgaaaa ttattccgaa gaattaggct   5640
gtgtcggatg ttatcaatac gatcccgtcg aatatcgaaa gtccagtgtt aagagaattg   5700
ctgccgaagc ggccaaatat acatcggact acatttttaa gaaattatat gaagaagata   5760
acggatgaat tatatcggct ccaaactaaa actttctaac tggctggaaa ctgaaataag   5820
caatgtggcc ggccattcgc tgtctgataa agtattttgt gatttatttg cagggacggg   5880
gattgtcgga agaaaattta aaacaaatgt aaagcaagtg attgcgaacg atatggaata   5940
ttacagttat gttttaaata gaaattatat cggcaattgc caaagtattc ttaaagcggg   6000
cgaacttctg caaaggctgg aacagttgcc gcccaaggaa gggttggttt atcggcatta   6060
ttgtttgggt tcgggctcgg aacgccaata tttcagtgat gaaaacggta aaaaaataga   6120
tgctgtccgg attcaaatcg aggagtggaa aaatacgcac tacattgatg aagacaccta   6180
ttattttta ctggcaactt tgctggagag tgcggataaa gtggcaaata cggcatctgt   6240
ttacggggct tttttgaaaa atctaaaaaa gtcggcatta aaaccattgt cgctcgaacc   6300
tgctttgttt gagattggca gtgacgggca tcaagtttat caggcggatg caaacaaact   6360
gataaaaaat atttcaggcg atattttgta cctcgatccg ccgtataacg cccgccaata   6420
tggtgcgaat tatcatctct taaacagcat cgcgctttat gatgatttta cgcccaaagg   6480
gaaaacgggc ttaagggaat atagccgctc gaaatattgc tcaaaatcgg atgtggttcc   6540
ggtatttgag gctttgatta gggatgcgga ctttcaatat atttttctca gctacaacaa   6600
cgaaggcttg atgtctatcg ggcaggtaag ggagattttt gagcgtttcg gcaaatatga   6660
tttggttcaa acggaatacc ggcggtttaa ggcagataaa acagaaaacc gtaaccataa   6720
ggcaaattcg acattcgaat atctgcatat tttagaaaag acctttttaaa aattcttgcc   6780
ggatactgca aacaacgccg gtttgcatct gaaggtattg tctattttcc atacgaatac   6840
ttgggttatc cgtttgattc gcaatctcag gtcggcaaag aagtatttgc caaattgggc   6900
ttgggcaaat tggtcgagac ctgcaggcat gcaagcttgg cgtaatcatg gtcatagctg   6960
tttcctgtgt gaaattgtta tccgctcaca attccacaca acatacgagc cggaagcata   7020
aagtgtaaag cctggggtgc ctaatgagtg agctaactca cattaattgc gttgcgctca   7080
ctgcccgctt tccagtcggg aaacctgtcg tgccagctgc attaatgaat cggccaacgc   7140
gcggggagag gcggtttgcg tattgggcgc                                  7170
```

<210> SEQ ID NO 22
<211> LENGTH: 6017
<212> TYPE: DNA
<213> ORGANISM: Artificial Sequence
<220> FEATURE:
<223> OTHER INFORMATION: Vector

<400> SEQUENCE: 22

```
tcttccgctt cctcgctcac tgactcgctg cgctcggtcg ttcggctgcg gcgagcggta     60
```

-continued

```
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aagaacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccatatg cggtgtgaaa taccgcacag atgcgtaagg   2220
agaaaatacc gcatcaggcg ccattcgcca ttcaggctgc gcaactgttg ggaagggcga   2280
tcggtgcggg cctcttcgct attacgccag ctggcgaaag ggggatgtgc tgcaaggcga   2340
ttaagttggg taacgccagg gttttcccag tcacgacgtt gtaaaacgac ggccagtgaa   2400
ttcgagctcg gtacccgggg atcctctaga gtcgccttac aagcagaatg tcggcggttc   2460
```

-continued

```
gactccgtca tcacccacca agtttccttt cattgttgca aacaatggat gcgcggtggt   2520
agctcagttg gttagagtac cggcctgtca cgccgggggt cgcgggttcg agccccgtcc   2580
gccgcgccaa gtttcaaaat actgactctg tcggtatttt ttatgttcgg gtgattagct   2640
cagttggtag agcgtctgcc ttacaagcag aatgtcggcg gttcgactcc gtcatcaccc   2700
accaagtttc ctttcattgt tgcaaacaat ggatgcgcgg tggtagctca gttggttaga   2760
gtaccggcct gtcacgccgg gggtcgcggg ttcgagcccc gtccgccgcg ccaaaagtta   2820
aaaaatacca acctccggtt ggtatttttt ttgtttgtac gctttaaaaa atgtttgttt   2880
ccggattttt ccattcccat ccggttttgc gctgtacaag gtgttttagc gcgggctttg   2940
gcgtatgttg caaaatgttc cgatattgca tcgtttgcca tattgccgga ggataacggc   3000
ggtgtgcctt gcattggcgt atggcaattg cggaatctat gggcgtgtca tccgaacggg   3060
aacggttttc ggcgtacggt acgacggaat tgtaatccat aaactgcctg tccccgccgc   3120
gccggcattc gttcagacgg catcggccca ataaaaatcc ccctttccag atgtctggcg   3180
gaagggcttt ccaagctgta aaactgccca aagccataaa attacacaat aaaacgcccg   3240
taaaccgggc agccggttcg cagaaagcca aaaataaagc cggatccgag gagggtaaaa   3300
caggatgttc cgcaccggac gaccgccttt atggcaaaat ccgaaggctg tattgtaacc   3360
atcgggcgat ttgggcggtt tgtccccgat tccgacgata cggtgcgtcc aatagtggtg   3420
actatatttt ttaaaaaagt gttttgagta tgaaaatcac aaaaacagaa ctatttttaa   3480
gattagccaa accaaatgaa caaggtattt cccgttgggt tagtacaagt gaatttgccg   3540
gggaatataa agatttgaaa ttaggtaatg ggggaagctg gtgtcggaaa gattctccat   3600
tggcgagaga atattcggca actgtcggaa tatctgctaa aattccgcat tttccgcacc   3660
gggtttccgc accgggacac tcgaggcgta tgttcaattt gtcggaatgg agtttaaagg   3720
aaatcatatg gccaaaatgc gcattagtcc ggaactgaaa aaattgattg aaaagtaccg   3780
ctgtgtcaaa gatactgagg gtatgtcgcc cgccaaagtc tacaagctgg tcggcgaaaa   3840
tgaaaacctg tacttgaaaa tgacagatag tcgctacaaa ggcaccacct acgacgtaga   3900
gcgcgagaaa gatatgatgt tatggctgga aggtaaactg cctgttccga aagttctgca   3960
tttcgaacgc cacgacggtt ggagcaacct gctgatgtcg gaagcagatg gcgtattgtg   4020
tagcgaagaa tacgaagacg aacaatcgcc ggagaaaatc atcgaattgt acgcggaatg   4080
catccgcttg tttcacagca tcgacatcag tgattgccct tacaccaact ccttagatag   4140
ccgcctggct gaacttgatt atttgttgaa taacgacttg gctgatgtag actgcgaaaa   4200
ctgggaggaa gatacaccct tcaaggaccc gcgcgagctc tacgactttc tgaaaactga   4260
aaaaccggaa gaagagctgg ttttctccca cggcgatctg ggcgactcga atattttcgt   4320
aaaagatggc aaagtttccg gctttatcga cttgggccgc agcgggcgcg cagataaatg   4380
gtacgacatt gcgttctgcg tccgcagcat ccgtgaagat atcggtgaag aacaatacgt   4440
cgagctcttt ttcgacttgc tgggtattaa accggattgg gaaaaaatca aatattatat   4500
cctgttggat gaattattct agatctatgc cgtctgaaat tgcggccgcg cggccaaata   4560
tacatcggac tacattttta agaaattata tgaagaagat aacggatgaa ttatatcggc   4620
tccaaactaa aactttctaa ctggctggaa actgaaataa gcaatgtggc cggccattcg   4680
ctgtctgata aagtattttg tgatttattt gcagggacgg ggattgtcgg aagaaaattt   4740
aaaacaaatg taaagcaagt gattgcgaac gatatggaat attacagtta tgttttaaat   4800
```

```
agaaattata tcggcaattg ccaaagtatt cttaaagcgg gcgaacttct gcaaaggctg   4860
gaacagttgc cgcccaagga agggttggtt tatcggcatt attgtttggg ttcgggctcg   4920
gaacgccaat atttcagtga tgaaaacggt aaaaaaatag atgctgtccg gattcaaatc   4980
gaggagtgga aaaatacgca ctacattgat gaagacacct attatttttt actggcaact   5040
ttgctggaga gtgcggataa agtggcaaat acggcatctg tttacggggc tttttgaaa   5100
aatctaaaaa agtcggcatt aaaaccattg tcgctcgaac ctgctttgtt tgagattggc   5160
agtgacgggc atcaagttta tcaggcggat gcaaacaaac tgataaaaaa tatttcaggc   5220
gatattttgt acctcgatcc gccgtataac gcccgccaat atggtgcgaa ttatcatctc   5280
ttaaacagca tcgcgcttta tgatgatttt acgcccaaag ggaaaacggg cttaagggaa   5340
tatagccgct cgaaatattg ctcaaaatcg gatgtggttc cggtatttga ggctttgatt   5400
agggatgcgg actttcaata tatttttctc agctacaaca acgaaggctt gatgtctatc   5460
gggcaggtaa gggagatttt tgagcgtttc ggcaaatatg atttggttca aacggaatac   5520
cggcggttta aggcagataa aacagaaaac cgtaaccata aggcaaattc gacattcgaa   5580
tatctgcata ttttagaaaa gaccttttaa aaattcttgc cggatactgc aaacaacgcc   5640
ggtttgcatc tgaaggtatt gtctattttc catacgaata cttgggttat ccgtttgatt   5700
cgcaatctca ggtcggcaaa gaagtatttg ccaaattggg cttgggcaaa ttggtcgatc   5760
tagagacctg caggcatgca agcttggcgt aatcatggtc atagctgttt cctgtgtgaa   5820
attgttatcc gctcacaatt ccacacaaca tacgagccgg aagcataaag tgtaaagcct   5880
ggggtgccta atgagtgagc taactcacat taattgcgtt gcgctcactg cccgctttcc   5940
agtcgggaaa cctgtcgtgc cagctgcatt aatgaatcgg ccaacgcgcg gggagaggcg   6000
gtttgcgtat tgggcgc                                                  6017
```

```
<210> SEQ ID NO 23
<211> LENGTH: 8152
<212> TYPE: DNA
<213> ORGANISM: Artificial Sequence
<220> FEATURE:
<223> OTHER INFORMATION: Vector

<400> SEQUENCE: 23

tcttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aagaacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
```

-continued

```
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccatatg cggtgtgaaa taccgcacag atgcgtaagg   2220
agaaaatacc gcatcaggcg ccattcgcca ttcaggctgc gcaactgttg ggaagggcga   2280
tcggtgcggg cctcttcgct attacgccag ctggcgaaag ggggatgtgc tgcaaggcga   2340
ttaagttggg taacgccagg gttttcccag tcacgacgtt gtaaaacgac ggccagtgaa   2400
ttcgagctcg gtacccgggg atcctctaga gtcctgatac cgagcttttc ccatggttta   2460
tcgcgactga tagtgttttc ggcgaggtag tcggcacgtg tttgagacca ccagcgagtg   2520
attgtgcttt cagctacaat aattttgctg cttgctctat gtttaaaaat ctatccatat   2580
tggatagttt agattagact taagtggatt tcaagtgagc tgtttaaccc ttagctagca   2640
agggttttgg tggcgtaagg ttactgaact taagcatatc ggcggccaaa gtaccgctgc   2700
cattgccaat ctcgccgggg aaatgaaaag gctcgctaaa aaatcaaaaa tgttactgaa   2760
aggactttgg tcatttttat cctctacaat atctacattt aaaaataaat cggtcattgt   2820
ttaaacctta ctgtaaaact gtacaactgc taaactgtaa acacagaaag aggcaatact   2880
aacagcacaa aacaacagat atccaaactc cataaagtgc attattctga ctttttttcgt   2940
tgcctgatgt atttatgcta tttgtgctgt tcttatatat gtgttgctgg ttacgttgcg   3000
ttttttcgga aaattcaacc ggtaggggac cgatacgcag tttcatctct ttgcttaggg   3060
agagtagggg ggtagattac gaccttagtt ttggtatccg taatatcatc atttttttcgt   3120
ctagggagta tatcgacttc agaaaacagg tattagatac tgccttttct tacgagagtg   3180
```

```
atggcaagat agttctcttc aagtcaatca aacaggaaag tatttctttt ctgtctgaag   3240
atttgaaaaa ggactgaatg tttcacaagg ttaaaactgg ggaaaaagat ggatatggtt   3300
cagatgaaat gctgagcgca ccccgtatct atttggaaat gatgtcgcgg aaaacggaag   3360
tcccctactc cagtattctt taaattctaa gcagaaaact tcttcgtcgg tctttttttt   3420
gttgtttggt ttgcatggag taaaactgtg caacgccgtc tgaagtcgac tattcggcaa   3480
ctgtcggaat atctgctaaa attccgcatt ttccgcaccg ggtttccgca ccgggacact   3540
cggggcgtat gttcaatttg tcggaatgga gtttaaagga atctcgagat ctattatata   3600
agcggccgca agtttgtttt ttcgggcggg aacatttata gtttcaaaca aggaatcgac   3660
gaaaacgtcg tcggtaaatg caaagctaag cggctcggaa agcccggttc gcttaaattt   3720
cttaaccaaa aaaggaatac acatatgtta ttagcgaatt attatcaaga tcctgaaatc   3780
acgagaatca atgcgttgcc gcaccatagc tattttatcc cttttgataa aaaagataag   3840
gtagatcagt tttctaggga aaattcttcg ttttttacat cattaaatgg aatgtggcaa   3900
ttcgcatatt atccgagtat gcaggatttg cctgaaagtc cggacgaaat cgcttttacg   3960
aaacaaatca atgtgccttc aaattggcag aatcacgggt ttgatgccca tcaatatact   4020
aatattaatt atcctttccc tttcgatccg ccttttgttc ctttagagaa cccttgcggg   4080
gtatatcaaa agcaggtcaa tctgaaaaag aatataaata agcggtattt attagtcctt   4140
gaaggggttg attcctgttc ttatatatat gtaaaccatc aatttgtagg atatggttct   4200
atcagccaca gtaccaatga atttgatatt accgattatc ttcacgatgg tgaaaacacc   4260
cttaccgtat ttgtcctgaa atggtgtgcc ggaagctact tggaagatca ggataaattt   4320
agaatgtcgg gaattttccg agatgtatat ttattggaaa gggagcatca ctatttgcaa   4380
gacttgaata ttcgaaccgt gctttctgaa gatttatcat tggggcagat ttgtctggat   4440
ttaaattttg cgggggatgc gggggatgtc ggagtgtcat tgtttgatac ggacgggcaa   4500
attgttcaag caggcagcgc aatcacgaca gataaacaac ggatgcaaat ccgccttgat   4560
aatattcctt taaccaaatc ccgactctgg aatgcggaaa accctgccct ttataccttg   4620
gtattaaaca caaaagaaga aatcattacc cagaagatcg gattccgcaa ggtagaggtc   4680
aaaaacgggg tattgctgct taataatcag cctattaaat tcaaaggggt aaaccggcac   4740
gatagcgatc ccaaaacggg atatgccatt tctgtcgctc aagcggtgac tgacttgtcg   4800
ttaatgaaga aacataatat taacgcgatt cgtaccgcgc attatccaaa ttcaccgtgg   4860
ttttgcgagc tttgcgataa gtatggtttc tatgtaatca gtgaaagcga cattgaaagt   4920
catggggcgg cattccaagc aatttcgcat cccgaaccga gtatctttct gaatgtggaa   4980
aatccgaatg aagagccgcg tatccgccaa caaactattg acaacttctg ttattttgcc   5040
cgagaaccat tgtatcgggc ggctttattg gagcggacta aagcaaatat agaacgtgat   5100
aagaaccgca gttctatttt aatttggtct ttaggcaatg aatcagggta tggtgagaat   5160
ttcgaatatt gtgcaaaatg ggtaaaagag cgggatccgg atcgattggt tcattacgaa   5220
agcagcattt atcagcattc tgcgtatcag aataacaccg ggcatttgga tttatacagt   5280
gaaatgtatt ccgacacaga agcaatcgat gcctattttg ccgatcattc acaaacgaaa   5340
aaaccattct tattatgcga atattcccat gcaatgggaa attcaaatgg agatatggaa   5400
gactatttcc aaacatttaa caaatattcg ggctgttgcg gtgggtttat ttgggagtgg   5460
tgcgatcatg cccaatatat taccccgaca aaattaggat atggcggtga cttcggcgaa   5520
aaaatccatg atgggaattt ctgtgtggat ggcttggttt cgcccgaacg cgtcccgcac   5580
```

-continued agcaacctgt tggaagtaaa aaatgtcaac cggcccgtac gggcaaactt gcgcggtgaa 5640
caaattgagt tatataacta ttttgatttc actaatttaa aagatattct ttgcgtcaaa 5700
tatgaatggg taaaaaatgg tcagataacc gggacgggaa cattggcggt tgattgcgaa 5760
ccccatcatt ctcaaatctt accgattcag cttcccaaag aacgggaagg attgctatgg 5820
ttgaacctat attactgcgc ttcccggcaa actgatttat tgccggcagg acatcatttc 5880
ggtttcgatc aaattatttt gagtaaggaa tacactcctg ccataggatc ggataaagat 5940
gattgcccgc cgttggaaat aaccgaaaca gtgagacaaa tcgttgttcg gaacaatcga 6000
tattattttg aatttaacaa gctcacgggg ataattgacg aaattaaagt caatggcaag 6060
gctttcatcc ataaaccatt ggcttggaat atttggcgcg cgccgacgga taatgaccgc 6120
ctgattcgtt cccaatggca aaatgccggt tatgatcaaa tgtattccaa ggtttacgat 6180
atttgcgcgc atcggcaagg aaacggtgtt gtcgtgtctg tgaaaagtgc attggttgcg 6240
gatgcaaaat caaaaatcat gacattggaa acacagtatc tgctgtctga aaatggtaaa 6300
ttggatattc aaacaaatgc tgttttccac gagcatttgc cattcctgcc ccgtttcggt 6360
ttgcgctttt tcttagacga acagaaaaca ccttttacct acttaggtta tggggcgggt 6420
gaaagctata ttgataaaca tcaggcgacc aaacttggta tttattcgac aacggcaggg 6480
gaaaatcatg ttggctatct caagcctcaa gagaacggca gccattatgg atgcttttat 6540
gttcaaaacg atatgatccg ggtggagtcg gggcagccgt ttagtttcaa cctgtcccct 6600
tatacgcaag aagaactgac gcagaaaaaa cattcttatg aattggtttg ttccgggtat 6660
gatgtattgt gtatcgacta taagatgagc ggtatcggtt cgaattcttg cgggcctaat 6720
ttgaagccgc aatatcgttt gattgaaaat aacatcaatt tcgatataag tatccggtta 6780
taagctttct gcaaagattg gtatcaacaa aaagcctgtc gtcagacagg cttttttttct 6840 gttttctgtt tttagatgcc gtctgaatgc tgaagtagaa aaccagcaag aaggtaaaaa 6900
gaaagaagca gtttttttgga ttttagatgt taccgcaatt ggtttccttt cctaaaattt 6960
gtttaaatta tttgcaatat taatataaac tggatattaa tgatgaggat tcaaaaaggc 7020
atactgaata taatttgtac aaaatatttg cagtatttaa aaatgttggt tcgtatatga 7080
aaagttaaaa atgccaaaat gtacagttgc taaactgtaa aactgctaaa gcaacaaaac 7140
ataaaaagga atgcagggat gcgatcacta catcttttta ttccgtaagc atttatgact 7200
ttacggtcaa ctgctactct atgtttccag cttttcagct ccctatttc gaatattgga 7260 cgaggcattt tcatcagtgt cgtaatgccg accgaaaccc tcacaaacca tattggttct 7320
tgtggcagca acacctatcc gtttgttcaa gcggccacaa gagtaacatg attggctggt 7380
ggcattggct ttaatctctt cgatatgaac tccattttta gctgcacctt ctttcagcgt 7440
atgcaacagt ggggatgggg caactatctt ctggtggagt ttgttgactt caatctgtat 7500
gcactgtagg ttgagcagat tcagtttttt gatacagatt atccggcttt gttcggcaat 7560
tctgttggcg aacgtatagt agagctgtcg tcttgccgct ttcaatttgc ggtaggtatt 7620
ttaccattcc atgcgtagcc gctcggtacg tttgagccaa atgttatctt cgccatttgt 7680
accaatttgt ttttacatta ggctgtgttt tagtaatcta ttgatttcaa ttatttgcaa 7740
gggaaaagac aattattttc cggttaggaa taaacctatc ctattgaata tattgaagcc 7800
aagtacgctt atcaacacta tattaaaaca cagccttttt taatatagta gacacaatct 7860
ttccttattt atgaaggtga tagcttcttt cagtctagag acctgcaggc atgcaagctt 7920

```
ggcgtaatca tggtcatagc tgtttcctgt gtgaaattgt tatccgctca caattccaca   7980

caacatacga gccggaagca taaagtgtaa agcctggggt gcctaatgag tgagctaact   8040

cacattaatt gcgttgcgct cactgcccgc tttccagtcg ggaaacctgt cgtgccagct   8100

gcattaatga atcggccaac gcgcggggag aggcggtttg cgtattgggc gc           8152


<210> SEQ ID NO 24
<211> LENGTH: 8152
<212> TYPE: DNA
<213> ORGANISM: Artificial Sequence
<220> FEATURE:
<223> OTHER INFORMATION: Vector

<400> SEQUENCE: 24

tcttccgctt cctcgctcac tgactcgctg cgctcggtcg ttcggctgcg gcgagcggta     60

tcagctcact caaaggcggt aatacggtta tccacagaat caggggataa cgcaggaaag    120

aacatgtgag caaaaggcca gcaaaaggcc aggaaccgta aaaaggccgc gttgctggcg    180

tttttccata ggctccgccc ccctgacgag catcacaaaa atcgacgctc aagtcagagg    240

tggcgaaacc cgacaggact ataaagatac caggcgtttc cccctggaag ctccctcgtg    300

cgctctcctg ttccgaccct gccgcttacc ggatacctgt ccgcctttct cccttcggga    360

agcgtggcgc tttctcatag ctcacgctgt aggtatctca gttcggtgta ggtcgttcgc    420

tccaagctgg gctgtgtgca cgaacccccc gttcagcccg accgctgcgc cttatccggt    480

aactatcgtc ttgagtccaa cccggtaaga cacgacttat cgccactggc agcagccact    540

ggtaacagga ttagcagagc gaggtatgta ggcggtgcta cagagttctt gaagtggtgg    600

cctaactacg gctacactag aagaacagta tttggtatct gcgctctgct gaagccagtt    660

accttcggaa aaagagttgg tagctcttga tccggcaaac aaaccaccgc tggtagcggt    720

ggtttttttg tttgcaagca gcagattacg cgcagaaaaa aaggatctca agaagatcct    780

ttgatctttt ctacggggtc tgacgctcag tggaacgaaa actcacgtta agggattttg    840

gtcatgagat tatcaaaaag gatcttcacc tagatccttt taaattaaaa atgaagtttt    900

aaatcaatct aaagtatata tgagtaaact tggtctgaca gttaccaatg cttaatcagt    960

gaggcaccta tctcagcgat ctgtctattt cgttcatcca tagttgcctg actccccgtc   1020

gtgtagataa ctacgatacg ggagggctta ccatctggcc ccagtgctgc aatgataccg   1080

cgagacccac gctcaccggc tccagattta tcagcaataa accagccagc cggaagggcc   1140

gagcgcagaa gtggtcctgc aactttatcc gcctccatcc agtctattaa ttgttgccgg   1200

gaagctagag taagtagttc gccagttaat agtttgcgca acgttgttgc cattgctaca   1260

ggcatcgtgg tgtcacgctc gtcgtttggt atggcttcat tcagctccgg ttcccaacga   1320

tcaaggcgag ttacatgatc ccccatgttg tgcaaaaaag cggttagctc cttcggtcct   1380

ccgatcgttg tcagaagtaa gttggccgca gtgttatcac tcatggttat ggcagcactg   1440

cataattctc ttactgtcat gccatccgta agatgctttt ctgtgactgg tgagtactca   1500

accaagtcat tctgagaata gtgtatgcgg cgaccgagtt gctcttgccc ggcgtcaata   1560

cgggataata ccgcgccaca tagcagaact ttaaaagtgc tcatcattgg aaaacgttct   1620

tcggggcgaa aactctcaag gatcttaccg ctgttgagat ccagttcgat gtaacccact   1680

cgtgcaccca actgatcttc agcatctttt actttcacca gcgtttctgg gtgagcaaaa   1740

acaggaaggc aaaatgccgc aaaaaaggga ataagggcga cacggaaatg ttgaatactc   1800

atactcttcc tttttcaata ttattgaagc atttatcagg gttattgtct catgagcgga   1860
```

-continued

```
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccatatg cggtgtgaaa taccgcacag atgcgtaagg   2220
agaaaatacc gcatcaggcg ccattcgcca ttcaggctgc gcaactgttg ggaagggcga   2280
tcggtgcggg cctcttcgct attacgccag ctggcgaaag ggggatgtgc tgcaaggcga   2340
ttaagttggg taacgccagg gttttcccag tcacgacgtt gtaaaacgac ggccagtgaa   2400
ttcgagctcg gtacccgggg atcctctaga gtcctgatac cgagcttttc ccatggttta   2460
tcgcgactga tagtgtttc ggcgaggtag tcggcacgtg tttgagacca ccagcgagtg   2520
attgtgcttt cagctacaat aattttgctg cttgctctat gtttaaaaat ctatccatat   2580
tggatagttt agattagact taagtggatt tcaagtgagc tgtttaaccc ttagctagca   2640
agggttttgg tggcgtaagg ttactgaact taagcatatc ggcggccaaa gtaccgctgc   2700
cattgccaat ctcgccgggg aaatgaaaag gctcgctaaa aatcaaaaa tgttactgaa   2760
aggactttgg tcatttttat cctctacaat atctacattt aaaaataaat cggtcattgt   2820
ttaaacctta ctgtaaaact gtacaactgc taaactgtaa acacagaaag aggcaatact   2880
aacagcacaa aacaacagat atccaaactc cataaagtgc attattctga ctttttcgt   2940
tgcctgatgt atttatgcta tttgtgctgt tcttatatat gtgttgctgg ttacgttgcg   3000
tttttcgga aaattcaacc ggtaggggac cgatacgcag tttcatctct ttgcttaggg   3060
agagtagggg ggtagattac gaccttagtt ttggtatccg taatatcatc attttttcgt   3120
ctagggagta tatcgacttc agaaaacagg tattagatac tgccttttct tacgagagtg   3180
atggcaagat agttctcttc aagtcaatca aacaggaaag tatttctttt ctgtctgaag   3240
atttgaaaaa ggactgaatg tttcacaagg ttaaaactgg ggaaaaagat ggatatggtt   3300
cagatgaaat gctgagcgca ccccgtatct atttggaaat gatgtcgcgg aaaacggaag   3360
tcccctactc cagtattctt taaattctaa gcagaaaact tcttcgtcgg tcttttttt   3420
gttgtttggt ttgcatggag taaaactgtg caacgccgtc tgaagtcgac agtttgtttt   3480
ttcgggcggg aacatttata gtttcaaaca aggaatcgac gaaaacgtcg tcggtaaatg   3540
caaagctaag cggctcggaa agcccggttc gcttaaattt cttaaccaaa aaaggaatct   3600
cgagatctat tatataagcg gccgcatatt cggcaactgt cggaatatct gctaaaattc   3660
cgcattttcc gcaccgggtt tccgcaccgg gacactcggg gcgtatgttc aatttgtcgg   3720
aatggagttt aaaggaatac acatatgtta ttagcgaatt attatcaaga tcctgaaatc   3780
acgagaatca atgcgttgcc gcaccatagc tattttatcc cttttgataa aaaagataag   3840
gtagatcagt tttctaggga aaattcttcg ttttttacat cattaaatgg aatgtggcaa   3900
ttcgcatatt atccgagtat gcaggatttg cctgaaagtc cggacgaaat cgcttttacg   3960
aaacaaatca atgtgccttc aaattggcag aatcacgggt ttgatgccca tcaatatact   4020
aatattaatt atcctttccc tttcgatccg ccttttgttc ctttagagaa cccttgcggg   4080
gtatatcaaa agcaggtcaa tctgaaaaag aatataaata agcggtattt attagtcctt   4140
gaaggggttg attcctgttc ttatatatat gtaaaccatc aatttgtagg atatggttct   4200
```

-continued

```
atcagccaca gtaccaatga atttgatatt accgattatc ttcacgatgg tgaaaacacc   4260
cttaccgtat ttgtcctgaa atggtgtgcc ggaagctact tggaagatca ggataaattt   4320
agaatgtcgg gaattttccg agatgtatat ttattggaaa gggagcatca ctatttgcaa   4380
gacttgaata ttcgaaccgt gctttctgaa gatttatcat tggggcagat ttgtctggat   4440
ttaaattttg cgggggatgc gggggatgtc ggagtgtcat tgtttgatac ggacgggcaa   4500
attgttcaag caggcagcgc aatcacgaca gataaacaac ggatgcaaat ccgccttgat   4560
aatattcctt taaccaaatc ccgactctgg aatgcggaaa accctgccct ttataccttg   4620
gtattaaaca caaaagaaga aatcattacc cagaagatcg gattccgcaa ggtagaggtc   4680
aaaaacgggg tattgctgct taataatcag cctattaaat tcaaaggggt aaaccggcac   4740
gatagcgatc ccaaaacggg atatgccatt tctgtcgctc aagcggtgac tgacttgtcg   4800
ttaatgaaga aacataatat taacgcgatt cgtaccgcgc attatccaaa ttcaccgtgg   4860
ttttgcgagc tttgcgataa gtatggtttc tatgtaatca gtgaaagcga cattgaaagt   4920
catggggcgg cattccaagc aatttcgcat cccgaaccga gtatctttct gaatgtggaa   4980
aatccgaatg aagagccgcg tatccgccaa caaactattg acaacttctg ttattttgcc   5040
cgagaaccat tgtatcgggc ggctttattg gagcggacta aagcaaatat agaacgtgat   5100
aagaaccgca gttctatttt aatttggtct ttaggcaatg aatcagggta tggtgagaat   5160
ttcgaatatt gtgcaaaatg ggtaaaagag cgggatccgg atcgattggt tcattacgaa   5220
agcagcattt atcagcattc tgcgtatcag aataacaccg ggcatttgga tttatacagt   5280
gaaatgtatt ccgacacaga agcaatcgat gcctattttg ccgatcattc acaaacgaaa   5340
aaaccattct tattatgcga atattcccat gcaatgggaa attcaaatgg agatatggaa   5400
gactatttcc aaacatttaa caaatattcg ggctgttgcg gtgggtttat ttgggagtgg   5460
tgcgatcatg cccaatatat taccccgaca aaattaggat atggcggtga cttcggcgaa   5520
aaaatccatg atgggaattt ctgtgtggat ggcttggttt cgcccgaacg cgtcccgcac   5580
agcaacctgt tggaagtaaa aaatgtcaac cggcccgtac gggcaaactt gcgcggtgaa   5640
caaattgagt tatataacta ttttgatttc actaatttaa aagatattct ttgcgtcaaa   5700
tatgaatggg taaaaaatgg tcagataacc gggacgggaa cattggcggt tgattgcgaa   5760
ccccatcatt ctcaaatctt accgattcag cttcccaaag aacgggaagg attgctatgg   5820
ttgaacctat attactgcgc ttcccggcaa actgatttat tgccggcagg acatcatttc   5880
ggtttcgatc aaattatttt gagtaaggaa tacactcctg ccataggatc ggataaagat   5940
gattgcccgc cgttggaaat aaccgaaaca gtgagacaaa tcgttgttcg gaacaatcga   6000
tattattttg aatttaacaa gctcacgggg ataattgacg aaattaaagt caatggcaag   6060
gctttcatcc ataaaccatt ggcttggaat atttggcgcg cgccgacgga taatgaccgc   6120
ctgattcgtt cccaatggca aaatgccggt tatgatcaaa tgtattccaa ggtttacgat   6180
atttgcgcgc atcggcaagg aaacggtgtt gtcgtgtctg tgaaaagtgc attggttgcg   6240
gatgcaaaat caaaaatcat gacattggaa acacagtatc tgctgtctga aaatggtaaa   6300
ttggatattc aaacaaatgc tgttttccac gagcatttgc cattcctgcc ccgtttcggt   6360
ttgcgctttt tcttagacga acagaaaaca ccttttacct acttaggtta tggggcgggt   6420
gaaagctata ttgataaaca tcaggcgacc aaacttggta tttattcgac aacggcaggg   6480
gaaaatcatg ttggctatct caagcctcaa gagaacggca gccattatgg atgcttttat   6540
gttcaaaacg atatgatccg ggtggagtcg gggcagccgt ttagtttcaa cctgtcccct   6600
```

```
tatacgcaag aagaactgac gcagaaaaaa cattcttatg aattggtttg ttccgggtat   6660
gatgtattgt gtatcgacta taagatgagc ggtatcggtt cgaattcttg cgggcctaat   6720
ttgaagccgc aatatcgttt gattgaaaat aacatcaatt tcgatataag tatccggtta   6780
taagctttct gcaaagattg gtatcaacaa aaagcctgtc gtcagacagg cttttttttct  6840
gttttctgtt tttagatgcc gtctgaatgc tgaagtagaa aaccagcaag aaggtaaaaa   6900
gaaagaagca gtttttttgga ttttagatgt taccgcaatt ggtttccttt cctaaaattt  6960
gtttaaatta tttgcaatat taatataaac tggatattaa tgatgaggat tcaaaaaggc   7020
atactgaata taatttgtac aaaatatttg cagtatttaa aaatgttggt tcgtatatga   7080
aaagttaaaa atgccaaaat gtacagttgc taaactgtaa aactgctaaa gcaacaaaac   7140
ataaaaagga atgcagggat gcgatcacta catcttttta ttccgtaagc atttatgact   7200
ttacggtcaa ctgctactct atgtttccag cttttcagct ccctattttc gaatattgga   7260
cgaggcattt tcatcagtgt cgtaatgccg accgaaaccc tcacaaacca tattggttct   7320
tgtggcagca acacctatcc gtttgttcaa gcggccacaa gagtaacatg attggctggt   7380
ggcattggct ttaatctctt cgatatgaac tccattttta gctgcacctt ctttcagcgt   7440
atgcaacagt ggggatgggg caactatctt ctggtggagt ttgttgactt caatctgtat   7500
gcactgtagg ttgagcagat tcagtttttt gatacagatt atccggcttt gttcggcaat   7560
tctgttggcg aacgtatagt agagctgtcg tcttgccgct ttcaatttgc ggtaggtatt   7620
ttaccattcc atgcgtagcc gctcggtacg tttgagccaa atgttatctt cgccatttgt   7680
accaatttgt ttttacatta ggctgtgttt tagtaatcta ttgatttcaa ttatttgcaa   7740
gggaaaagac aattattttc cggttaggaa taaacctatc ctattgaata tattgaagcc   7800
aagtacgctt atcaacacta tattaaaaca cagccttttt taatatagta gacacaatct   7860
ttccttattt atgaaggtga tagcttcttt cagtctagag acctgcaggc atgcaagctt   7920
ggcgtaatca tggtcatagc tgtttcctgt gtgaaattgt tatccgctca caattccaca   7980
caacatacga gccggaagca taaagtgtaa agcctggggt gcctaatgag tgagctaact   8040
cacattaatt gcgttgcgct cactgcccgc tttccagtcg ggaaacctgt cgtgccagct   8100
gcattaatga atcggccaac gcgcggggag aggcggtttg cgtattgggc gc           8152
```

```
<210> SEQ ID NO 25
<211> LENGTH: 7256
<212> TYPE: DNA
<213> ORGANISM: Artificial Sequence
<220> FEATURE:
<223> OTHER INFORMATION: Vector

<400> SEQUENCE: 25

tctagagcaa aaggccagca aaaggccagg aaccgtaaaa aggccgcgtt gctggcgttt     60
ttccataggc tccgcccccc tgacgagcat cacaaaaatc gacgctcaag tcagaggtgg    120
cgaaacccga caggactata aagataccag gcgtttcccc ctggaagctc cctcgtgcgc    180
tctcctgttc cgaccctgcc gcttaccgga tacctgtccg cctttctccc ttcgggaagc    240
gtggcgcttt ctcatagctc acgctgtagg tatctcagtt cggtgtaggt cgttcgctcc    300
aagctgggct gtgtgcacga accccccgtt cagcccgacc gctgcgcctt atccggtaac    360
tatcgtcttg agtccaaccc ggtaagacac gacttatcgc cactggcagc agccactggt    420
aacaggatta gcagagcgag gtatgtaggc ggtgctacag agttcttgaa gtggtggcct    480
```

aactacggct acactagaag aacagtattt ggtatctgcg ctctgctgaa gccagttacc 540
ttcggaaaaa gagttggtag ctcttgatcc ggcaaacaaa ccaccgctgg tagcggtggt 600 tttttgttt gcaagcagca gattacgcgc agaaaaaaag gatctcaaga agatcctttg 660
atcttttcta cggggtctga cgctcagtgg aacgaaaact cacgttaagg gattttggtc 720
atgagattat caaaaaggat cttcacctag atccttttaa attaaaaatg aagttttaaa 780
tcaatctaaa gtatatatga gtaaacttgg tctgacagtt accaatgctt aatcagtgag 840
gcacctatct cagcgatctg tctatttcgt tcatccatag ttgcctgact ccccgtcgtg 900
tagataacta cgatacggga gggcttacca tctggcccca gtgctgcaat gataccgcga 960
gacccacgct caccggctcc agatttatca gcaataaacc agccagccgg aagggccgag 1020
cgcagaagtg gtcctgcaac tttatccgcc tccatccagt ctattaattg ttgccgggaa 1080
gctagagtaa gtagttcgcc agttaatagt ttgcgcaacg ttgttgccat tgctacaggc 1140
atcgtggtgt cacgctcgtc gtttggtatg gcttcattca gctccggttc ccaacgatca 1200
aggcgagtta catgatcccc catgttgtgc aaaaaagcgg ttagctcctt cggtcctccg 1260
atcgttgtca gaagtaagtt ggccgcagtg ttatcactca tggttatggc agcactgcat 1320
aattctctta ctgtcatgcc atccgtaaga tgcttttctg tgactggtga gtactcaacc 1380
aagtcattct gagaatagtg tatgcggcga ccgagttgct cttgcccggc gtcaatacgg 1440
gataataccg cgccacatag cagaacttta aaagtgctca tcattggaaa acgttcttcg 1500
gggcgaaaac tctcaaggat cttaccgctg ttgagatcca gttcgatgta acccactcgt 1560
gcacccaact gatcttcagc atcttttact ttcaccagcg tttctgggtg agcaaaaaca 1620
ggaaggcaaa atgccgcaaa aaagggaata agggcgacac ggaaatgttg aatactcata 1680
ctcttccttt ttcaatatta ttgaagcatt tatcagggtt attgtctcat gagcggatac 1740
atatttgaat gtatttagaa aaataaacaa ataggggttc cgcgcacatt tccccgaaaa 1800
gtgccacctt ctagacgggc cggaagacga ttatatgaat gacgatcatc tggctttttt 1860
ccgcgaattg ctggtaaaaa tgcaagacga actcatcgaa aatgcttccg ctacgacagg 1920
gcatctccaa gaacatgaat cagcccccga tcctgccgac cgtgccacac aggaagaaga 1980
gtacgcattg gaactccgta cccgcgatcg ggaacgaaaa cttctcagta aaatacaggc 2040
gaccatccgc aatattgaca ggggcgatta tggattctgc gccgatacgg gagaacctat 2100
cgggctgaag cggctgttgg cgcgcccgac cgccactttg tccgtagagg cgcaagagcg 2160
tcgtgagaga atgaaaaaac agtttgccga ctaatagcgg caaacgaaaa tgccgtctga 2220
agccccgagt ttcagacggc atattcacaa aggcgcacca gccagaggag aagaggaagg 2280
gatttttgga ggcggcgcag catttggcgg aaataaaaaa ccttatctga cagggatatg 2340
acgaatttcc ccaaaaaatc ccgctgaaag tgttgaccgc ctccgtcttc gggcgtatag 2400
ttcggttctt cgctgccgac gaagcggcgg aatgaaacgg acaagtatat cacggtttgc 2460
aggatgtttg acgcatcggc cgtacatacc gacagtttca aacgctcttt aacaaaacag 2520
attaccgata agtgtgagtg cctcgggcct cacactgttt gaaagacaga caagataatg 2580
ttttgaacat tgtcctgtcg gtttctttga agcagaccag aagttaaaaa gttagagatt 2640
gaacataaga gtttgatcct ggctcagatt gaacgctggc ggcatgcttt acacatgcaa 2700
gtcggacggc agcggggtag tgcttgcact actgccggcg agtggcgaac gggtgagtaa 2760
catatcggaa cgtaccgggc agtgggggat aactgatcga aagatcagct aataccgcat 2820
attttctgag gaagaaagca gggggacgtc gccgtctgaa gtcgactatt cggcaactgt 2880

-continued cggaatatct gctaaaattc cgcattttcc gcaccgggtt tccgcaccgg gacactcggg 2940
gcgtatgttc aatttgtcgg aatggagttt aaaggaatct cgagatctat tatataagcg 3000
gccgcaagtt tgtttttttcg ggcgggaaca tttatagttt caaacaagga atcgacgaaa 3060
acgtcgtcgg taaatgcaaa gctaagcggc tcggaaagcc cggttcgctt aaatttctta 3120
accaaaaaag gaatacacat atgttattag cgaattatta tcaagatcct gaaatcacga 3180
gaatcaatgc gttgccgcac catagctatt ttatcccttt tgataaaaaa gataaggtag 3240
atcagttttc tagggaaaat tcttcgtttt ttacatcatt aaatggaatg tggcaattcg 3300
catattatcc gagtatgcag gatttgcctg aaagtccgga cgaaatcgct tttacgaaac 3360
aaatcaatgt gccttcaaat tggcagaatc acgggtttga tgcccatcaa tatactaata 3420
ttaattatcc tttccctttc gatccgcctt ttgttccttt agagaaccct tgcggggtat 3480
atcaaaagca ggtcaatctg aaaaagaata taaataagcg gtatttatta gtccttgaag 3540
gggttgattc ctgttcttat atatatgtaa accatcaatt tgtaggatat ggttctatca 3600
gccacagtac caatgaattt gatattaccg attatcttca cgatggtgaa aacaccctta 3660
ccgtatttgt cctgaaatgg tgtgccggaa gctacttgga agatcaggat aaatttagaa 3720
tgtcgggaat tttccgagat gtatatttat tggaaaggga gcatcactat ttgcaagact 3780
tgaatattcg aaccgtgctt tctgaagatt tatcattggg gcagatttgt ctggatttaa 3840
attttgcggg ggatgcgggg gatgtcggag tgtcattgtt tgatacggac gggcaaattg 3900
ttcaagcagg cagcgcaatc acgacagata aacaacggat gcaaatccgc cttgataata 3960
ttcctttaac caaatcccga ctctggaatg cggaaaaccc tgccctttat accttggtat 4020
taaacacaaa agaagaaatc attacccaga agatcggatt ccgcaaggta gaggtcaaaa 4080
acggggtatt gctgcttaat aatcagccta ttaaattcaa aggggtaaac cggcacgata 4140
gcgatcccaa aacgggatat gccatttctg tcgctcaagc ggtgactgac ttgtcgttaa 4200
tgaagaaaca taatattaac gcgattcgta ccgcgcatta tccaaattca ccgtggtttt 4260
gcgagctttg cgataagtat ggtttctatg taatcagtga aagcgacatt gaaagtcatg 4320
gggcggcatt ccaagcaatt tcgcatcccg aaccgagtat ctttctgaat gtggaaaatc 4380
cgaatgaaga gccgcgtatc cgccaacaaa ctattgacaa cttctgttat tttgcccgag 4440
aaccattgta tcgggcggct ttattggagc ggactaaagc aaatatagaa cgtgataaga 4500
accgcagttc tattttaatt tggtctttag gcaatgaatc agggtatggt gagaatttcg 4560
aatattgtgc aaaatgggta aaagagcggg atccggatcg attggttcat tacgaaagca 4620
gcatttatca gcattctgcg tatcagaata acaccgggca tttggattta tacagtgaaa 4680
tgtattccga cacagaagca atcgatgcct attttgccga tcattcacaa acgaaaaaac 4740
cattcttatt atgcgaatat tcccatgcaa tgggaaattc aaatggagat atggaagact 4800
atttccaaac atttaacaaa tattcgggct gttgcggtgg gtttatttgg gagtggtgcg 4860
atcatgccca atatattacc ccgacaaaat taggatatgg cggtgacttc ggcgaaaaaa 4920
tccatgatgg gaatttctgt gtggatggct tggtttcgcc cgaacgcgtc ccgcacagca 4980
acctgttgga agtaaaaaat gtcaaccggc ccgtacgggc aaacttgcgc ggtgaacaaa 5040
ttgagttata taactatttt gatttcacta atttaaaaga tattctttgc gtcaaatatg 5100
aatgggtaaa aaatggtcag ataaccggga cgggaacatt ggcggttgat tgcgaacccc 5160
atcattctca aatcttaccg attcagcttc ccaaagaacg ggaaggattg ctatggttga 5220
acctatatta ctgcgcttcc cggcaaactg atttattgcc ggcaggacat catttcggtt 5280
tcgatcaaat tattttgagt aaggaataca ctcctgccat aggatcggat aaagatgatt 5340
gcccgccgtt ggaaataacc gaaacagtga gacaaatcgt tgttcggaac aatcgatatt 5400
attttgaatt taacaagctc acggggataa ttgacgaaat taaagtcaat ggcaaggctt 5460
tcatccataa accattggct tggaatattt ggcgcgcgcc gacggataat gaccgcctga 5520
ttcgttccca atggcaaaat gccggttatg atcaaatgta ttccaaggtt tacgatattt 5580
gcgcgcatcg gcaaggaaac ggtgttgtcg tgtctgtgaa aagtgcattg gttgcggatg 5640
caaaatcaaa aatcatgaca ttggaaacac agtatctgct gtctgaaaat ggtaaattgg 5700
atattcaaac aaatgctgtt ttccacgagc atttgccatt cctgccccgt ttcggtttgc 5760
gctttttctt agacgaacag aaaacacctt ttacctactt aggttatggg gcgggtgaaa 5820
gctatattga taaacatcag gcgaccaaac ttggtattta ttcgacaacg gcaggggaaa 5880
atcatgttgg ctatctcaag cctcaagaga acggcagcca ttatggatgc ttttatgttc 5940
aaaacgatat gatccgggtg gagtcggggc agccgtttag tttcaacctg tccccttata 6000
cgcaagaaga actgacgcag aaaaaacatt cttatgaatt ggtttgttcc gggtatgatg 6060
tattgtgtat cgactataag atgagcggta tcggttcgaa ttcttgcggg cctaatttga 6120
agccgcaata tcgtttgatt gaaaataaca tcaatttcga tataagtatc cggttataag 6180
ctttctgcaa agattggtat caacaaaaag cctgtcgtca gacaggcttt ttttctgttt 6240
tctgttttta gatgccgtct gaagacgtca ccatttggcc ttgcgctatc cgagcggccg 6300
atatctgatt agcttgttgg cggggtaagg gcccaccaag gcgacgatca gtagcgggtc 6360
tgagaggacg atccgccaca ctgggactga gacacggccc agactcctac gggaggcagc 6420
agtggggaat tttggacaat gggcgcaagc ctgatccagc catgccgcgt gtctgaagaa 6480
ggccttcggg ttgtaaagga cttttgtcgg ggaagaaaag gctgttgcta atatcagcgg 6540
ctgatgacgg tacccgaaga ataagcaccg gctaactacg tgccagcagc cgcggtaata 6600
cgtagggtgc gagcgttaat cggaattact gggcgtaaag cgggcgcaga cggttactta 6660
agcaggatgt gaaatccccg ggctcaaccc gggaattgcg ttctgaactg ggtggctaga 6720
gtgtgtcaga gggaggtaga attccacgtg tagcagtgaa atgcgtagag atgtggagga 6780
ataccgatgg cgaaggcagc ctcctgggat aacactgacg ttcatgtccg aaagcgtggg 6840
tagcaaacag gattagatac cctggtagtc cacgccctaa acgatgtcga ttagctgttg 6900
ggcagcctga ctgcttggta gcgaagctaa cgcgtgaaat cgaccgcctg gggagtacgg 6960
tcgcaagatt aaaactcaaa ggaattgacg gggacccgca caagcggtgg atgatgtgga 7020
ttaattcgat gcaacgcgaa gaaccttacc cggttttgac atgtacggaa tcctccggag 7080
acggaggagt gccttcggga gccgtaacac aggtgctgca tggctgtcgt cagctcgtgt 7140
cgtgagatgt tgggttaagt cccgcaacga gcgcaaccct tgtcattagt tgccatcatt 7200
cagttgggca ctctaatgag actgccggtg acaagccgga ggaaggtggg gatgac 7256

<210> SEQ ID NO 26
<211> LENGTH: 9385
<212> TYPE: DNA
<213> ORGANISM: Artificial Sequence
<220> FEATURE:
<223> OTHER INFORMATION: Vector

<400> SEQUENCE: 26
tcttccgctt cctcgctcac tgactcgctg cgctcggtcg ttcggctgcg gcgagcggta 60

-continued

```
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aagaacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccatatg cggtgtgaaa taccgcacag atgcgtaagg   2220
agaaaatacc gcatcaggcg ccattcgcca ttcaggctgc gcaactgttg ggaagggcga   2280
tcggtgcggg cctcttcgct attacgccag ctggcgaaag ggggatgtgc tgcaaggcga   2340
ttaagttggg taacgccagg gttttcccag tcacgacgtt gtaaaacgac ggccagtgaa   2400
```

-continued

```
ttcgagctcg gtacccgggg atcctctaga gtcctgatac cgagcttttc ccatggttta   2460
tcgcgactga tagtgttttc ggcgaggtag tcggcacgtg tttgagacca ccagcgagtg   2520
attgtgcttt cagctacaat aattttgctg cttgctctat gtttaaaaat ctatccatat   2580
tggatagttt agattagact taagtggatt tcaagtgagc tgtttaaccc ttagctagca   2640
agggttttgg tggcgtaagg ttactgaact taagcatatc ggcggccaaa gtaccgctgc   2700
cattgccaat ctcgccgggg aaatgaaaag gctcgctaaa aaatcaaaaa tgttactgaa   2760
aggactttgg tcatttttat cctctacaat atctacattt aaaaataaat cggtcattgt   2820
ttaaacctta ctgtaaaact gtacaactgc taaactgtaa acacagaaag aggcaatact   2880
aacagcacaa aacaacagat atccaaactc cataaagtgc attattctga ctttttttcgt   2940
tgcctgatgt atttatgcta tttgtgctgt tcttatatat gtgttgctgg ttacgttgcg   3000
tttttcgga aaattcaacc ggtaggggac cgatacgcag tttcatctct ttgcttaggg   3060
agagtagggg ggtagattac gaccttagtt ttggtatccg taatatcatc attttttcgt   3120
ctagggagta tatcgacttc agaaaacagg tattagatac tgccttttct tacgagagtg   3180
atggcaagat agttctcttc aagtcaatca aacaggaaag tatttctttt ctgtctgaag   3240
atttgaaaaa ggactgaatg tttcacaagg ttaaaactgg ggaaaaagat ggatatggtt   3300
cagatgaaat gctgagcgca ccccgtatct atttggaaat gatgtcgcgg aaaacggaag   3360
tcccctactc cagtattctt taaattctaa gcagaaaact tcttcgtcgg tctttttttt   3420
gttgtttggt ttgcatggag taaaactgtg caacgccgtc tgaagtcgac gttgtagaaa   3480
cacaacgttt ttgaaaaaat aagctattgt tttatatcaa aatataatca tttttaaaat   3540
aaaggttgcg gcatttatca gatatttgtt ctgaaaaatg gttttttgcg gggggggggt   3600
ataattgaag acgtatcggg tgtttgcccg atgtttttag gtttttatca aatttacaaa   3660
aggaagccga tatgcgaaaa aaacttaccg ccctcgtatt gtccgcactg ccgcttgcgg   3720
ccgttgccga tgtcagccta tacggcgaaa tcaaagccgg cgtggaaggc aggaactacc   3780
agctgcaatt gactgaagca caagccgcta acggtggagc gagcggtcag gtaaaagtta   3840
ctaaagttac taaggccaaa agccgcatca ggacgaaaat cagtgatttc ggctcgttta   3900
tcggctttaa ggggagtgag gatttgggcg acgggctgaa ggctgtttgg cagcttgagc   3960
aagacgtatc cgttgccggc ggcggcgcga cccagtgggg caacagggaa tcctttatcg   4020
gcttggcagg cgaattcggt acgctgcgcg ccggtcgcgt tgcgaatcag tttgacgatg   4080
ccagccaagc cattgatcct tgggacagca ataatgatgt ggcttcgcaa ttgggtattt   4140
tcaaacgcca cgacgacatg ccggtttccg tacgctacga ttcccccgaa ttttccggtt   4200
tcagcggcag cgttcaattc gttccgatcc aaaacagcaa gtccgcctat acgccggctt   4260
attatactaa ggatacaaac aataatctta ctctcgttcc ggctgttgtc ggcaagcccg   4320
gatcggatgt gtattatgcc ggtctgaatt acaaaaatgg cggttttgcc gggaactatg   4380
cctttaaata tgcgagacac gccaatgtcg gacgtaatgc ttttgagttg ttcttgatcg   4440
gcagcgggag tgatcaagcc aaaggtaccg atcccttgaa aaaccatcag gtacaccgtc   4500
tgacgggcgg ctatgaggaa ggcggcttga atctcgcctt ggcggctcag ttggatttgt   4560
ctgaaaatgg cgacaaaacc aaaaacagta cgaccgaaat tgccgccact gcttcctacc   4620
gcttcggtaa tgcagttcca cgcatcagct atgcccatgg tttcgacttt atcgaacgcg   4680
gtaaaaaagg cgaaaatacc agctacgatc aaatcatcgc cggcgttgat tatgattttt   4740
ccaaacgcac ttccgccatc gtgtctggcg cttggctgaa acgcaatacc ggcatcggca   4800
```

-continued

```
actacactca aattaatgcc gcctccgtcg gtttgcgcca caaattctaa gcggccgcat   4860
attcggcaac tgtcggaata tctgctaaaa ttccgcattt tccgcaccgg gtttccgcac   4920
cgggacactc ggggcgtatg ttcaatttgt cggaatggag tttaaaggaa tacacatatg   4980
ttattagcga attattatca agatcctgaa atcacgagaa tcaatgcgtt gccgcaccat   5040
agctatttta tccctttga taaaaaagat aaggtagatc agttttctag ggaaaattct   5100
tcgtttttta catcattaaa tggaatgtgg caattcgcat attatccgag tatgcaggat   5160
ttgcctgaaa gtccggacga aatcgctttt acgaaacaaa tcaatgtgcc ttcaaattgg   5220
cagaatcacg ggtttgatgc ccatcaatat actaatatta attatccttt ccctttcgat   5280
ccgcctttg ttcctttaga gaacccttgc ggggtatatc aaaagcaggt caatctgaaa   5340
aagaatataa ataagcggta tttattagtc cttgaagggg ttgattcctg ttcttatata   5400
tatgtaaacc atcaatttgt aggatatggt tctatcagcc acagtaccaa tgaatttgat   5460
attaccgatt atcttcacga tggtgaaaac acccttaccg tatttgtcct gaaatggtgt   5520
gccggaagct acttggaaga tcaggataaa tttagaatgt cgggaatttt ccgagatgta   5580
tatttattgg aaagggagca tcactatttg caagacttga atattcgaac cgtgctttct   5640
gaagatttat cattggggca gatttgtctg gatttaaatt ttgcgggga tgcgggggat   5700
gtcggagtgt cattgtttga tacggacggg caaattgttc aagcaggcag cgcaatcacg   5760
acagataaac aacggatgca aatccgcctt gataatattc ctttaaccaa atcccgactc   5820
tggaatgcgg aaaaccctgc cctttatacc ttggtattaa acacaaaaga agaaatcatt   5880
acccagaaga tcggattccg caaggtagag gtcaaaaacg gggtattgct gcttaataat   5940
cagcctatta aattcaaagg ggtaaaccgg cacgatagcg atcccaaaac gggatatgcc   6000
atttctgtcg ctcaagcggt gactgacttg tcgttaatga agaaacataa tattaacgcg   6060
attcgtaccg cgcattatcc aaattcaccg tggttttgcg agctttgcga taagtatggt   6120
ttctatgtaa tcagtgaaag cgacattgaa agtcatgggg cggcattcca agcaatttcg   6180
catcccgaac cgagtatctt tctgaatgtg gaaaatccga atgaagagcc gcgtatccgc   6240
caacaaacta ttgacaactt ctgttatttt gcccgagaac cattgtatcg ggcggcttta   6300
ttggagcgga ctaaagcaaa tatagaacgt gataagaacc gcagttctat tttaatttgg   6360
tctttaggca atgaatcagg gtatggtgag aatttcgaat attgtgcaaa atgggtaaaa   6420
gagcgggatc cggatcgatt ggttcattac gaaagcagca tttatcagca ttctgcgtat   6480
cagaataaca ccgggcattt ggatttatac agtgaaatgt attccgacac agaagcaatc   6540
gatgcctatt ttgccgatca ttcacaaacg aaaaaaccat tcttattatg cgaatattcc   6600
catgcaatgg gaaattcaaa tggagatatg gaagactatt tccaaacatt taacaaatat   6660
tcgggctgtt gcggtgggtt tatttgggag tggtgcgatc atgcccaata tattaccccg   6720
acaaaattag gatatggcgg tgacttcggc gaaaaaatcc atgatgggaa tttctgtgtg   6780
gatggcttgg tttcgcccga acgcgtcccg cacagcaacc tgttggaagt aaaaaatgtc   6840
aaccggcccg tacgggcaaa cttgcgcggt gaacaaattg agttatataa ctattttgat   6900
ttcactaatt taaaagatat tctttgcgtc aaatatgaat gggtaaaaaa tggtcagata   6960
accgggacgg gaacattggc ggttgattgc gaaccccatc attctcaaat cttaccgatt   7020
cagcttccca aagaacggga aggattgcta tggttgaacc tatattactg cgcttcccgg   7080
caaactgatt tattgccggc aggacatcat ttcggtttcg atcaaattat tttgagtaag   7140
```

-continued

```
gaatacactc ctgccatagg atcggataaa gatgattgcc cgccgttgga aataaccgaa   7200
acagtgagac aaatcgttgt tcggaacaat cgatattatt ttgaatttaa caagctcacg   7260
gggataattg acgaaattaa agtcaatggc aaggctttca tccataaacc attggcttgg   7320
aatatttggc gcgcgccgac ggataatgac cgcctgattc gttcccaatg gcaaaatgcc   7380
ggttatgatc aaatgtattc caaggtttac gatatttgcg cgcatcggca aggaaacggt   7440
gttgtcgtgt ctgtgaaaag tgcattggtt gcggatgcaa aatcaaaaat catgacattg   7500
gaaacacagt atctgctgtc tgaaaatggt aaattggata ttcaaacaaa tgctgttttc   7560
cacgagcatt tgccattcct gccccgtttc ggtttgcgct tttcttaga cgaacagaaa    7620
acacctttta cctacttagg ttatggggcg ggtgaaagct atattgataa acatcaggcg   7680
accaaacttg gtatttattc gacaacggca ggggaaaatc atgttggcta tctcaagcct   7740
caagagaacg gcagccatta tggatgcttt tatgttcaaa acgatatgat ccgggtggag   7800
tcggggcagc cgtttagttt caacctgtcc ccttatacgc aagaagaact gacgcagaaa   7860
aaacattctt atgaattggt ttgttccggg tatgatgtat tgtgtatcga ctataagatg   7920
agcggtatcg gttcgaattc ttgcgggcct aatttgaagc cgcaatatcg tttgattgaa   7980
aataacatca atttcgatat aagtatccgg ttataagctt tctgcaaaga ttggtatcaa   8040
caaaaagcct gtcgtcagac aggctttttt tctgttttct gtttttagat gccgtctgaa   8100
tgctgaagta gaaaaccagc aagaaggtaa aaagaaagaa gcagtttttt ggattttaga   8160
tgttaccgca attggtttcc tttcctaaaa tttgtttaaa ttatttgcaa tattaatata   8220
aactggatat taatgatgag gattcaaaaa ggcatactga atataatttg tacaaaatat   8280
ttgcagtatt taaaaatgtt ggttcgtata tgaaaagtta aaaatgccaa aatgtacagt   8340
tgctaaactg taaaactgct aaagcaacaa aacataaaaa ggaatgcagg gatgcgatca   8400
ctacatcttt ttattccgta agcatttatg actttacggt caactgctac tctatgtttc   8460
cagcttttca gctccctatt ttcgaatatt ggacgaggca ttttcatcag tgtcgtaatg   8520
ccgaccgaaa ccctcacaaa ccatattggt tcttgtggca gcaacaccta tccgtttgtt   8580
caagcggcca caagagtaac atgattggct ggtggcattg gctttaatct cttcgatatg   8640
aactccattt ttagctgcac cttctttcag cgtatgcaac agtggggatg gggcaactat   8700
cttctggtgg agtttgttga cttcaatctg tatgcactgt aggttgagca gattcagttt   8760
tttgatacag attatccggc tttgttcggc aattctgttg gcgaacgtat agtagagctg   8820
tcgtcttgcc gctttcaatt tgcggtaggt attttaccat tccatgcgta gccgctcggt   8880
acgtttgagc caaatgttat cttcgccatt tgtaccaatt tgtttttaca ttaggctgtg   8940
ttttagtaat ctattgattt caattatttg caagggaaaa gacaattatt ttccggttag   9000
gaataaacct atcctattga atatattgaa gccaagtacg cttatcaaca ctatattaaa   9060
acacagcctt ttttaatata gtagacacaa tctttcctta tttatgaagg tgatagcttc   9120
tttcagtcta gagacctgca ggcatgcaag cttggcgtaa tcatggtcat agctgtttcc   9180
tgtgtgaaat tgttatccgc tcacaattcc acacaacata cgagccggaa gcataaagtg   9240
taaagcctgg ggtgcctaat gagtgagcta actcacatta attgcgttgc gctcactgcc   9300
cgctttccag tcgggaaacc tgtcgtgcca gctgcattaa tgaatcggcc aacgcgcggg   9360
gagaggcggt ttgcgtattg ggcgc                                         9385
```

<210> SEQ ID NO 27
<211> LENGTH: 9395

-continued

<212> TYPE: DNA
<213> ORGANISM: Artificial Sequence
<220> FEATURE:
<223> OTHER INFORMATION: Vector

<400> SEQUENCE: 27
tcttccgctt cctcgctcac tgactcgctg cgctcggtcg ttcggctgcg gcgagcggta 60
tcagctcact caaaggcggt aatacggtta tccacagaat caggggataa cgcaggaaag 120
aacatgtgag caaaaggcca gcaaaaggcc aggaaccgta aaaaggccgc gttgctggcg 180
tttttccata ggctccgccc ccctgacgag catcacaaaa atcgacgctc aagtcagagg 240
tggcgaaacc cgacaggact ataaagatac caggcgtttc cccctggaag ctccctcgtg 300
cgctctcctg ttccgaccct gccgcttacc ggatacctgt ccgcctttct cccttcggga 360
agcgtggcgc tttctcatag ctcacgctgt aggtatctca gttcggtgta ggtcgttcgc 420
tccaagctgg gctgtgtgca cgaacccccc gttcagcccg accgctgcgc cttatccggt 480
aactatcgtc ttgagtccaa cccggtaaga cacgacttat cgccactggc agcagccact 540
ggtaacagga ttagcagagc gaggtatgta ggcggtgcta cagagttctt gaagtggtgg 600
cctaactacg gctacactag aagaacagta tttggtatct gcgctctgct gaagccagtt 660
accttcggaa aaagagttgg tagctcttga tccggcaaac aaaccaccgc tggtagcggt 720
ggtttttttg tttgcaagca gcagattacg cgcagaaaaa aaggatctca agaagatcct 780
ttgatctttt ctacggggtc tgacgctcag tggaacgaaa actcacgtta agggattttg 840
gtcatgagat tatcaaaaag gatcttcacc tagatccttt taaattaaaa atgaagtttt 900
aaatcaatct aaagtatata tgagtaaact tggtctgaca gttaccaatg cttaatcagt 960
gaggcaccta tctcagcgat ctgtctattt cgttcatcca tagttgcctg actccccgtc 1020
gtgtagataa ctacgatacg ggagggctta ccatctggcc ccagtgctgc aatgataccg 1080
cgagacccac gctcaccggc tccagattta tcagcaataa accagccagc cggaagggcc 1140
gagcgcagaa gtggtcctgc aactttatcc gcctccatcc agtctattaa ttgttgccgg 1200
gaagctagag taagtagttc gccagttaat agtttgcgca acgttgttgc cattgctaca 1260
ggcatcgtgg tgtcacgctc gtcgtttggt atggcttcat tcagctccgg ttcccaacga 1320
tcaaggcgag ttacatgatc ccccatgttg tgcaaaaaag cggttagctc cttcggtcct 1380
ccgatcgttg tcagaagtaa gttggccgca gtgttatcac tcatggttat ggcagcactg 1440
cataattctc ttactgtcat gccatccgta agatgctttt ctgtgactgg tgagtactca 1500
accaagtcat tctgagaata gtgtatgcgg cgaccgagtt gctcttgccc ggcgtcaata 1560
cgggataata ccgcgccaca tagcagaact ttaaaagtgc tcatcattgg aaaacgttct 1620
tcggggcgaa aactctcaag gatcttaccg ctgttgagat ccagttcgat gtaacccact 1680
cgtgcaccca actgatcttc agcatctttt actttcacca gcgtttctgg gtgagcaaaa 1740
acaggaaggc aaaatgccgc aaaaaaggga ataagggcga cacggaaatg ttgaatactc 1800
atactcttcc tttttcaata ttattgaagc atttatcagg gttattgtct catgagcgga 1860
tacatatttg aatgtattta gaaaaataaa caaatagggg ttccgcgcac atttccccga 1920
aaagtgccac ctgacgtcta agaaaccatt attatcatga cattaaccta taaaaatagg 1980
cgtatcacga ggccctttcg tctcgcgcgt ttcggtgatg acggtgaaaa cctctgacac 2040
atgcagctcc cggagacggt cacagcttgt ctgtaagcgg atgccgggag cagacaagcc 2100
cgtcagggcg cgtcagcggg tgttggcggg tgtcggggct ggcttaacta tgcggcatca 2160

```
gagcagattg tactgagagt gcaccatatg cggtgtgaaa taccgcacag atgcgtaagg   2220
agaaaatacc gcatcaggcg ccattcgcca ttcaggctgc gcaactgttg ggaagggcga   2280
tcggtgcggg cctcttcgct attacgccag ctggcgaaag ggggatgtgc tgcaaggcga   2340
ttaagttggg taacgccagg gttttcccag tcacgacgtt gtaaaacgac ggccagtgaa   2400
ttcgagctcg gtacccgggg atcctctaga gtcctgatac cgagcttttc ccatggttta   2460
tcgcgactga tagtgttttc ggcgaggtag tcggcacgtg tttgagacca ccagcgagtg   2520
attgtgcttt cagctacaat aattttgctg cttgctctat gtttaaaaat ctatccatat   2580
tggatagttt agattagact taagtggatt tcaagtgagc tgtttaaccc ttagctagca   2640
agggttttgg tggcgtaagg ttactgaact taagcatatc ggcggccaaa gtaccgctgc   2700
cattgccaat ctcgccgggg aaatgaaaag gctcgctaaa aaatcaaaaa tgttactgaa   2760
aggactttgg tcatttttat cctctacaat atctacattt aaaaataaat cggtcattgt   2820
ttaaacctta ctgtaaaact gtacaactgc taaactgtaa acacagaaag aggcaatact   2880
aacagcacaa aacaacagat atccaaactc cataaagtgc attattctga ctttttttcgt   2940
tgcctgatgt atttatgcta tttgtgctgt tcttatatat gtgttgctgg ttacgttgcg   3000
tttttttcgga aaattcaacc ggtaggggac cgatacgcag tttcatctct ttgcttaggg   3060
agagtagggg ggtagattac gaccttagtt ttggtatccg taatatcatc attttttcgt   3120
ctagggagta tatcgacttc agaaaacagg tattagatac tgccttttct tacgagagtg   3180
atggcaagat agttctcttc aagtcaatca aacaggaaag tatttctttt ctgtctgaag   3240
atttgaaaaa ggactgaatg tttcacaagg ttaaaactgg ggaaaaagat ggatatggtt   3300
cagatgaaat gctgagcgca ccccgtatct atttggaaat gatgtcgcgg aaaacggaag   3360
tcccctactc cagtattctt taaattctaa gcagaaaact tcttcgtcgg tctttttttt   3420
gttgtttggt ttgcatggag taaaactgtg caacgccgtc tgaagtcgac gtgccgcgtg   3480
tgttttttta tggcgtttta aaaagccgag actgcatccg ggcagcagcg catcggctcg   3540
cacgaggtct gcgcttgaat tgtgttgtag aaacacaacg tttttgaaaa aataagctat   3600
tgttttatat caaaatataa tcatttttaa aataaaggtt gcggcattta tcagatattt   3660
gttctgaaaa atggtttttc gggcgggaac atttataatt gaagacgtat cgggtgtttg   3720
cccgatgttt ttaggttttt atcaaattta caaaaggaac tcgagatgag catgaaacac   3780
tttccgtcga aagtactgac aaccgcaatt ttagctacat tttgtagcgg cgccttggca   3840
gccaccagcg acgatgacgt aaaaaaagcc gccactgtcg ctatcgtggc ggcctacaac   3900
aacggccagg aaatcaacgg ttttaaagcc ggtgaaacca tctatgacat cggcgaagac   3960
ggtactatca cccaaaaaga tgctacggcg gcagacgttg aagcagacga tttcaaaggc   4020
ttgggcctga aaaaagtggt caccaacttg accaagaccg tgaacgaaaa taaacagaac   4080
gtcgatgcca aagtaaaagc agcggaaagc gaaattgaaa agttgaccac gaaattagca   4140
gataccgacg cggctctggc cgataccgac gctgcgctgg acgagaccac caatgcattg   4200
aataaactgg gtgaaaatat caccacgttc gccgaagaaa cgaaaaccaa catcgtgaaa   4260
attgacgaga aattggaagc ggtggccgac accgtcgata aacacgcgga agcgttcaat   4320
gacatcgccg atagcttgga cgaaaccaac acaaaggcag atgaagcggt taagacggcc   4380
aatgaagcaa agcaaactgc cgaagagaca aaacagaacg tggacgccaa agtcaaagcg   4440
gccgaaacag cggccggcaa agctgaagca gccgcaggca cagcgaacac agccgcggat   4500
aaagcagaag cagtagcggc caaagtcacc gacatcaaag ccgatatcgc gactaacaaa   4560
```

```
gcggatatcg ccaaaaactc agcacgtatc gactctttgg acaaaaacgt agcgaactta   4620
cgtaaagaaa cccgccaggg tttggctgaa caagcggctt tgtctggatt gttccaaccc   4680
tataacgtcg gtcgctttaa cgtcacggca gccgttggcg ggtataaaag cgaatcggct   4740
gtcgctatag gcaccggttt ccgcttcact gagaactttg ccgcgaaagc cggcgttgcc   4800
gtaggcacct cctccggctc atccgccgct tatcacgttg gcgtcaacta cgaatggtaa   4860
gcggccgcat attcggcaac tgtcggaata tctgctaaaa ttccgcattt tccgcaccgg   4920
gtttccgcac cgggacactc ggggcgtatg ttcaatttgt cggaatggag tttaaaggaa   4980
tacacatatg ttattagcga attattatca agatcctgaa atcacgagaa tcaatgcgtt   5040
gccgcaccat agctatttta tcccttttga taaaaaagat aaggtagatc agttttctag   5100
ggaaaattct tcgtttttta catcattaaa tggaatgtgg caattcgcat attatccgag   5160
tatgcaggat ttgcctgaaa gtccggacga aatcgctttt acgaaacaaa tcaatgtgcc   5220
ttcaaattgg cagaatcacg ggtttgatgc ccatcaatat actaatatta attatccttt   5280
ccctttcgat ccgccttttg ttcctttaga gaacccttgc ggggtatatc aaaagcaggt   5340
caatctgaaa aagaatataa ataagcggta tttattagtc cttgaagggg ttgattcctg   5400
ttcttatata tatgtaaacc atcaatttgt aggatatggt tctatcagcc acagtaccaa   5460
tgaatttgat attaccgatt atcttcacga tggtgaaaac acccttaccg tatttgtcct   5520
gaaatggtgt gccggaagct acttggaaga tcaggataaa tttagaatgt cgggaatttt   5580
ccgagatgta tatttattgg aaagggagca tcactatttg caagacttga atattcgaac   5640
cgtgctttct gaagatttat cattggggca gatttgtctg gatttaaatt ttgcgggggga   5700
tgcgggggat gtcggagtgt cattgtttga tacggacggg caaattgttc aagcaggcag   5760
cgcaatcacg acagataaac aacggatgca aatccgcctt gataatattc ctttaaccaa   5820
atcccgactc tggaatgcgg aaaaccctgc cctttatacc ttggtattaa acacaaaaga   5880
agaaatcatt acccagaaga tcggattccg caaggtagag gtcaaaaacg gggtattgct   5940
gcttaataat cagcctatta aattcaaagg ggtaaaccgg cacgatagcg atcccaaaac   6000
gggatatgcc atttctgtcg ctcaagcggt gactgacttg tcgttaatga agaaacataa   6060
tattaacgcg attcgtaccg cgcattatcc aaattcaccg tggttttgcg agctttgcga   6120
taagtatggt ttctatgtaa tcagtgaaag cgacattgaa agtcatgggg cggcattcca   6180
agcaatttcg catcccgaac cgagtatctt tctgaatgtg gaaaatccga atgaagagcc   6240
gcgtatccgc caacaaacta ttgacaactt ctgttatttt gcccgagaac cattgtatcg   6300
ggcggcttta ttggagcgga ctaaagcaaa tatagaacgt gataagaacc gcagttctat   6360
tttaatttgg tctttaggca atgaatcagg gtatggtgag aatttcgaat attgtgcaaa   6420
atgggtaaaa gagcgggatc cggatcgatt ggttcattac gaaagcagca tttatcagca   6480
ttctgcgtat cagaataaca ccgggcattt ggatttatac agtgaaatgt attccgacac   6540
agaagcaatc gatgcctatt ttgccgatca ttcacaaacg aaaaaaccat tcttattatg   6600
cgaatattcc catgcaatgg gaaattcaaa tggagatatg gaagactatt tccaaacatt   6660
taacaaatat tcgggctgtt gcggtgggtt tatttgggag tggtgcgatc atgcccaata   6720
tattaccccg acaaaattag gatatggcgg tgacttcggc gaaaaaatcc atgatgggaa   6780
tttctgtgtg gatggcttgg tttcgcccga acgcgtcccg cacagcaacc tgttggaagt   6840
aaaaaatgtc aaccggcccg tacgggcaaa cttgcgcggt gaacaaattg agttatataa   6900
```

-continued ctattttgat ttcactaatt taaaagatat tctttgcgtc aaatatgaat gggtaaaaaa 6960
tggtcagata accgggacgg gaacattggc ggttgattgc gaaccccatc attctcaaat 7020
cttaccgatt cagcttccca aagaacggga aggattgcta tggttgaacc tatattactg 7080
cgcttcccgg caaactgatt tattgccggc aggacatcat ttcggtttcg atcaaattat 7140
tttgagtaag gaatacactc ctgccatagg atcggataaa gatgattgcc cgccgttgga 7200
aataaccgaa acagtgagac aaatcgttgt tcggaacaat cgatattatt ttgaatttaa 7260
caagctcacg gggataattg acgaaattaa agtcaatggc aaggctttca tccataaacc 7320
attggcttgg aatatttggc gcgcgccgac ggataatgac cgcctgattc gttcccaatg 7380
gcaaaatgcc ggttatgatc aaatgtattc caaggtttac gatatttgcg cgcatcggca 7440
aggaaacggt gttgtcgtgt ctgtgaaaag tgcattggtt gcggatgcaa aatcaaaaat 7500
catgacattg gaaacacagt atctgctgtc tgaaaatggt aaattggata ttcaaacaaa 7560
tgctgttttc cacgagcatt tgccattcct gccccgtttc ggtttgcgct tttcttaga 7620
cgaacagaaa acacctttta cctacttagg ttatggggcg ggtgaaagct atattgataa 7680
acatcaggcg accaaacttg gtatttattc gacaacggca ggggaaaatc atgttggcta 7740
tctcaagcct caagagaacg gcagccatta tggatgcttt tatgttcaaa acgatatgat 7800
ccgggtggag tcggggcagc cgtttagttt caacctgtcc ccttatacgc aagaagaact 7860
gacgcagaaa aaacattctt atgaattggt ttgttccggg tatgatgtat tgtgtatcga 7920
ctataagatg agcggtatcg gttcgaattc ttgcgggcct aatttgaagc cgcaatatcg 7980
tttgattgaa aataacatca atttcgatat aagtatccgg ttataagctt tctgcaaaga 8040
ttggtatcaa caaaaagcct gtcgtcagac aggcttttt tctgttttct gtttttagat 8100
gccgtctgaa tgctgaagta gaaaaccagc aagaaggtaa aaagaaagaa gcagttttt 8160
ggattttaga tgttaccgca attggtttcc tttcctaaaa tttgtttaaa ttatttgcaa 8220
tattaatata aactggatat taatgatgag gattcaaaaa ggcatactga atataatttg 8280
tacaaaatat ttgcagtatt taaaaatgtt ggttcgtata tgaaaagtta aaaatgccaa 8340
aatgtacagt tgctaaactg taaaactgct aaagcaacaa aacataaaaa ggaatgcagg 8400
gatgcgatca ctacatcttt ttattccgta agcatttatg actttacggt caactgctac 8460
tctatgtttc cagcttttca gctccctatt ttcgaatatt ggacgaggca ttttcatcag 8520
tgtcgtaatg ccgaccgaaa ccctcacaaa ccatattggt tcttgtggca gcaacaccta 8580
tccgtttgtt caagcggcca caagagtaac atgattggct ggtggcattg gctttaatct 8640
cttcgatatg aactccattt ttagctgcac cttctttcag cgtatgcaac agtggggatg 8700
gggcaactat cttctggtgg agtttgttga cttcaatctg tatgcactgt aggttgagca 8760
gattcagttt tttgatacag attatccggc tttgttcggc aattctgttg gcgaacgtat 8820
agtagagctg tcgtcttgcc gctttcaatt tgcggtaggt attttaccat tccatgcgta 8880
gccgctcggt acgtttgagc caaatgttat cttcgccatt tgtaccaatt tgtttttaca 8940
ttaggctgtg ttttagtaat ctattgattt caattatttg caagggaaaa gacaattatt 9000
ttccggttag gaataaacct atcctattga atatattgaa gccaagtacg cttatcaaca 9060
ctatattaaa acacagcctt ttttaatata gtagacacaa tctttcctta tttatgaagg 9120
tgatagcttc tttcagtcta gagacctgca ggcatgcaag cttggcgtaa tcatggtcat 9180
agctgtttcc tgtgtgaaat tgttatccgc tcacaattcc acacaacata cgagccggaa 9240
gcataaagtg taaagcctgg ggtgcctaat gagtgagcta actcacatta attgcgttgc 9300
gctcactgcc cgctttccag tcgggaaacc tgtcgtgcca gctgcattaa tgaatcggcc 9360
aacgcgcggg gagaggcggt ttgcgtattg ggcgc 9395

<210> SEQ ID NO 28
<211> LENGTH: 8314
<212> TYPE: DNA
<213> ORGANISM: Artificial Sequence
<220> FEATURE:
<223> OTHER INFORMATION: Vector

<400> SEQUENCE: 28
tcttccgctt cctcgctcac tgactcgctg cgctcggtcg ttcggctgcg gcgagcggta 60
tcagctcact caaaggcggt aatacggtta tccacagaat caggggataa cgcaggaaag 120
aacatgtgag caaaaggcca gcaaaaggcc aggaaccgta aaaaggccgc gttgctggcg 180
tttttccata ggctccgccc ccctgacgag catcacaaaa atcgacgctc aagtcagagg 240
tggcgaaacc cgacaggact ataaagatac caggcgtttc cccctggaag ctccctcgtg 300
cgctctcctg ttccgaccct gccgcttacc ggatacctgt ccgcctttct cccttcggga 360
agcgtggcgc tttctcatag ctcacgctgt aggtatctca gttcggtgta ggtcgttcgc 420
tccaagctgg gctgtgtgca cgaacccccc gttcagcccg accgctgcgc cttatccggt 480
aactatcgtc ttgagtccaa cccggtaaga cacgacttat cgccactggc agcagccact 540
ggtaacagga ttagcagagc gaggtatgta ggcggtgcta cagagttctt gaagtggtgg 600
cctaactacg gctacactag aagaacagta tttggtatct gcgctctgct gaagccagtt 660
accttcggaa aaagagttgg tagctcttga tccggcaaac aaaccaccgc tggtagcggt 720
ggtttttttg tttgcaagca gcagattacg cgcagaaaaa aaggatctca agaagatcct 780
ttgatctttt ctacggggtc tgacgctcag tggaacgaaa actcacgtta agggattttg 840
gtcatgagat tatcaaaaag gatcttcacc tagatccttt taaattaaaa atgaagtttt 900
aaatcaatct aaagtatata tgagtaaact tggtctgaca gttaccaatg cttaatcagt 960
gaggcaccta tctcagcgat ctgtctattt cgttcatcca tagttgcctg actccccgtc 1020
gtgtagataa ctacgatacg ggagggctta ccatctggcc ccagtgctgc aatgataccg 1080
cgagacccac gctcaccggc tccagattta tcagcaataa accagccagc cggaagggcc 1140
gagcgcagaa gtggtcctgc aactttatcc gcctccatcc agtctattaa ttgttgccgg 1200
gaagctagag taagtagttc gccagttaat agtttgcgca acgttgttgc cattgctaca 1260
ggcatcgtgg tgtcacgctc gtcgtttggt atggcttcat tcagctccgg ttcccaacga 1320
tcaaggcgag ttacatgatc ccccatgttg tgcaaaaaag cggttagctc cttcggtcct 1380
ccgatcgttg tcagaagtaa gttggccgca gtgttatcac tcatggttat ggcagcactg 1440
cataattctc ttactgtcat gccatccgta agatgctttt ctgtgactgg tgagtactca 1500
accaagtcat tctgagaata gtgtatgcgg cgaccgagtt gctcttgccc ggcgtcaata 1560
cgggataata ccgcgccaca tagcagaact ttaaaagtgc tcatcattgg aaaacgttct 1620
tcggggcgaa aactctcaag gatcttaccg ctgttgagat ccagttcgat gtaacccact 1680
cgtgcaccca actgatcttc agcatctttt actttcacca gcgtttctgg gtgagcaaaa 1740
acaggaaggc aaaatgccgc aaaaaaggga ataagggcga cacggaaatg ttgaatactc 1800
atactcttcc tttttcaata ttattgaagc atttatcagg gttattgtct catgagcgga 1860
tacatatttg aatgtattta gaaaaataaa caaatagggg ttccgcgcac atttccccga 1920
aaagtgccac ctgacgtcta agaaaccatt attatcatga cattaaccta taaaaatagg 1980
cgtatcacga ggccctttcg tctcgcgcgt ttcggtgatg acggtgaaaa cctctgacac 2040
atgcagctcc cggagacggt cacagcttgt ctgtaagcgg atgccgggag cagacaagcc 2100
cgtcagggcg cgtcagcggg tgttggcggg tgtcggggct ggcttaacta tgcggcatca 2160
gagcagattg tactgagagt gcaccatatg cggtgtgaaa taccgcacag atgcgtaagg 2220
agaaaatacc gcatcaggcg ccattcgcca ttcaggctgc gcaactgttg ggaagggcga 2280
tcggtgcggg cctcttcgct attacgccag ctggcgaaag ggggatgtgc tgcaaggcga 2340
ttaagttggg taacgccagg gttttcccag tcacgacgtt gtaaaacgac ggccagtgaa 2400
ttcgagctcg gtacccgggg atcctctaga gtcctgatac cgagcttttc ccatggttta 2460
tcgcgactga tagtgttttc ggcgaggtag tcggcacgtg tttgagacca ccagcgagtg 2520
attgtgcttt cagctacaat aattttgctg cttgctctat gtttaaaaat ctatccatat 2580
tggatagttt agattagact taagtggatt tcaagtgagc tgtttaaccc ttagctagca 2640
agggttttgg tggcgtaagg ttactgaact taagcatatc ggcggccaaa gtaccgctgc 2700
cattgccaat ctcgccgggg aaatgaaaag gctcgctaaa aaatcaaaaa tgttactgaa 2760
aggactttgg tcatttttat cctctacaat atctacattt aaaaataaat cggtcattgt 2820
ttaaacctta ctgtaaaact gtacaactgc taaactgtaa acacagaaag aggcaatact 2880
aacagcacaa aacaacagat atccaaactc cataaagtgc attattctga ctttttttcgt 2940
tgcctgatgt atttatgcta tttgtgctgt tcttatatat gtgttgctgg ttacgttgcg 3000
tttttcgga aaattcaacc ggtaggggac cgatacgcag tttcatctct ttgcttaggg 3060
agagtagggg ggtagattac gaccttagtt ttggtatccg taatatcatc attttttcgt 3120
ctagggagta tatcgacttc agaaaacagg tattagatac tgccttttct tacgagagtg 3180
atggcaagat agttctcttc aagtcaatca aacaggaaag tatttctttt ctgtctgaag 3240
atttgaaaaa ggactgaatg tttcacaagg ttaaaactgg ggaaaaagat ggatatggtt 3300
cagatgaaat gctgagcgca ccccgtatct atttggaaat gatgtcgcgg aaaacggaag 3360
tcccctactc cagtattctt taaattctaa gcagaaaact tcttcgtcgg tctttttttt 3420
gttgtttggt ttgcatggag taaaactgtg caacgccgtc tgaagtcgac gtgccgcgtg 3480
tgttttttta tggcgtttta aaaagccgag actgcatccg ggcagcagcg catcggctcg 3540
cacgaggtct gcgcttgaat tgtgttgtag aaacacaacg tttttgaaaa aataagctat 3600
tgttttatat caaaatataa tcatttttaa aataaaggtt gcggcattta tcagatattt 3660
gttctgaaaa atggttttc gggcgggaac atttataatt gaagacgtat cgggtgtttg 3720
cccgatgttt ttaggttttt atcaaattta caaaaggaac tcgagatcta ttatataacg 3780
cggccgcata ttcggcaact gtcggaatat ctgctaaaat tccgcatttt ccgcaccggg 3840
tttccgcacc gggacactcg gggcgtatgt tcaatttgtc ggaatggagt ttaaaggaat 3900
acacatatgt tattagcgaa ttattatcaa gatcctgaaa tcacgagaat caatgcgttg 3960
ccgcaccata gctattttat cccttttgat aaaaaagata aggtagatca gttttctagg 4020
gaaaattctt cgttttttac atcattaaat ggaatgtggc aattcgcata ttatccgagt 4080
atgcaggatt tgcctgaaag tccggacgaa atcgctttta cgaaacaaat caatgtgcct 4140
tcaaattggc agaatcacgg gtttgatgcc catcaatata ctaatattaa ttatcctttc 4200
cctttcgatc cgccttttgt tcctttagag aacccttgcg ggtatatcaa aaagcaggtc 4260
aatctgaaaa agaatataaa taagcggtat ttattagtcc ttgaaggggt tgattcctgt 4320
tcttatatat atgtaaacca tcaatttgta ggatatggtt ctatcagcca cagtaccaat 4380
gaatttgata ttaccgatta tcttcacgat ggtgaaaaca cccttaccgt atttgtcctg 4440
aaatggtgtg ccggaagcta cttggaagat caggataaat ttagaatgtc gggaattttc 4500
cgagatgtat atttattgga aagggagcat cactatttgc aagacttgaa tattcgaacc 4560
gtgctttctg aagatttatc attggggcag atttgtctgg atttaaattt tgcgggggat 4620
gcgggggatg tcggagtgtc attgtttgat acggacgggc aaattgttca agcaggcagc 4680
gcaatcacga cagataaaca acggatgcaa atccgccttg ataatattcc tttaaccaaa 4740
tcccgactct ggaatgcgga aaccctgcc ctttatacct tggtattaaa cacaaaagaa 4800
gaaatcatta cccagaagat cggattccgc aaggtagagg tcaaaaacgg ggtattgctg 4860
cttaataatc agcctattaa attcaaaggg gtaaaccggc acgatagcga tcccaaaacg 4920
ggatatgcca tttctgtcgc tcaagcggtg actgacttgt cgttaatgaa gaaacataat 4980
attaacgcga ttcgtaccgc gcattatcca aattcaccgt ggttttgcga gctttgcgat 5040
aagtatggtt tctatgtaat cagtgaaagc gacattgaaa gtcatggggc ggcattccaa 5100
gcaatttcgc atcccgaacc gagtatcttt ctgaatgtgg aaaatccgaa tgaagagccg 5160
cgtatccgcc aacaaactat tgacaacttc tgttattttg cccgagaacc attgtatcgg 5220
gcggctttat tggagcggac taaagcaaat atagaacgtg ataagaaccg cagttctatt 5280
ttaatttggt ctttaggcaa tgaatcaggg tatggtgaga atttcgaata ttgtgcaaaa 5340
tgggtaaaag agcgggatcc ggatcgattg gttcattacg aaagcagcat ttatcagcat 5400
tctgcgtatc agaataacac cggcatttg gatttataca gtgaaatgta ttccgacaca 5460
gaagcaatcg atgcctattt tgccgatcat tcacaaacga aaaaaccatt cttattatgc 5520
gaatattccc atgcaatggg aaattcaaat ggagatatgg aagactattt ccaaacattt 5580
aacaaatatt cgggctgttg cggtgggttt atttgggagt ggtgcgatca tgcccaatat 5640
attaccccga caaaattagg atatggcggt gacttcggcg aaaaaatcca tgatgggaat 5700
ttctgtgtgg atggcttggt ttcgcccgaa cgcgtcccgc acagcaacct gttggaagta 5760
aaaaatgtca accggcccgt acgggcaaac ttgcgcggtg aacaaattga gttatataac 5820
tattttgatt tcactaattt aaaagatatt ctttgcgtca aatatgaatg ggtaaaaaat 5880
ggtcagataa ccgggacggg aacattggcg gttgattgcg aaccccatca ttctcaaatc 5940
ttaccgattc agcttcccaa agaacgggaa ggattgctat ggttgaacct atattactgc 6000
gcttcccggc aaactgattt attgccggca ggacatcatt tcggtttcga tcaaatttatt 6060 ttgagtaagg aatacactcc tgccatagga tcggataaag atgattgccc gccgttggaa 6120
ataaccgaaa cagtgagaca aatcgttgtt cggaacaatc gatattattt tgaatttaac 6180
aagctcacgg ggataattga cgaaattaaa gtcaatggca aggctttcat ccataaacca 6240
ttggcttgga atatttggcg cgcgccgacg gataatgacc gcctgattcg ttcccaatgg 6300
caaaatgccg gttatgatca aatgtattcc aaggtttacg atatttgcgc gcatcggcaa 6360
ggaaacggtg ttgtcgtgtc tgtgaaaagt gcattggttg cggatgcaaa atcaaaaatc 6420
atgacattgg aaacacagta tctgctgtct gaaaatggta aattggatat tcaaacaaat 6480
gctgttttcc acgagcattt gccattcctg ccccgtttcg gtttgcgctt tttcttagac 6540
gaacagaaaa caccttttac ctacttaggt tatggggcgg gtgaaagcta tattgataaa 6600
catcaggcga ccaaacttgg tatttattcg acaacggcag ggaaaaatca tgttggctat 6660

```
ctcaagcctc aagagaacgg cagccattat ggatgctttt atgttcaaaa cgatatgatc   6720

cgggtggagt cggggcagcc gtttagtttc aacctgtccc cttatacgca agaagaactg   6780

acgcagaaaa aacattctta tgaattggtt tgttccgggt atgatgtatt gtgtatcgac   6840

tataagatga gcggtatcgg ttcgaattct tgcgggccta atttgaagcc gcaatatcgt   6900

ttgattgaaa ataacatcaa tttcgatata agtatccggt tataagcttt ctgcaaagat   6960

tggtatcaac aaaaagcctg tcgtcagaca ggcttttttt ctgttttctg tttttagatg   7020

ccgtctgaat gctgaagtag aaaaccagca agaaggtaaa aagaaagaag cagttttttg   7080

gattttagat gttaccgcaa ttggtttcct ttcctaaaat ttgtttaaat tatttgcaat   7140

attaatataa actggatatt aatgatgagg attcaaaaag gcatactgaa tataatttgt   7200

acaaaatatt tgcagtattt aaaaatgttg gttcgtatat gaaaagttaa aaatgccaaa   7260

atgtacagtt gctaaactgt aaaactgcta aagcaacaaa acataaaaag gaatgcaggg   7320

atgcgatcac tacatctttt tattccgtaa gcatttatga ctttacggtc aactgctact   7380

ctatgtttcc agcttttcag ctccctattt tcgaatattg gacgaggcat tttcatcagt   7440

gtcgtaatgc cgaccgaaac cctcacaaac catattggtt cttgtggcag caacacctat   7500

ccgtttgttc aagcggccac aagagtaaca tgattggctg gtggcattgg ctttaatctc   7560

ttcgatatga actccatttt tagctgcacc ttctttcagc gtatgcaaca gtggggatgg   7620

ggcaactatc ttctggtgga gtttgttgac ttcaatctgt atgcactgta ggttgagcag   7680

attcagtttt ttgatacaga ttatccggct ttgttcggca attctgttgg cgaacgtata   7740

gtagagctgt cgtcttgccg ctttcaattt gcggtaggta ttttaccatt ccatgcgtag   7800

ccgctcggta cgtttgagcc aaatgttatc ttcgccattt gtaccaattt gtttttacat   7860

taggctgtgt tttagtaatc tattgatttc aattatttgc aagggaaaag acaattattt   7920

tccggttagg aataaaccta tcctattgaa tatattgaag ccaagtacgc ttatcaacac   7980

tatattaaaa cacagccttt tttaatatag tagacacaat ctttccttat ttatgaaggt   8040

gatagcttct ttcagtctag agacctgcag gcatgcaagc ttggcgtaat catggtcata   8100

gctgtttcct gtgtgaaatt gttatccgct cacaattcca cacaacatac gagccggaag   8160

cataaagtgt aaagcctggg gtgcctaatg agtgagctaa ctcacattaa ttgcgttgcg   8220

ctcactgccc gctttccagt cgggaaacct gtcgtgccag ctgcattaat gaatcggcca   8280

acgcgcgggg agaggcggtt tgcgtattgg gcgc                               8314
```

<210> SEQ ID NO 29
<211> LENGTH: 9506
<212> TYPE: DNA
<213> ORGANISM: Artificial Sequence
<220> FEATURE:
<223> OTHER INFORMATION: Vector

<400> SEQUENCE: 29

```
cataagaacc tcagatcctt ccgtatttag ccagtatgtt ctctagtgtg gttcgttgtt     60

tttgcgtgag ccatgagaac gaaccattga gatcatactt actttgcatg tcactcaaaa    120

attttgcctc aaaactggtg agctgaattt ttgcagttaa agcatcgtgt agtgtttttc    180

ttagtccgtt atgtaggtag gaatctgatg taatggttgt tggtattttg tcaccattca    240

tttttatctg gttgttctca agttcggtta cgagatccat ttgtctatct agttcaactt    300

ggaaaatcaa cgtatcagtc gggcggcctc gcttatcaac caccaatttc atattgctgt    360

aagtgtttaa atctttactt attggtttca aaacccattg gttaagcctt ttaaactcat    420
```

```
ggtagttatt ttcaagcatt aacatgaact taaattcatc aaggctaatc tctatatttg    480
ccttgtgagt tttcttttgt gttagttctt ttaataacca ctcataaatc ctcatagagt    540
atttgttttc aaaagactta acatgttcca gattatattt tatgaatttt tttaactgga    600
aaagataagg caatatctct tcactaaaaa ctaattctaa tttttcgctt gagaacttgg    660
catagtttgt ccactggaaa atctcaaagc ctttaaccaa aggattcctg atttccacag    720
ttctcgtcat cagctctctg gttgctttag ctaatacacc ataagcattt tccctactga    780
tgttcatcat ctgagcgtat tggttataag tgaacgatac cgtccgttct ttccttgtag    840
ggttttcaat cgtggggttg agtagtgcca cacagcataa aattagcttg gtttcatgct    900
ccgttaagtc atagcgacta atcgctagtt catttgcttt gaaaacaact aattcagaca    960
tacatctcaa ttggtctagg tgattttaat cactatacca attgagatgg gctagtcaat   1020
gataattact agtccttttc ctttgagttg tgggtatctg taaattctgc tagacctttg   1080
ctggaaaact tgtaaattct gctagaccct ctgtaaattc cgctagacct ttgtgtgttt   1140
tttttgttta tattcaagtg gttataattt atagaataaa gaaagaataa aaaaagataa   1200
aaagaataga tcccagccct gtgtataact cactacttta gtcagttccg cagtattaca   1260
aaaggatgtc gcaaacgctg tttgctcctc tacaaaacag accttaaaac cctaaaggct   1320
taagtagcac cctcgcaagc tcgggcaaat cgaagatcct ttgatctttt ctacggggtc   1380
tgacgctcag tggaacgaaa actcacgtta agggattttg gtcatgagat tatcaaaaag   1440
gatcttcacc tagatccttt taaattaaaa atgaagtttt aaatcaatct aaagtatata   1500
tgagtaaact tggtctgaca gttaccaatg cttaatcagt gaggcaccta tctcagcgat   1560
ctgtctattt cgttcatcca tagttgcctg actccccgtc gtgtagataa ctacgatacg   1620
ggagggctta ccatctggcc ccagtgctgc aatgataccg cgagacccac gctcaccggc   1680
tccagattta tcagcaataa accagccagc cggaagggcc gagcgcagaa gtggtcctgc   1740
aactttatcc gcctccatcc agtctattaa ttgttgccgg gaagctagag taagtagttc   1800
gccagttaat agtttgcgca acgttgttgc cattgctaca ggcatcgtgg tgtcacgctc   1860
gtcgtttggt atggcttcat tcagctccgg ttcccaacga tcaaggcgag ttacatgatc   1920
ccccatgttg tgcaaaaaag cggttagctc cttcggtcct ccgatcgttg tcagaagtaa   1980
gttggccgca gtgttatcac tcatggttat ggcagcactg cataattctc ttactgtcat   2040
gccatccgta agatgctttt ctgtgactgg tgagtactca accaagtcat tctgagaata   2100
gtgtatgcgg cgaccgagtt gctcttgccc ggcgtcaata cgggataata ccgcgccaca   2160
tagcagaact ttaaaagtgc tcatcattgg aaaacgttct tcggggcgaa aactctcaag   2220
gatcttaccg ctgttgagat ccagttcgat gtaacccact cgtgcaccca actgatcttc   2280
agcatctttt actttcacca gcgtttctgg gtgagcaaaa acaggaaggc aaaatgccgc   2340
aaaaaaggga ataagggcga cacggaaatg ttgaatactc atactcttcc tttttcaata   2400
ttattgaagc atttatcagg gttattgtct catgagcgga tacatatttg aatgtattta   2460
gaaaaataaa caaatagggg ttccgcgcac atttccccga aaagtgccac ctgacgtcta   2520
agaaaccatt attatcatga cattaaccta taaaaatagg cgtatcacga ggccctttcg   2580
tctcgcgcgt ttcggtgatg acggtgaaaa cctctgacac atgcagctcc cggagacggt   2640
cacagcttgt ctgtaagcgg atgccgggag cagacaagcc cgtcagggcg cgtcagcggg   2700
tgttggcggg tgtcggggct ggcttaacta tgcggcatca gagcagattg tactgagagt   2760
```

-continued

```
gcaccatatg cggtgtgaaa taccgcacag atgcgtaagg agaaaatacc gcatcaggcg   2820
ccattcgcca ttcaggctgc gcaactgttg ggaagggcga tcggtgcggg cctcttcgct   2880
attacgccag ctggcgaaag ggggatgtgc tgcaaggcga ttaagttggg taacgccagg   2940
gttttcccag tcacgacgtt gtaaaacgac ggccagtgaa ttcgagctcg gtacccgggg   3000
atcctctaga gtcctgatac cgagcttttc ccatggttta tcgcgactga tagtgttttc   3060
ggcgaggtag tcggcacgtg tttgagacca ccagcgagtg attgtgcttt cagctacaat   3120
aattttgctg cttgctctat gtttaaaaat ctatccatat tggatagttt agattagact   3180
taagtggatt tcaagtgagc tgtttaaccc ttagctagca agggttttgg tggcgtaagg   3240
ttactgaact taagcatatc ggcggccaaa gtaccgctgc cattgccaat ctcgccgggg   3300
aaatgaaaag gctcgctaaa aaatcaaaaa tgttactgaa aggactttgg tcatttttat   3360
cctctacaat atctacattt aaaaataaat cggtcattgt ttaaacctta ctgtaaaact   3420
gtacaactgc taaactgtaa acacagaaag aggcaatact aacagcacaa aacaacagat   3480
atccaaactc cataaagtgc attattctga ctttttttcgt tgcctgatgt atttatgcta   3540
tttgtgctgt tcttatatat gtgttgctgg ttacgttgcg ttttttcgga aaattcaacc   3600
ggtaggggac cgatacgcag tttcatctct ttgcttaggg agagtagggg ggtagattac   3660
gaccttagtt ttggtatccg taatatcatc attttttcgt ctagggagta tatcgacttc   3720
agaaaacagg tattagatac tgccttttct tacgagagtg atggcaagat agttctcttc   3780
aagtcaatca aacaggaaag tatttctttt ctgtctgaag atttgaaaaa ggactgaatg   3840
tttcacaagg ttaaaactgg ggaaaaagat ggatatggtt cagatgaaat gctgagcgca   3900
ccccgtatct atttggaaat gatgtcgcgg aaaacggaag tcccctactc cagtattctt   3960
taaattctaa gcagaaaact tcttcgtcgg tctttttttt gttgtttggt ttgcatggag   4020
taaaactgtg caacgccgtc tgaagtcgac gtgccgcgtg tgttttttta tggcgtttta   4080
aaaagccgag actgcatccg ggcagcagcg catcggctcg cacgaggtct gcgcttgaat   4140
tgtgttgtag aaacacaacg tttttgaaaa aataagctat tgttttatat caaaatataa   4200
tcatttttaa aataaaggtt gcggcattta tcagatattt gttctgaaaa atggtttttc   4260
gggcgggaac atttataatt gaagacgtat cgggtgtttg cccgatgttt ttaggttttt   4320
atcaaattta caaaaggaac tcgagatgaa gaaaactgtc ttcacctgcg ctatgattgc   4380
cctgaccggc accgccgccg ctgcgcaaga attacaaacc gcgaatgaat tcaccgtcca   4440
caccgacctg agcagcatta gcagcacccg tgccttcttg aaagaaaaac acaaagcagc   4500
caaacacatc tcggtacgcg ctgatatccc cttcgatgcg aaccaaggca tccgcctcga   4560
agcaggcttc ggtcgctcaa agaaaaacat tatcaactta gaaactgacg aaaataaact   4620
gggcaaaact aaaaatgtga aactgcccac cggcgttcct gaaaaccgca tcgacttgta   4680
cacaggttac acatacaccc aaaccctttc cgatagcctg aattttaggg ttggcgcggg   4740
cttgggtttc gaatcctcca aagacagcat taaaaccacc aaacacaccc tccactcctc   4800
tcgtcaaagc tggctggcga aggtgcacgc ggatttgttg agccaacttg gtaacggctg   4860
gtacattaac ccctggtccg aagtgaaatt cgacttgaac agccgttata aattgaacac   4920
cggtgtcacc aatttgaaga aagatatcaa ccagaaaact aatggctggg gctttggcct   4980
cggagctaac attggcaaga aattgggtga aagcgccagc attgaagcgg gtcctttttta   5040
caaacaacgg acttacaaag aatccggcga attctccgtg accacaaaat ccggtgacgt   5100
aagtctgaca atcccgaaaa cctctattcg cgaatatggt ctgcgtgtgg gtatcaaatt   5160
```

```
ctgagcggcc gcatattcgg caactgtcgg aatatctgct aaaattccgc attttccgca   5220
ccgggtttcc gcaccgggac actcggggcg tatgttcaat ttgtcggaat ggagtttaaa   5280
ggaatacaca tatgttatta gcgaattatt atcaagatcc tgaaatcacg agaatcaatg   5340
cgttgccgca ccatagctat tttatccctt ttgataaaaa agataaggta gatcagtttt   5400
ctagggaaaa ttcttcgttt tttacatcat taaatggaat gtggcaattc gcatattatc   5460
cgagtatgca ggatttgcct gaaagtccgg acgaaatcgc ttttacgaaa caaatcaatg   5520
tgccttcaaa ttggcagaat cacgggtttg atgcccatca atatactaat attaattatc   5580
ctttcccttt cgatccgcct tttgttcctt tagagaaccc ttgcggggta tatcaaaagc   5640
aggtcaatct gaaaaagaat ataaataagc ggtatttatt agtccttgaa ggggttgatt   5700
cctgttctta tatatatgta aaccatcaat ttgtaggata tggttctatc agccacagta   5760
ccaatgaatt tgatattacc gattatcttc acgatggtga aaacaccctt accgtatttg   5820
tcctgaaatg gtgtgccgga agctacttgg aagatcagga taaatttaga atgtcgggaa   5880
ttttccgaga tgtatattta ttggaaaggg agcatcacta tttgcaagac ttgaatattc   5940
gaaccgtgct ttctgaagat ttatcattgg ggcagatttg tctggattta aattttgcgg   6000
gggatgcggg ggatgtcgga gtgtcattgt ttgatacgga cgggcaaatt gttcaagcag   6060
gcagcgcaat cacgacagat aaacaacgga tgcaaatccg ccttgataat attcctttaa   6120
ccaaatcccg actctggaat gcggaaaacc ctgcccttta taccttggta ttaaacacaa   6180
aagaagaaat cattacccag aagatcggat tccgcaaggt agaggtcaaa aacggggtat   6240
tgctgcttaa taatcagcct attaaattca aaggggtaaa ccggcacgat agcgatccca   6300
aaacgggata tgccatttct gtcgctcaag cggtgactga cttgtcgtta atgaagaaac   6360
ataatattaa cgcgattcgt accgcgcatt atccaaattc accgtggttt tgcgagcttt   6420
gcgataagta tggtttctat gtaatcagtg aaagcgacat tgaaagtcat ggggcggcat   6480
tccaagcaat ttcgcatccc gaaccgagta tctttctgaa tgtggaaaat ccgaatgaag   6540
agccgcgtat ccgccaacaa actattgaca acttctgtta ttttgcccga gaaccattgt   6600
atcgggcggc tttattggag cggactaaag caaatataga acgtgataag aaccgcagtt   6660
ctattttaat ttggtcttta ggcaatgaat cagggtatgg tgagaatttc gaatattgtg   6720
caaaatgggt aaaagagcgg gatccggatc gattggttca ttacgaaagc agcatttatc   6780
agcattctgc gtatcagaat aacaccgggc atttggattt atacagtgaa atgtattccg   6840
acacagaagc aatcgatgcc tattttgccg atcattcaca aacgaaaaaa ccattcttat   6900
tatgcgaata ttcccatgca atgggaaatt caaatggaga tatggaagac tatttccaaa   6960
catttaacaa atattcgggc tgttgcggtg ggtttatttg ggagtggtgc gatcatgccc   7020
aatatattac cccgacaaaa ttaggatatg gcggtgactt cggcgaaaaa atccatgatg   7080
ggaatttctg tgtggatggc ttggtttcgc ccgaacgcgt cccgcacagc aacctgttgg   7140
aagtaaaaaa tgtcaaccgg cccgtacggg caaacttgcg cggtgaacaa attgagttat   7200
ataactattt tgatttcact aatttaaaag atattctttg cgtcaaatat gaatgggtaa   7260
aaaatggtca gataaccggg acgggaacat tggcggttga ttgcgaaccc catcattctc   7320
aaatcttacc gattcagctt cccaaagaac gggaaggatt gctatggttg aacctatatt   7380
actgcgcttc ccggcaaact gatttattgc cggcaggaca tcatttcggt ttcgatcaaa   7440
ttattttgag taaggaatac actcctgcca taggatcgga taaagatgat tgcccgccgt   7500
```

tggaaataac cgaaacagtg agacaaatcg ttgttcggaa caatcgatat tattttgaat 7560
ttaacaagct cacggggata attgacgaaa ttaaagtcaa tggcaaggct ttcatccata 7620
aaccattggc ttggaatatt tggcgcgcgc cgacggataa tgaccgcctg attcgttccc 7680
aatggcaaaa tgccggttat gatcaaatgt attccaaggt ttacgatatt tgcgcgcatc 7740
ggcaaggaaa cggtgttgtc gtgtctgtga aaagtgcatt ggttgcggat gcaaaatcaa 7800
aaatcatgac attggaaaca cagtatctgc tgtctgaaaa tggtaaattg gatattcaaa 7860
caaatgctgt tttccacgag catttgccat tcctgccccg tttcggtttg cgcttttttct 7920 tagacgaaca gaaaacacct tttacctact taggttatgg ggcgggtgaa agctatattg 7980
ataaacatca ggcgaccaaa cttggtattt attcgacaac ggcaggggaa aatcatgttg 8040
gctatctcaa gcctcaagag aacggcagcc attatggatg cttttatgtt caaaacgata 8100
tgatccgggt ggagtcgggg cagccgttta gtttcaacct gtccccttat acgcaagaag 8160
aactgacgca gaaaaaacat tcttatgaat tggtttgttc cgggtatgat gtattgtgta 8220
tcgactataa gatgagcggt atcggttcga attcttgcgg gcctaatttg aagccgcaat 8280
atcgtttgat tgaaaataac atcaatttcg atataagtat ccggttataa gctttctgca 8340
aagattggta tcaacaaaaa gcctgtcgtc agacaggctt tttttctgtt ttctgttttt 8400
agatgccgtc tgaatgctga agtagaaaac cagcaagaag gtaaaaagaa agaagcagtt 8460
ttttggattt tagatgttac cgcaattggt ttcctttcct aaaatttgtt taaattattt 8520
gcaatattaa tataaactgg atattaatga tgaggattca aaaaggcata ctgaatataa 8580
tttgtacaaa atatttgcag tatttaaaaa tgttggttcg tatatgaaaa gttaaaaatg 8640
ccaaaatgta cagttgctaa actgtaaaac tgctaaagca acaaaacata aaaaggaatg 8700
cagggatgcg atcactacat ctttttattc cgtaagcatt tatgacttta cggtcaactg 8760
ctactctatg tttccagctt ttcagctccc tattttcgaa tattggacga ggcattttca 8820
tcagtgtcgt aatgccgacc gaaaccctca caaaccatat tggttcttgt ggcagcaaca 8880
cctatccgtt tgttcaagcg gccacaagag taacatgatt ggctggtggc attggcttta 8940
atctcttcga tatgaactcc atttttagct gcaccttctt tcagcgtatg caacagtggg 9000
gatggggcaa ctatcttctg gtggagtttg ttgacttcaa tctgtatgca ctgtaggttg 9060
agcagattca gtttttgat acagattatc cggctttgtt cggcaattct gttggcgaac 9120
gtatagtaga gctgtcgtct tgccgctttc aatttgcggt aggtatttta ccattccatg 9180
cgtagccgct cggtacgttt gagccaaatg ttatcttcgc catttgtacc aatttgtttt 9240
tacattaggc tgtgttttag taatctattg atttcaatta tttgcaaggg aaaagacaat 9300
tattttccgg ttaggaataa acctatccta ttgaatatat tgaagccaag tacgcttatc 9360
aacactatat taaaacacag cctttttttaa tatagtagac acaatctttc cttatttatg 9420
aaggtgatag cttctttcag tctagagacc tgcaggcatg caagcttggc gtaatcatgg 9480
tcatagctgt ttcctgtgtg aaattg 9506

<210> SEQ ID NO 30
<211> LENGTH: 7024
<212> TYPE: DNA
<213> ORGANISM: Artificial Sequence
<220> FEATURE:
<223> OTHER INFORMATION: Vector

<400> SEQUENCE: 30
tctagagcaa aaggccagca aaaggccagg aaccgtaaaa aggccgcgtt gctggcgttt 60

-continued

```
ttccataggc tccgcccccc tgacgagcat cacaaaaatc gacgctcaag tcagaggtgg    120
cgaaacccga caggactata aagataccag gcgtttcccc ctggaagctc cctcgtgcgc    180
tctcctgttc cgaccctgcc gcttaccgga tacctgtccg cctttctccc ttcgggaagc    240
gtggcgcttt ctcatagctc acgctgtagg tatctcagtt cggtgtaggt cgttcgctcc    300
aagctgggct gtgtgcacga accccccgtt cagcccgacc gctgcgcctt atccggtaac    360
tatcgtcttg agtccaaccc ggtaagacac gacttatcgc cactggcagc agccactggt    420
aacaggatta gcagagcgag gtatgtaggc ggtgctacag agttcttgaa gtggtggcct    480
aactacggct acactagaag aacagtattt ggtatctgcg ctctgctgaa gccagttacc    540
ttcggaaaaa gagttggtag ctcttgatcc ggcaaacaaa ccaccgctgg tagcggtggt    600
tttttgttt gcaagcagca gattacgcgc agaaaaaaag gatctcaaga agatcctttg    660
atcttttcta cggggtctga cgctcagtgg aacgaaaact cacgttaagg gattttggtc    720
atgagattat caaaaaggat cttcacctag atccttttaa attaaaaatg aagttttaaa    780
tcaatctaaa gtatatatga gtaaacttgg tctgacagtt accaatgctt aatcagtgag    840
gcacctatct cagcgatctg tctatttcgt tcatccatag ttgcctgact ccccgtcgtg    900
tagataacta cgatacggga gggcttacca tctggcccca gtgctgcaat gataccgcga    960
gacccacgct caccggctcc agatttatca gcaataaacc agccagccgg aagggccgag   1020
cgcagaagtg gtcctgcaac tttatccgcc tccatccagt ctattaattg ttgccgggaa   1080
gctagagtaa gtagttcgcc agttaatagt ttgcgcaacg ttgttgccat tgctacaggc   1140
atcgtggtgt cacgctcgtc gtttggtatg gcttcattca gctccggttc ccaacgatca   1200
aggcgagtta catgatcccc catgttgtgc aaaaaagcgg ttagctcctt cggtcctccg   1260
atcgttgtca gaagtaagtt ggccgcagtg ttatcactca tggttatggc agcactgcat   1320
aattctctta ctgtcatgcc atccgtaaga tgcttttctg tgactggtga gtactcaacc   1380
aagtcattct gagaatagtg tatgcggcga ccgagttgct cttgcccggc gtcaatacgg   1440
gataataccg cgccacatag cagaacttta aaagtgctca tcattggaaa acgttcttcg   1500
gggcgaaaac tctcaaggat cttaccgctg ttgagatcca gttcgatgta acccactcgt   1560
gcacccaact gatcttcagc atcttttact ttcaccagcg tttctgggtg agcaaaaaca   1620
ggaaggcaaa atgccgcaaa aaagggaata agggcgacac ggaaatgttg aatactcata   1680
ctcttccttt ttcaatatta ttgaagcatt tatcagggtt attgtctcat gagcggatac   1740
atatttgaat gtatttagaa aaataaacaa ataggggttc cgcgcacatt tccccgaaaa   1800
gtgccacctt ctagaggaga tgatgatgtt taaacgcagc gtaatcgcaa tggcttgtat   1860
ttttgccctt tcagcctgcg gggcggcgg tggcggatcg cccgatgtca agtcggcgga   1920
cacgctgtca aaaccggctg ttcctgttgt tgctgaagat gccggggaag aggtgctgcc   1980
gaaagaaaag aaagatgagg aggcagtggg cggtgcgccg caagccgata cgcaggacgc   2040
aaccgccgga gaaggcagtc aagatatggc ggcagtttcg gcggaaaata caggcaatgg   2100
cggtgcggca acaacggaca aacccaaaaa tgaagacgca ggggcgcaaa atgatatgcc   2160
gcaaaatgcc gccgatacag atagtttgac accgaattac accacggcac cgaatatgcc   2220
ggccgtagat atgggaaacc aagcaccgga ttccggggaa tcggcacaac cggcaaacca   2280
accggatatg gcaaatgcgg cggacggaat acagggggac gatccgtcgg taggggaaaa   2340
tgccggcaat acggcagatc aagctgaaaa tcaagctgaa aacaatcaag tcggcggctc   2400
```

-continued

```
tcaaaatcct gcctcttcaa ccaatcctaa cgccacgaat ggcggcggcg attttggaag   2460
gacgaacgtg ggcaattctg ttgtgattga cgggccgtcg caaaatataa cgttgaccca   2520
ctgtaaaggc gattcttgta atgatgataa tttattgtat gaagaagcac cgtcaaaatc   2580
agaatttgaa tcgttaaatg actctgggcg aattgataaa tataaaaaag atggacagga   2640
taaatttact aatttggttg cgacaaaagt tgaaaagaaa ggattgaata aatatgtcat   2700
cttttatacg gacacccccg acgtcgccgt ctgaagtcga ctattcggca actgtcggaa   2760
tatctgctaa aattccgcat tttccgcacc gggtttccgc accgggacac tcggggcgta   2820
tgttcaattt gtcggaatgg agtttaaagg aatctcgaga tctattatat aagcggccgc   2880
aagtttgttt tttcgggcgg gaacatttat agtttcaaac aaggaatcga cgaaaacgtc   2940
gtcggtaaat gcaaagctaa gcggctcgga aagcccggtt cgcttaaatt tcttaaccaa   3000
aaaaggaata cacatatgtt attagcgaat tattatcaag atcctgaaat cacgagaatc   3060
aatgcgttgc cgcaccatag ctattttatc ccttttgata aaaaagataa ggtagatcag   3120
ttttctaggg aaaattcttc gtttttttaca tcattaaatg gaatgtggca attcgcatat   3180
tatccgagta tgcaggattt gcctgaaagt ccggacgaaa tcgcttttac gaaacaaatc   3240
aatgtgcctt caaattggca gaatcacggg tttgatgccc atcaatatac taatattaat   3300
tatcctttcc ctttcgatcc gccttttgtt cctttagaga acccttgcgg ggtatatcaa   3360
aagcaggtca atctgaaaaa gaatataaat aagcggtatt tattagtcct tgaaggggtt   3420
gattcctgtt cttatatata tgtaaaccat caatttgtag gatatggttc tatcagccac   3480
agtaccaatg aatttgatat taccgattat cttcacgatg gtgaaaacac ccttaccgta   3540
tttgtcctga aatggtgtgc cggaagctac ttggaagatc aggataaatt tagaatgtcg   3600
ggaattttcc gagatgtata tttattggaa agggagcatc actatttgca agacttgaat   3660
attcgaaccg tgctttctga agatttatca ttggggcaga tttgtctgga tttaaatttt   3720
gcgggggatg cgggggatgt cggagtgtca ttgtttgata cggacgggca aattgttcaa   3780
gcaggcagcg caatcacgac agataaacaa cggatgcaaa tccgccttga taatattcct   3840
ttaaccaaat cccgactctg gaatgcggaa aaccctgccc tttatacctt ggtattaaac   3900
acaaaagaag aaatcattac ccagaagatc ggattccgca aggtagaggt caaaaacggg   3960
gtattgctgc ttaataatca gcctattaaa ttcaaagggg taaaccggca cgatagcgat   4020
cccaaaacgg gatatgccat ttctgtcgct caagcggtga ctgacttgtc gttaatgaag   4080
aaacataata ttaacgcgat tcgtaccgcg cattatccaa attcaccgtg gttttgcgag   4140
ctttgcgata agtatggttt ctatgtaatc agtgaaagcg acattgaaag tcatggggcg   4200
gcattccaag caatttcgca tcccgaaccg agtatctttc tgaatgtgga aaatccgaat   4260
gaagagccgc gtatccgcca acaaactatt gacaacttct gttattttgc ccgagaacca   4320
ttgtatcggg cggctttatt ggagcggact aaagcaaata tagaacgtga taagaaccgc   4380
agttctattt taatttggtc tttaggcaat gaatcagggt atggtgagaa tttcgaatat   4440
tgtgcaaaat gggtaaaaga gcgggatccg gatcgattgg ttcattacga aagcagcatt   4500
tatcagcatt ctgcgtatca gaataacacc gggcatttgg atttatacag tgaaatgtat   4560
tccgacacag aagcaatcga tgcctatttt gccgatcatt cacaaacgaa aaaaccattc   4620
ttattatgcg aatattccca tgcaatggga aattcaaatg gagatatgga agactatttc   4680
caaacattta acaaatattc gggctgttgc ggtgggttta tttgggagtg gtgcgatcat   4740
gcccaatata ttaccccgac aaaattagga tatggcggtg acttcggcga aaaaaatccat   4800
```

gatgggaatt tctgtgtgga tggcttggtt tcgcccgaac gcgtcccgca cagcaacctg 4860
ttggaagtaa aaaatgtcaa ccggcccgta cgggcaaact tgcgcggtga acaaattgag 4920
ttatataact attttgattt cactaattta aaagatattc tttgcgtcaa atatgaatgg 4980
gtaaaaaatg gtcagataac cgggacggga acattggcgg ttgattgcga accccatcat 5040
tctcaaatct taccgattca gcttcccaaa gaacgggaag gattgctatg gttgaaccta 5100
tattactgcg cttcccggca aactgattta ttgccggcag gacatcattt cggtttcgat 5160
caaattattt tgagtaagga atacactcct gccataggat cggataaaga tgattgcccg 5220
ccgttggaaa taaccgaaac agtgagacaa atcgttgttc ggaacaatcg atattatttt 5280
gaatttaaca agctcacggg gataattgac gaaattaaag tcaatggcaa ggctttcatc 5340
cataaaccat tggcttggaa tatttggcgc gcgccgacgg ataatgaccg cctgattcgt 5400
tcccaatggc aaaatgccgg ttatgatcaa atgtattcca aggtttacga tatttgcgcg 5460
catcggcaag gaaacggtgt tgtcgtgtct gtgaaaagtg cattggttgc ggatgcaaaa 5520
tcaaaaatca tgacattgga aacacagtat ctgctgtctg aaaatggtaa attggatatt 5580
caaacaaatg ctgttttcca cgagcatttg ccattcctgc cccgtttcgg tttgcgcttt 5640
ttcttagacg aacagaaaac accttttacc tacttaggtt atggggcggg tgaaagctat 5700
attgataaac atcaggcgac caaacttggt atttattcga caacggcagg ggaaaatcat 5760
gttggctatc tcaagcctca agagaacggc agccattatg gatgctttta tgttcaaaac 5820
gatatgatcc gggtggagtc ggggcagccg tttagtttca acctgtcccc ttatacgcaa 5880
gaagaactga cgcagaaaaa acattcttat gaattggttt gttccgggta tgatgtattg 5940
tgtatcgact ataagatgag cggtatcggt tcgaattctt gcgggcctaa tttgaagccg 6000
caatatcgtt tgattgaaaa taacatcaat ttcgatataa gtatccggtt ataagctttc 6060
tgcaaagatt ggtatcaaca aaaagcctgt cgtcagacag gctttttttc tgttttctgt 6120
ttttagatgc cgtctgaaga cgtccccact cgttctgcac ggtcgagacg gttgaggcgg 6180
tcgcttccgg ctgagatgcc gctgatcccc gtcaatcagg cggatacgct gattgtcgat 6240
ggggaagcgg tcagcctgac ggggcattcc ggcaatatct tcgcgcccga agggaattac 6300
cggtatctga cttacagggc ggaaaaattg tccggaggat cgtatgccct ccgtgtgcaa 6360
ggcgaaccgg caaaaggcga aatgcttgcg ggcacggccg tgtacaacgg cgaagtgctg 6420
catttccata cggaaaacgg ccgtccgtac ccgtccggag gcaggtttgc cgcaaaagtc 6480
gatttcggca gcaaatctgt ggacggcatt atcgacagcg gcgatgattt gcatatgggt 6540
acgcaaaaat tcaaagccgc catcgatgga aacggcttta aggggacttg gacggaaaat 6600
ggcggcgggg atgtttccgg aaggttttac ggcccggccg gcgaggaagt ggcggggaaa 6660
tacagctatc gcccgacaga tgcggaaaag ggcggattcg gcgtgtttgc cggcaaaaaa 6720
gagcaggatt gatattgatg ccgcgcgtat cggcggcatc ccgcccgcct tttcagacc 6780 gttgaaatat gaaagtgaag cacaggccgt ccgaatgttc agacggcctg ttttttttaaa 6840 cggctgcgtt ttaacaaaaa gaatctcatc ggcatttcct taacgcttga atacccgcac 6900
tcggggcggt acaacggggt gtgccttatg tgccgaaagg gcttgcggaa acggtatgcc 6960
gtctgaagcg ggggcgttca gacggcattg tgatgtttgg gttgcgaatc cggttcaaat 7020
ccgc 7024

<210> SEQ ID NO 31

<211> LENGTH: 3613
<212> TYPE: DNA
<213> ORGANISM: Artificial Sequence
<220> FEATURE:
<223> OTHER INFORMATION: Vector

<400> SEQUENCE: 31

```
tctagagcaa aaggccagca aaaggccagg aaccgtaaaa aggccgcgtt gctggcgttt     60
ttccataggc tccgcccccc tgacgagcat cacaaaaatc gacgctcaag tcagaggtgg    120
cgaaacccga caggactata aagataccag gcgtttcccc ctggaagctc cctcgtgcgc    180
tctcctgttc cgaccctgcc gcttaccgga tacctgtccg cctttctccc ttcgggaagc    240
gtggcgcttt ctcatagctc acgctgtagg tatctcagtt cggtgtaggt cgttcgctcc    300
aagctgggct gtgtgcacga accccccgtt cagcccgacc gctgcgcctt atccggtaac    360
tatcgtcttg agtccaaccc ggtaagacac gacttatcgc cactggcagc agccactggt    420
aacaggatta gcagagcgag gtatgtaggc ggtgctacag agttcttgaa gtggtggcct    480
aactacggct acactagaag aacagtattt ggtatctgcg ctctgctgaa gccagttacc    540
ttcggaaaaa gagttggtag ctcttgatcc ggcaaacaaa ccaccgctgg tagcggtggt    600
tttttgttt gcaagcagca gattacgcgc agaaaaaaag gatctcaaga agatcctttg    660
atcttttcta cggggtctga cgctcagtgg aacgaaaact cacgttaagg gattttggtc    720
atgagattat caaaaaggat cttcacctag atccttttaa attaaaaatg aagttttaaa    780
tcaatctaaa gtatatatga gtaaacttgg tctgacagtt accaatgctt aatcagtgag    840
gcacctatct cagcgatctg tctatttcgt tcatccatag ttgcctgact ccccgtcgtg    900
tagataacta cgatacggga gggcttacca tctggcccca gtgctgcaat gataccgcga    960
gacccacgct caccggctcc agatttatca gcaataaacc agccagccgg aagggccgag   1020
cgcagaagtg gtcctgcaac tttatccgcc tccatccagt ctattaattg ttgccgggaa   1080
gctagagtaa gtagttcgcc agttaatagt ttgcgcaacg ttgttgccat tgctacaggc   1140
atcgtggtgt cacgctcgtc gtttggtatg gcttcattca gctccggttc ccaacgatca   1200
aggcgagtta catgatcccc catgttgtgc aaaaaagcgg ttagctcctt cggtcctccg   1260
atcgttgtca gaagtaagtt ggccgcagtg ttatcactca tggttatggc agcactgcat   1320
aattctctta ctgtcatgcc atccgtaaga tgcttttctg tgactggtga gtactcaacc   1380
aagtcattct gagaatagtg tatgcggcga ccgagttgct cttgcccggc gtcaatacgg   1440
gataataccg cgccacatag cagaacttta aaagtgctca tcattggaaa acgttcttcg   1500
gggcgaaaac tctcaaggat cttaccgctg ttgagatcca gttcgatgta acccactcgt   1560
gcacccaact gatcttcagc atcttttact ttcaccagcg tttctgggtg agcaaaaaca   1620
ggaaggcaaa atgccgcaaa aaagggaata agggcgacac ggaaatgttg aatactcata   1680
ctcttccttt ttcaatatta ttgaagcatt tatcagggtt attgtctcat gagcggatac   1740
atatttgaat gtatttagaa aaataaacaa ataggggttc cgcgcacatt tccccgaaaa   1800
gtgccacctt ctagaggaga tgatgatgtt taaacgcagc gtaatcgcaa tggcttgtat   1860
ttttgccctt tcagcctgcg ggggcggcgg tggcggatcg cccgatgtca agtcggcgga   1920
cacgctgtca aaaccggctg ttcctgttgt tgctgaagat gccggggaag aggtgctgcc   1980
gaaagaaaag aaagatgagg aggcagtggg cggtgcgccg caagccgata cgcaggacgc   2040
aaccgccgga gaaggcagtc aagatatggc ggcagtttcg gcggaaaata caggcaatgg   2100
cggtgcggca acaacggaca aacccaaaaa tgaagacgca ggggcgcaaa atgatatgcc   2160
```

gcaaaatgcc gccgatacag atagtttgac accgaattac accacggcac cgaatatgcc 2220
ggccgtagat atgggaaacc aagcaccgga ttccggggaa tcggcacaac cggcaaacca 2280
accggatatg gcaaatgcgg cggacggaat acagggggac gatccgtcgg taggggaaaa 2340
tgccggcaat acggcagatc aagctgaaaa tcaagctgaa aacaatcaag tcggcggctc 2400
tcaaaatcct gcctcttcaa ccaatcctaa cgccacgaat ggcggcggcg attttggaag 2460
gacgaacgtg ggcaattctg ttgtgattga cgggccgtcg caaaatataa cgttgaccca 2520
ctgtaaaggc gattcttgta atgatgataa tttattgtat gaagaagcac cgtcaaaatc 2580
agaatttgaa tcgttaaatg actctgggcg aattgataaa tataaaaaag atggacagga 2640
taaatttact aatttggttg cgacaaaagt tgaaaagaaa ggattgaata aatatgtcat 2700
cttttatacg gacacatcta tgccgtctga aattgcactc gttctgcacg gtcgagacgg 2760
ttgaggcggt cgcttccggc tgagatgccg ctgatccccg tcaatcaggc ggatacgctg 2820
attgtcgatg gggaagcggt cagcctgacg gggcattccg gcaatatctt cgcgcccgaa 2880
gggaattacc ggtatctgac ttacagggcg gaaaaattgt ccggaggatc gtatgccctc 2940
cgtgtgcaag gcgaaccggc aaaaggcgaa atgcttgcgg gcacggccgt gtacaacggc 3000
gaagtgctgc atttccatac ggaaaacggc cgtccgtacc cgtccggagg caggtttgcc 3060
gcaaaagtcg atttcggcag caaatctgtg gacggcatta tcgacagcgg cgatgatttg 3120
catatgggta cgcaaaaatt caaagccgcc atcgatggaa acggctttaa ggggacttgg 3180
acggaaaatg gcggcgggga tgtttccgga aggttttacg gcccggccgg cgaggaagtg 3240
gcggggaaat acagctatcg cccgacagat gcggaaaagg gcggattcgg cgtgtttgcc 3300
ggcaaaaaag agcaggattg atattgatgc cgcgcgtatc ggcggcatcc cgcccgcctt 3360
tttcagaccg ttgaaatatg aaagtgaagc acaggccgtc cgaatgttca gacggcctgt 3420
ttttttaaac ggctgcgttt taacaaaaag aatctcatcg gcatttcctt aacgcttgaa 3480
tacccgcact cggggcggta caacggggtg tgccttatgt gccgaaaggg cttgcggaaa 3540
cggtatgccg tctgaagcgg gggcgttcag acggcattgt gatgtttggg ttgcgaatcc 3600
ggttcaaatc cgc 3613

<210> SEQ ID NO 32
<211> LENGTH: 6223
<212> TYPE: DNA
<213> ORGANISM: Artificial Sequence
<220> FEATURE:
<223> OTHER INFORMATION: Vector

<400> SEQUENCE: 32
cataagaacc tcagatcctt ccgtatttag ccagtatgtt ctctagtgtg gttcgttgtt 60
tttgcgtgag ccatgagaac gaaccattga gatcatactt actttgcatg tcactcaaaa 120
attttgcctc aaaactggtg agctgaattt ttgcagttaa agcatcgtgt agtgtttttc 180
ttagtccgtt atgtaggtag gaatctgatg taatggttgt tggtattttg tcaccattca 240
tttttatctg gttgttctca agttcggtta cgagatccat ttgtctatct agttcaactt 300
ggaaaatcaa cgtatcagtc gggcggcctc gcttatcaac caccaatttc atattgctgt 360
aagtgtttaa atctttactt attggtttca aaacccattg gttaagcctt ttaaactcat 420
ggtagttatt ttcaagcatt aacatgaact taaattcatc aaggctaatc tctatatttg 480
ccttgtgagt tttcttttgt gttagttctt ttaataacca ctcataaatc ctcatagagt 540

-continued

```
atttgttttc aaaagactta acatgttcca gattatattt tatgaatttt tttaactgga    600
aaagataagg caatatctct tcactaaaaa ctaattctaa tttttcgctt gagaacttgg    660
catagtttgt ccactggaaa atctcaaagc ctttaaccaa aggattcctg atttccacag    720
ttctcgtcat cagctctctg gttgctttag ctaatacacc ataagcattt tccctactga    780
tgttcatcat ctgagcgtat tggttataag tgaacgatac cgtccgttct ttccttgtag    840
ggttttcaat cgtggggttg agtagtgcca cacagcataa aattagcttg gtttcatgct    900
ccgttaagtc atagcgacta atcgctagtt catttgcttt gaaaacaact aattcagaca    960
tacatctcaa ttggtctagg tgattttaat cactatacca attgagatgg gctagtcaat   1020
gataattact agtccttttc ctttgagttg tgggtatctg taaattctgc tagacctttg   1080
ctggaaaact tgtaaattct gctagaccct ctgtaaattc cgctagacct ttgtgtgttt   1140
tttttgttta tattcaagtg gttataattt atagaataaa gaaagaataa aaaaagataa   1200
aaagaataga tcccagccct gtgtataact cactacttta gtcagttccg cagtattaca   1260
aaaggatgtc gcaaacgctg tttgctcctc tacaaaacag accttaaaac cctaaaggct   1320
taagtagcac cctcgcaagc tcgggcaaat cgaagatcct ttgatctttt ctacggggtc   1380
tgacgctcag tggaacgaaa actcacgtta agggattttg gtcatgagat tatcaaaaag   1440
gatcttcacc tagatccttt taaattaaaa atgaagtttt aaatcaatct aaagtatata   1500
tgagtaaact tggtctgaca gttaccaatg cttaatcagt gaggcaccta tctcagcgat   1560
ctgtctattt cgttcatcca tagttgcctg actccccgtc gtgtagataa ctacgatacg   1620
ggagggctta ccatctggcc ccagtgctgc aatgataccg cgagacccac gctcaccggc   1680
tccagattta tcagcaataa accagccagc cggaagggcc gagcgcagaa gtggtcctgc   1740
aactttatcc gcctccatcc agtctattaa ttgttgccgg gaagctagag taagtagttc   1800
gccagttaat agtttgcgca acgttgttgc cattgctaca ggcatcgtgg tgtcacgctc   1860
gtcgtttggt atggcttcat tcagctccgg ttcccaacga tcaaggcgag ttacatgatc   1920
ccccatgttg tgcaaaaaag cggttagctc cttcggtcct ccgatcgttg tcagaagtaa   1980
gttggccgca gtgttatcac tcatggttat ggcagcactg cataattctc ttactgtcat   2040
gccatccgta agatgctttt ctgtgactgg tgagtactca accaagtcat tctgagaata   2100
gtgtatgcgg cgaccgagtt gctcttgccc ggcgtcaata cgggataata ccgcgccaca   2160
tagcagaact ttaaaagtgc tcatcattgg aaaacgttct tcggggcgaa aactctcaag   2220
gatcttaccg ctgttgagat ccagttcgat gtaacccact cgtgcaccca actgatcttc   2280
agcatctttt actttcacca gcgtttctgg gtgagcaaaa acaggaaggc aaaatgccgc   2340
aaaaaaggga ataagggcga cacggaaatg ttgaatactc atactcttcc tttttcaata   2400
ttattgaagc atttatcagg gttattgtct catgagcgga tacatatttg aatgtattta   2460
gaaaaataaa caaatagggg ttccgcgcac atttccccga aaagtgccac ctgacgtcta   2520
agaaaccatt attatcatga cattaaccta taaaaatagg cgtatcacga ggccctttcg   2580
tctcgcgcgt ttcggtgatg acggtgaaaa cctctgacac atgcagctcc cggagacggt   2640
cacagcttgt ctgtaagcgg atgccgggag cagacaagcc cgtcagggcg cgtcagcggg   2700
tgttggcggg tgtcggggct ggcttaacta tgcggcatca gagcagattg tactgagagt   2760
gcaccatatg cggtgtgaaa taccgcacag atgcgtaagg agaaaatacc gcatcaggcg   2820
ccattcgcca ttcaggctgc gcaactgttg ggaagggcga tcggtgcggg cctcttcgct   2880
attacgccag ctggcgaaag ggggatgtgc tgcaaggcga ttaagttggg taacgccagg   2940
```

gttttcccag tcacgacgtt gtaaaacgac ggccagtgaa ttcgagctcg gtacccgggg 3000
atcctctaga gcgaattatt atcaagatcc tgaaatcacg agaatcaatg cgttgccgca 3060
ccatagctat tttatccctt ttgataaaaa agataaggta gatcagtttt ctagggaaaa 3120
ttcttcgttt tttacatcat taaatggaat gtggcaattc gcatattatc cgagtatgca 3180
ggatttgcct gaaagtccgg acgaaatcgc ttttacgaaa caaatcaatg tgccttcaaa 3240
ttggcagaat cacgggtttg atgcccatca atatactaat attaattatc ctttcccttt 3300
cgatccgcct tttgttcctt tagagaaccc ttgcggggta tatcaaaagc aggtcaatct 3360
gaaaaagaat ataaataagc ggtatttatt agtccttgaa ggggttgatt cctgttctta 3420
tatatatgta aaccatcaat ttgtaggata tggttctatc agccacagta ccaatgaatt 3480
tgatattacc gattatcttc acgatggtga aaacaccctt accgtatttg tcctgaaatg 3540
gtgtgccgga agctacttgg aagatcagga taaatttaga atgtcgggaa ttttccgaga 3600
tgtatattta ttggaaaggg agcatcacta tttgcaagac ttgaatattc gaaccgtgct 3660
ttctgaagat ttatcattgg ggcagatttg tctggattta aattttgcgg gggatgcggg 3720
ggatgtcgga gtgtcattgt ttgatacgga cgggcaaatt gttcaagcag gcagcgcaat 3780
cacgacagat aaacaacgga tgcaaatccg ccttgataat attcctttaa ccaaatcccg 3840
actctggaat gcggaaaacc ctgcccttta taccttggta ttaaacacaa aagaagaaat 3900
cattacccag aagatcggat tccgcaaggt agaggtcaaa aacggggtat tgctgcttaa 3960
taatcagcct attaaattca aaggggtaaa ccggcacgat agcgatcccg ccgtctgaag 4020
tcgacgtgcc gcgtgtgttt ttttatggcg ttttaaaaag ccgagactgc atccgggcag 4080
cagcgcatcg gctcgcacga ggtctgcgct tgaattgtgt tgtagaaaca caacgttttt 4140
gaaaaaataa gctattgttt tatatcaaaa tataatcatt tttaaaataa aggttgcggc 4200
atttatcaga tatttgttct gaaaaatggt ttttcgggcg ggaacattta taattgaaga 4260
cgtatcgggt gtttgcccga tgtttttagg tttttatcaa atttacaaaa ggaactcgag 4320
atgaagaaaa ctgtcttcac ctgcgctatg attgccctga ccggcaccgc cgccgctgcg 4380
caagaattac aaaccgcgaa tgaattcacc gtccacaccg acctgagcag cattagcagc 4440
acccgtgcct tcttgaaaga aaaacacaaa gcagccaaac acatctcggt acgcgctgat 4500
atccccttcg atgcgaacca aggcatccgc ctcgaagcag gcttcggtcg ctcaaagaaa 4560
aacattatca acttagaaac tgacgaaaat aaactgggca aaactaaaaa tgtgaaactg 4620
cccaccggcg ttcctgaaaa ccgcatcgac ttgtacacag gttacacata cacccaaacc 4680
ctttccgata gcctgaattt tagggttggc gcgggcttgg gtttcgaatc ctccaaagac 4740
agcattaaaa ccaccaaaca caccctccac tcctctcgtc aaagctggct ggcgaaggtg 4800
cacgcggatt tgttgagcca acttggtaac ggctggtaca ttaacccctg gtccgaagtg 4860
aaattcgact tgaacagccg ttataaattg aacaccggtg tcaccaattt gaagaaagat 4920
atcaaccaga aaactaatgg ctggggcttt ggcctcggag ctaacattgg caagaaattg 4980
ggtgaaagcg ccagcattga agcgggtcct ttttacaaac aacggactta caaagaatcc 5040
ggcgaattct ccgtgaccac aaaatccggt gacgtaagtc tgacaatccc gaaaacctct 5100
attcgcgaat atggtctgcg tgtgggtatc aaattctgag cggccgcgcc gtctgaaccg 5160
attcagcttc ccaaagaacg ggaaggattg ctatggttga acctatatta ctgcgcttcc 5220
cggcaaactg atttattgcc ggcaggacat catttcggtt tcgatcaaat tattttgagt 5280

-continued aaggaataca ctcctgccat aggatcggat aaagatgatt gcccgccgtt ggaaataacc 5340
gaaacagtga gacaaatcgt tgttcggaac aatcgatatt attttgaatt taacaagctc 5400
acggggataa ttgacgaaat taaagtcaat ggcaaggctt tcatccataa accattggct 5460
tggaatattt ggcgcgcgcc gacggataat gaccgcctga ttcgttccca atggcaaaat 5520
gccggttatg atcaaatgta ttccaaggtt tacgatattt gcgcgcatcg gcaaggaaac 5580
ggtgttgtcg tgtctgtgaa aagtgcattg gttgcggatg caaaatcaaa aatcatgaca 5640
ttggaaacac agtatctgct gtctgaaaat ggtaaattgg atattcaaac aaatgctgtt 5700
ttccacgagc atttgccatt cctgccccgt ttcggtttgc gctttttctt agacgaacag 5760
aaaacacctt ttacctactt aggttatggg gcgggtgaaa gctatattga taaacatcag 5820
gcgaccaaac ttggtattta ttcgacaacg gcaggggaaa atcatgttgg ctatctcaag 5880
cctcaagaga acggcagcca ttatggatgc ttttatgttc aaaacgatat gatccgggtg 5940
gagtcggggc agccgtttag tttcaacctg tccccttata cgcaagaaga actgacgcag 6000
aaaaaacatt cttatgaatt ggtttgttcc gggtatgatg tattgtgtat cgactataag 6060
atgagcggta tcggttcgaa ttcttgcggg cctaatttga agccgcaata tcgtttgatt 6120
gaaaataaca tcaatttcga tataagtatc cggttataag cttgacctgc aggcatgcaa 6180
gcttggcgta atcatggtca tagctgtttc ctgtgtgaaa ttg 6223

<210> SEQ ID NO 33
<211> LENGTH: 8356
<212> TYPE: DNA
<213> ORGANISM: Artificial Sequence
<220> FEATURE:
<223> OTHER INFORMATION: Vector

<400> SEQUENCE: 33
cataagaacc tcagatcctt ccgtatttag ccagtatgtt ctctagtgtg gttcgttgtt 60
tttgcgtgag ccatgagaac gaaccattga gatcatactt actttgcatg tcactcaaaa 120
attttgcctc aaaactggtg agctgaattt ttgcagttaa agcatcgtgt agtgtttttc 180
ttagtccgtt atgtaggtag gaatctgatg taatggttgt tggtattttg tcaccattca 240
tttttatctg gttgttctca agttcggtta cgagatccat ttgtctatct agttcaactt 300
ggaaaatcaa cgtatcagtc gggcggcctc gcttatcaac caccaatttc atattgctgt 360
aagtgtttaa atctttactt attggtttca aaacccattg gttaagcctt ttaaactcat 420
ggtagttatt ttcaagcatt aacatgaact taaattcatc aaggctaatc tctatatttg 480
ccttgtgagt tttcttttgt gttagttctt ttaataacca ctcataaatc ctcatagagt 540
atttgttttc aaaagactta acatgttcca gattatattt tatgaatttt tttaactgga 600
aaagataagg caatatctct tcactaaaaa ctaattctaa tttttcgctt gagaacttgg 660
catagtttgt ccactggaaa atctcaaagc ctttaaccaa aggattcctg atttccacag 720
ttctcgtcat cagctctctg gttgctttag ctaatacacc ataagcattt tccctactga 780
tgttcatcat ctgagcgtat tggttataag tgaacgatac cgtccgttct ttccttgtag 840
ggttttcaat cgtggggttg agtagtgcca cacagcataa aattagcttg gtttcatgct 900
ccgttaagtc atagcgacta atcgctagtt catttgcttt gaaaacaact aattcagaca 960
tacatctcaa ttggtctagg tgattttaat cactatacca attgagatgg gctagtcaat 1020
gataattact agtccttttc ctttgagttg tgggtatctg taaattctgc tagacctttg 1080
ctggaaaact tgtaaattct gctagaccct ctgtaaattc cgctagacct ttgtgtgttt 1140

-continued

```
tttttgttta tattcaagtg gttataattt atagaataaa gaaagaataa aaaaagataa   1200
aaagaataga tcccagccct gtgtataact cactacttta gtcagttccg cagtattaca   1260
aaaggatgtc gcaaacgctg tttgctcctc tacaaaacag accttaaaac cctaaaggct   1320
taagtagcac cctcgcaagc tcgggcaaat cgaagatcct ttgatctttt ctacggggtc   1380
tgacgctcag tggaacgaaa actcacgtta agggattttg gtcatgagat tatcaaaaag   1440
gatcttcacc tagatccttt taaattaaaa atgaagtttt aaatcaatct aaagtatata   1500
tgagtaaact tggtctgaca gttaccaatg cttaatcagt gaggcaccta tctcagcgat   1560
ctgtctattt cgttcatcca tagttgcctg actccccgtc gtgtagataa ctacgatacg   1620
ggagggctta ccatctggcc ccagtgctgc aatgataccg cgagacccac gctcaccggc   1680
tccagattta tcagcaataa accagccagc cggaagggcc gagcgcagaa gtggtcctgc   1740
aactttatcc gcctccatcc agtctattaa ttgttgccgg gaagctagag taagtagttc   1800
gccagttaat agtttgcgca acgttgttgc cattgctaca ggcatcgtgg tgtcacgctc   1860
gtcgtttggt atggcttcat tcagctccgg ttcccaacga tcaaggcgag ttacatgatc   1920
ccccatgttg tgcaaaaaag cggttagctc cttcggtcct ccgatcgttg tcagaagtaa   1980
gttggccgca gtgttatcac tcatggttat ggcagcactg cataattctc ttactgtcat   2040
gccatccgta agatgctttt ctgtgactgg tgagtactca accaagtcat tctgagaata   2100
gtgtatgcgg cgaccgagtt gctcttgccc ggcgtcaata cgggataata ccgcgccaca   2160
tagcagaact ttaaaagtgc tcatcattgg aaaacgttct tcggggcgaa aactctcaag   2220
gatcttaccg ctgttgagat ccagttcgat gtaacccact cgtgcaccca actgatcttc   2280
agcatctttt actttcacca gcgtttctgg gtgagcaaaa acaggaaggc aaaatgccgc   2340
aaaaaaggga ataagggcga cacggaaatg ttgaatactc atactcttcc tttttcaata   2400
ttattgaagc atttatcagg gttattgtct catgagcgga tacatatttg aatgtattta   2460
gaaaaataaa caaatagggg ttccgcgcac atttccccga aaagtgccac ctgacgtcta   2520
agaaaccatt attatcatga cattaaccta taaaaatagg cgtatcacga ggccctttcg   2580
tctcgcgcgt ttcggtgatg acggtgaaaa cctctgacac atgcagctcc cggagacggt   2640
cacagcttgt ctgtaagcgg atgccgggag cagacaagcc cgtcagggcg cgtcagcggg   2700
tgttggcggg tgtcggggct ggcttaacta tgcggcatca gagcagattg tactgagagt   2760
gcaccatatg cggtgtgaaa taccgcacag atgcgtaagg agaaaatacc gcatcaggcg   2820
ccattcgcca ttcaggctgc gcaactgttg ggaagggcga tcggtgcggg cctcttcgct   2880
attacgccag ctggcgaaag ggggatgtgc tgcaaggcga ttaagttggg taacgccagg   2940
gttttcccag tcacgacgtt gtaaaacgac ggccagtgaa ttcgagctcg gtacccgggg   3000
atcctctaga gccgtctgaa ccgattcagc ttcccaaaga acgggaagga ttgctatggt   3060
tgaacctata ttactgcgct tcccggcaaa ctgatttatt gccggcagga catcatttcg   3120
gtttcgatca aattattttg agtaaggaat acactcctgc cataggatcg gataaagatg   3180
attgcccgcc gttggaaata accgaaacag tgagacaaat cgttgttcgg aacaatcgat   3240
attattttga atttaacaag ctcacgggga taattgacga aattaaagtc aatggcaagg   3300
ctttcatcca taaaccattg gcttggaata tttggcgcgc gccgacggat aatgaccgcc   3360
tgattcgttc ccaatggcaa aatgccggtt atgatcaaat gtattccaag gtttacgata   3420
tttgcgcgca tcggcaagga aacggtgttg tcgtgtctgt gaaaagtgca ttggttgcgg   3480
```

-continued

```
atgcaaaatc aaaaatcatg acattggaaa cacagtatct gctgtctgaa aatggtaaat   3540
tggatattca aacaaatgct gttttccacg agcatttgcc attcctgccc cgtttcggtt   3600
tgcgcttttt cttagacgaa cagaaaacac cttttaccta cttaggttat ggggcgggtg   3660
aaagctatat tgataaacat caggcgacca aacttggtat ttattcgaca acggcagggg   3720
aaaatcatgt tggctatctc aagcctcaag agaacggcag ccattatgga tgcttttatg   3780
ttcaaaacga tatgatccgg gtggagtcgg ggcagccgtt tagtttcaac ctgtcccctt   3840
atacgcaaga agaactgacg cagaaaaaac attcttatga attggtttgt tccgggtatg   3900
atgtattgtg tatcgactat aagatgagcg gtatcggttc gaattcttgc gggcctaatt   3960
tgaagccgca atatcgtttg attgaaaata acatcaattt cgatataagt atccggttat   4020
aagcttatat tcggcaactg tcggaatatc tgctaaaatt ccgcattttc cgcaccgggt   4080
ttccgcaccg ggacactcgg ggcgtatgtt caatttgtcg gaatggagtt taaaggaata   4140
cacatatgct gttggcaaac tactaccaag acccggaaat tacccgcatc aacgcactcc   4200
cgcatcattc ctacttcatc ccattcgaca agaaagacaa agttgaccaa ttttcgcgcg   4260
agaactccag cttcttcaca tccctgaacg gcatgtggca gttcgcttac tacccttcta   4320
tgcaagacct gccggaatct cccgatgaga ttgcgttcac taaacagata aacgtaccga   4380
gcaactggca aaaccatggc ttcgacgcgc accagtacac caacatcaac tacccgtttc   4440
catttgaccc tccgttcgta cccctggaaa atccgtgtgg tgtctaccag aaacaagtta   4500
acctgaagaa aaacatcaac aaacgttacc tcctggttct ggagggcgtg gacagctgca   4560
gctacatcta cgtgaatcac cagttcgttg gttacggcag catttcccat tccacgaacg   4620
agttcgacat cactgactac ttgcatgacg gcgagaatac gctcactgtc ttcgtattga   4680
agtggtgcgc gggctcctat ctggaggacc aagacaagtt ccgcatgtcc ggtatctttc   4740
gggacgtcta cttgctcgag cgcgaacacc attacctgca ggatctcaac atccgcactg   4800
tcctgagcga ggacctcagc ctcggccaaa tctgccttga cctgaacttc gccggtgacg   4860
ccggcgacgt gggtgtcagt ctcttcgaca ccgatggcca gatcgtgcag gccggttccg   4920
ccattactac ggacaagcag cgtatgcaga ttcgtctgga caacatcccg ttgactaaaa   4980
gtcgtttgtg gaacgccgag aatccggcat tgtacacgct tgttctgaat accaaagagg   5040
agattatcac gcaaaaaatt ggctttcgta aagttgaagt gaagaatggc gtgctgttgc   5100
tgaacaacca accgatcaag tttaagggtg ttaatcgcca tgactccgac cctaaaacgg   5160
ggtacgctat ttccgtcgcc caagccgtca cggacctgtc actgatgaaa aaacacaata   5220
tcaacgcgat tcgcactgca cattatccga attccccctg gttctgcgaa ctgtgtgaca   5280
aatatgggtt ttacgtgatc agtgaaagcg acattgaatc acacggtgca gccttccagg   5340
ctatctccca tccggaaccg tcaattttcc ttaacgtgga aaaccccaac gaagaaccgc   5400
ggatccgcca acaaacaatc gacaactttt gctacttcgc tcgtgaaccg ttgtatcgtg   5460
cggcactgct ggaacgtacc aaagccaaca ttgaacgtga caaaaaccgc tcttccattt   5520
tgatttggtc tttgggcaac gagagcggct acggcgaaaa cttcgaatac tgcgcaaaat   5580
gggttaaaga acgcgatcct gatcgtttgg tccactacga atcaagcatc tatcagcata   5640
gcgcatacca aaataacacc ggtcatttgg atctatacag tgaaatgtac tccgatacgg   5700
aagccattga tgcctacttt gcagaccaca gccagaccaa aaaaccgttc ctgctatgtg   5760
aatacagcca cgccatgggc aattccaacg gtgacatgga agattacttt caaaccttta   5820
acaaatactc cggctgttgc ggcggtttca tctgggaatg gtgtgaccac gcacaatata   5880
```

tcaccccgac gaaattgggc tacggtggcg actttggaga gaaaatccat gatggcaatt 5940
tctgtgtcga tgggttggtt agccctgaac gcgtacccca ctcgaatctg ttggaggtta 6000
agaacgttaa ccgcccggtc cgcgctaacc tgaggggtga acaaatagaa ttgtacaact 6060
acttcgattt caccaactta aaagacatct tgtgcgtaaa atacgaatgg gtcaaaaatg 6120
gtcaaattac tggcaccggt acactggcgg tcgactgcga accccaccac tcccagattt 6180
tgcctatcca actgccgaag gagcgtgagg gtctcttgtg gcttaatctg tactattgtg 6240
ccagccgtca gaccgacctg ctccctgcgg gccaccactt tggctttgac cagatcatcc 6300
tgtcaaaaga gtataccccc gcgattggca gcgacaagga cgactgtcca cctctggaga 6360
tcactgagac cgtccgccag attgtggtcc gtaataaccg ttactacttc gagttcaata 6420
aattgactgg tattatcgat gagatcaagg tgaacggtaa agcctttatt cacaaaccgc 6480
tcgcctggaa catctggcgt gcccccaccg acaacgatcg tttgatccgc tcacagtggc 6540
agaacgcggg ctacgaccag atgtactcta aagtctatga catctgtgca caccgccagg 6600
gcaatggcgt cgttgtctcg gtaaagtcgg cgctcgtcgc agacgccaaa tcgaagatta 6660
tgacgctgga gacccaatac ttgctcagcg agaacggcaa actggacatc cagaccaacg 6720
cagtgtttca tgaacacctc ccgtttttac cacgctttgg cctccgtttc tttctggatg 6780
agcaaaagac cccgttcact tatctgggct acggcgccgg cgagtcttac atcgacaagc 6840
accaagccac gaaattgggc atctactcca ccaccgccgg cgagaaccat gtcggttacc 6900
tgaaaccgca ggaaaatggt tcccactacg gctgtttcta cgtgcagaat gacatgattc 6960
gcgtagaaag cggccaaccc ttctccttta atttaagccc gtacacccag gaagagttga 7020
cccaaaagaa acactcctac gagctcgtct gcagcggata cgacgtcctc tgcattgatt 7080
acaaaatgtc tggcattggc tccaacagct gtggccccaa cctgaaacct cagtaccgcc 7140
tcatcgagaa caatattaac tttgacattt ccattcgcct ctagtctgca aagattggta 7200
tcaacaaaaa gcctgtcgtc agacaggctt tttttctgtt ttctgttttt agatgccgtc 7260
tgaatgctga agtagaaaac cagcaagaag gtaaaaagaa agaagcagtt ttttggattt 7320
tagatgttac cgcaattggt ttcctttcct aaaatttgtt taaattattt gcaatattaa 7380
tataaactgg atattaatga tgaggattca aaaaggcata ctgaatataa tttgtacaaa 7440
atatttgcag tatttaaaaa tgttggttcg tatatgaaaa gttaaaaatg ccaaaatgta 7500
cagttgctaa actgtaaaac tgctaaagca acaaaacata aaaaggaatg cagggatgcg 7560
atcactacat ctttttattc cgtaagcatt tatgacttta cggtcaactg ctactctatg 7620
tttccagctt ttcagctccc tattttcgaa tattggacga ggcattttca tcagtgtcgt 7680
aatgccgacc gaaaccctca caaaccatat tggttcttgt ggcagcaaca cctatccgtt 7740
tgttcaagcg gccacaagag taacatgatt ggctggtggc attggcttta atctcttcga 7800
tatgaactcc atttttagct gcaccttctt tcagcgtatg caacagtggg gatggggcaa 7860
ctatcttctg gtggagtttg ttgacttcaa tctgtatgca ctgtaggttg agcagattca 7920 gtttttgat acagattatc cggctttgtt cggcaattct gttggcgaac gtatagtaga 7980
gctgtcgtct tgccgctttc aatttgcggt aggtatttta ccattccatg cgtagccgct 8040
cggtacgttt gagccaaatg ttatcttcgc catttgtacc aatttgtttt tacattaggc 8100
tgtgttttag taatctattg atttcaatta tttgcaaggg aaaagacaat tattttccgg 8160
ttaggaataa acctatccta ttgaatatat tgaagccaag tacgcttatc aacactatat 8220
taaaacacag cctttttaa tatagtagac acaatctttc cttatttatg aaggtgatag 8280
cttctttcag tctagagacc tgcaggcatg caagcttggc gtaatcatgg tcatagctgt 8340
ttcctgtgtg aaattg 8356

<210> SEQ ID NO 34
<211> LENGTH: 9864
<212> TYPE: DNA
<213> ORGANISM: Artificial Sequence
<220> FEATURE:
<223> OTHER INFORMATION: Vector

<400> SEQUENCE: 34
cataagaacc tcagatcctt ccgtatttag ccagtatgtt ctctagtgtg gttcgttgtt 60
tttgcgtgag ccatgagaac gaaccattga gatcatactt actttgcatg tcactcaaaa 120
attttgcctc aaaactggtg agctgaattt ttgcagttaa agcatcgtgt agtgtttttc 180
ttagtccgtt atgtaggtag gaatctgatg taatggttgt tggtattttg tcaccattca 240
tttttatctg gttgttctca agttcggtta cgagatccat ttgtctatct agttcaactt 300
ggaaaatcaa cgtatcagtc gggcggcctc gcttatcaac caccaatttc atattgctgt 360
aagtgtttaa atctttactt attggtttca aaacccattg gttaagcctt ttaaactcat 420
ggtagttatt ttcaagcatt aacatgaact taaattcatc aaggctaatc tctatatttg 480
ccttgtgagt tttcttttgt gttagttctt ttaataacca ctcataaatc ctcatagagt 540
atttgttttc aaaagactta acatgttcca gattatattt tatgaatttt tttaactgga 600
aaagataagg caatatctct tcactaaaaa ctaattctaa tttttcgctt gagaacttgg 660
catagtttgt ccactggaaa atctcaaagc ctttaaccaa aggattcctg atttccacag 720
ttctcgtcat cagctctctg gttgctttag ctaatacacc ataagcattt tccctactga 780
tgttcatcat ctgagcgtat tggttataag tgaacgatac cgtccgttct ttccttgtag 840
ggttttcaat cgtggggttg agtagtgcca cacagcataa aattagcttg gtttcatgct 900
ccgttaagtc atagcgacta atcgctagtt catttgcttt gaaaacaact aattcagaca 960
tacatctcaa ttggtctagg tgattttaat cactatacca attgagatgg gctagtcaat 1020
gataattact agtccttttc ctttgagttg tgggtatctg taaattctgc tagacctttg 1080
ctggaaaact tgtaaattct gctagaccct ctgtaaattc cgctagacct ttgtgtgttt 1140
tttttgttta tattcaagtg gttataattt atagaataaa gaaagaataa aaaaagataa 1200
aaagaataga tcccagccct gtgtataact cactacttta gtcagttccg cagtattaca 1260
aaaggatgtc gcaaacgctg tttgctcctc tacaaaacag accttaaaac cctaaaggct 1320
taagtagcac cctcgcaagc tcgggcaaat cgaagatcct ttgatctttt ctacggggtc 1380
tgacgctcag tggaacgaaa actcacgtta agggattttg gtcatgagat tatcaaaaag 1440
gatcttcacc tagatccttt taaattaaaa atgaagtttt aaatcaatct aaagtatata 1500
tgagtaaact tggtctgaca gttaccaatg cttaatcagt gaggcaccta tctcagcgat 1560
ctgtctattt cgttcatcca tagttgcctg actccccgtc gtgtagataa ctacgatacg 1620
ggagggctta ccatctggcc ccagtgctgc aatgataccg cgagacccac gctcaccggc 1680
tccagattta tcagcaataa accagccagc cggaagggcc gagcgcagaa gtggtcctgc 1740
aactttatcc gcctccatcc agtctattaa ttgttgccgg gaagctagag taagtagttc 1800
gccagttaat agtttgcgca acgttgttgc cattgctaca ggcatcgtgg tgtcacgctc 1860
gtcgtttggt atggcttcat tcagctccgg ttcccaacga tcaaggcgag ttacatgatc 1920

```
ccccatgttg tgcaaaaaag cggttagctc cttcggtcct ccgatcgttg tcagaagtaa   1980
gttggccgca gtgttatcac tcatggttat ggcagcactg cataattctc ttactgtcat   2040
gccatccgta agatgctttt ctgtgactgg tgagtactca accaagtcat tctgagaata   2100
gtgtatgcgg cgaccgagtt gctcttgccc ggcgtcaata cgggataata ccgcgccaca   2160
tagcagaact ttaaaagtgc tcatcattgg aaaacgttct tcggggcgaa aactctcaag   2220
gatcttaccg ctgttgagat ccagttcgat gtaacccact cgtgcaccca actgatcttc   2280
agcatctttt actttcacca gcgtttctgg gtgagcaaaa acaggaaggc aaaatgccgc   2340
aaaaaaggga ataagggcga cacggaaatg ttgaatactc atactcttcc tttttcaata   2400
ttattgaagc atttatcagg gttattgtct catgagcgga tacatatttg aatgtattta   2460
gaaaaataaa caaatagggg ttccgcgcac atttccccga aaagtgccac ctgacgtcta   2520
agaaaccatt attatcatga cattaaccta taaaaatagg cgtatcacga ggccctttcg   2580
tctcgcgcgt ttcggtgatg acggtgaaaa cctctgacac atgcagctcc cggagacggt   2640
cacagcttgt ctgtaagcgg atgccgggag cagacaagcc cgtcagggcg cgtcagcggg   2700
tgttggcggg tgtcggggct ggcttaacta tgcggcatca gagcagattg tactgagagt   2760
gcaccatatg cggtgtgaaa taccgcacag atgcgtaagg agaaaatacc gcatcaggcg   2820
ccattcgcca ttcaggctgc gcaactgttg ggaagggcga tcggtgcggg cctcttcgct   2880
attacgccag ctggcgaaag ggggatgtgc tgcaaggcga ttaagttggg taacgccagg   2940
gttttcccag tcacgacgtt gtaaaacgac ggccagtgaa ttcgagctcg gtacccgggg   3000
atcctctaga gtcctgatac cgagcttttc ccatggttta tcgcgactga tagtgttttc   3060
ggcgaggtag tcggcacgtg tttgagacca ccagcgagtg attgtgcttt cagctacaat   3120
aattttgctg cttgctctat gtttaaaaat ctatccatat tggatagttt agattagact   3180
taagtggatt tcaagtgagc tgtttaaccc ttagctagca agggttttgg tggcgtaagg   3240
ttactgaact taagcatatc ggcggccaaa gtaccgctgc cattgccaat ctcgccgggg   3300
aaatgaaaag gctcgctaaa aaatcaaaaa tgttactgaa aggactttgg tcatttttat   3360
cctctacaat atctacattt aaaaataaat cggtcattgt ttaaacctta ctgtaaaact   3420
gtacaactgc taaactgtaa acacagaaag aggcaatact aacagcacaa aacaacagat   3480
atccaaactc cataaagtgc attattctga ctttttttcgt tgcctgatgt atttatgcta   3540
tttgtgctgt tcttatatat gtgttgctgg ttacgttgcg ttttttcgga aaattcaacc   3600
ggtaggggac cgatacgcag tttcatctct ttgcttaggg agagtagggg ggtagattac   3660
gaccttagtt ttggtatccg taatatcatc attttttcgt ctagggagta tatcgacttc   3720
agaaaacagg tattagatac tgccttttct tacgagagtg atggcaagat agttctcttc   3780
aagtcaatca aacaggaaag tatttctttt ctgtctgaag atttgaaaaa ggactgaatg   3840
tttcacaagg ttaaaactgg ggaaaaagat ggatatggtt cagatgaaat gctgagcgca   3900
ccccgtatct atttggaaat gatgtcgcgg aaaacggaag tcccctactc cagtattctt   3960
taaattctaa gcagaaaact tcttcgtcgg tctttttttt gttgtttggt ttgcatggag   4020
taaaactgtg caacgccgtc tgagtcgacg tgccgcgtgt gtttttttat ggcgttttaa   4080
aaagccgaga ctgcatccgg gcagcagcgc atcggctcgc acgaggtctg cgcttgaatt   4140
gtgttgtaga aacacaacgt tttgaaaaa ataagctatt gttttatatc aaaatataat   4200
catttttaaa ataaaggttg cggcatttat cagatatttg ttctgaaaaa tggtttttcg   4260
```

-continued

```
ggcgggaaca tttataattg aagacgtatc gggtgtttgc ccgatgtttt taggtttttta   4320
tcaaatttac aaaaggaact cgagatgcgc aagaaactta ccgccctcgt attgtccgca   4380
ctgccgcttg cggccgttgc cgatgtcagc ctatacggcg aaatcaaagc cggcgtggaa   4440
ggcaggaact accagctgca attgactgaa gcacaagccg ctaacggtgg agcgagcggt   4500
caggtaaaag ttactaaagt tactaaggcc aaaagccgca tcaggacgaa aatcagtgat   4560
ttcggctcgt ttatcggctt taaagggagt gaggatttgg gcgacgggct gaaagctgtt   4620
tggcagcttg agcaagacgt atccgttgcc ggcggcggcg cgacccagtg gggcaacagg   4680
gaatccttta tcggcttggc aggcgaattt ggtacgctgc gcgccggtcg cgttgcgaat   4740
cagtttgacg atgccagcca agccattgat ccttgggaca gcaataatga tgtggcttcg   4800
caattgggta ttttcaaacg ccacgacgac atgccggttt ccgtacgcta cgattccccc   4860
gaattttccg gtttcagcgg cagcgttcaa ttcgttccga tccaaaacag caagtccgcc   4920
tatacgccgg cttattatac taaagataca aacaataatc ttactctcgt tccggctgtt   4980
gtcggcaaac ccggatcgga tgtgtattat gccggtctga attacaagaa tggcggtttt   5040
gccgggaact atgcctttaa atatgcgaga cacgccaatg tcggacgtaa tgcttttgag   5100
ttgttcttga tcggcagcgg gagtgatcaa gccaaaggta ccgatccctt gaagaaccat   5160
caggtacacc gtctgacggg cggctatgag gaaggcggct tgaatctcgc cttggcggct   5220
cagttggatt tgtctgaaaa tggcgacaaa accaagaaca gtacgaccga aattgccgcc   5280
actgcttcct accgcttcgg taatgcagtt ccacgcatca gctatgccca tggtttcgac   5340
tttatcgaac gcggtaagaa aggcgaaaat accagctacg atcaaatcat cgccggcgtt   5400
gattatgatt tctccaaacg cacttccgcc atcgtgtctg gcgcttggct gaaacgcaat   5460
accggcatcg gcaactacac tcaaattaat gccgcctccg tcggtttgcg ccacaaattc   5520
taagcggccg catatcggca actgtcggaa tatctgctaa aattccgcat tttccgcacc   5580
gggtttccgc accgggacac tcggggcgta tgttcaattt gtcggaatgg agtttaaagg   5640
aatacacata tgttattagc gaattattat caagatcctg aaatcacgag aatcaatgcg   5700
ttgccgcacc atagctattt tatccctttt gataaaaaag ataaggtaga tcagttttct   5760
agggaaaatt cttcgttttt tacatcatta aatggaatgt ggcaattcgc atattatccg   5820
agtatgcagg atttgcctga aagtccggac gaaatcgctt ttacgaaaca aatcaatgtg   5880
ccttcaaatt ggcagaatca cgggtttgat gcccatcaat atactaatat taattatcct   5940
ttccctttcg atccgccttt tgttccttta gagaaccctt gcggggtata tcaaaagcag   6000
gtcaatctga aaaagaatat aaataagcgg tatttattag tccttgaagg ggttgattcc   6060
tgttcttata tatatgtaaa ccatcaattt gtaggatatg gttctatcag ccacagtacc   6120
aatgaatttg atattaccga ttatcttcac gatggtgaaa acacccttac cgtatttgtc   6180
ctgaaatggt gtgccggaag ctacttggaa gatcaggata aatttagaat gtcgggaatt   6240
ttccgagatg tatatttatt ggaaagggag catcactatt tgcaagactt gaatattcga   6300
accgtgcttt ctgaagattt atcattgggg cagatttgtc tggatttaaa ttttgcgggg   6360
gatgcggggg atgtcggagt gtcattgttt gatacggacg ggcaaattgt tcaagcaggc   6420
agcgcaatca cgacagataa acaacggatg caaatccgcc ttgataatat tcctttaacc   6480
aaatcccgac tctggaatgc ggaaaaccct gccctttata ccttggtatt aaacacaaaa   6540
gaagaaatca ttacccagaa gatcggattc cgcaaggtag aggtcaaaaa cggggtattg   6600
ctgcttaata atcagcctat taaattcaaa ggggtaaacc ggcacgatag cgatcccaaa   6660
```

acgggatatg ccatttctgt cgctcaagcg gtgactgact tgtcgttaat gaagaaacat 6720
aatattaacg cgattcgtac cgcgcattat ccaaattcac cgtggttttg cgagctttgc 6780
gataagtatg gtttctatgt aatcagtgaa agcgacattg aaagtcatgg ggcggcattc 6840
caagcaattt cgcatcccga accgagtatc tttctgaatg tggaaaatcc gaatgaagag 6900
ccgcgtatcc gccaacaaac tattgacaac ttctgttatt ttgcccgaga accattgtat 6960
cgggcggctt tattggagcg gactaaagca aatatagaac gtgataagaa ccgcagttct 7020
attttaattt ggtctttagg caatgaatca gggtatggtg agaatttcga atattgtgca 7080
aaatgggtaa aagagcggga tccggatcga ttggttcatt acgaaagcag catttatcag 7140
cattctgcgt atcagaataa caccgggcat ttggatttat acagtgaaat gtattccgac 7200
acagaagcaa tcgatgccta ttttgccgat cattcacaaa cgaaaaaacc attcttatta 7260
tgcgaatatt cccatgcaat gggaaattca aatggagata tggaagacta tttccaaaca 7320
tttaacaaat attcgggctg ttgcggtggg tttatttggg agtggtgcga tcatgcccaa 7380
tatattaccc cgacaaaatt aggatatggc ggtgacttcg gcgaaaaaat ccatgatggg 7440
aatttctgtg tggatggctt ggtttcgccc gaacgcgtcc cgcacagcaa cctgttggaa 7500
gtaaaaaatg tcaaccggcc cgtacgggca aacttgcgcg gtgaacaaat tgagttatat 7560
aactattttg atttcactaa tttaaaagat attctttgcg tcaaatatga atgggtaaaa 7620
aatggtcaga taaccgggac gggaacattg gcggttgatt gcgaacccca tcattctcaa 7680
atcttaccga ttcagcttcc caaagaacgg gaaggattgc tatggttgaa cctatattac 7740
tgcgcttccc ggcaaactga tttattgccg gcaggacatc atttcggttt cgatcaaatt 7800
attttgagta aggaatacac tcctgccata ggatcggata aagatgattg cccgccgttg 7860
gaaataaccg aaacagtgag acaaatcgtt gttcggaaca atcgatatta ttttgaattt 7920
aacaagctca cggggataat tgacgaaatt aaagtcaatg gcaaggcttt catccataaa 7980
ccattggctt ggaatatttg gcgcgcgccg acggataatg accgcctgat tcgttcccaa 8040
tggcaaaatg ccggttatga tcaaatgtat tccaaggttt acgatatttg cgcgcatcgg 8100
caaggaaacg gtgttgtcgt gtctgtgaaa agtgcattgg ttgcggatgc aaaatcaaaa 8160
atcatgacat tggaaacaca gtatctgctg tctgaaaatg gtaaattgga tattcaaaca 8220
aatgctgttt tccacgagca tttgccattc ctgccccgtt tcggtttgcg ctttttctta 8280
gacgaacaga aaacaccttt tacctactta ggttatgggg cgggtgaaag ctatattgat 8340
aaacatcagg cgaccaaact tggtatttat tcgacaacgg caggggaaaa tcatgttggc 8400
tatctcaagc ctcaagagaa cggcagccat tatggatgct tttatgttca aaacgatatg 8460
atccgggtgg agtcggggca gccgtttagt ttcaacctgt ccccttatac gcaagaagaa 8520
ctgacgcaga aaaaacattc ttatgaattg gtttgttccg ggtatgatgt attgtgtatc 8580
gactataaga tgagcggtat cggttcgaat tcttgcgggc ctaatttgaa gccgcaatat 8640
cgtttgattg aaaataacat caatttcgat ataagtatcc ggttataagc tttctgcaaa 8700
gattggtatc aacaaaaagc ctgtcgtcag acaggctttt tttctgtttt ctgtttttag 8760
atgccgtctg aatgctgaag tagaaaacca gcaagaaggt aaaaagaaag aagcagtttt 8820
ttggatttta gatgttaccg caattggttt cctttcctaa aatttgttta aattatttgc 8880
aatattaata taaactggat attaatgatg aggattcaaa aaggcatact gaatataatt 8940
tgtacaaaat atttgcagta tttaaaaatg ttggttcgta tatgaaaagt taaaaatgcc 9000
aaaatgtaca gttgctaaac tgtaaaactg ctaaagcaac aaaacataaa aaggaatgca 9060
gggatgcgat cactacatct ttttattccg taagcattta tgactttacg gtcaactgct 9120
actctatgtt tccagctttt cagctcccta ttttcgaata ttggacgagg cattttcatc 9180
agtgtcgtaa tgccgaccga aaccctcaca aaccatattg gttcttgtgg cagcaacacc 9240
tatccgtttg ttcaagcggc cacaagagta acatgattgg ctggtggcat tggctttaat 9300
ctcttcgata tgaactccat tttagctgc accttctttc agcgtatgca acagtgggga 9360
tggggcaact atcttctggt ggagtttgtt gacttcaatc tgtatgcact gtaggttgag 9420
cagattcagt tttttgatac agattatccg gctttgttcg gcaattctgt tggcgaacgt 9480
atagtagagc tgtcgtcttg ccgctttcaa tttgcggtag gtattttacc attccatgcg 9540
tagccgctcg gtacgtttga gccaaatgtt atcttcgcca tttgtaccaa tttgttttta 9600
cattaggctg tgttttagta atctattgat ttcaattatt tgcaagggaa aagacaatta 9660
ttttccggtt aggaataaac ctatcctatt gaatatattg aagccaagta cgcttatcaa 9720
cactatatta aaacacagcc ttttttaata tagtagacac aatctttcct tatttatgaa 9780
ggtgatagct tctttcagtc tagagacctg caggcatgca agcttggcgt aatcatggtc 9840
atagctgttt cctgtgtgaa attg 9864

<210> SEQ ID NO 35
<211> LENGTH: 9864
<212> TYPE: DNA
<213> ORGANISM: Artificial Sequence
<220> FEATURE:
<223> OTHER INFORMATION: Vector

<400> SEQUENCE: 35
cataagaacc tcagatcctt ccgtatttag ccagtatgtt ctctagtgtg gttcgttgtt 60
tttgcgtgag ccatgagaac gaaccattga gatcatactt actttgcatg tcactcaaaa 120
attttgcctc aaaactggtg agctgaattt ttgcagttaa agcatcgtgt agtgtttttc 180
ttagtccgtt atgtaggtag gaatctgatg taatggttgt tggtattttg tcaccattca 240
tttttatctg gttgttctca agttcggtta cgagatccat ttgtctatct agttcaactt 300
ggaaaatcaa cgtatcagtc gggcggcctc gcttatcaac caccaatttc atattgctgt 360
aagtgtttaa atctttactt attggtttca aaacccattg gttaagcctt ttaaactcat 420
ggtagttatt ttcaagcatt aacatgaact taaattcatc aaggctaatc tctatatttg 480
ccttgtgagt tttcttttgt gttagttctt ttaataacca ctcataaatc ctcatagagt 540
atttgttttc aaaagactta acatgttcca gattatattt tatgaatttt tttaactgga 600
aaagataagg caatatctct tcactaaaaa ctaattctaa tttttcgctt gagaacttgg 660
catagtttgt ccactggaaa atctcaaagc ctttaaccaa aggattcctg atttccacag 720
ttctcgtcat cagctctctg gttgctttag ctaatacacc ataagcattt tccctactga 780
tgttcatcat ctgagcgtat tggttataag tgaacgatac cgtccgttct ttccttgtag 840
ggttttcaat cgtggggttg agtagtgcca cacagcataa aattagcttg gtttcatgct 900
ccgttaagtc atagcgacta atcgctagtt catttgcttt gaaaacaact aattcagaca 960
tacatctcaa ttggtctagg tgattttaat cactatacca attgagatgg gctagtcaat 1020
gataattact agtccttttc ctttgagttg tgggtatctg taaattctgc tagacctttg 1080
ctggaaaact tgtaaattct gctagaccct ctgtaaattc cgctagacct ttgtgtgttt 1140
tttttgttta tattcaagtg gttataattt atagaataaa gaaagaataa aaaaagataa 1200

```
aaagaataga tcccagccct gtgtataact cactacttta gtcagttccg cagtattaca   1260
aaaggatgtc gcaaacgctg tttgctcctc tacaaaacag accttaaaac cctaaaggct   1320
taagtagcac cctcgcaagc tcgggcaaat cgaagatcct ttgatctttt ctacggggtc   1380
tgacgctcag tggaacgaaa actcacgtta agggattttg gtcatgagat tatcaaaaag   1440
gatcttcacc tagatccttt taaattaaaa atgaagtttt aaatcaatct aaagtatata   1500
tgagtaaact tggtctgaca gttaccaatg cttaatcagt gaggcaccta tctcagcgat   1560
ctgtctattt cgttcatcca tagttgcctg actccccgtc gtgtagataa ctacgatacg   1620
ggagggctta ccatctggcc ccagtgctgc aatgataccg cgagacccac gctcaccggc   1680
tccagattta tcagcaataa accagccagc cggaagggcc gagcgcagaa gtggtcctgc   1740
aactttatcc gcctccatcc agtctattaa ttgttgccgg gaagctagag taagtagttc   1800
gccagttaat agtttgcgca acgttgttgc cattgctaca ggcatcgtgg tgtcacgctc   1860
gtcgtttggt atggcttcat tcagctccgg ttcccaacga tcaaggcgag ttacatgatc   1920
ccccatgttg tgcaaaaaag cggttagctc cttcggtcct ccgatcgttg tcagaagtaa   1980
gttggccgca gtgttatcac tcatggttat ggcagcactg cataattctc ttactgtcat   2040
gccatccgta agatgctttt ctgtgactgg tgagtactca accaagtcat tctgagaata   2100
gtgtatgcgg cgaccgagtt gctcttgccc ggcgtcaata cgggataata ccgcgccaca   2160
tagcagaact ttaaaagtgc tcatcattgg aaaacgttct tcggggcgaa aactctcaag   2220
gatcttaccg ctgttgagat ccagttcgat gtaacccact cgtgcaccca actgatcttc   2280
agcatctttt actttcacca gcgtttctgg gtgagcaaaa acaggaaggc aaaatgccgc   2340
aaaaaaggga ataagggcga cacggaaatg ttgaatactc atactcttcc tttttcaata   2400
ttattgaagc atttatcagg gttattgtct catgagcgga tacatatttg aatgtattta   2460
gaaaaataaa caaatagggg ttccgcgcac atttccccga aaagtgccac ctgacgtcta   2520
agaaaccatt attatcatga cattaaccta taaaaatagg cgtatcacga ggccctttcg   2580
tctcgcgcgt ttcggtgatg acggtgaaaa cctctgacac atgcagctcc cggagacggt   2640
cacagcttgt ctgtaagcgg atgccgggag cagacaagcc cgtcagggcg cgtcagcggg   2700
tgttggcggg tgtcggggct ggcttaacta tgcggcatca gagcagattg tactgagagt   2760
gcaccatatg cggtgtgaaa taccgcacag atgcgtaagg agaaaatacc gcatcaggcg   2820
ccattcgcca ttcaggctgc gcaactgttg ggaagggcga tcggtgcggg cctcttcgct   2880
attacgccag ctggcgaaag ggggatgtgc tgcaaggcga ttaagttggg taacgccagg   2940
gttttcccag tcacgacgtt gtaaaacgac ggccagtgaa ttcgagctcg gtacccgggg   3000
atcctctaga gtcctgatac cgagcttttc ccatggttta tcgcgactga tagtgttttc   3060
ggcgaggtag tcggcacgtg tttgagacca ccagcgagtg attgtgcttt cagctacaat   3120
aattttgctg cttgctctat gtttaaaaat ctatccatat tggatagttt agattagact   3180
taagtggatt tcaagtgagc tgtttaaccc ttagctagca agggttttgg tggcgtaagg   3240
ttactgaact taagcatatc ggcggccaaa gtaccgctgc cattgccaat ctcgccgggg   3300
aaatgaaaag gctcgctaaa aaatcaaaaa tgttactgaa aggactttgg tcatttttat   3360
cctctacaat atctacattt aaaaataaat cggtcattgt ttaaacctta ctgtaaaact   3420
gtacaactgc taaactgtaa acacagaaag aggcaatact aacagcacaa aacaacagat   3480
atccaaactc cataaagtgc attattctga ctttttttcgt tgcctgatgt atttatgcta   3540
```

-continued

```
tttgtgctgt tcttatatat gtgttgctgg ttacgttgcg ttttttcgga aaattcaacc   3600
ggtaggggac cgatacgcag tttcatctct ttgcttaggg agagtagggg ggtagattac   3660
gaccttagtt ttggtatccg taatatcatc attttttcgt ctagggagta tatcgacttc   3720
agaaaacagg tattagatac tgccttttct tacgagagtg atggcaagat agttctcttc   3780
aagtcaatca aacaggaaag tatttctttt ctgtctgaag atttgaaaaa ggactgaatg   3840
tttcacaagg ttaaaactgg ggaaaaagat ggatatggtt cagatgaaat gctgagcgca   3900
ccccgtatct atttggaaat gatgtcgcgg aaaacggaag tcccctactc cagtattctt   3960
taaattctaa gcagaaaact tcttcgtcgg tcttttttt gttgtttggt ttgcatggag   4020
taaaactgtg caacgccgtc tgagtcgacg tgccgcgtgt gttttttat ggcgttttaa   4080
aaagccgaga ctgcatccgg gcagcagcgc atcggctcgc acgaggtctg cgcttgaatt   4140
gtgttgtaga aacacaacgt tttgaaaaa ataagctatt gttttatatc aaaatataat   4200
catttttaaa ataaaggttg cggcatttat cagatatttg ttctgaaaaa tggtttttttg  4260
cgggggggg ggtataattg aagacgtatc gggtgtttgc ccgatgtttt taggtttta   4320
tcaaatttac aaaaggaagc cgatatgcga aaaaaactta ccgccctcgt attgtccgca   4380
ctgccgcttg cggccgttgc cgatgtcagc ctatacggcg aaatcaaagc cggcgtggaa   4440
ggcaggaact accagctgca attgactgaa gcacaagccg ctaacggtgg agcgagcggt   4500
caggtaaaag ttactaaagt tactaaggcc aaaagccgca tcaggacgaa aatcagtgat   4560
ttcggctcgt ttatcggctt taaggggagt gaggatttgg gcgacgggct gaaggctgtt   4620
tggcagcttg agcaagacgt atccgttgcc ggcggcggcg cgacccagtg gggcaacagg   4680
gaatccttta tcggcttggc aggcgaattc ggtacgctgc gcgccggtcg cgttgcgaat   4740
cagtttgacg atgccagcca agccattgat ccttgggaca gcaataatga tgtggcttcg   4800
caattgggta ttttcaaacg ccacgacgac atgccggttt ccgtacgcta cgattccccc   4860
gaattttccg gtttcagcgg cagcgttcaa ttcgttccga tccaaaacag caagtccgcc   4920
tatacgccgg cttattatac taaggataca aacaataatc ttactctcgt tccggctgtt   4980
gtcggcaagc ccggatcgga tgtgtattat gccggtctga attacaaaaa tggcggtttt   5040
gccgggaact atgcctttaa atatgcgaga cacgccaatg tcggacgtaa tgcttttgag   5100
ttgttcttga tcggcagcgg gagtgatcaa gccaaaggta ccgatccctt gaaaaaccat   5160
caggtacacc gtctgacggg cggctatgag gaaggcggct tgaatctcgc cttggcggct   5220
cagttggatt tgtctgaaaa tggcgacaaa accaaaaaca gtacgaccga aattgccgcc   5280
actgcttcct accgcttcgg taatgcagtt ccacgcatca gctatgccca tggtttcgac   5340
tttatcgaac gcggtaaaaa aggcgaaaat accagctacg atcaaatcat cgccggcgtt   5400
gattatgatt tttccaaacg cacttccgcc atcgtgtctg gcgcttggct gaaacgcaat   5460
accggcatcg gcaactacac tcaaattaat gccgcctccg tcggtttgcg ccacaaattc   5520
taagcggccg catatcggca actgtcggaa tatctgctaa aattccgcat tttccgcacc   5580
gggtttccgc accgggacac tcggggcgta tgttcaattt gtcggaatgg agtttaaagg   5640
aatacacata tgttattagc gaattattat caagatcctg aaatcacgag aatcaatgcg   5700
ttgccgcacc atagctattt tatccctttt gataaaaaag ataaggtaga tcagttttct   5760
agggaaaatt cttcgttttt tacatcatta aatggaatgt ggcaattcgc atattatccg   5820
agtatgcagg atttgcctga aagtccggac gaaatcgctt ttacgaaaca aatcaatgtg   5880
ccttcaaatt ggcagaatca cgggtttgat gcccatcaat atactaatat taattatcct   5940
```

-continued

```
ttccctttcg atccgccttt tgttccttta gagaaccctt gcggggtata tcaaaagcag   6000
gtcaatctga aaaagaatat aaataagcgg tatttattag tccttgaagg ggttgattcc   6060
tgttcttata tatatgtaaa ccatcaattt gtaggatatg gttctatcag ccacagtacc   6120
aatgaatttg atattaccga ttatcttcac gatggtgaaa acacccttac cgtatttgtc   6180
ctgaaatggt gtgccggaag ctacttggaa gatcaggata aatttagaat gtcgggaatt   6240
ttccgagatg tatatttatt ggaaagggag catcactatt tgcaagactt gaatattcga   6300
accgtgcttt ctgaagattt atcattgggg cagatttgtc tggatttaaa ttttgcgggg   6360
gatgcggggg atgtcggagt gtcattgttt gatacggacg ggcaaattgt tcaagcaggc   6420
agcgcaatca cgacagataa acaacggatg caaatccgcc ttgataatat tcctttaacc   6480
aaatcccgac tctggaatgc ggaaaaccct gccctttata ccttggtatt aaacacaaaa   6540
gaagaaatca ttacccagaa gatcggattc cgcaaggtag aggtcaaaaa cggggtattg   6600
ctgcttaata atcagcctat taaattcaaa ggggtaaacc ggcacgatag cgatcccaaa   6660
acgggatatg ccatttctgt cgctcaagcg gtgactgact tgtcgttaat gaagaaacat   6720
aatattaacg cgattcgtac cgcgcattat ccaaattcac cgtggttttg cgagctttgc   6780
gataagtatg gtttctatgt aatcagtgaa agcgacattg aaagtcatgg ggcggcattc   6840
caagcaattt cgcatcccga accgagtatc tttctgaatg tggaaaatcc gaatgaagag   6900
ccgcgtatcc gccaacaaac tattgacaac ttctgttatt ttgcccgaga accattgtat   6960
cgggcggctt tattggagcg gactaaagca aatatagaac gtgataagaa ccgcagttct   7020
attttaattt ggtctttagg caatgaatca gggtatggtg agaatttcga atattgtgca   7080
aaatgggtaa aagagcggga tccggatcga ttggttcatt acgaaagcag catttatcag   7140
cattctgcgt atcagaataa caccgggcat ttggatttat acagtgaaat gtattccgac   7200
acagaagcaa tcgatgccta ttttgccgat cattcacaaa cgaaaaaacc attcttatta   7260
tgcgaatatt cccatgcaat gggaaattca aatggagata tggaagacta tttccaaaca   7320
tttaacaaat attcgggctg ttgcggtggg tttatttggg agtggtgcga tcatgcccaa   7380
tatattaccc cgacaaaatt aggatatggc ggtgacttcg gcgaaaaaat ccatgatggg   7440
aatttctgtg tggatggctt ggtttcgccc gaacgcgtcc cgcacagcaa cctgttggaa   7500
gtaaaaaatg tcaaccggcc cgtacgggca aacttgcgcg gtgaacaaat tgagttatat   7560
aactattttg atttcactaa tttaaaagat attctttgcg tcaaatatga atgggtaaaa   7620
aatggtcaga taaccgggac gggaacattg gcggttgatt gcgaaccccca tcattctcaa   7680
atcttaccga ttcagcttcc caaagaacgg gaaggattgc tatggttgaa cctatattac   7740
tgcgcttccc ggcaaactga tttattgccg gcaggacatc atttcggttt cgatcaaatt   7800
attttgagta aggaatacac tcctgccata ggatcggata aagatgattg cccgccgttg   7860
gaaataaccg aaacagtgag acaaatcgtt gttcggaaca atcgatatta ttttgaattt   7920
aacaagctca cggggataat tgacgaaatt aaagtcaatg gcaaggcttt catccataaa   7980
ccattggctt ggaatatttg gcgcgcgccg acggataatg accgcctgat tcgttcccaa   8040
tggcaaaatg ccggttatga tcaaatgtat tccaaggttt acgatatttg cgcgcatcgg   8100
caaggaaacg gtgttgtcgt gtctgtgaaa agtgcattgg ttgcggatgc aaaatcaaaa   8160
atcatgacat tggaaacaca gtatctgctg tctgaaaatg gtaaattgga tattcaaaca   8220
aatgctgttt tccacgagca tttgccattc ctgccccgtt tcggtttgcg ctttttctta   8280
```

-continued

```
gacgaacaga aaacaccttt tacctactta ggttatgggg cgggtgaaag ctatattgat   8340
aaacatcagg cgaccaaact tggtatttat tcgacaacgg caggggaaaa tcatgttggc   8400
tatctcaagc ctcaagagaa cggcagccat tatggatgct tttatgttca aaacgatatg   8460
atccgggtgg agtcggggca gccgtttagt ttcaacctgt ccccttatac gcaagaagaa   8520
ctgacgcaga aaaaacattc ttatgaattg gtttgttccg ggtatgatgt attgtgtatc   8580
gactataaga tgagcggtat cggttcgaat tcttgcgggc ctaatttgaa gccgcaatat   8640
cgtttgattg aaaataacat caatttcgat ataagtatcc ggttataagc tttctgcaaa   8700
gattggtatc aacaaaaagc ctgtcgtcag acaggctttt tttctgtttt ctgtttttag   8760
atgccgtctg aatgctgaag tagaaaacca gcaagaaggt aaaaagaaag aagcagtttt   8820
ttggatttta gatgttaccg caattggttt cctttcctaa aatttgttta aattatttgc   8880
aatattaata taaactggat attaatgatg aggattcaaa aaggcatact gaatataatt   8940
tgtacaaaat atttgcagta tttaaaaatg ttggttcgta tatgaaaagt taaaaatgcc   9000
aaaatgtaca gttgctaaac tgtaaaactg ctaaagcaac aaaacataaa aaggaatgca   9060
gggatgcgat cactacatct ttttattccg taagcattta tgactttacg gtcaactgct   9120
actctatgtt tccagctttt cagctcccta ttttcgaata ttggacgagg cattttcatc   9180
agtgtcgtaa tgccgaccga aaccctcaca aaccatattg gttcttgtgg cagcaacacc   9240
tatccgtttg ttcaagcggc cacaagagta acatgattgg ctggtggcat tggctttaat   9300
ctcttcgata tgaactccat ttttagctgc accttctttc agcgtatgca acagtgggga   9360
tggggcaact atcttctggt ggagtttgtt gacttcaatc tgtatgcact gtaggttgag   9420
cagattcagt tttttgatac agattatccg gctttgttcg gcaattctgt tggcgaacgt   9480
atagtagagc tgtcgtcttg ccgctttcaa tttgcggtag gtattttacc attccatgcg   9540
tagccgctcg gtacgtttga gccaaatgtt atcttcgcca tttgtaccaa tttgttttta   9600
cattaggctg tgttttagta atctattgat ttcaattatt tgcaagggaa aagacaatta   9660
ttttccggtt aggaataaac ctatcctatt gaatatattg aagccaagta cgcttatcaa   9720
cactatatta aaacacagcc ttttttaata tagtagacac aatctttcct tatttatgaa   9780
ggtgatagct tctttcagtc tagagacctg caggcatgca agcttggcgt aatcatggtc   9840
atagctgttt cctgtgtgaa attg                                          9864
```

MENINGOCOCCAL INFECTION AND MODIFIED *NEISSERIA LACTAMICA*

CROSS REFERENCE TO RELATED APPLICATIONS

This is the U.S. National Stage of International Application No. PCT/GB2016/053944, filed Dec. 15, 2016, which was published in English under PCT Article 21(2), which in turn claims the benefit of GB Application No. 1522153.4, filed Dec. 15, 2015. The prior GB Application No. 1522153.4 is incorporated herein in its entirety.

The present invention relates to a modified *Neisseria lactamica*, methods of prophylactic treatment with modified *Neisseria lactamica*, methods of mutagenesis of *Neisseria lactamica*, a series of cloning vectors for modifying *Neisseria lactamica*, and modified *Neisseria lactamica*-generated outer membrane vesicles (OMVs).

Asymptomatic oropharyngeal carriage of *Neisseria meningitidis* is common in many communities and in high income counties the highest rates are seen in young adults, particularly in semi closed communities with active social mixing such as educational facilities. In contrast, invasive meningococcal disease, in the form of septicaemia and/or meningitis, has an incidence of <1 per 100,000 persons per annum in most high income countries. In populations vaccinated with glycoconjugate vaccines, disease incidence of the vaccine serogroups is dramatically reduced due to herd protection conferred by reduced carriage and transmission. A large proportion of current meningococcal carriage and disease is due to bacteria expressing serogroup B capsule, for which no glycoconjugate vaccines exist. A new sub-capsular vaccine 4CMenB induces bactericidal antibodies against a range of strains, but the effect on carriage of serogroup B *N. meningitidis* is relatively modest. Reduction of carriage of *N. meningitidis* will be a key strategy in future control of meningococcal disease. A number of studies indicate that carriage of the related but non-invasive *Neisseria lactamica* may confer natural herd protection of infants. Age-specific rates of *N. meningitidis* carriage and disease were inversely proportional to carriage of *N. lactamica* and a modelling study has suggested a mean 4.7 year delay in meningococcal carriage following carriage of *N. lactamica*. The mechanism of this relationship is undetermined, but is unlikely to be due to cross-protective antibody production, as the early years of life that are associated with high rates of *N. lactamica* carriage pre-date considerably the development of natural bactericidal antibodies to *N. meningitidis*. Furthermore, in a controlled infection study, intranasal inoculation of young adults with live *N. lactamica* was followed by development of humoral immunity to *N. lactamica* in those who carried the inoculated strain, but this did not induce significant cross reactive antibodies against *N. meningitidis*.

Outer Membrane Vesicles (OMV) are generated during the growth of the Gram negative bacterium, *Neisseria lactamica* and have been demonstrated to induce immunity to protein antigens following administration to humans. The components of OMV-based vaccines are naturally packaged in a manner that promotes a strong immune response, and have been successfully trialled for use in vaccination against meningococcal disease. The problem with OMV-based vaccines is that the immunity they elicit is constrained by the genetic repertoire of the bacterium from which the OMV is derived, so cross-protective immunity generated in response to exposure to OMV-based vaccine is only against immunogenic antigens that are highly similar in both *Neisseria lactamica* and the closely-related bacterium *Neisseria meningitidis* (the meningococcus). Comparative genomic analyses have repeatedly demonstrated there a large number of important, immunogenic virulence determinants coded for in the meningococcal genome that are absent in the *N. lactamica* genome, meaning that vaccines based on wild type *N. lactamica* OMV would require supplementation with exogenously-derived meningococcal antigens in order to provoke cross-protective immunity to *Neisseria meningitidis* (e.g. a situation similar to 4CMenB vaccine—aka Bexsero™, in which two exogenously-derived meningococcal outer membrane protein conjugates are supplemented into a meningococcal-derived OMV preparation).

In order to modify the outer membrane components of *Neisseria lactamica*, and to have them presented in a biologically and immunologically relevant ('native') orientation in the membrane, it is preferential to introduce genetic material into the genome of *Neisseria lactamica*. This material would contain genes that encode the desired protein components, under the control of either constitutive or inducible gene promoters depending on the relevant application. The transcriptional and translational machinery of the bacterium would then produce the desired antigen and direct it to the membrane. However, despite being a naturally competent bacterial species, which constitutively takes up exogenous DNA from the environment, *Neisseria lactamica* has proven to be refractory to targeted mutagenesis or directed genetic change. As such, there are currently no molecular systems for the manipulation of the *Neisseria lactamica* genome.

An aim of the invention is to improve, or at least provide alternatives to, current methods of treatment or prevention of meningococcal infection and to provide modified *Neisseria lactamica* having enhanced properties for use in such methods.

INVENTION SUMMARY

According to a first aspect of the invention, there is provided a modified *Neisseria lactamica*, wherein the modified *Neisseria lactamica* is transformed with recombinant DNA encoding a heterologous protein.

According to another aspect of the invention, there is provided a method of prophylactic treatment for meningococcal infection of a subject comprising nasopharyngeal inoculation of a modified *Neisseria lactamica*, wherein the modified *Neisseria lactamica* is transformed with recombinant DNA encoding a heterologous protein.

According to another aspect of the invention, there is provided a method of reducing or preventing meningococcal colonisation of a subject comprising nasopharyngeal inoculation of a modified *Neisseria lactamica*, wherein the modified *Neisseria lactamica* is transformed with recombinant DNA encoding a heterologous protein.

According to another aspect of the invention, there is provided a method of modifying the microbiome of a subject comprising nasopharyngeal inoculation of a modified *Neisseria lactamica*, wherein the modified *Neisseria lactamica* is transformed with recombinant DNA encoding a heterologous protein.

According to another aspect of the invention, there is provided a method of modifying the microbiome of a subject comprising nasopharyngeal inoculation of wild-type *Neisseria lactamica.*

According to another aspect of the invention, there is provided a method of preventing meningococcal colonisation of a subject comprising nasopharyngeal inoculation of a wild-type *Neisseria lactamica*.

According to another aspect of the invention, there is provided a method of prophylactic treatment for pathogenic infection of a subject comprising nasopharyngeal inoculation of a modified *Neisseria lactamica*, wherein the modified *Neisseria lactamica* is transformed with recombinant DNA encoding a heterologous protein.

According to another aspect of the invention, there is provided a modified *Neisseria lactamica* for use for the prophylactic treatment of meningococcal infection of a subject, wherein the prophylactic treatment comprises nasopharyngeal inoculation of the modified *Neisseria lactamica*, wherein the modified *Neisseria lactamica* is transformed with recombinant DNA encoding a heterologous protein.

According to another aspect of the invention, there is provided a wild-type *Neisseria lactamica* for use for the prophylactic treatment of meningococcal infection of a subject, wherein the prophylactic treatment comprises nasopharyngeal inoculation of the *Neisseria lactamica*.

According to another aspect of the invention, there is provided a modified *Neisseria lactamica* for use for reducing or preventing colonisation of *Neisseria meningitidis* in a subject, the use comprising nasopharyngeal inoculation of the modified *Neisseria lactamica*, wherein the modified *Neisseria lactamica* is transformed with recombinant DNA encoding a heterologous protein.

According to another aspect of the invention, there is provided a cloning vector for modification of *Neisseria lactamica* comprising one or more Heterologous Antigen Expression Cassettes (HAEC), wherein the HAEC comprises:

- a heterologous nucleic acid sequence insertion site;
- a first promoter, upstream of the heterologous nucleic acid sequence;
- a second promoter, downstream of the heterologous nucleic acid sequence; and
- a selection marker downstream of the second promoter;
- wherein the HAEC is flanked by a sequence homologous to a region of *Neisseria lactamica* chromosome.

According to another aspect of the invention, there is provided a cloning vector for modification of *Neisseria lactamica* comprising one or more *Neisseria* Heterologous Antigen Expression Cassettes (HAEC), wherein the HAEC comprises:

- a heterologous nucleic acid sequence insertion site;
- a selection marker; and
- a promoter upstream of the heterologous nucleic acid sequence insertion site and selection marker;

wherein the HAEC is flanked by a sequence homologous to a region of *Neisseria lactamica* chromosome.

According to another aspect of the invention, there is provided a cloning vector for mutagenesis of *Neisseria lactamica* comprising one or more Heterologous Antigen Expression Cassettes (HAEC), wherein the HAEC comprises:

- a heterologous nucleic acid sequence;
- a first promoter upstream of the heterologous nucleic acid sequence;
- a second promoter downstream of the heterologous nucleic acid sequence; and
- a selection marker downstream of the second promoter;
- wherein the HAEC is flanked by a sequence homologous to a region of *Neisseria lactamica* chromosome.

According to another aspect of the invention, there is provided a cloning vector for mutagenesis of *Neisseria lactamica* comprising one or more Heterologous Antigen Expression Cassettes (HAEC), wherein the HAEC comprises:

- a heterologous nucleic acid sequence;
- a selection marker; and
- a promoter upstream of the heterologous nucleic acid sequence and selection marker;
- wherein the HAEC is flanked by a sequence homologous to a region of *Neisseria lactamica* chromosome.

According to another aspect of the invention, there is provided a nucleic acid for mutagenesis of *Neisseria lactamica* comprising one or more Heterologous Antigen Expression Cassettes (HAEC), wherein the HAEC comprises:

- a heterologous nucleic acid sequence;
- a first promoter upstream of the heterologous nucleic acid sequence;
- a second promoter downstream of the heterologous nucleic acid sequence; and
- a selection marker downstream of the second promoter;
- wherein the HAEC is flanked by a sequence homologous to a region of *Neisseria lactamica* chromosome.

According to another aspect of the invention, there is provided a nucleic acid for mutagenesis of *Neisseria lactamica* comprising one or more Heterologous Antigen Expression Cassettes (HAEC), wherein the HAEC comprises:

- a heterologous nucleic acid sequence;
- a selection marker; and
- a promoter upstream of the heterologous nucleic acid sequence and selection marker;
- wherein the HAEC is flanked by a sequence homologous to a region of *Neisseria lactamica* genome.

According to another aspect of the invention, there is provided a method of mutagenesis of *Neisseria lactamica* comprising transformation of *Neisseria lactamica* with the cloning vector according the invention herein.

According to another aspect of the invention, there is provided a method of mutagenesis of *Neisseria lactamica* comprising transformation of *Neisseria lactamica* with hypermethylated nucleic acid.

According to another aspect of the invention, there is provided an outer membrane vesicle (OMV) vaccine, wherein the OMV is an OMV of the modified *Neisseria lactamica* described herein.

According to another aspect of the invention, there is provided a composition comprising the OMV according to the invention herein; or the modified *Neisseria lactamica* according to the invention herein.

According to another aspect of the invention, there is provided an OMV; modified *Neisseria lactamica*; or composition according to the invention herein for use in a vaccine/vaccination.

According to another aspect of the invention, there is provided a method of vaccination of a subject for the prevention of infection or colonisation of a pathogen comprising the administration of the OMV or the modified *Neisseria lactamica* or the composition according to the invention herein.

This invention describes a process to circumvent the barriers to transformation of *Neisseria lactamica* and allow targeted genetic modification of this organism to be performed for the first time. The invention allows stable integration of DNA constructs into loci of the *Neisseria lactamica* chromosome, with utility for both deletion of existing genes (i.e. targeted mutagenesis) or insertion of genes from other biotic sources.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. The Sequence Listing is submitted as an ASCII text file in the form of the file named "Sequence.txt" (~173 kb), which was created on Jun. 13, 2018 which is incorporated by reference herein.

DETAILED DESCRIPTION

It is understood that reference to protein or nucleic acid "variants", it is understood to mean a protein or nucleic acid sequence that has at least 70%, 80%, 90%, 95%, 98%, 99%, 99.9% identity with the sequence of the fore mentioned protein or nucleic acid. The percentage identity may be calculated under standard NCBI blast p/n alignment parameters. "Variants" may also include truncations of a protein or nucleic acid sequence. The skilled person will understand that various truncations of a protein can still provide a protein which retains its function and/or antigenic activity.

The term "colonisation" is defined as the synthesis of multiple cellular and subcellular processes leading to the retention of a given living organism in close association within, upon or beneath host cells or extracellular matrix. An organism, colonising a surface within a human or animal host, may or may not cause disease, and may be recoverable from that surface by various detection techniques, which would verify the fact that colonization has occurred. Colonisation can be induced by inoculating an organism into the human, so that it lives on a given surface within the body.

The term "heterologous protein" or "heterologous DNA" or "heterologous nucleic acid sequence" is understood to mean that the protein or sequence is derived from a different species or strain relative to the organism, e.g. it is not homologous. In the context of the invention, heterologous may be used interchangeably with "exogenous".

The term "exogenous" refers to any nucleic acid or protein that originates outside of the organism of concern. The term "endogenous" refers to nucleic acid or protein that is originating or produced within the same organism.

The term "homologous DNA" or "homologous nucleic acid sequence" is understood to mean that the sequence is derived from or is of the same structure as the DNA/nucleic acid sequence found in the species or strain of concern.

The term "recombinant DNA" refers to DNA molecules formed by laboratory methods of genetic recombination (such as molecular cloning) to bring together genetic material, perhaps from multiple sources, creating sequences that would not otherwise be found in the organism.

The term "infection", in particular "meningococcal infection" may refer both to the invasive disease state, wherein the meningococcus has penetrated into the blood stream from a colonized mucosal surface and is actively growing within the host, inducing sepsis; and the benign carriage of the meningococcus in the nasopharynx with no adverse effects.

The term "meningococcal colonisation" may refer to benign carriage of the meningococcus in the nasopharynx with no adverse effects.

The term "cassette" may refer to a genetic element that may contain a selection of genetic features such as a gene, a gene insert site, a recombination site, restriction sites, selection markers, promoters and enhancers.

The term "selection marker" is intended to cover a "screening marker" and the terms may be used interchangeably herein. The selection marker is a genetic element, such as an antibiotic resistance gene, that can be used to identify cells carry and expressing the selection marker.

In some of the descriptions herein, the term 'phase variation' will be used to refer to a variety of genetic mechanisms that cause a subset of bacterial cells from a given Neisserial population to silence expression of a narrow range of genes, whilst retaining the nucleotide sequence of the appropriate gene in the chromosome. Phase variation is a stochastic process, driven by a range of molecular mechanisms, and takes place at the level of individual bacteria, such that given populations of bacteria are phenotypically heterologous for a "phase variable" gene product.

In some of the descriptions herein, the term 'construct' may be used in reference to the plasmid/cloning vector under discussion. The term 'cassette' may be used in reference to the part of the construct intended for uptake and assimilation into the genome of *Neisseria lactamica.*

In some of the descriptions herein, the term 'DUS' may be used to refer to the canonical Neisserial DNA Uptake Sequence (5'-GCCGTCTGAA-3') (SEQ ID NO: 1) and 'AT-DUS' may be used to refer to the canonical AT-flanked Neisserial DNA Uptake Sequence (5'-ATGCCGTCTGAA-3') (SEQ ID NO: 2). Where the inverse (i.e. the reverse complement) of either sequence is present and noted as part of any construct (i.e. the canonical version of either element is present in the complementary DNA strand to that containing the coding sequences of the appropriate genes), the prefix 'inv-' may precede the appropriate acronym. In other aspects of the invention, other forms of the Neisserial DNA Uptake Sequences could be substituted (though they would work at reduced efficiency).

In some of the descriptions herein, the term 'NHCIS(X)' may be used to refer to "*Neisseria* Heterologous Construct Insertion Site X", where X represents a number, arbitrarily assigned to an appropriate chromosomal locus in the order of development. NHCIS are areas of relative gene paucity in the *N. lactamica* chromosome, to where exogenous genetic material can be targeted for integration into the genome with minimal disruption to other open reading frames (hereafter, ORF). It should be noted that although there are multiple potential NHCIS loci (based upon data on the size of *N. lactamica* intergenic gaps), the transformation procedure described herein, and detailed in PROTOCOL A allows for any locus to be targeted for chromosomal integration of Cassettes.

In some of the descriptions herein, the term 'HAEC(Y)' may be used to refer to "Heterologous Antigen Expression Construct Y", where Y represents a number, arbitrarily assigned to the HAEC sequence in the order of development. HAEC are tandemly-linked promoter sequences that drive gene expression in *N. lactamica* (but are not necessarily of *N. lactamica* derivation), flanked and punctuated by restriction sites for ease of downstream cloning. The skilled person will understand that any promoter sequence that enables gene expression in bacteria could be incorporated into a HAEC. Constructs and cassettes containing HAEC are referred to as HAEC(Y):(Z)-(Z'), whereby Z and Z' represent the genes placed downstream and under the control of each of the respective promoters contained in the HAEC, in the order of 5' to 3' on the coding strand.

In some of the descriptions herein, the term 'donor material' shall be used to refer to a nucleic acid molecule suitable for uptake by and for chromosomal integration into *N. lactamica*. These molecules can be from any source, including but not limited to: (hypermethylated) PCR products, extracted chromosomal or linearised, plasmid DNA.

Modified *Neisseria lactamica*

According to a first aspect of the invention, there is provided a modified *Neisseria lactamica*, wherein the modified *Neisseria lactamica* is transformed with recombinant DNA encoding a heterologous protein.

In one embodiment, the modified *Neisseria lactamica* is capable of expressing the heterologous protein encoded by the recombinant DNA. In another embodiment, the modified *Neisseria lactamica* expresses the heterologous protein encoded by the recombinant DNA. The expression of the heterologous protein encoded by the recombinant DNA may be inducible or constitutive.

The heterologous protein may comprise a eukaryote protein. The heterologous protein may comprise a viral protein, such as a capsid protein. The heterologous protein may comprise a protein of a non-*Neisseria* prokaryote. The heterologous protein may comprise a protein. The heterologous protein may comprise a protein of a different strain of *Neisseria*. The DNA encoding the heterologous protein may comprise eukaryote DNA. The DNA encoding the heterologous protein may comprise a processed coding sequence (for example, a gene sequence with introns removed). The DNA encoding the heterologous protein may comprise of sequence not found in wild-type *N. lactamica*. The modified *Neisseria lactamica* may be transformed with recombinant DNA encoding two or more heterologous proteins.

The heterologous protein may comprise fluorescent protein, such as green, red, cyan, yellow fluorescent protein, or the like, and their derivatives. The heterologous protein may be CLOVER. The heterologous protein may comprise a protein capable of enabling or enhancing *Neisseria lactamica* colonisation of a subject, for example nasopharyngeal colonisation of the subject. The heterologous protein may comprise meningococcal adhesin NadA, or a functional homologue, variant or derivative thereof. The heterologous protein may comprise an antigen, for example a disease-associated antigen. The heterologous protein may comprise a *Neisseria meningitidis* protein, or a variant or part thereof. The heterologous protein may comprise a *Neisseria meningitidis* antigen. The heterologous protein may comprise a *Neisseria meningitidis* outer membrane protein, or a variant or part thereof. The *Neisseria meningitidis* protein/antigen may comprise *Neisseria meningitidis* serotype A, B, C, Y, W135 and X protein/antigen. The *Neisseria meningitidis* protein/antigen may comprise protein/antigen of non-typeable isolates of *Neisseria meningitidis*. The *Neisseria meningitidis* protein/antigen may comprise PorA. The PorA may comprise (P1.7,16) or PorA (P1.7-2,4). The *Neisseria meningitidis* protein/antigen may comprise any protein/antigen selected from the group comprising heparin sulphate proteoglycan binding protein, Opc (encoded by the opcA gene); NadA; factor H binding protein, fHbp; Heparin-Binding Antigen, NHBA, or Gna2123 (encoded by gna2132 or nhba gene) (see Serruto et al., *Proc Natl Acad Sci USA*. 2010 Feb. 23; 107(8):3770-5); hia/hsf homologue, NhhA (coded for by gna0992) (see Scarselli et al., *Mol Microbiol*. 2006 August; 61(3):631-44. Epub 2006 Jun. 27.); tbpA (transferrin binding protein A); lbpAB (lactoferrin binding protein); *Morexella* IgD binding protein (MID); and variants, derivatives, hybrids or partial fragments thereof; or combinations thereof. In one embodiment, the *Neisseria meningitidis* protein/antigen may comprise Opc. In another embodiment, both Opc and NadA may be provided.

In one embodiment, two or more, such as a plurality of, heterologous proteins may be encoded and/or expressed by the modified *Neisseria lactamica*. In another embodiment, three or more heterologous proteins are encoded and/or expressed by the modified *Neisseria lactamica*.

The recombinant DNA may be stably transformed to provide the modified *Neisseria lactamica*. The recombinant DNA may be chromosomally integrated. The recombinant DNA may be inserted into an intergenic chromosomal sequence. The intergenic chromosomal sequence may be between genes NLY_27080 and NLY_27100 of *Neisseria lactamica* strain Y92-1009, or equivalent loci thereof in other *Neisseria lactamica* strains. The intergenic chromosomal sequence may be between genes NLY_36160 and NLY_36180 of *Neisseria lactamica* strain Y92-1009, or equivalent loci thereof in other *Neisseria lactamica* strains. In one embodiment, the recombinant DNA is inserted into the NHCIS loci of the modified *Neisseria lactamica*. The recombinant DNA may be inserted into NHCIS1 or NHCIS2. The recombinant DNA may be inserted into NHCIS1 or NHCIS2, or an equivalent thereof in other *Neisseria lactamica* strains. NHCIS1 and NHCIS2 may allow expression of protein/antigen at different levels relative to each other. Therefore, if a high level of protein expression is desired, then the gene coding for the heterologous protein can be inserted into NHCIS2; conversely, genes coding for either potentially toxic products, or proteins that have a detrimental, concentration-dependent effect on the host organism can be inserted into NHCIS1 for a lower level of expression relative to NHCIS2 inserts. Alternatively if a high level of protein expression is desired, then the gene coding for the heterologous protein can be inserted into NHCIS1; conversely, genes coding for either potentially toxic products, or proteins that have a detrimental, concentration-dependent effect on the host organism can be inserted into NHCIS2 for a lower level of expression relative to NHCIS1 inserts.

In another embodiment, the recombinant DNA may not be inserted into an intergenic chromosomal sequence. The recombinant DNA may not be inserted into an essential gene (i.e. a gene essential for survival and/or growth of *N. lactamica*). The recombinant DNA may not be inserted into a wild-type *N. lactamica* gene. The recombinant DNA may not be inserted into a wild-type *N. lactamica* operon. The recombinant DNA may not be inserted into a wild-type *N. lactamica* regulatory sequence. The recombinant DNA may comprise part of a gene or genes flanking an intergenic sequence.

The DNA encoding the heterologous protein (i.e. the endogenous or heterologous gene to be inserted) may be at least 600 bp in length. In another embodiment, the DNA encoding the heterologous protein may be at least 800 bp in length. In another embodiment, the DNA encoding the heterologous protein may be at least lkbp in length. In another embodiment, the DNA encoding the heterologous protein may be at least 1.5 kbp in length.

The *Neisseria lactamica* may comprise *Neisseria lactamica* Y92-1009. The skilled person will understand that other *Neisseria lactamica* isolates may be suitable for modification according to the invention herein.

In one embodiment the modified *Neisseria lactamica* is a β-galactosidase (lacZ) deficient mutant (ΔlacZ). The modified *Neisseria lactamica* may not comprise a functional or non-functional wild-type lacZ gene. The modified *Neisseria lactamica* may not comprise any substantial parts of the wild-type lacZ gene. Substantial parts of the wild-type lacZ gene sequence may comprise at least 10 nucleotides of the wild-type lacZ gene sequence.

Advantageously, providing a modified *Neisseria lactamica* with no wild-type lacZ gene or parts thereof, minimises the chance of undesirable homologous recombinations where lacZ may be used as a selection marker on a cloning vector for transforming the modified *Neisseria lactamica*.

Therefore, according to another aspect of the present invention, there is provided a modified *Neisseria lactamica*, wherein the modified *Neisseria lactamica* does not comprise wild type lacZ gene sequence, or substantial parts thereof.

The modified *Neisseria lactamica* may have been derived from a wild-type strain of *Neisseria lactamica* that normally has a functional lacZ gene. Such a wild-type strain may be modified to form the modified *Neisseria lactamica* by lacZ gene knockout or substantial removal of lacZ gene sequence.

Advantageously, the provision of a modified *Neisseria lactamica* with wild type lacZ gene sequence, or substantial parts thereof removed from the chromosome can avoid non-specific recombination events with Nlac lacZ-containing Cassettes and concomitant mis-targeting of the Cassette to loci other than that intended. This strain provides a background for insertion of genes coding for heterologous proteins without need for antibiotic resistance markers, a preferred state for potential human challenge with recombinant *Neisseria lactamica*.

In one embodiment the modified *Neisseria lactamica* is a β-galactosidase (lacZ) deficient mutant (ΔlacZ), which is also deficient for the *Neisseria* Heparin Binding Antigen (NHBA or Gna2132). The modified *Neisseria lactamica* may not comprise a functional or non-functional wild-type lacZ gene. The modified *Neisseria lactamica* may not comprise any substantial parts of the wild-type lacZ gene. Substantial parts of the wild-type lacZ gene sequence may comprise at least 10 nucleotides of the wild-type lacZ gene sequence. The modified *Neisseria lactamica* may not comprise a functional or non-functional wild-type nhba gene. The modified *Neisseria lactamica* may not comprise any substantial parts of the wild-type nhba gene. Substantial parts of the wild-type nhba gene sequence may comprise at least 10 nucleotides of the wild-type nhba gene sequence.

The modified *Neisseria lactamica* may comprise a synthetic version (i.e. not wild-type) of the lacZ gene (synth-.lacZ), in which the coding sequence has been modified to diversify the sequence from the endogenous Nlac version of the lacZ gene, whilst maintaining the fidelity of the encoded amino acid sequence of β-galactosidase. In one embodiment, the synthetic version of the lacZ gene may comprise the sequence of SEQ ID NO: 20 (FIG. 37) or a variant thereof. A variant of the synthetic version of the lacZ gene may comprise may comprise a sequence of at least 80% identity with the sequence of SEQ ID NO: 20 (FIG. 37), whilst maintaining β-galactosidase function. In another embodiment, a variant of the synthetic version of the lacZ gene may comprise a sequence of at least 85%, 90%, 95%, 98%, 99%, or 99.5% identity with the sequence of SEQ ID NO: 20 (FIG. 37), whilst maintaining β-galactosidase function. The skilled person will understand that fewer or more amino acid substitutions which either diversify the sequence away from wild-type or conform the sequence back towards wild-type may be envisaged, and still retain function and sufficient diversity to avoid inadvertent recombination with wild-type sequence. For example, up to 40% of the substitutions to form the synthetic lacZ gene may be reverted back to wild-type (although with an increased likelihood of inadvertent recombination). In another embodiment, up to 5%, 10%, 15%, 20%, 25% or 30% of the substitutions to form the synthetic lacZ gene may be reverted back to wild-type.

Providing a synthetic version of the lacZ gene advantageously introduces a functional copy of the lacZ gene back into the chromosome of a modified Nlac strain having a previously knocked out lacZ gene via an heterologous nucleic acid insertion, so that 3-galactosidase activity is maintained. For example, double mutants encoding heterologous NadA and Opc can retain β-galactosidase activity.

The recombinant DNA may further comprise a selection marker. The selection marker may be expressed under the control of an exogenous promoter. The selection marker may be heterologous to wild-type *N. lactamica*. The selection marker may comprise a *Neisseria lactamica* β-galactosidase (lacZ) gene or a non-*Neisseria lactamica* β-galactosidase (lacZ) gene. The selection marker may comprise the synthetic lacZ gene described herein. In one embodiment, the selection marker may not comprise an antibiotic resistance marker/gene. In one embodiment, the selection marker may comprise any one of kanamycin, spectinomycin, erythromycin, tetracycline, or gentamycin resistance genes.

The recombinant DNA may encode a promoter. In one embodiment, the recombinant DNA encodes at least two promoters. The promoter may promote expression of the gene encoding the heterologous protein and/or the selection marker. In embodiments where at least two promoters are encoded, a first promotor may promote expression of the heterologous protein and a second promoter may promote expression of the selection marker, or vice versa. The first and second promoters may be constitutive promoters. Alternatively, the first and second promoters may be inducible promoters. Alternatively, first promoter may be constitutive and the second promoter may be inducible, or vice versa.

The first and/or second promoter may comprise a *Neisseria lactamica* promoter. i.e. a promoter that is recognised by the transcriptional apparatus of *Neisseria lactamica* and capable of promoting expression in *Neisseria lactamica*. The first and second promoters may be different, for example, a different promoter sequence. The first and second promotors may be promotors originating from different genes.

The first promoter may comprise the promoter from the α-2,3 sialyltransferase (lst) gene. Alternatively, the second promoter may comprise the promoter from the α-2,3 sialyltransferase (lst) gene.

The second promotor may comprise the promotor for the gene coding for Porin B (porB). Alternatively, the second promotor may comprise the promotor for the gene coding for Porin B (porB).

In one embodiment, the first promoter comprises the promoter from the α-2,3 sialyltransferase (lst) gene and the second promotor comprises the promotor for the gene coding for Porin B (porB). In an alternative embodiment, the first promoter comprises the promoter for the gene coding for Porin B (porB) and the second promotor comprises the promotor from the α-2,3 sialyltransferase (lst) gene.

The first promotor may be a constitutive or inducible gene promoter. The second promoter may be a constitutive or inducible gene promoter. The first promotor may be a constitutive promoter and the second promoter may be an inducible promoter, or vice versa. The inducible promoter may be a phase variable promoter.

Advantageously, using a first promoter, such as a constitutive promoter or an inducible promoter, would express a large amount of an antigen, for example in quantities similar to wild type *N. meningitidis*. In instances where the host develops an immune response against that antigen, then it could potentially lead to immune clearance of the modified *N. lactamica* and a termination of colonisation. In an alternative embodiment using a phase variable promoter, a subset of the modified *N. lactamica* population—those with the antigen in the phase OFF position—may escape immunological clearance, persist in the nasopharynx and be present later on to re-express the gene (in the subset of the survivor population that revert to the phase ON phenotype). This can effectively constitute a re-challenge with the antigen of choice and potentially serve to mature an immune response against the target protein.

The first promoter may comprise the hybrid porA/porB promoter described herein. Alternatively, the second promoter may comprise hybrid porA/porB promoter described herein. The porA sequence may be a modified form having the 5' polyadenosine tract removed.

An enhancer sequence may also be provided with the promoter. The enhancer may comprise a 200 bp sequence upstream of the −35 box of the RNA Polymerase binding site. The enhancer may comprise a 250 bp sequence upstream of the −35 box of the RNA Polymerase binding site. In one embodiment, the enhancer is a native enhancer for the promoter. In one embodiment, the enhancer is a porA enhancer (see FIG. 25 and FIG. 26).

A hybrid promoter may be provided having a hybrid porA/porB promoter coupled with a porA enhancer (for example see FIG. 25 and FIG. 26). The hybrid porA/porB promoter may comprise a porA sequence wherein the homopolymeric tract of 'G' nucleotides (that renders the wild type porA gene phase variable) has been replaced with sequence derived from the wild type, non-phase variable porB promoter of *N. lactamica*. A hybrid promoter may be provided having the promoter from the sialyltransferase gene coupled with aporA enhancer (see FIG. 21).

The promoter with enhancer sequence may comprise or consist of the sequence of any one of lst:lacZ; lst(50):lacZ; lst(100):lacZ; lst(150):lacZ; lst(200):lacZ; lst(250):lacZ; or lst(400):lacZ as depicted in FIG. 21. Variants of such promoter and enhancer sequences may be provided, for example lst(1-400):lacZ with 1-400 denoting the length of the sequence extending 5' from the promoter in accordance to FIG. 21. The variant may comprise lst(50-400):lacZ or lst(100-300):lacZ or lst(150-250):lacZ.

The hybrid porA/porB promoter may be preceded by 200 bp or 250 bp of transcriptional enhancer sequence, derived from the wild type porA gene of *N. meningitidis*. The porA/porB hybrid promoter may be followed (3') by a second hybrid promoter, wherein the 17 bp that separate the −10 and −35 boxes of the RNA Polymerase binding site of the wild type porB gene have been replaced with 17 bp of sequence derived from the lst promoter.

The hybrid, synthetic promoters advantageously combine elements of the various wild type promoters, along with the enhancer sequence of porA to ensure they remain phase on, and express the genes they control to high levels.

In one embodiment, the promoter sequence comprises a homopolymeric 'G' tract, which separates the −10 and −35 boxes of the promoter, such as the wild type porA promoter. The homopolymeric 'G' tract may comprise about 9 to 17 contiguous guanosine nucleotide residues. The homopolymeric 'G' tract may comprise about 9 to 15 contiguous guanosine nucleotide residues. The homopolymeric 'G' tract may comprise about 10 to 15 contiguous guanosine nucleotide residues. The homopolymeric 'G' tract may comprise about 10 to 12 contiguous guanosine nucleotide residues. In one embodiment, the homopolymeric 'G' tract comprises or consists of 11 contiguous guanosine nucleotide residues. In another embodiment, the homopolymeric 'G' tract comprises or consists of 10 contiguous guanosine nucleotide residues.

In another embodiment, the recombinant DNA may be promoterless, but is inserted into a chromosomal site under the influence of an endogenous promoter.

In one embodiment, the modified *N. lactamica* is modified by chromosomal integration of an endogenous gene to enhance expression of the endogenous gene. In another embodiment, the modified *N. lactamica* is modified by chromosomal integration of an endogenous gene that has been modified to enhance a property and/or expression of the endogenous gene. In another embodiment, the modified *N. lactamica* is modified by chromosomal integration of a regulatory element, such as a promoter and/or enhancer, which can enhance expression of an endogenous gene.

Reducing meningococcal colonisation and prophylactic inoculation of modified *Neisseria lactamica*

According to another aspect of the invention, there is provided a method of prophylactic treatment for pathogenic infection of a subject comprising nasopharyngeal inoculation of a modified *Neisseria lactamica*, wherein the modified *Neisseria lactamica* is transformed with recombinant DNA encoding a heterologous protein.

The pathogenic infection may comprise meningococcal infection.

According to another aspect of the invention, there is provided a method of reducing or preventing meningococcal colonisation of a subject comprising nasopharyngeal inoculation of a modified *Neisseria lactamica*, wherein the modified *Neisseria lactamica* is transformed with recombinant DNA encoding a heterologous protein.

The meningococcal colonisation may comprise colonisation of *Neisseria meningitidis.*

According to another aspect of the invention, there is provided a method of modifying the microbiome of a subject comprising nasopharyngeal inoculation of a modified *Neisseria lactamica*, wherein the modified *Neisseria lactamica* is transformed with recombinant DNA encoding a heterologous protein.

According to another aspect of the invention, there is provided a method of modifying the microbiome of a subject comprising nasopharyngeal inoculation of wild-type *Neisseria lactamica.*

According to another aspect of the invention, there is provided a method of preventing meningococcal colonisation of a subject comprising nasopharyngeal inoculation of a wild-type *Neisseria lactamica.*

According to another aspect of the invention, there is provided a method of prophylactic treatment for pathogenic infection of a subject comprising nasopharyngeal inoculation of a modified *Neisseria lactamica*, wherein the modified *Neisseria lactamica* is transformed with recombinant DNA encoding a heterologous protein.

According to another aspect of the invention, there is provided a modified *Neisseria lactamica* for use for the prophylactic treatment of meningococcal infection of a subject, wherein the prophylactic treatment comprises nasopharyngeal inoculation of the modified *Neisseria lactamica*, wherein the modified *Neisseria lactamica* is transformed with recombinant DNA encoding a heterologous protein.

According to another aspect of the invention, there is provided a wild-type *Neisseria lactamica* for use for the prophylactic treatment of meningococcal infection of a subject, wherein the prophylactic treatment comprises nasopharyngeal inoculation of the *Neisseria lactamica.*

According to another aspect of the invention, there is provided a modified *Neisseria lactamica* for use for reducing or preventing colonisation of *Neisseria meningitidis* in a subject, the use comprising nasopharyngeal inoculation of the modified *Neisseria lactamica*, wherein the modified *Neisseria lactamica* is transformed with recombinant DNA encoding a heterologous protein.

Advantageously, the invention provides a prophylactic means of displacing resident *N. meningitidis* and preventing the (re-)acquisition of new *N. meningitidis* into the nasopharynx. The invention promotes herd immunity in a given population of humans, on the basis that the presence of *Neisseria lactamica* in the nasopharynx prevents co-colonisation with the more pathogenic *N. meningitidis*. If the *N. meningitidis* is not present in an individual's nasopharynx then it cannot be transmitted to other individuals; meaning it cannot possibly cause disease in these other individuals. During epidemic spread of a meningococcal outbreak, close contacts of patients with meningococcal disease can be prophylactically administered *Neisseria lactamica*, as a cheap alternative to antibiotic prophlyaxis.

The modified *Neisseria lactamica* for use for the prophylactic treatment of meningococcal infection may be according the invention herein described. The modified *Neisseria lactamica* for use for reducing or preventing colonisation of *Neisseria meningitidis* in a subject may be according the invention herein described.

The meningococcal infection may comprise *Neisseria meningitidis* serotype A, B, C, Y, W-135, and/or X infection. The meningococcal infection may comprise non-typeable *Neisseria meningitidis*. The *Neisseria meningitidis* colonisation may comprise *Neisseria meningitidis* serotype A, B, C, Y, W135 and/or X colonisation. The *Neisseria meningitidis* colonisation may comprise non-typeable *Neisseria meningitidis*. In one embodiment, the *Neisseria meningitidis* comprises *Neisseria meningitidis* serotype B.

The modified or wild-type *Neisseria lactamica* may be provided in a suspension. The suspension may comprise between about $2\times10^2$ per ml and about $2\times10^8$ per ml of the modified or wild-type *Neisseria lactamica*. The suspension may comprise between about $2\times10^2$ per ml and about $2\times10^7$ per ml of the modified or wild-type *Neisseria lactamica*. The suspension may comprise between about $2\times10^2$ per ml and about $2\times10^6$ per ml of the modified or wild-type *Neisseria lactamica*. Alternatively, the suspension may comprise between about $2\times10^3$ per ml and about $2\times10^5$ per ml of the modified or wild-type *Neisseria lactamica*. Alternatively, the suspension may comprise about $2\times10^4$ per ml of the modified or wild-type *Neisseria lactamica*. The suspension may comprise PBS buffer. The suspension of modified or wild-type *Neisseria lactamica* may comprise a pharmaceutically acceptable carrier. In one embodiment, the pharmaceutically acceptable carrier comprises glycerol. The pharmaceutically acceptable carrier may comprise Frantz medium. Alternatively, the pharmaceutically acceptable carrier may comprise Frantz medium with glycerol. The glycerol may be provided in an amount of between 20% and 40% v/v. The glycerol may be provided in an amount of about 30% v/v.

In one embodiment, the nasopharyngeal inoculation of the modified *Neisseria lactamica* comprises exposing nasopharyngeal tissue of the subject to the modified *Neisseria lactamica*. In one embodiment, the nasopharyngeal inoculation of the modified *Neisseria lactamica* comprises applying a suspension of the modified *Neisseria lactamica* onto nasopharyngeal tissue of the subject. The exposure/application may be by spraying, or by droplet of a modified *Neisseria lactamica* suspension. The exposure/application may be by drinking and swilling a suspension of the modified *Neisseria lactamica* around the mouth.

The modified *Neisseria lactamica* may comprise an inducible promoter, which only promotes significant expression of a gene in the presence of an inducer agent. Additionally or alternatively, the modified *Neisseria lactamica* may comprise a transient gene, which is only expressed in one, two or three generations of the modified *Neisseria lactamica.*

In an embodiment, wherein the modified *Neisseria lactamica* comprises an inducible promoter the subject may be administered with an agent capable of inducing the promoter. The administration may be concurrent with inoculation of the modified *Neisseria lactamica*, pre-inoculation of the modified *Neisseria lactamica*, or post-inoculation of the modified *Neisseria lactamica.*

*Neisseria lactamica* Cloning Vector

According to another aspect of the invention, there is provided a cloning vector for modification of *Neisseria lactamica* comprising one or more Heterologous Antigen Expression Cassettes (HAEC), wherein the HAEC comprises:

- a heterologous nucleic acid sequence insertion site;
- a first promoter, upstream of the heterologous nucleic acid sequence;
- a second promoter, downstream of the heterologous nucleic acid sequence; and
- a selection marker downstream of the second promoter;
- wherein the HAEC is flanked by a sequence homologous to a region of *Neisseria lactamica* chromosome.

Each flanking sequence homologous to a region of *Neisseria lactamica* genome may be between about 50 bp and about 1500 bp. In another embodiment, each flanking sequence homologous to a region of *Neisseria lactamica* genome may be between about 75 bp and about 1200 bp. In another embodiment, each flanking sequence homologous to a region of *Neisseria lactamica* genome may be between about 100 bp and about 1200 bp. In another embodiment, each flanking sequence homologous to a region of *Neisseria lactamica* genome may be between about 200 bp and about 1200 bp. In another embodiment, each flanking sequence homologous to a region of *Neisseria lactamica* genome may be between about 100 bp and about 1000 bp.

According to another aspect of the invention, there is provided a cloning vector for modification of *Neisseria lactamica* comprising one or more *Neisseria* Heterologous Antigen Expression Cassettes (HAEC), wherein the HAEC comprises:

- a heterologous nucleic acid sequence insertion site;
- a selection marker; and
- a promoter upstream of the heterologous nucleic acid sequence insertion site and selection marker;
- wherein the HAEC is flanked by a sequence homologous to a region of *Neisseria lactamica* chromosome.

In one embodiment, the modification of *Neisseria lactamica* may be mutagenesis of *Neisseria lactamica*. The mutagenesis may comprise a double crossover event, leading to recombination of the heterologous expression construct into the chromosome of *Neisseria lactamica.*

The heterologous nucleic acid sequence insertion site may comprise a restriction enzyme recognition sequence. The heterologous nucleic acid sequence insertion site may comprise a multiple cloning site, for example, a region of DNA comprising a plurality of different restriction enzyme recognition sequences. The restriction enzyme recognition sequence may be for recognition of a restriction enzyme which leaves blunt ends, or nucleotide overhangs. The restriction enzyme recognition sequence may be for recognition of a restriction enzyme selected from BamHI, XbaI, SalI, XhoI, NotI, NdeI, and HindIII, or combinations thereof.

Advantageously, providing nucleotide overhangs provides the ability to select or design heterologous nucleic acid sequences that will orientate in a preferred orientation (directional cloning).

In one embodiment, a heterologous nucleic acid sequence may be provided in the heterologous nucleic acid sequence insertion site.

Therefore, according to another aspect of the invention, there is provided a cloning vector for mutagenesis of *Neisseria lactamica* comprising one or more Heterologous Antigen Expression Cassettes (HAEC), wherein the HAEC comprises:
- a heterologous nucleic acid sequence;
- a first promoter upstream of the heterologous nucleic acid sequence;
- a second promoter downstream of the heterologous nucleic acid sequence; and
- a selection marker downstream of the second promoter;
- wherein the HAEC is flanked by a sequence homologous to a region of *Neisseria lactamica* chromosome.

According to another aspect of the invention, there is provided a cloning vector for mutagenesis of *Neisseria lactamica* comprising one or more Heterologous Antigen Expression Cassettes (HAEC), wherein the HAEC comprises:
- a heterologous nucleic acid sequence;
- a selection marker; and
- a promoter upstream of the heterologous nucleic acid sequence and selection marker;
- wherein the HAEC is flanked by a sequence homologous to a region of *Neisseria lactamica* chromosome.

According to another aspect of the invention, there is provided a nucleic acid for mutagenesis of *Neisseria lactamica* comprising one or more Heterologous Antigen Expression Cassettes (HAEC), wherein the HAEC comprises:
- a heterologous nucleic acid sequence;
- a first promoter upstream of the heterologous nucleic acid sequence;
- a second promoter downstream of the heterologous nucleic acid sequence; and
- a selection marker downstream of the second promoter;
- wherein the HAEC is flanked by a sequence homologous to a region of *Neisseria lactamica* chromosome.

According to another aspect of the invention, there is provided a nucleic acid for mutagenesis of *Neisseria lactamica* comprising one or more Heterologous Antigen Expression Cassettes (HAEC), wherein the HAEC comprises:
- a heterologous nucleic acid sequence;
- a selection marker; and
- a promoter upstream of the heterologous nucleic acid sequence and selection marker;
- wherein the HAEC is flanked by a sequence homologous to a region of *Neisseria lactamica* genome.

The nucleic acid may be a cloning vector. The nucleic acid may be a PCR product. The nucleic acid may be a hypermethlyated PCR product. Additionally or alternatively, the nucleic acid may be devoid of one or more restriction enzyme recognition sites selected from NlaI, NlaII, Drg, NlaIII, NlaIV and NgoMIV recognition sites, or combinations thereof.

The heterologous expression construct may comprise a Heterologous Antigen Expression Cassette (HAEC). The heterologous expression construct may comprise the sequence of HAEC1 (see FIG. 12), HAEC2 (see FIG. 13), HAEC3 (see FIG. 25), or HAEC4 (see FIG. 26).

The HAEC may encode an antigen, for example which is heterologous for *Neisseria lactamica*. Alternatively, the HAEC may encode an antigen, for example which is homologous for *Neisseria lactamica.*

The promoter, such as the first and/or second promoter may comprise a *Neisseria lactamica* promoter. i.e. a promoter that is recognised and capable of promoting expression in *Neisseria lactamica*. The first and second promoters may be different, for example, a different promoter sequence. The first and second promotors may be promotors originating from different genes.

The promoter, such as the first promoter, may comprise the promoter from the sialyltransferase gene. Alternatively, the second promoter may comprise the promoter from the sialyltransferase gene.

The promoter, such as the first promoter, may comprise the promoter for the gene coding for Porin B (porB). Alternatively, the second promoter may comprise the promoter for the gene coding for Porin B (porB). The first promoter may comprise the hybrid porA/porB promoter described herein. Alternatively, the second promoter may comprise hybrid porA/porB promoter described herein.

An enhancer sequence may also be provided with the promoter. The enhancer may comprise a 200 bp sequence upstream of the −35 box of the RNA Polymerase binding site. The enhancer may comprise a 250 bp sequence upstream of the −35 box of the RNA Polymerase binding site. In one embodiment, the enhancer is a native enhancer for the promoter. In one embodiment, the enhancer is a porA enhancer (see FIG. 25 and FIG. 26).

A hybrid promoter may be provided having a hybrid porA/porB promoter coupled with a porA enhancer (for example see FIG. 25 and FIG. 26). The hybrid porA/porB promoter may comprise a porA sequence wherein the homopolymeric tract of 'G' nucleotides (that renders the wild type porA gene phase variable) has been replaced with sequence derived from the wild type, non-phase variable porB promoter of *N. lactamica.*

A hybrid promoter may be provided having the promoter from the sialyltransferase gene coupled with aporA enhancer (see FIG. 21).

The promoter with enhancer sequence may comprise or consist of the sequence of any one of lst:lacZ; lst(50):lacZ; lst(100):lacZ; lst(150):lacZ; lst(200):lacZ; lst(250):lacZ; or lst(400):lacZ as depicted in FIG. 21. Variants of such promoter and enhancer sequences may be provided, for example lst(1-400):lacZ with 1-400 denoting the length of the sequence extending 5' from the promoter in accordance to FIG. 21. The variant may comprise lst(50-400):lacZ or lst(100-300):lacZ or lst(150-250):lacZ.

The hybrid porA/porB promoter may be preceded by 200 bp or 250 bp of transcriptional enhancer sequence, derived from the wild type porA gene of *N. meningitidis*. The porA/porB hybrid promoter may be followed (3') by a second hybrid promoter, wherein the 17 bp that separate the −10 and −35 boxes of the RNA Polymerase binding site of the wild type porB gene have been replaced with 17 bp of sequence derived from the lst promoter.

The hybrid, synthetic promoters advantageously combine elements of the various wild type promoters, along with the enhancer sequence of porA to ensure they remain phase on, and express the genes they control to high levels.

In one embodiment, the promoter sequence comprises a homopolymeric 'G' tract, which separates the −10 and −35 boxes of the promoter, such as the wild type porA promoter. The homopolymeric 'G' tract may comprise about 9 to 17 contiguous guanosine nucleotide residues. The homopolymeric 'G' tract may comprise about 9 to 15 contiguous guanosine nucleotide residues. The homopolymeric 'G' tract may comprise about 10 to 15 contiguous guanosine nucleotide residues. The homopolymeric 'G' tract may comprise about 10 to 12 contiguous guanosine nucleotide residues. In one embodiment, the homopolymeric 'G' tract comprises or consists of 11 contiguous guanosine nucleotide residues. In another embodiment, the homopolymeric 'G' tract comprises or consists of 10 contiguous guanosine nucleotide residues.

In one embodiment, the first promoter comprises the promoter from the sialyltransferase (lst) gene and the second promotor comprises the promotor for the gene coding for Porin B (porB). In an alternative embodiment, the first promoter comprises the promoter for the gene coding for Porin B (porB) and the second promotor comprises the promotor from the sialyltransferase (lst) gene.

The first promotor may be a constitutive or inducible gene promoter. The second promoter may be a constitutive or inducible gene promoter. The first promotor may be a constitutive promoter and the second promoter may be an inducible promoter, or vice versa.

The selection marker may comprise a β-galactosidase (lacZ) gene. In one embodiment, the selection marker comprises a *Neisseria lactamica* β-galactosidase (lacZ) gene. In an embodiment wherein two or more HAEC are provided, each HAEC may comprise a different β-galactosidase (lacZ) gene, for example from different natural or synthetic sources. In one embodiment, the selection marker may not comprise an antibiotic resistance marker. In one embodiment, the selection marker may comprise any one of kanamycin, spectinomycin, erythromycin, tetracycline, or gentamycin resistance genes.

The promoter, such as the first and/or second promoter sequences may be flanked by a plurality of unique restriction sites. The term "unique" is understood to mean that a restriction site is provided only once in the cloning vector sequence.

The nucleic acid, such as the cloning vector, PCR product or heterologous expression construct, may comprise a canonical Neisserial DNA Uptake Sequence (DUS), for example 5'-GCCGTCTGAA-3' (SEQ ID NO: 1), or a reverse compliment thereof. The nucleic acid may comprise a canonical AT-flanked Neisserial DNA Uptake Sequence (AT-DUS), for example 5'-ATGCCGTCTGAA-3' (SEQ ID NO: 2), or a reverse compliment thereof.

Figure 9:
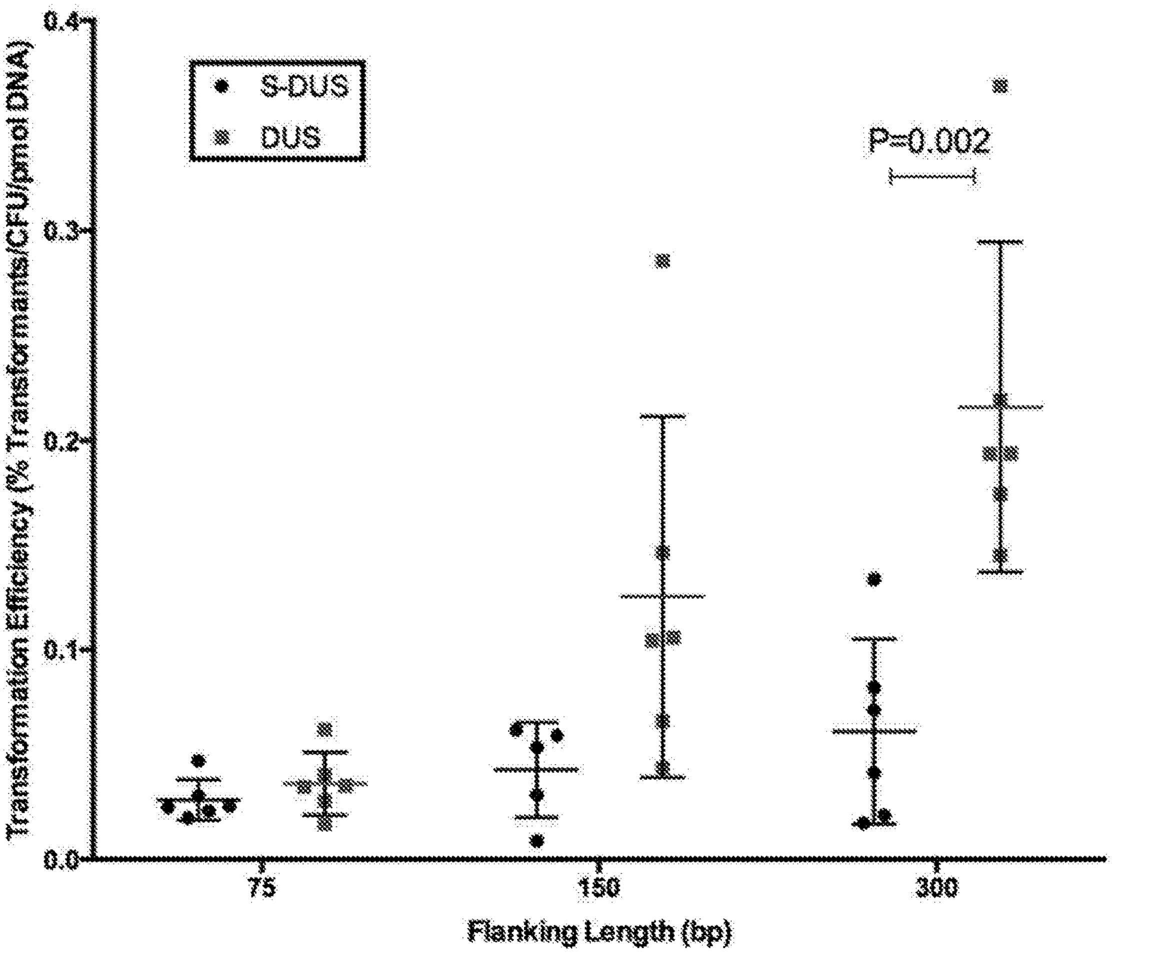

Advantageously, the provision of a Neisserial DNA Uptake Sequence (DUS) or AT-flanked Neisserial DNA Uptake Sequence (AT-DUS) in the nucleic acid can enhance uptake of the nucleic acid during transformation (see FIG. 9).

The nucleic acid may be suitable for uptake by, and for chromosomal integration into, *N. lactamica*. The nucleic acid may be from any source, for example selected from PCR product, hypermethylated PCR product, extracted chromosomal DNA, or plasmid DNA. The nucleic acid may be provided in linearised form.

The heterologous nucleic acid may be hypermethylated, whereby all the deoxycytosine residues of the heterologous nucleic acid have been replaced with methyl-deoxycytosine. The heterologous expression construct and flanking homologous sequences may be hypermethylated, whereby all the deoxycytosine residues of the heterologous nucleic acid have been replaced with methyl-deoxycytosine. In one embodiment, the cloning vector may be hypermethylated, whereby all the deoxycytosine residues of the cloning vector have been replaced with methyl-deoxycytosine.

In one embodiment, the heterologous expression cassette and flanking homologous sequences may not comprise one or more NlaIII restriction recognition sites. The heterologous expression construct and flanking homologous sequences may not comprise the sequence 5'-CATG-3'. In one embodiment, the heterologous expression construct and flanking homologous sequences may not comprise any one of NlaI, NlaII, Drg, NlaIII, NlaIV and NgoMIV recognition sites, or combinations thereof. In one embodiment, the heterologous nucleic acid may not comprise a NlaIII restriction recognition site. The heterologous nucleic acid may not comprise the sequence 5'-CATG-3'. In one embodiment, heterologous nucleic acid may not comprise any one of NlaI, NlaII, Drg, NlaIII, NlaIV and NgoMIV recognition sites, or combinations thereof. In one embodiment, the cloning vector may not comprise a NlaIII restriction recognition site. The cloning vector may not comprise the sequence 5'-CATG-3'. In one embodiment, the cloning vector may not comprise any one of NlaI, NlaII, Drg, NlaIII, NlaIV and NgoMIV recognition sites, or combinations thereof.

The transformation efficiency of *N. lactamica* is highest when the cloning vector is hypermethylated PCR product, but other sources of nucleic acid can successfully transform *N. lactamica*, albeit at lower efficiency. With properly-designed constructs that are free of 'CATG' sequences (NlaIII restriction enzyme cut sites), it is possible to successfully transform *N. lactamica* with normal PCR products (at very low efficiency). In particular, despite being a naturally competent bacterial species, which constitutively takes up exogenous DNA from the environment, *Neisseria lactamica* has proven to be refractory to targeted mutagenesis or directed genetic change. The most likely cause of this is the battery of restriction enzymes encoded in the genome of *Neisseria lactamica*, most notably the 4-cutter restriction enzyme, NlaIII, which cuts dsDNA at the short palindromic sequence 'CATG'. In the absence of selective pressure against the accumulation of these sequences, this motif can occur with relatively high frequency in a given stretch of nucleotides, meaning that uptake of DNA containing one or more of these sequences results in the intracellular degradation of the material before homologous recombination can take place and integrate the exogenous DNA into the *Neisseria lactamica* chromosome. As such, there are currently no molecular systems for the manipulation of the *Neisseria lactamica* genome. Advantageously, this invention circumvents the barriers to transformation of *Neisseria lactamica* and allows targeted genetic modification of this organism for the first time. In particular, methylation of restriction sites can inhibit the DNA cleavage action of restriction endonucleases (see FIG. 7), which prevents degradation of the product following uptake and therefore provides sufficient time for homologous recombination to take place and the construct to become integrated into the chromosomal locus of choice. This allows stable integration of DNA constructs into loci of the *Neisseria lactamica* chromosome, with utility for both deletion of existing genes (i.e. targeted mutagenesis) or insertion of genes from other sources, such as genes from other Gram negative bacteria and eukaryotic proteins.

The cloning vector may be modified from the standard cloning vector pUC19 (Norrander et al, Gene 1983 December; 26(1):101-6.). For example, the cloning vector may comprise pUC19 sequence, or substantial parts thereof. The cloning vector may comprise pUC19 sequence, or substantial parts thereof, with the lacZ promotor encoding sequence removed. The cloning vector may comprise the pUC19NHCIS(X)::HAEC(Y):(Z)-lacZ vector system described herein. In one embodiment, the cloning vector may comprise pUC19NHCIS1::HAEC1:(Z)-lacZ. In another embodiment, the cloning vector may comprise pUC19NHCIS2::HAEC1:(Z)-lacZ. In another embodiment, the cloning vector may comprise pUC19NHCIS1::HAEC2: porAplusprom-lacZ. In another embodiment, the cloning vector may comprise pUC19NHCIS1::HAEC4:nadA-lacZ. In another embodiment, the cloning vector may comprise pUC19NHCIS1::HAEC4:nadA-lacZ. In another embodiment, the cloning vector may comprise pSC101NHCIS1:: HAEC4:opcA-lacZ. In another embodiment, the cloning vector may comprise pUC19Δnhba::HAEC3:(Z)-lacZ. In another embodiment, the cloning vector may comprise pNHCIS(X)::HAEC(Y):(Z)-lacZ. In another embodiment, the cloning vector may comprise pNHCIS2::HAEC1:(Z)-lacZ. In another embodiment, the cloning vector may comprise pUC19Δnhba::HAEC1:(Z)-lacZ. In another embodiment, the cloning vector may comprise pUC19Δnhba.

The cloning vector may comprise pUC19 sequence, or substantial parts thereof, comprising the pUC origin of replication (pMB1). Alternatively, the cloning vector may comprise pUC19 sequence, or substantial parts thereof, with the pUC origin of replication (pMB1) has been substituted for the repA/ori, minimally-required replicatory region of plasmid pSC101. (see Chang and Cohen J. 1978. Construction and characterisation of amplifiable multicopy DNA cloning vehicles derived from the P15A cryptic miniplasmid. J Bacteriol. 1978 June; 134(3): 1141-1156; and Vocke and Bastia 1983. Primary Structure of the essential replicon of the plasmid pSC101. PNAS, 80(21): 6557-6561). In one embodiment, the cloning vector comprises pSC101NHCIS1::HAEC4:opcA-lacZ.

The cloning vector may comprise an *N. lactamica* codon-optimized version of the opcA gene (eg. NMB1053), optionally under the control of the optimally enhanced, modified porA/porB hybrid promoter, and further optionally flanked on either side by sequences derived from the 5' and 3' ends of the Nlac lacZ gene. In one embodiment, the cloning vector comprises pSC101::AlacZ:opcA.

The cloning vector may comprise a synthetic version (i.e. not wild-type) of the lacZ gene (synth.lacZ), in which the coding sequence has been modified to diversify the sequence from the endogenous Nlac version of the lacZ gene, whilst maintaining the fidelity of the encoded amino acid sequence of β-galactosidase. In one embodiment, the synthetic version of the lacZ gene may comprise the sequence of SEQ ID NO: 20 (FIG. 37) or a variant thereof. A variant of the synthetic version of the lacZ gene may comprise may comprise a sequence of at least 80% identity with the sequence of SEQ ID NO: 20 (FIG. 37), whilst maintaining β-galactosidase function. In another embodiment, a variant of the synthetic version of the lacZ gene may comprise a sequence of at least 85%, 90%, 95%, 98%, 99%, or 99.5% identity with the sequence of SEQ ID NO: 20 (FIG. 37), whilst maintaining β-galactosidase function. The skilled person will understand that fewer or more amino acid substitutions which either diversify the sequence away from wild-type or conform the sequence back towards wild-type may be envisaged, and still retain function and sufficient diversity to avoid inadvertent recombination with wild-type sequence. For example, up to 40% of the substitutions to form the synthetic lacZ gene may be reverted back to wild-type (although with an increased likelihood of inadvertent recombination). In another embodiment, up to 5%, 10%, 15%, 20%, 25% or 30% of the substitutions to form the synthetic lacZ gene may be reverted back to wild-type.

In one embodiment, the cloning vector comprises pSC101::AlacZ-synth.lacZ-3'ENDNHCIS1.

Providing a synthetic version of the lacZ gene, for example in the AlacZ-synth.lacZ-3'ENDNHCIS1 construct, advantageously introduces a functional copy of the lacZ gene back into the chromosome of an Nlac strain having a previously knocked out lacZ gene via an heterologous nucleic acid insertion, for example Nlac strain ΔlacZ NHCIS1::HAEC4:nadA-AlacZ:opcA, so that β-galactosidase activity is maintained. For example, double mutants encoding heterologous NadA and Opc can retain (3-galactosidase activity.

In one embodiment, the cloning vector comprises pSC101NHCIS1::HAEC4:porA(P1.7,16)-lacZ. In another embodiment, the cloning vector comprises pSC101NHCIS1::PVporA(P1.7,16)-lacZ.

Advantageously, the copy number of pSC101-derived plasmids is tightly controlled by the presence of the self-encoded RepA protein, and the plasmids exist at a much lower copy number per bacterial cell (=5) than the pUC plasmids (=50-300), which can facilitate successful transformation of constructs encoding gene products that are potentially toxic to the host cell.

The sequence homologous to a region of *Neisseria lactamica* genome may comprise a sequence of NHCIS1 or NHCIS2. In one embodiment, the sequence homologous to a region of *Neisseria lactamica* genome comprise a sequence of NHCIS1.

Method of Mutagenesis

According to another aspect of the invention, there is provided a method of mutagenesis of *Neisseria lactamica* comprising transformation of *Neisseria lactamica* with the cloning vector according to the invention herein.

According to another aspect of the invention, there is provided a method of mutagenesis of *Neisseria lactamica* comprising transformation of *Neisseria lactamica* with hypermethylated nucleic acid.

The hypermethylated nucleic acid may comprise or consist of a hypermethylated PCR product. The hypermethylated nucleic acid may comprise or consist of a hypermethylated cloning vector.

The method of mutagenesis may further comprise screening for successful transformants. Successful transformants may be screened by the use of the selection marker. For example, where the selection marker comprises a β-galactosidase (lacZ) gene, the screening may comprise the testing for β-galactosidase activity. Where the selection marker comprises an antibiotic resistance gene, the screening may comprise the testing for ability to grow or survive in the presence of the antibiotic. Other selection methods may be used, for example restoration of function for auxotrophic mutants. In one embodiment, successful transformants may be selected for by screening in a ΔlacZ mutant of *Neisseria lactamica*, for example a ΔlacZ mutant of Y92-1009. In one embodiment, successful transformants may be selected for by screening in a ΔlacZ Δnhba mutant of *Neisseria lactamica*, for example a ΔlacZ Δnhba mutant of Y92-1009.

Advantageously, the use of a non-antibiotic related selection marker, such as 0-galactosidase (lacZ) provides a more clinically acceptable strain of a modified *Neisseria lactamica* resulting from this method. The resulting modified *Neisseria lactamica* strain may be used as a platform for the generation of outer membrane vesicles (OMV), for example for vaccines. An antibiotic selection marker may be used for strains that may ultimately be used as a platform for the generation of outer membrane vesicles (OMV).

Outer Membrane Vesicle (OMV) vaccine

According to another aspect of the invention, there is provided an outer membrane vesicle (OMV) vaccine, wherein the OMV is an OMV of the modified *Neisseria lactamica* described herein.

The OMV may comprise a protein, or a variant or part thereof, which is heterologous to the modified *Neisseria lactamica*. The heterologous protein may comprise PorA, such as PorA of *N. meningitidis*.

According to another aspect of the invention, there is provided a composition comprising the OMV according to the invention herein; or the modified *Neisseria lactamica* according to the invention herein.

The composition may be a pharmaceutically acceptable composition.

According to another aspect of the invention, there is provided an OMV; modified *Neisseria lactamica*; or composition according to the invention herein for use in a vaccine/vaccination.

According to another aspect of the invention, there is provided a method of vaccination of a subject for the prevention of infection or colonisation of a pathogen comprising the administration of the OMV or the modified *Neisseria lactamica* or the composition according to the invention herein.

The vaccination may be for prevention of infection or colonisation of *Neisseria meningitidis* in the subject.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1: Plasmid map of pUC19ΔnlaIII::CLOVER-aphA3.

FIG. 2: Nucleotide sequence (SEQ ID NO: 3) of tandemly-expressed, *N. lactamica*-codon-optimised CLOVER and aphA3 genes. The sequence of the CLOVER gene is shown as white text against a black background and the aphA3 sequence is shown as boxed black text. The NotI and NdeI restriction sites are shown as black text against a grey background. The DUS and RBS are shown in lower case letters, with the DUS sequence underlined.

FIGS. 3A and 3B: Confocal microscopy of wild type (FIG. 3A) and CLOVER-expressing strains (FIG. 3B) of *Neisseria lactamica* Y91-1009.

Figure 4:
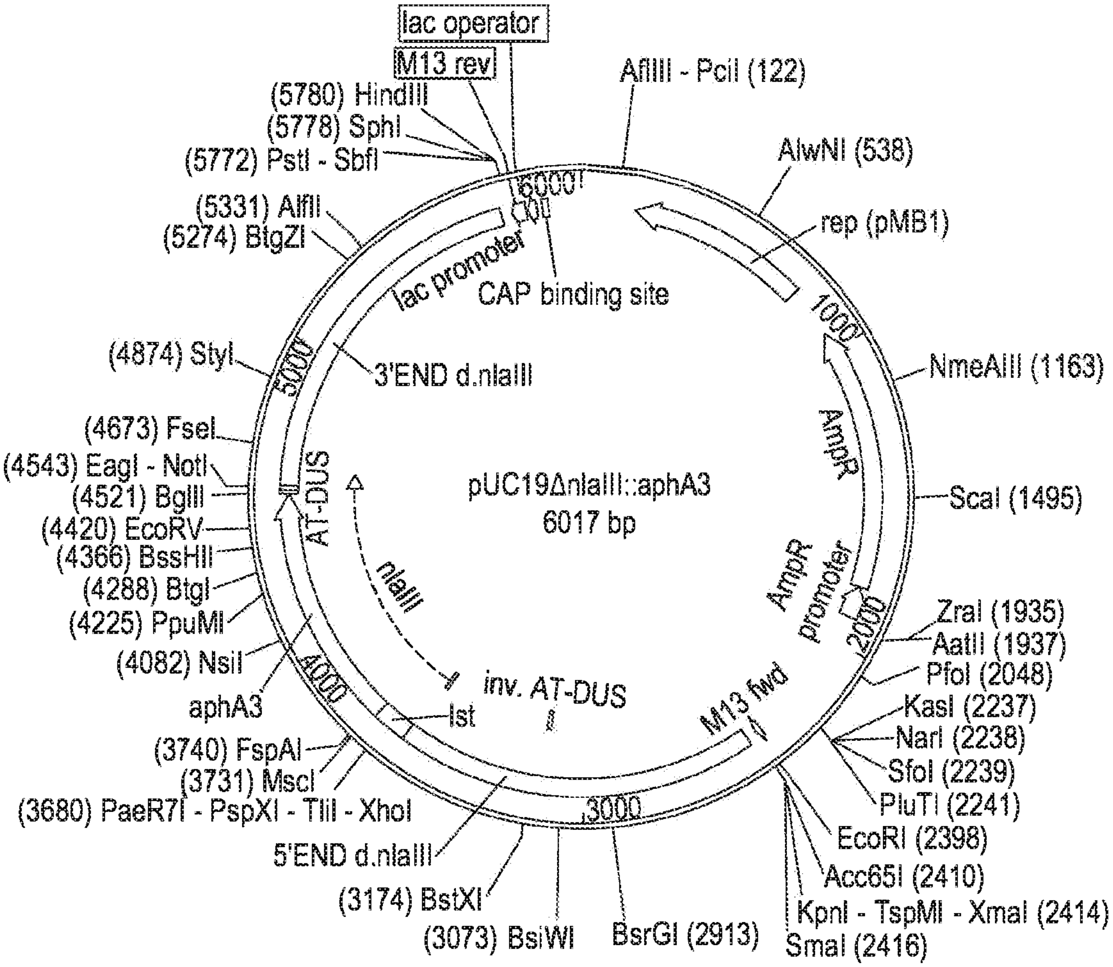

FIG. 4: Plasmid map of pUC19ΔnlaIII::aphA3.

Figure 5:
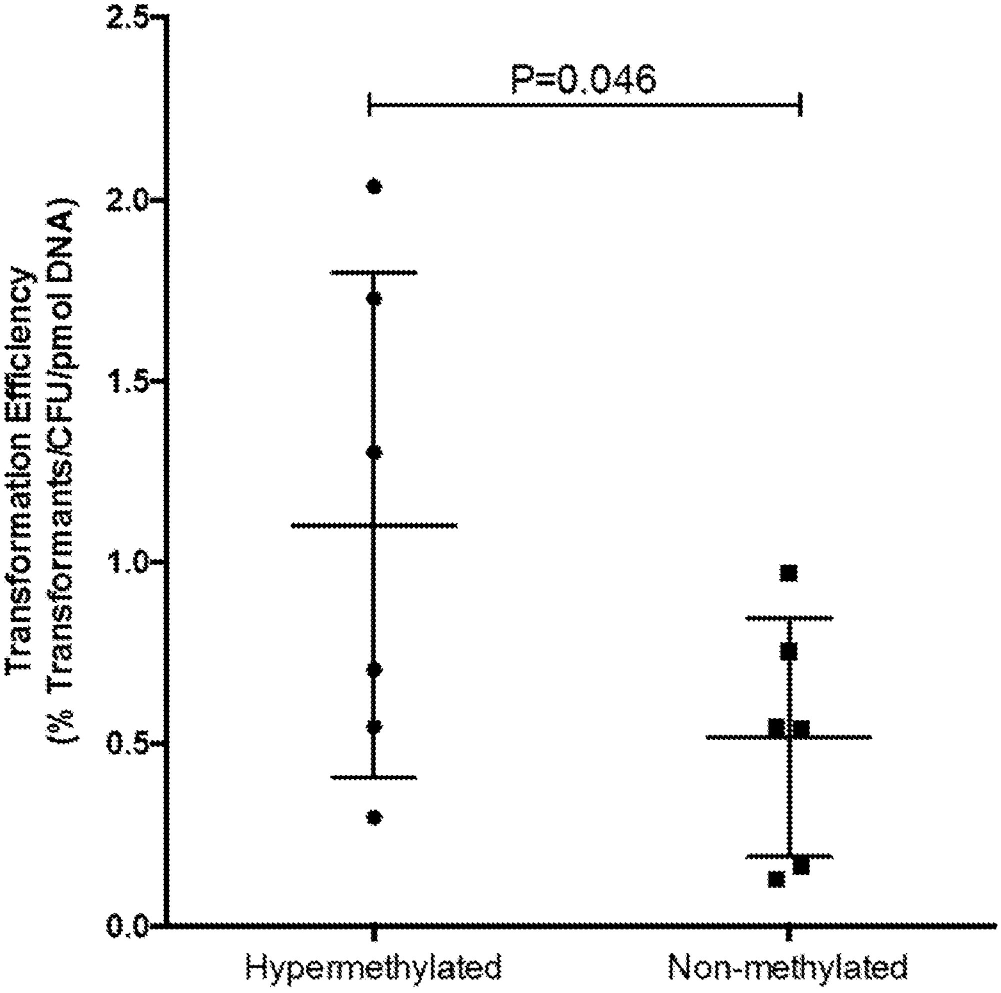

FIG. 5: Transformation efficiency of wild type *Neisseria lactamica* using (hypermethylated) PCR products amplified from pUC19ΔnlaIII::aphA3.

Figure 6:
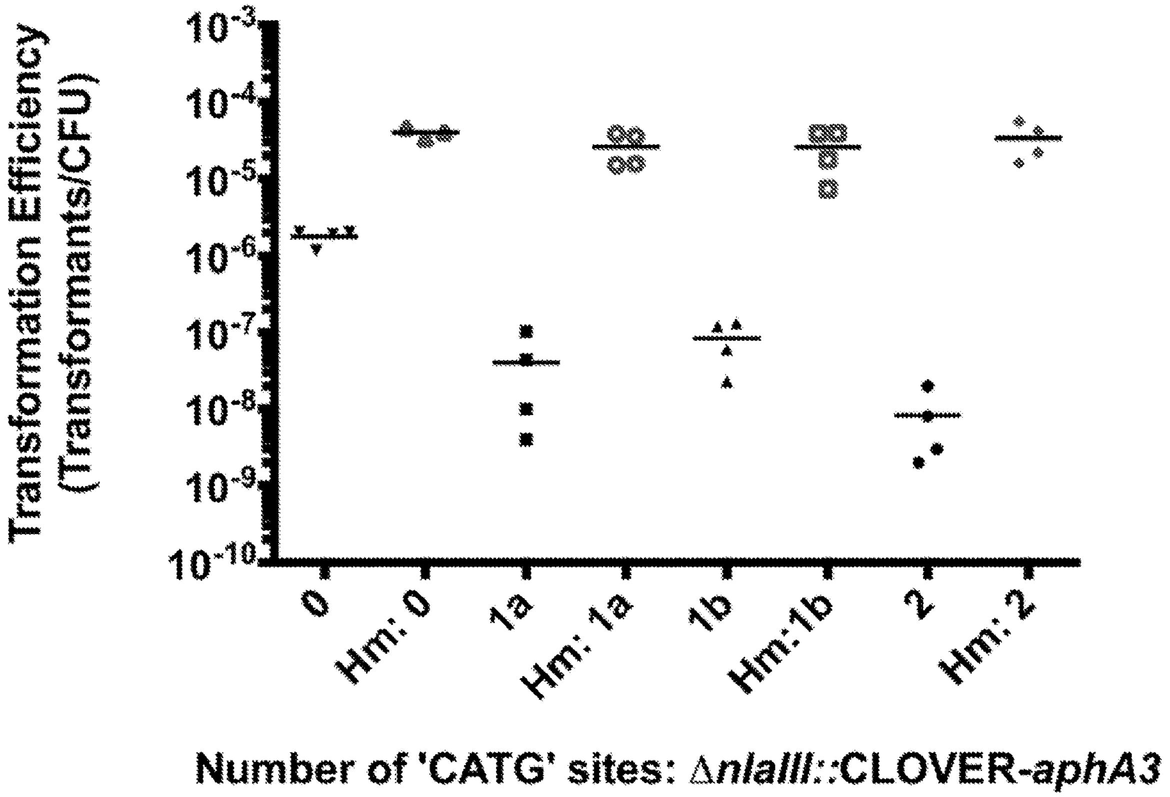

FIG. 6: Transformation efficiency of wild type *Neisseria lactamica* using (hypermethylated) PCR products amplified from pUC19ΔnlaIII::CLOVER-aphA3 and derivatives thereof, wherein site-directed mutagenesis has been used to remove 'CATG' sequences from the CLOVER coding sequence. Hm=hypermethylated; 0=PCR product contains no sequences of CATG; 1a and 1b=duplicates for PCR products containing one sequence of CATG; 2=PCR product contains two sequences of CATG.

Figure 7:
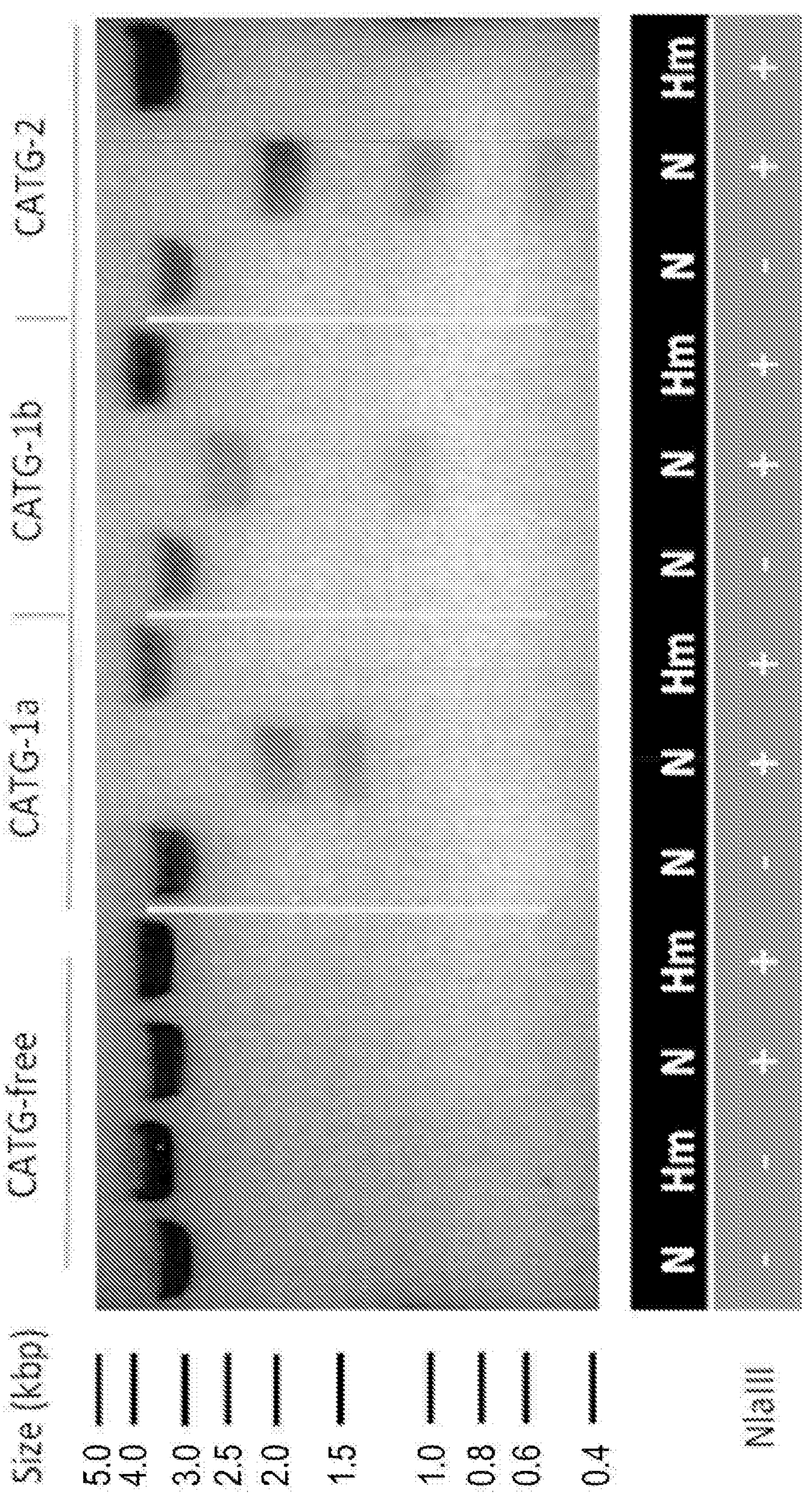

FIG. 7: Hypermethylation of PCR product blocks restriction activity of NlaIII. Hm=hypermethylated. N=normal, non-hypermethylated. CATG free=no CATG sequence present; CATG=1a and CATG-1b=duplicates for PCR products containing one sequence of CATG; CATG-2=PCR product contains two sequences of CATG.

Figure 8:
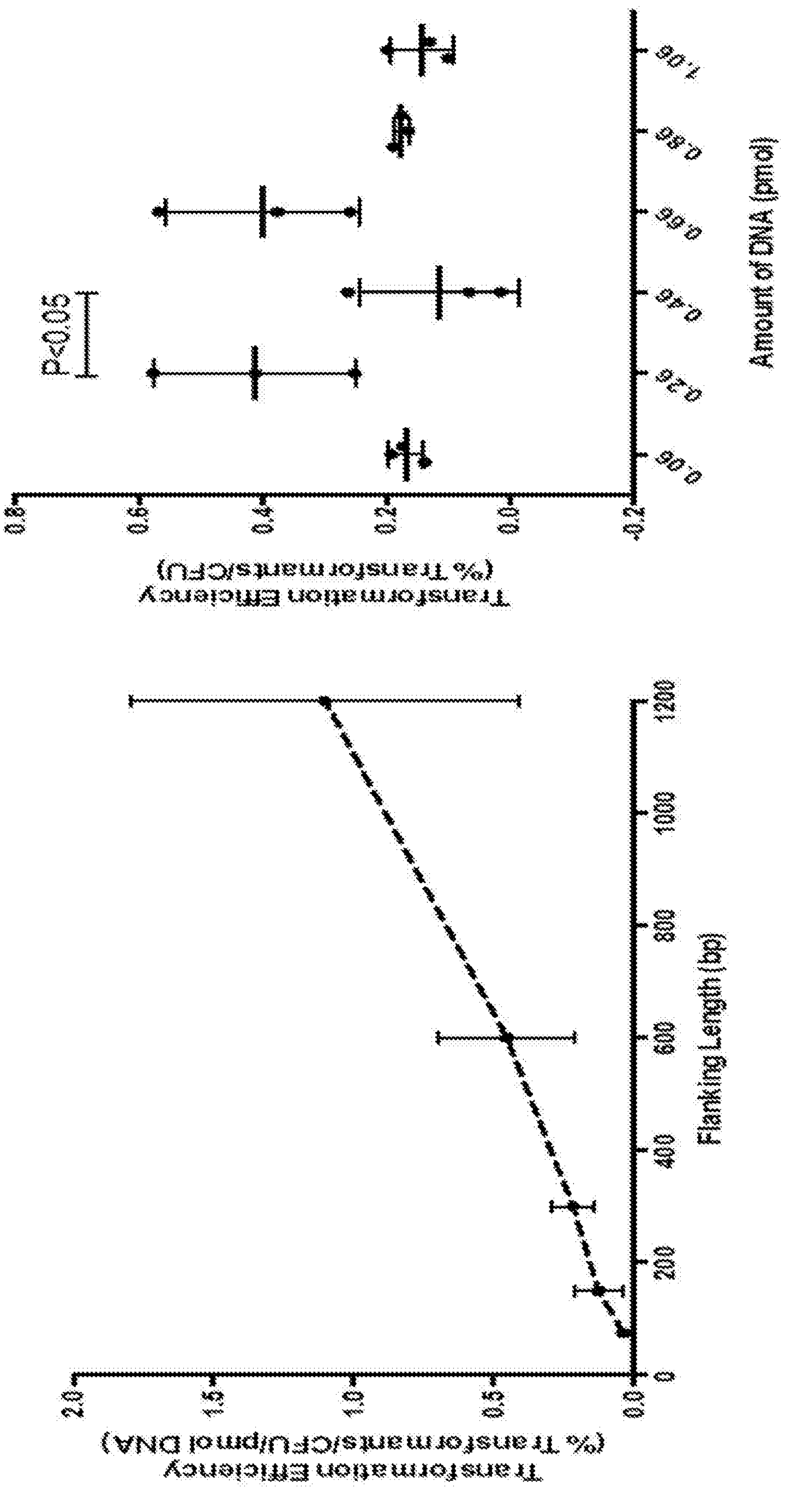

FIG. 8: Effect of the length of the flanking region and amount of DNA used to transform wild type *Neisseria lactamica* using PROTOCOL A.

FIG. 9: Effect of the neisserial DNA Uptake Sequence (DUS) on the transformation efficiency of *Neisseria lactamica* using PROTOCOL A. S-DUS=scrambled DUS.

FIG. 10: Chromosomal schematic and nucleotide sequence of NHCIS1 (*N. lactamica* Y92-1009) (SEQ ID NOs: 4 and 5).

FIG. 11: Chromosomal schematic and nucleotide sequence of NHCIS2 (*N. lactamica* Y92-1009) (SEQ ID NOs: 6 and 7).

FIG. 12: Annotated nucleotide sequence of HAEC1 (SEQ ID NO: 8).

FIG. 13: Annotated nucleotide sequence of HAEC2 (SEQ ID NO: 9). AT-DUS=AT-variant of DUS.

Figure 14:
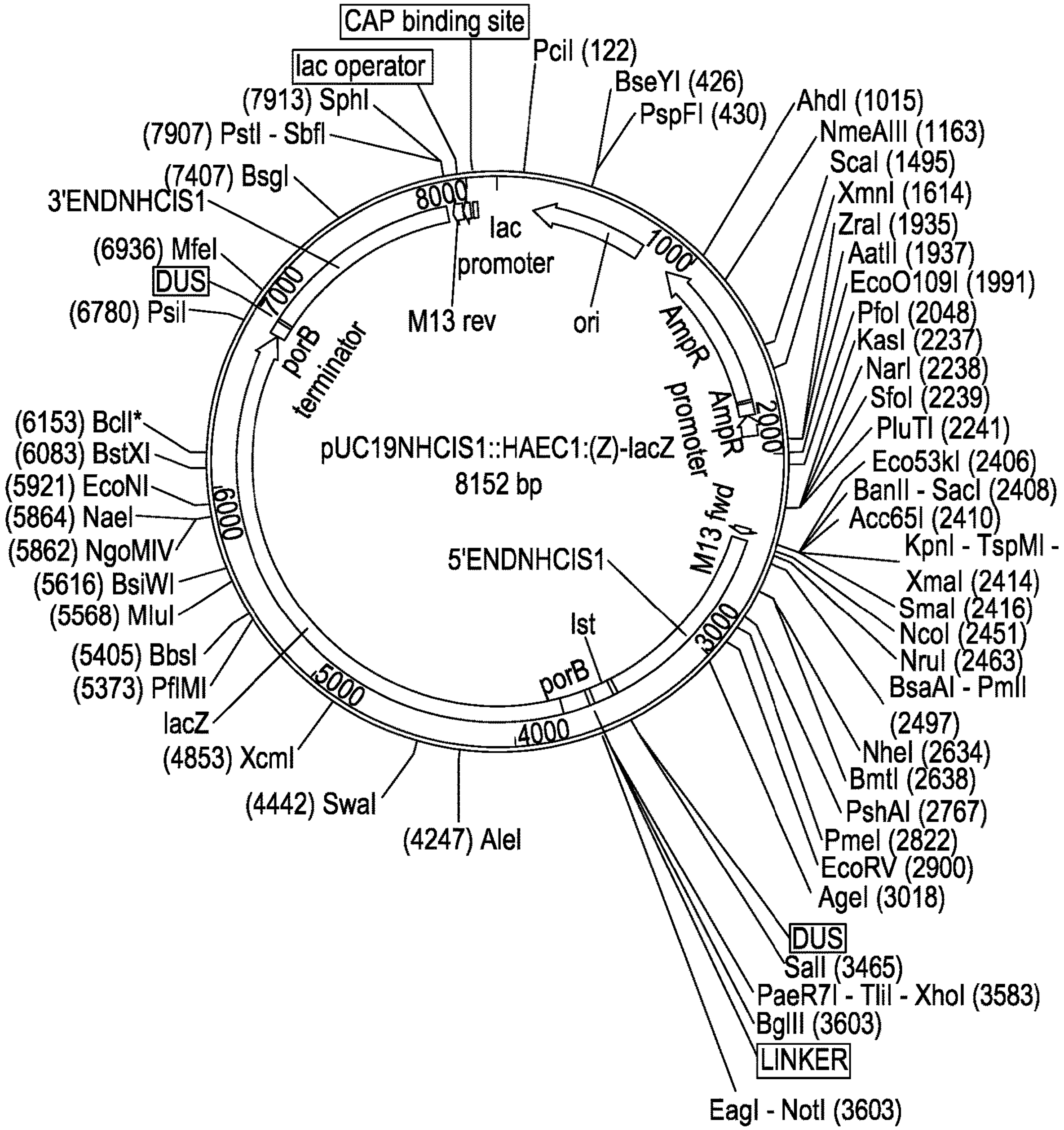

FIG. 14: Plasmid map of pUC19NHCIS1::HAEC1:(Z)-lacZ.

Figure 15:
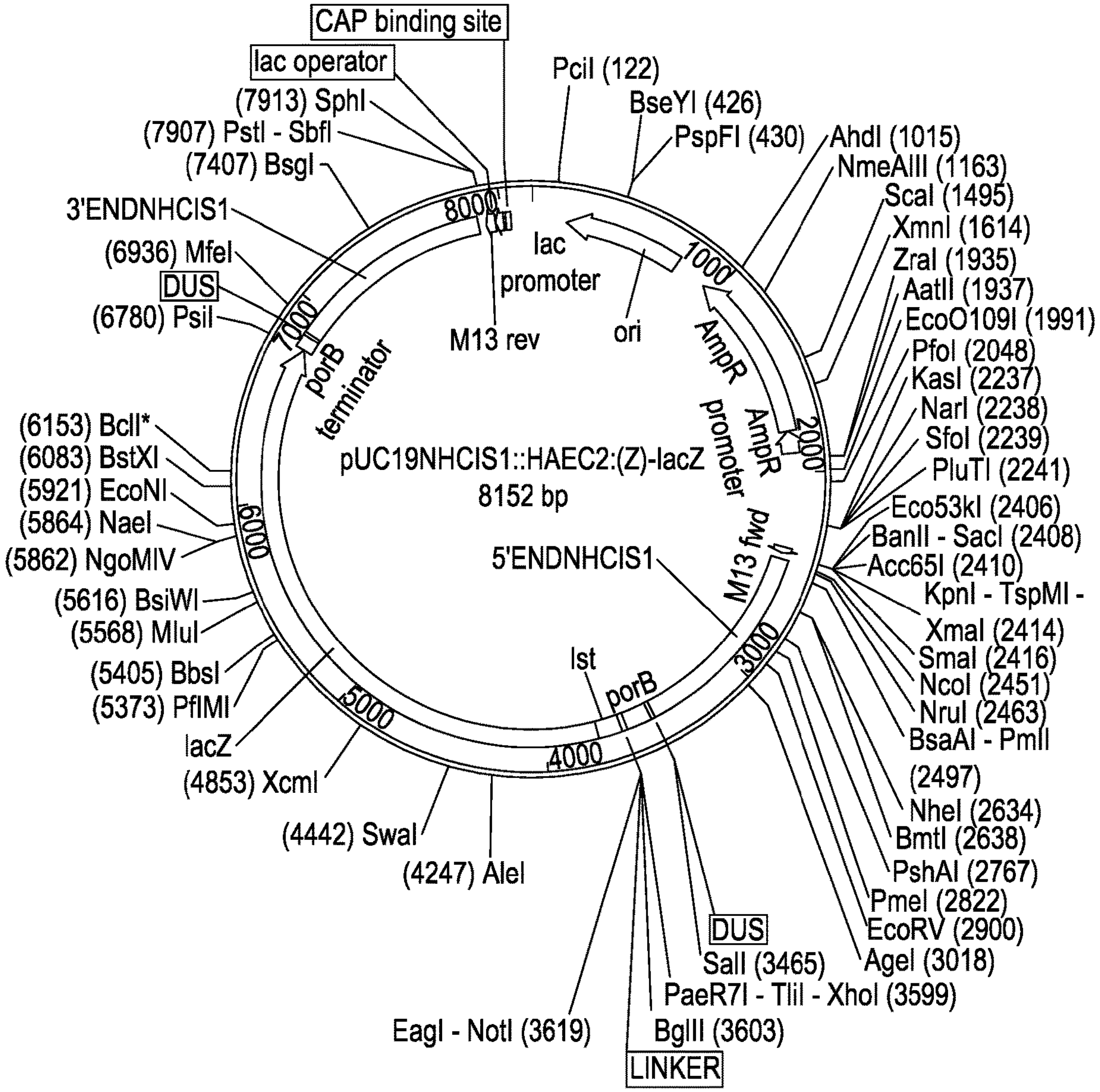

FIG. 15: Plasmid map of pUC19NHCIS1::HAEC2:(Z)-lacZ.

Figure 16:
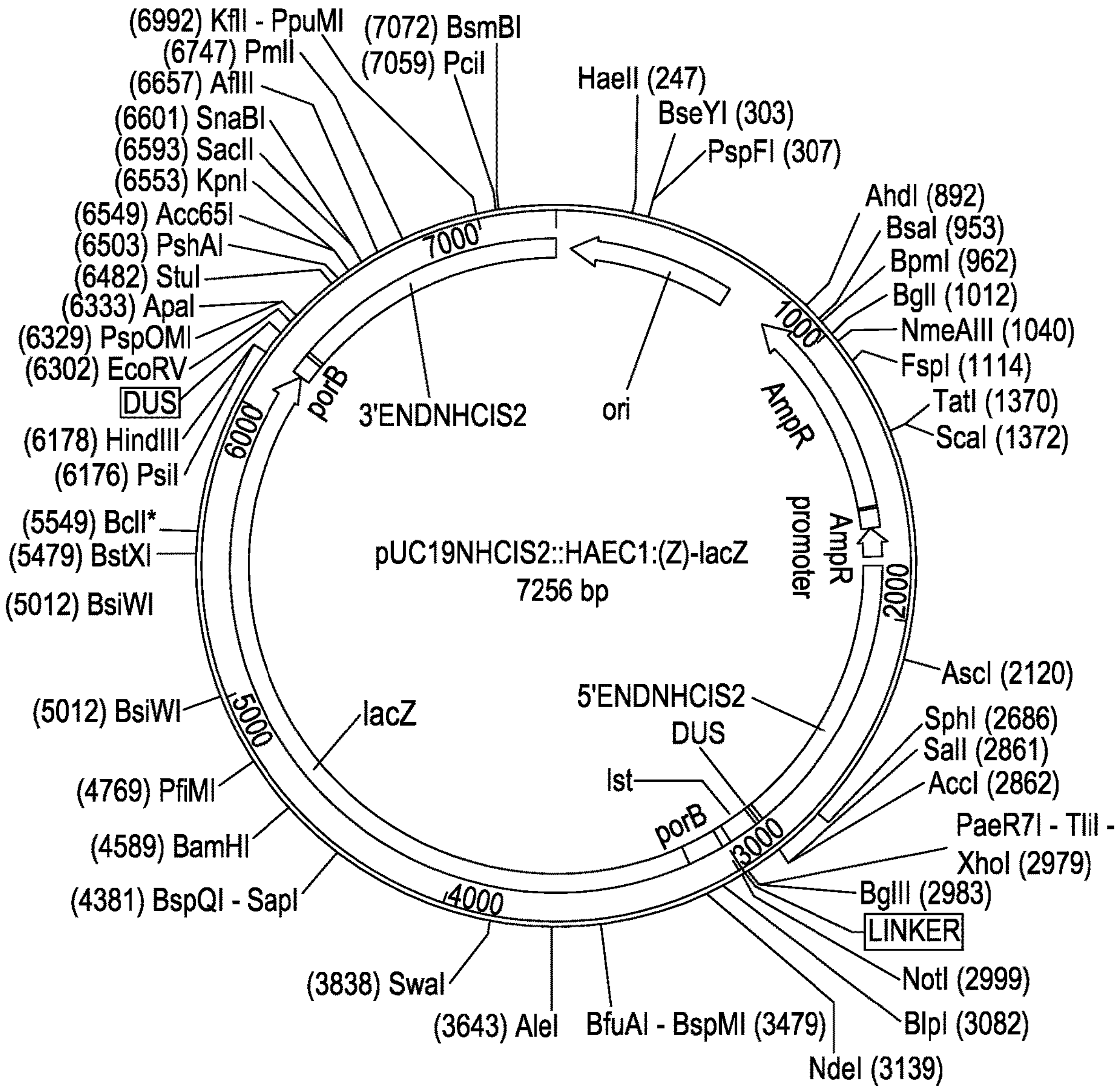

FIG. 16: Plasmid map of pUC19NHCIS2::HAEC1:(Z)-lacZ.

Figure 17:
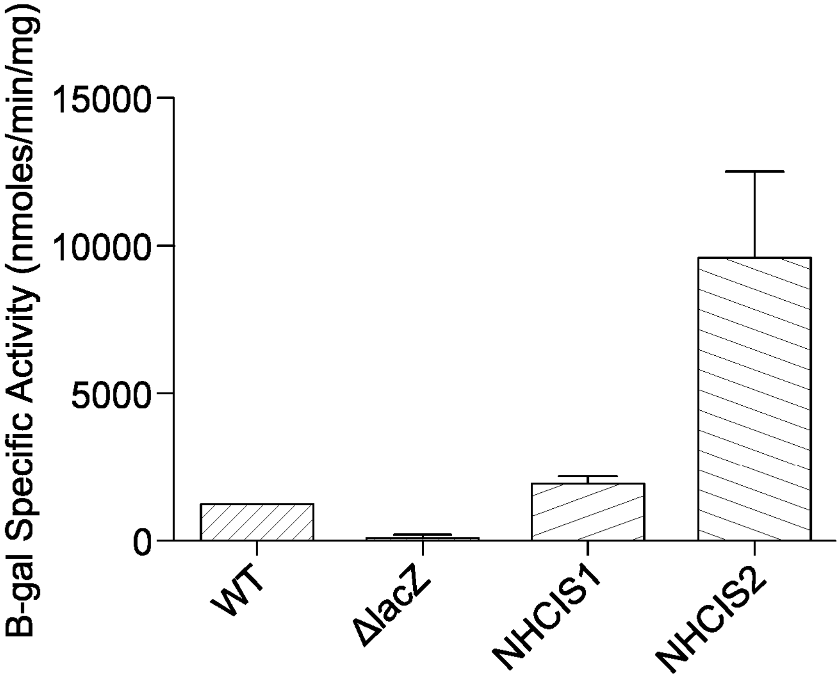

FIG. 17: Bar graph showing Specific Activity of lacZ, expressed from different NHCIS loci.

Figure 18:
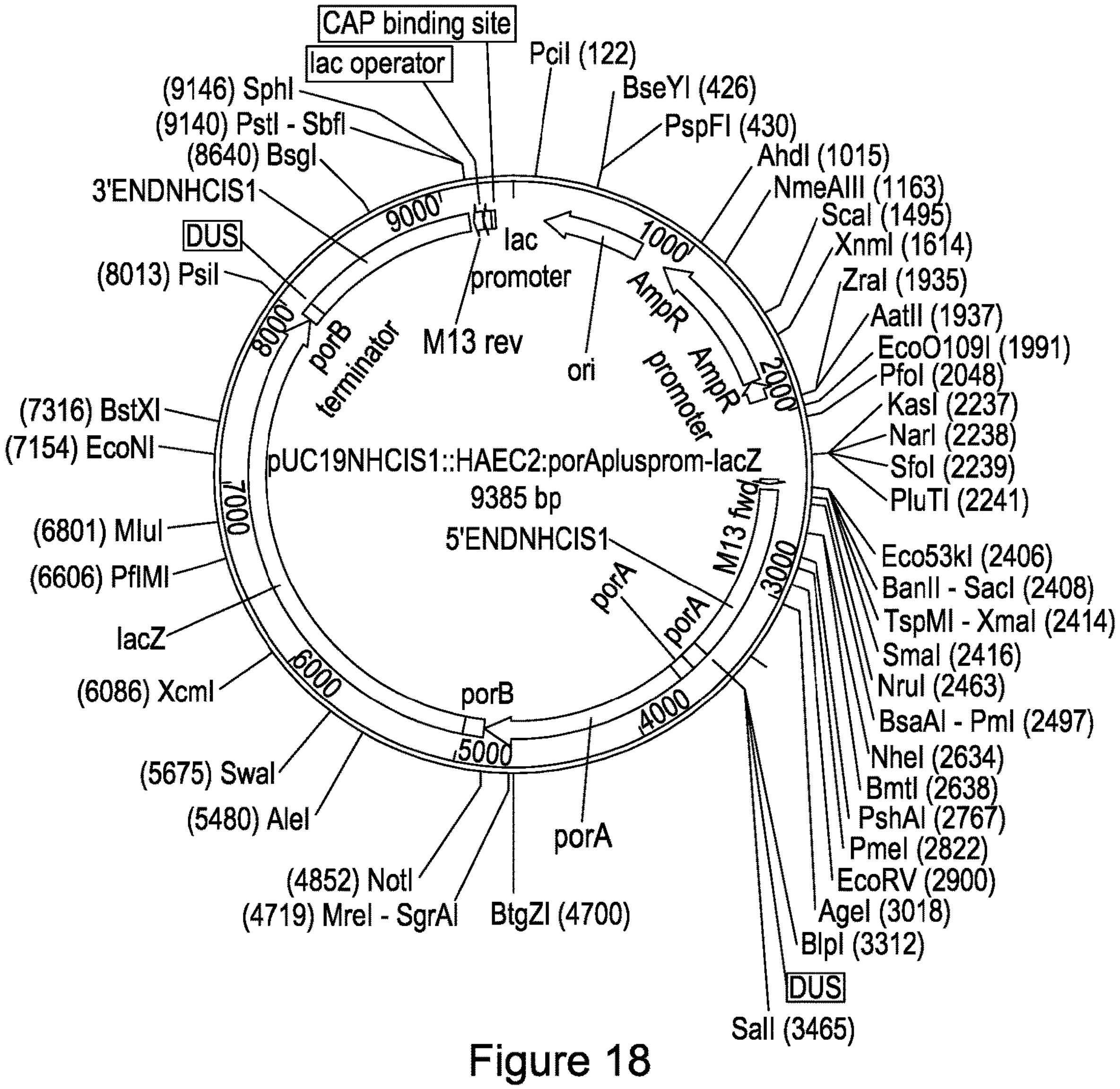

FIG. 18: Plasmid map of pUC19NHCIS1::HAEC2:porAplusprom-lacZ.

Figure 19A:
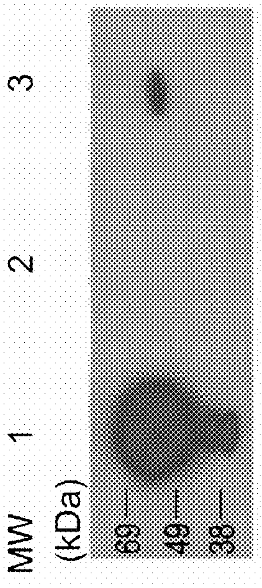
Figure 19B:
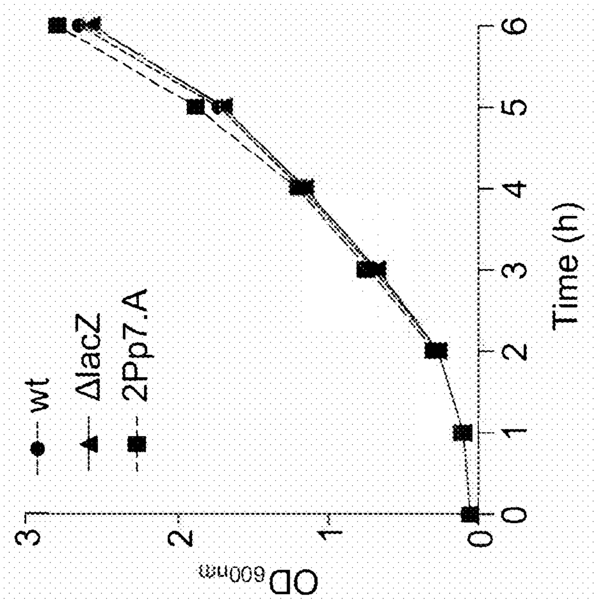

FIGS. 19A and 19B: Expression of PorA in recombinant *N. lactamica* has no appreciable effect on growth rate in TSB.

Figure 20:
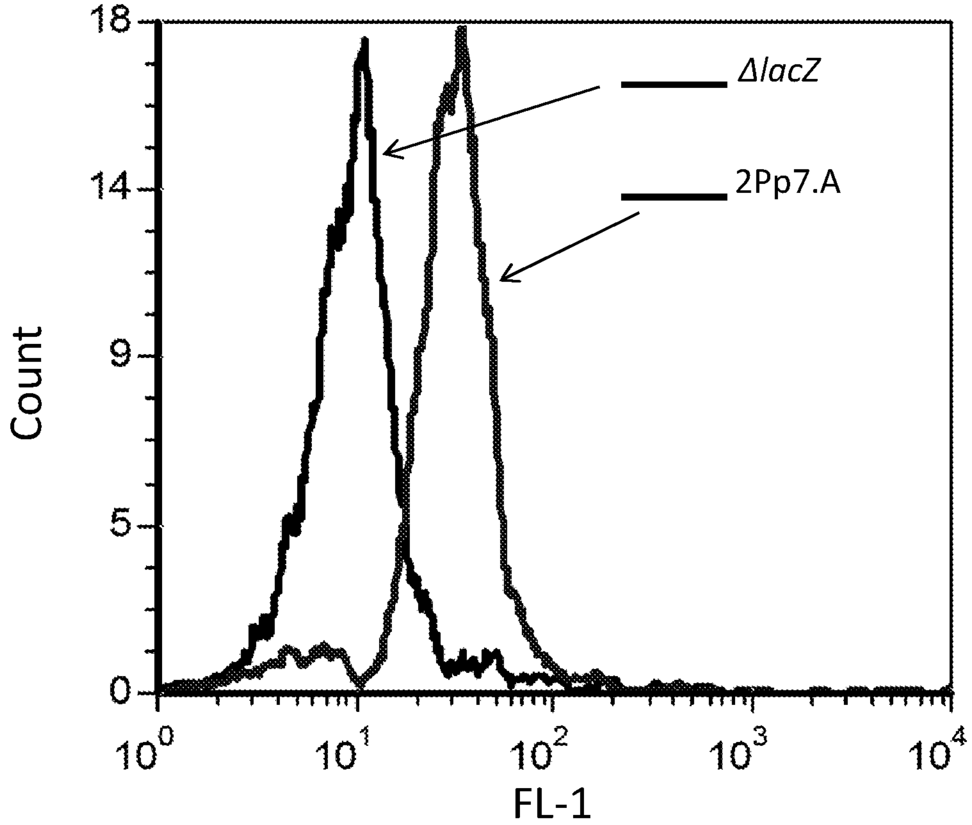

FIG. 20: PorA is surface-expressed in recombinant *N. lactamica* strain 2Pp7.A.

FIG. 21: Promoter constructs for investigating transcriptional enhancement by sequence associated with the *N. meningitidis* porA gene (SEQ ID NOs: 10-16).

Figure 22:
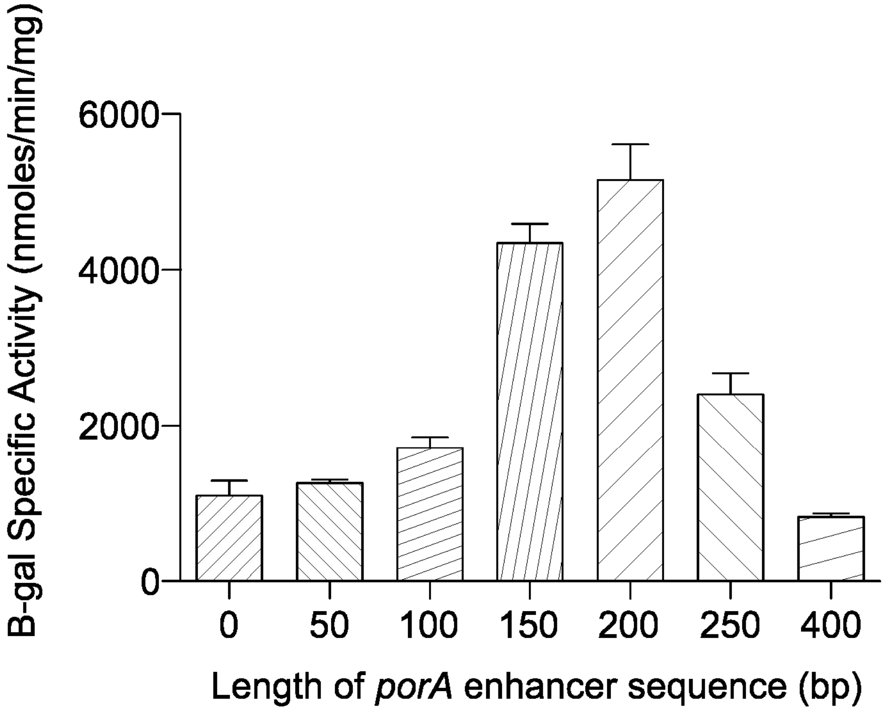

FIG. 22: Transcriptional enhancement of the lst promoter by sequence cloned from upstream of the porA gene from *Neisseria meningitidis* strain MC58.

FIG. 23: Promoter construct designed to investigate the mechanism of porA transcriptional enhancement (SEQ ID NO: 17).

Figure 24:
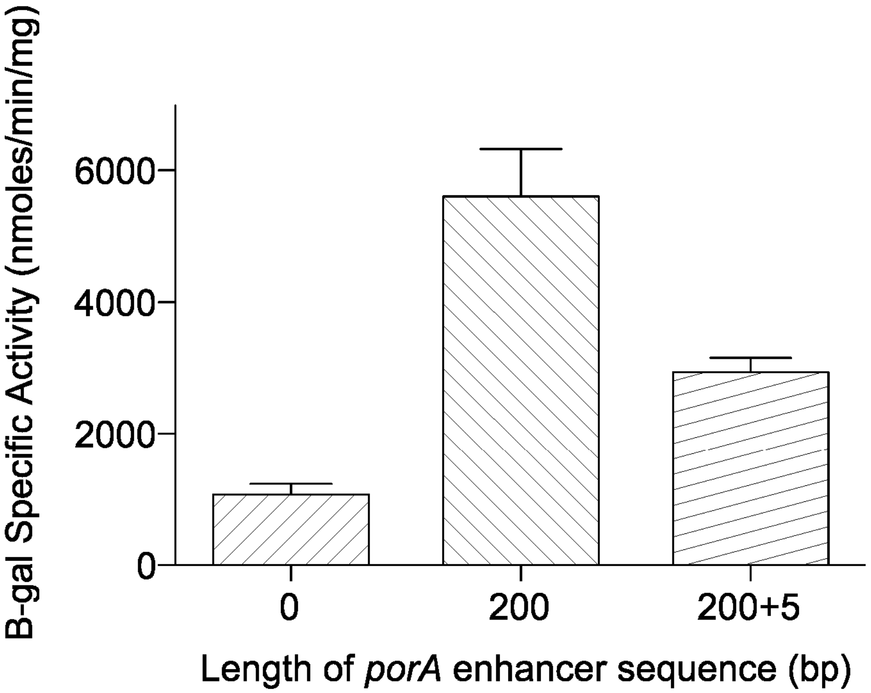

FIG. 24: DNA bending is partially responsible for the transcriptional enhancement activity of the porA enhancer sequence.

FIG. 25: Annotated nucleotide sequence of HAEC3 (SEQ ID NO: 18).

FIG. 26: Annotated nucleotide sequence of HAEC4 (SEQ ID NO: 19).

Figure 27:
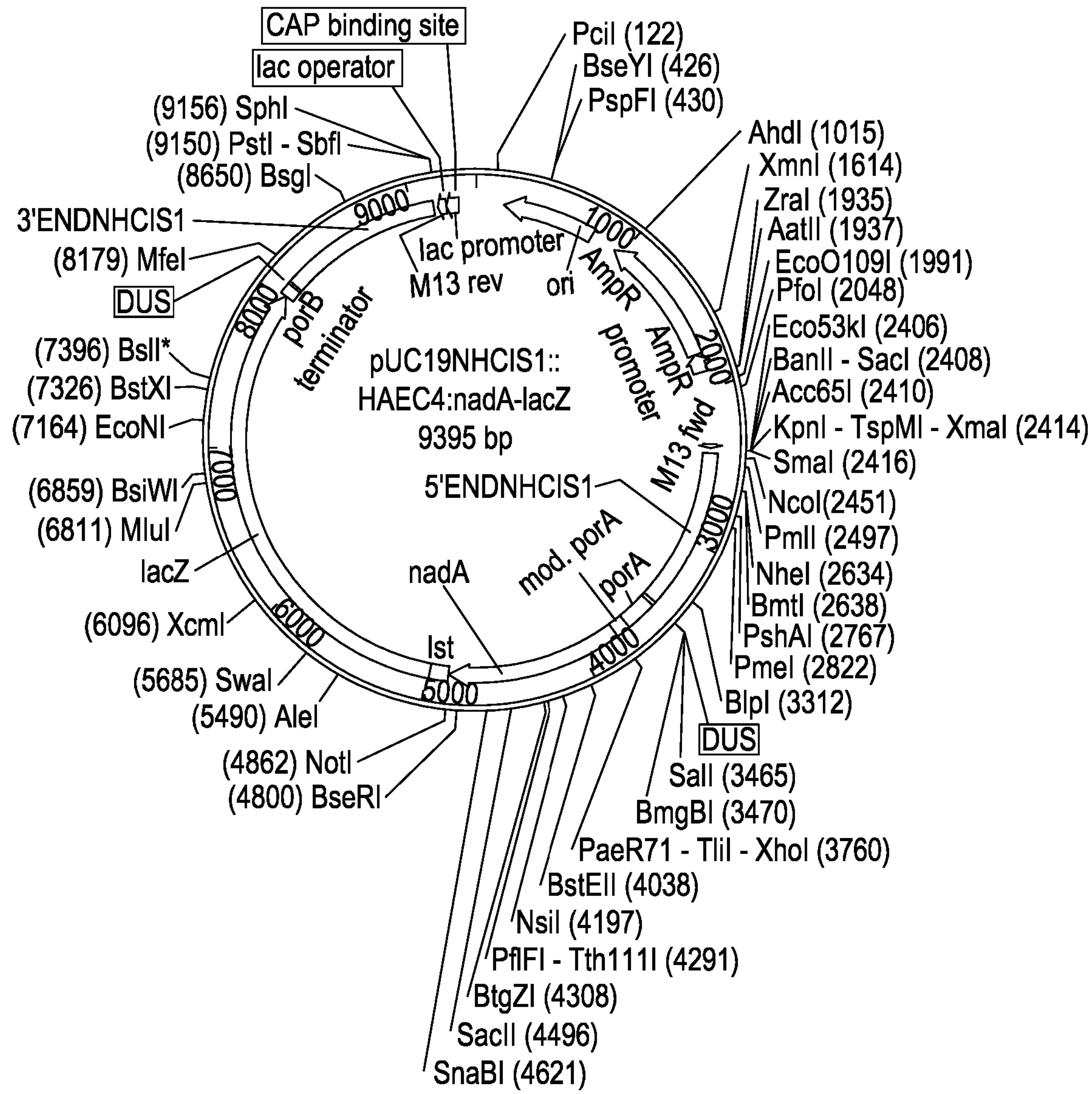

FIG. 27: Plasmid map of pUC19NHCIS1::HAEC4:nadA-lacZ

Figure 28:
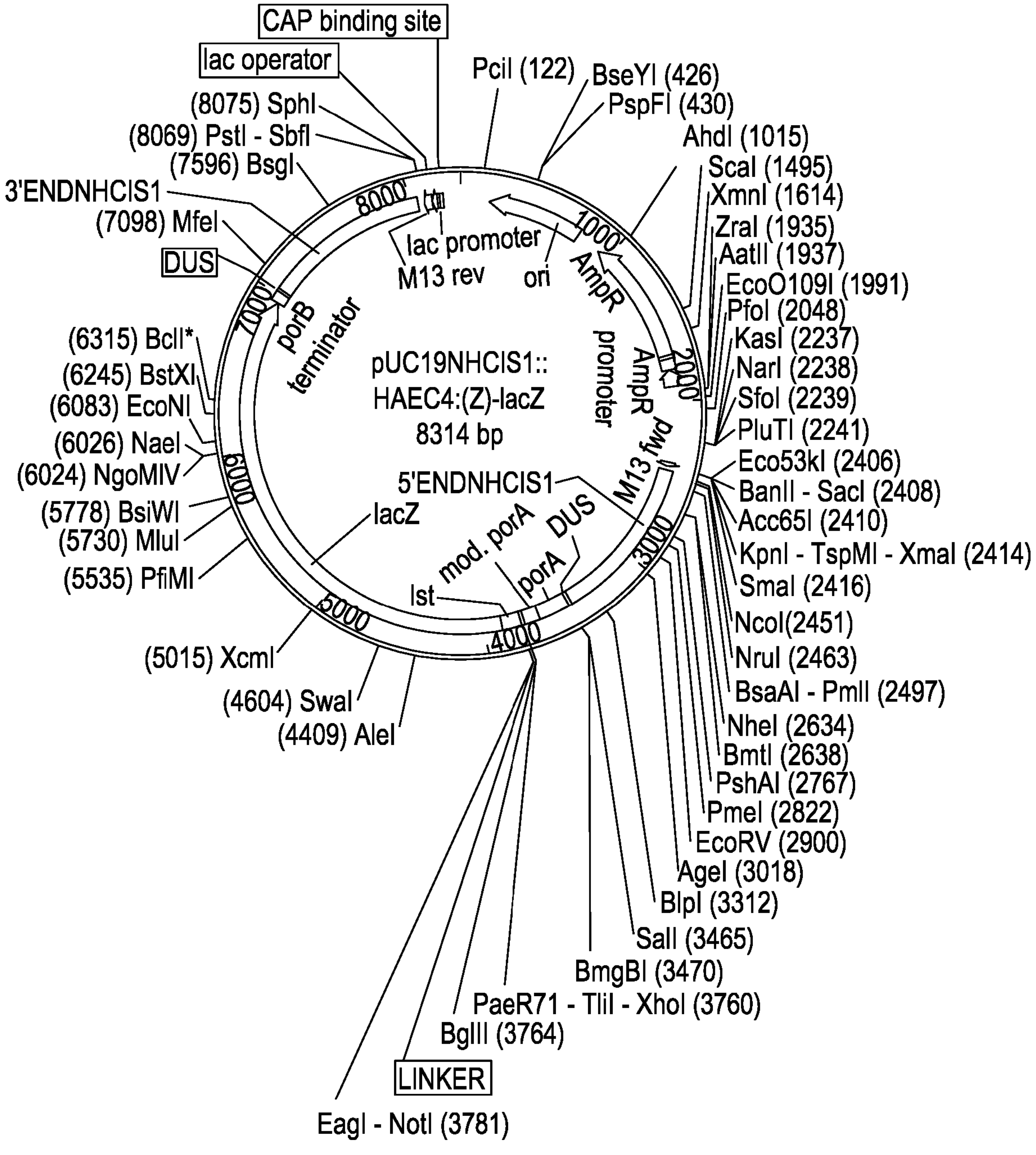

FIG. 28: Plasmid map of pUC19NHCIS1::HAEC4:(Z)-lacZ

Figure 29:
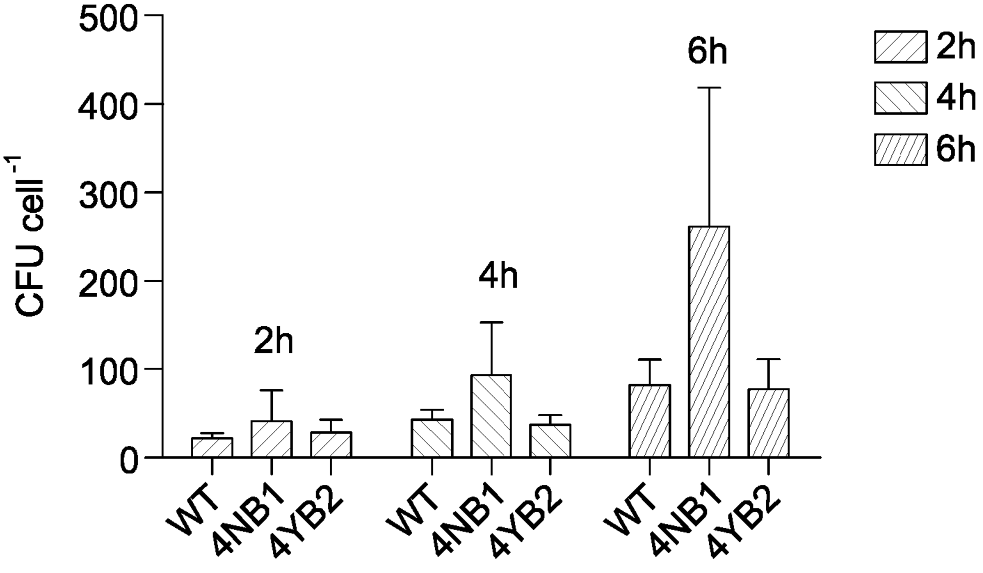

FIG. 29: NadA-expressing *N. lactamica* have increased adherence to HEP-2 cells.

Figure 30:
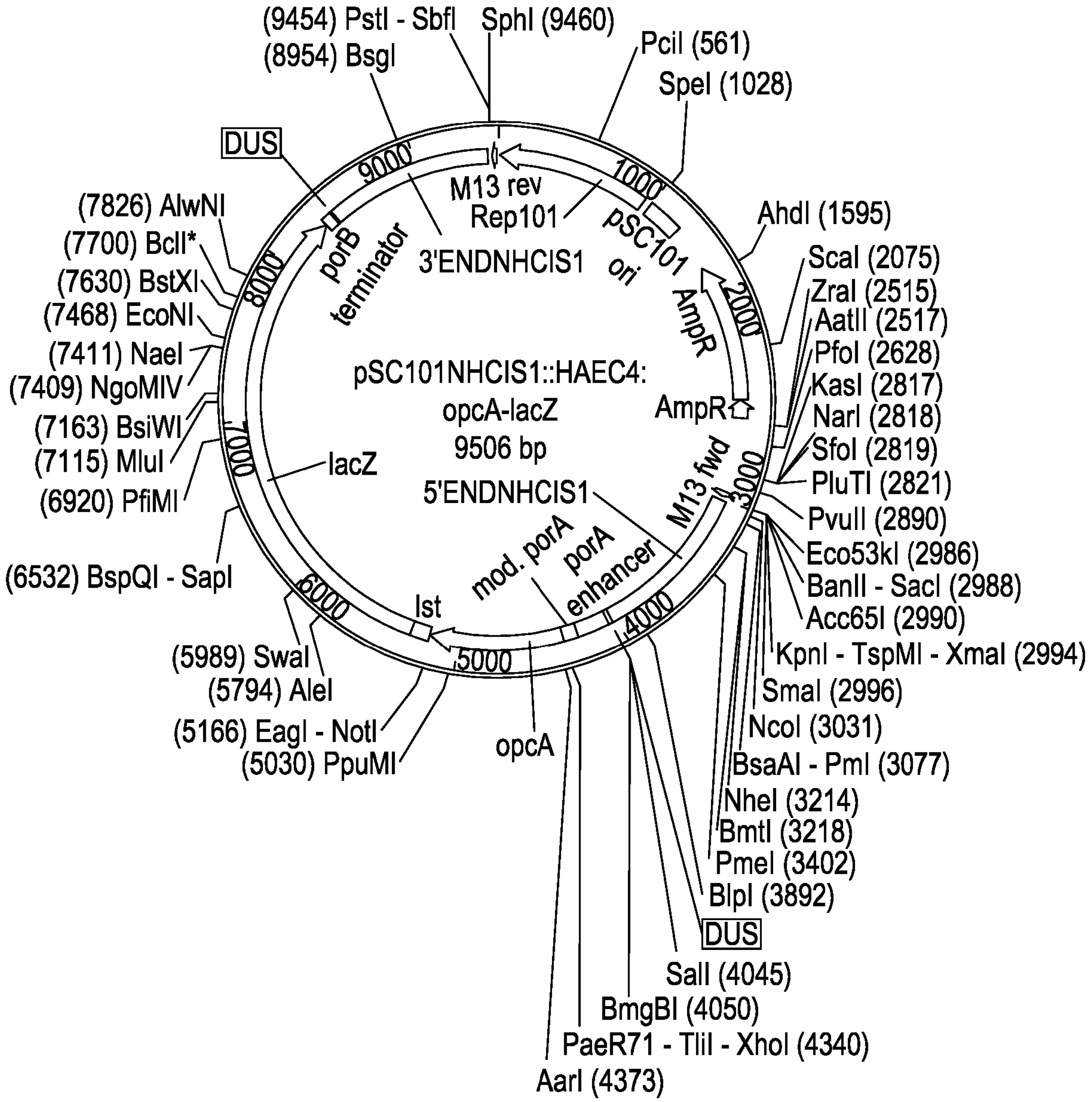

FIG. 30: Plasmid map of pSC101NHCIS1::HAEC4:opc-lacZ

Figure 31:
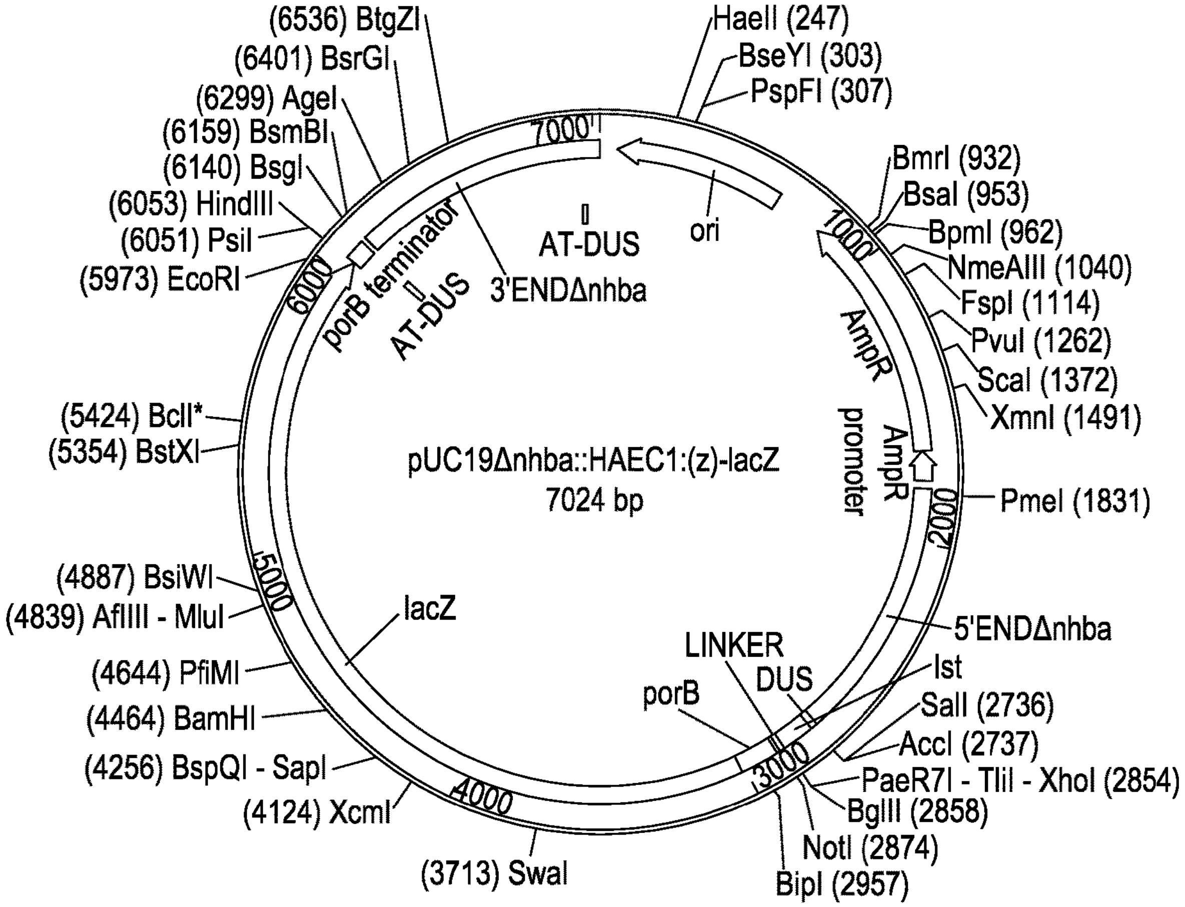

FIG. 31: Plasmid map of pUC19Δnhba::HAEC3:(Z)-lacZ

Figure 32:
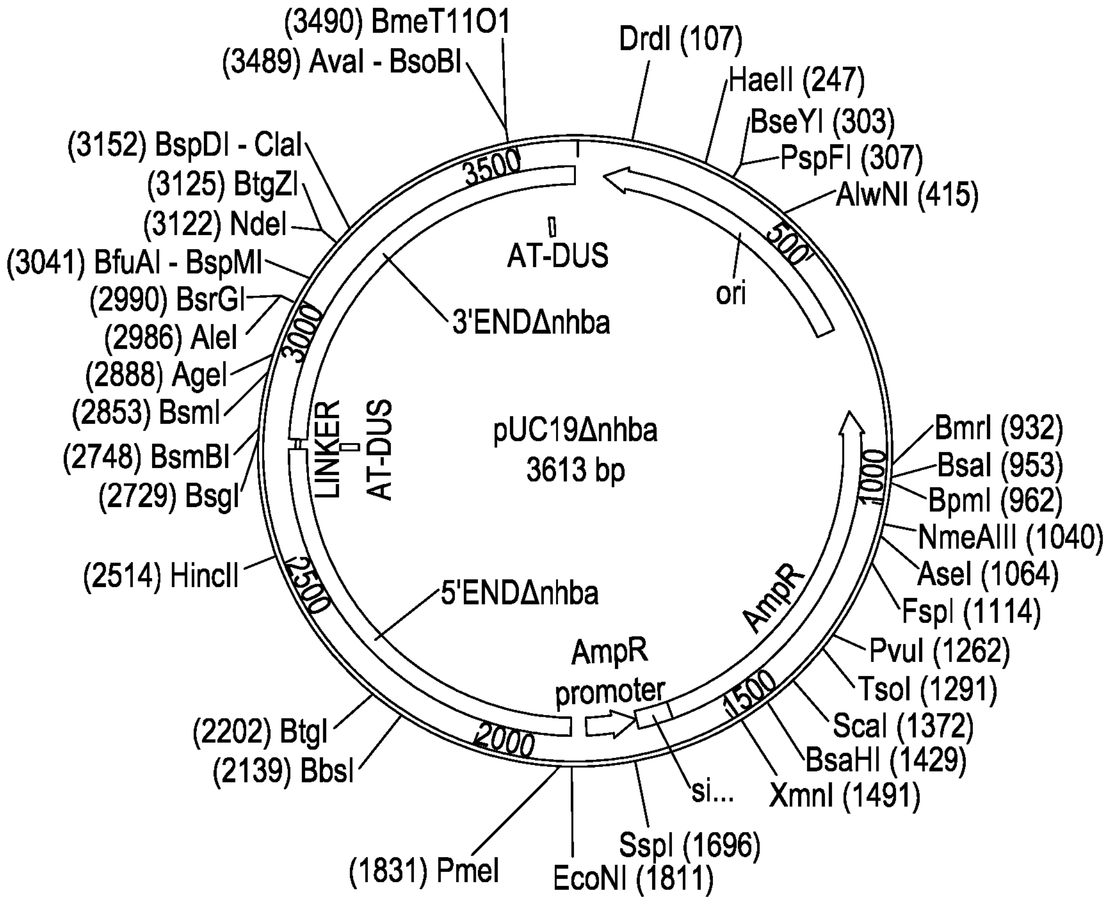

FIG. 32: Plasmid map of pUC19Δnhba

Figure 33:
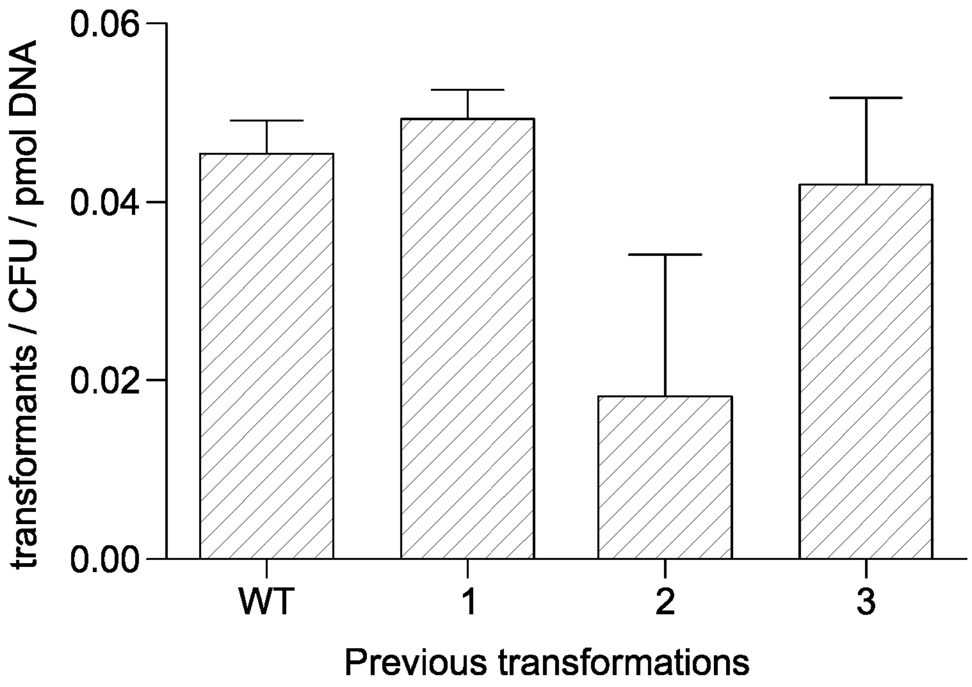

FIG. 33: Repeated transformation of *N. lactamica* does NOT select for a more transformable phenotype.

Figure 34:
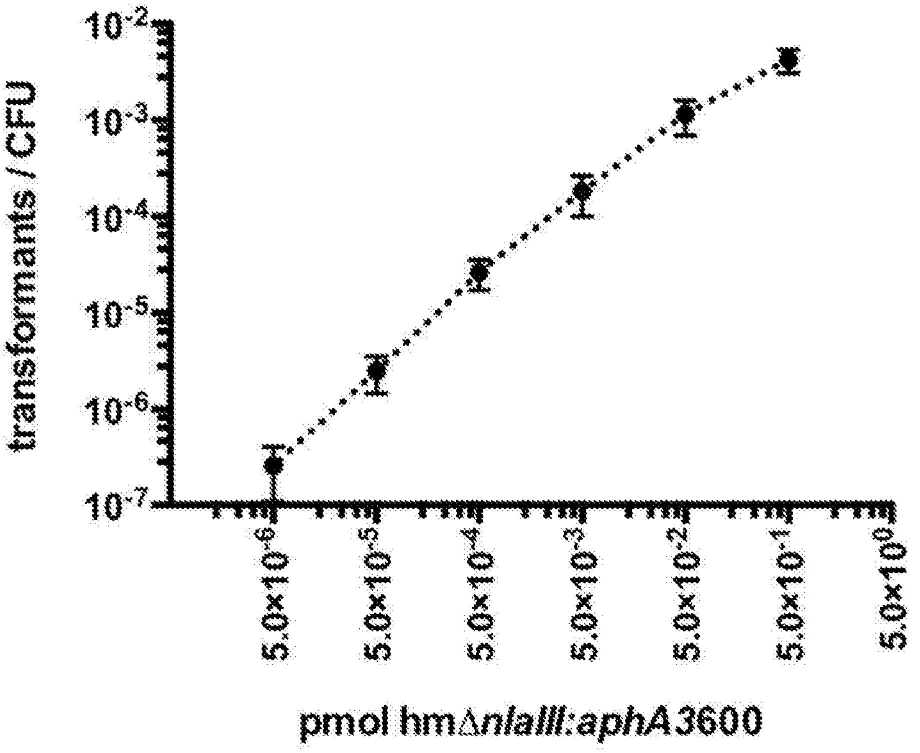

FIG. 34: Effect of the amount of donor material used to transform wild type *Neisseria lactamica*: supplemental.

Figure 35:
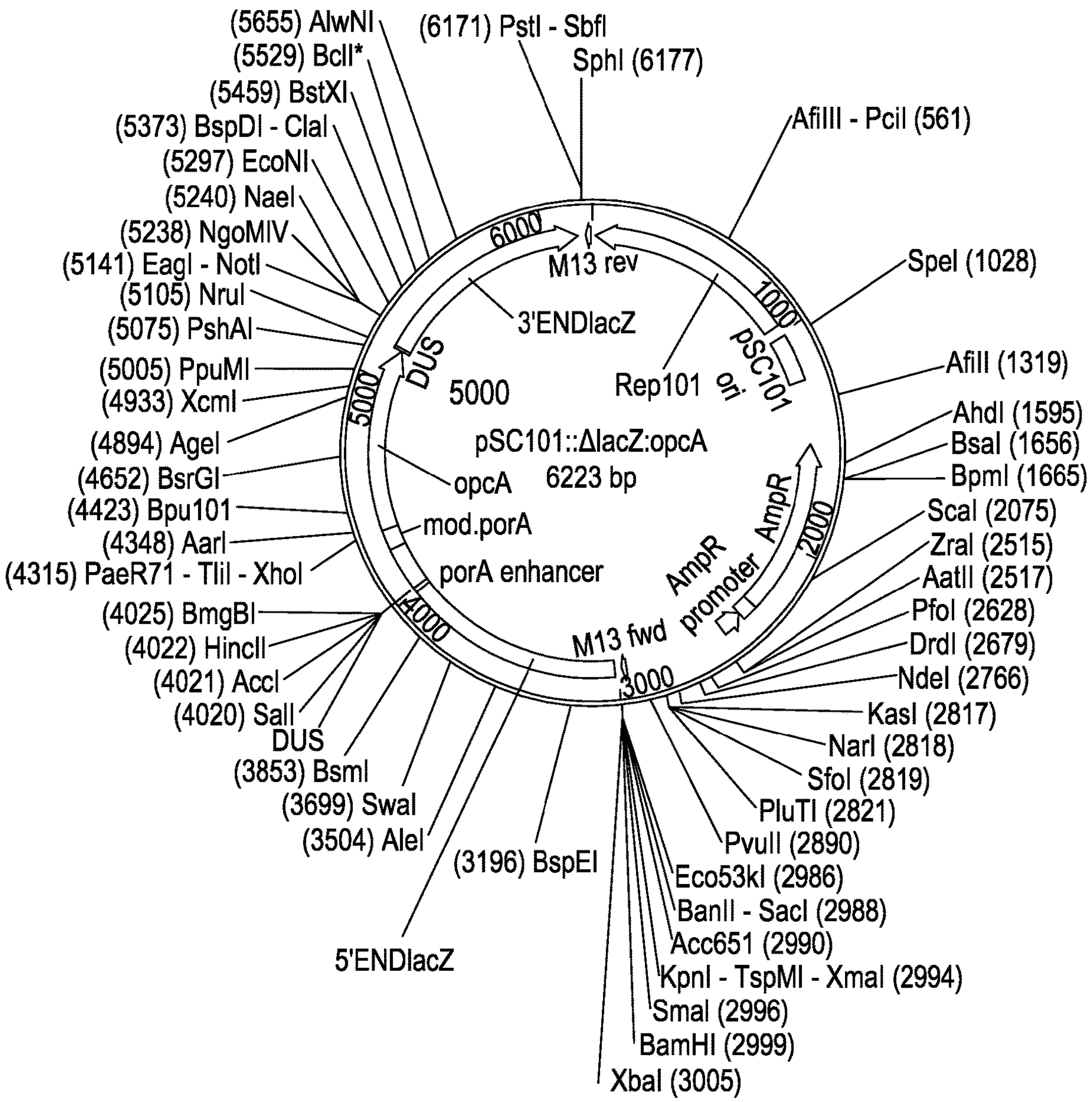

FIG. 35: Plasmid map of pSC101::ΔlacZ:opcA

Figure 36:
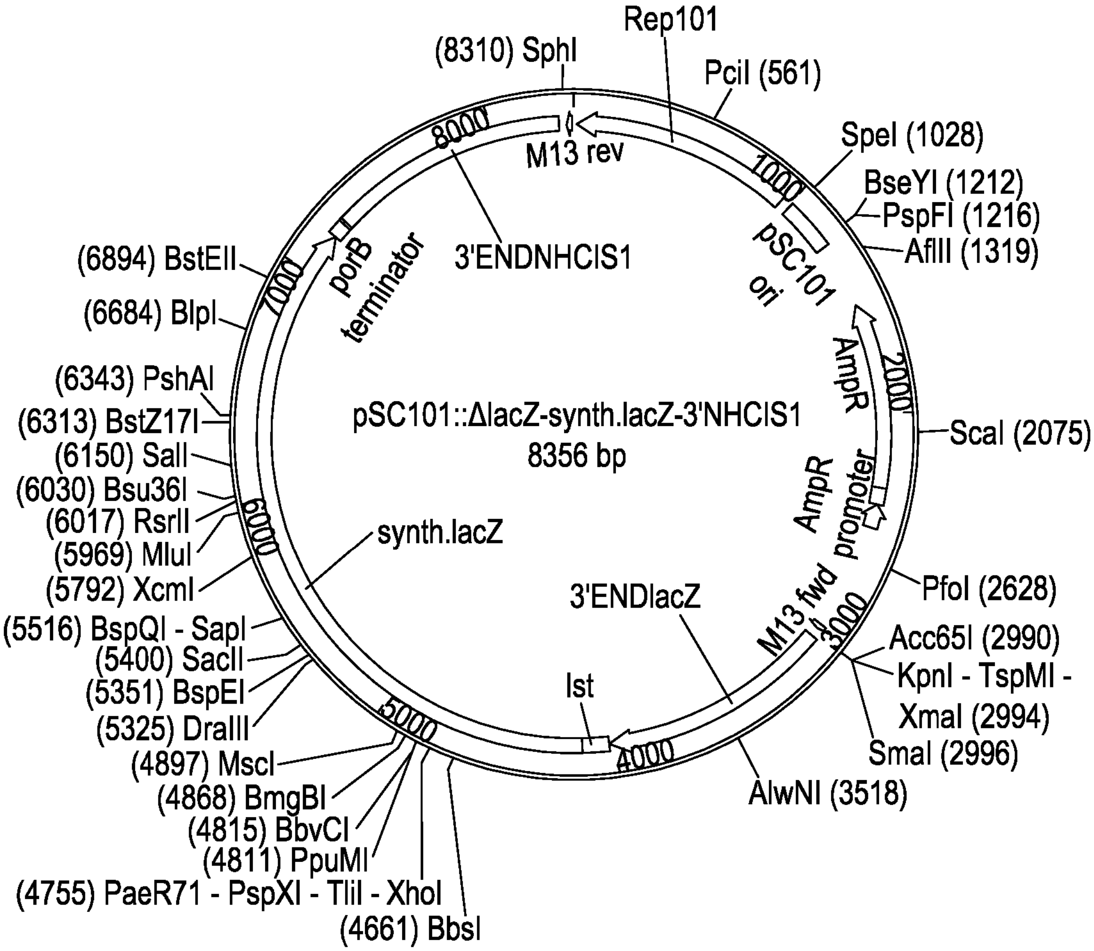

FIG. 36: Plasmid map of pSC101::ΔlacZ-synth.lacZ-3'ENDNHCIS1

FIG. 37 (SEQ ID NO: 20): Coding sequence of synth.lacZ

Figure 38:
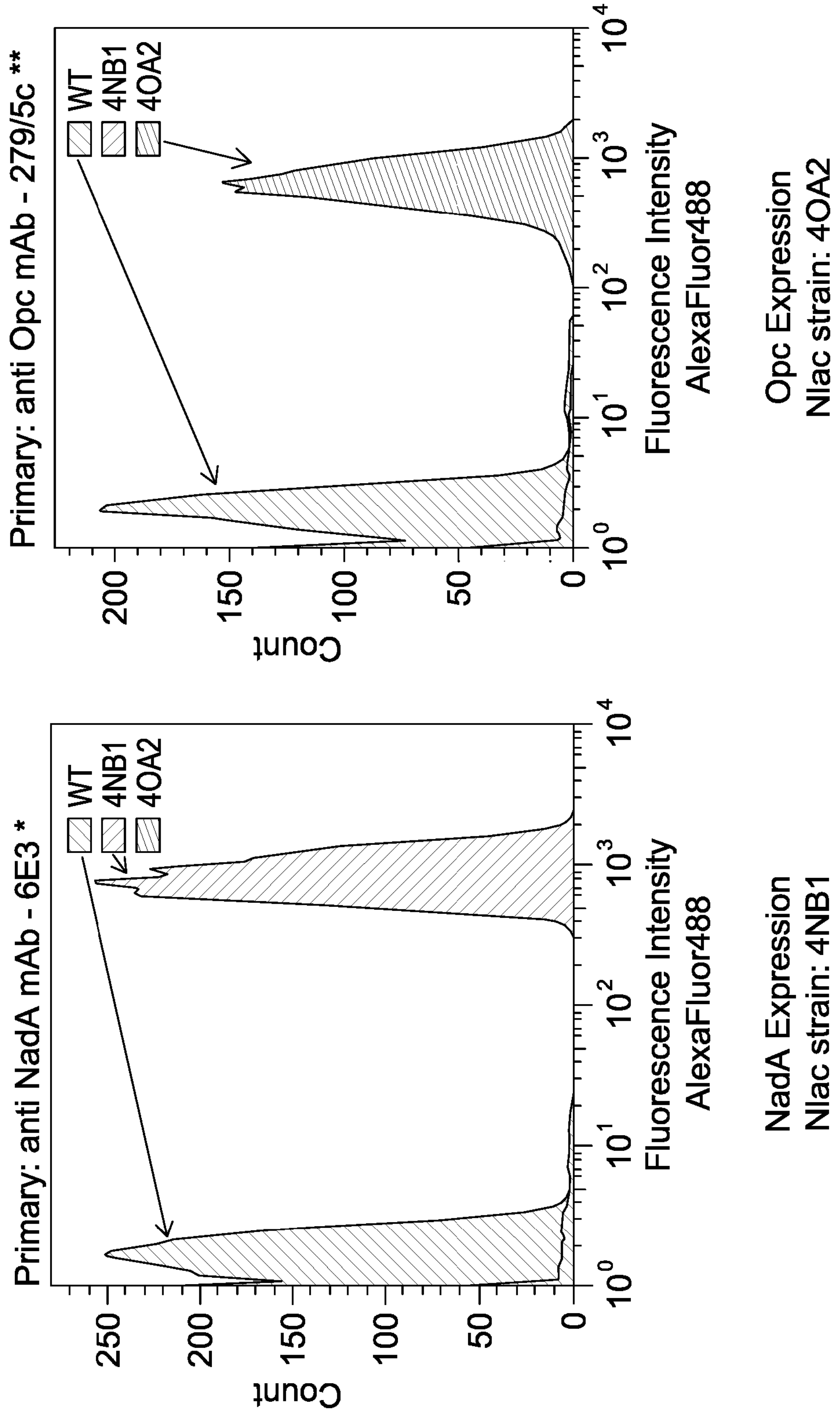

FIG. 38: Expression of NadA and Opc outer membrane proteins on the surface of recombinant strains of *N. lactamica*

Figure 39:
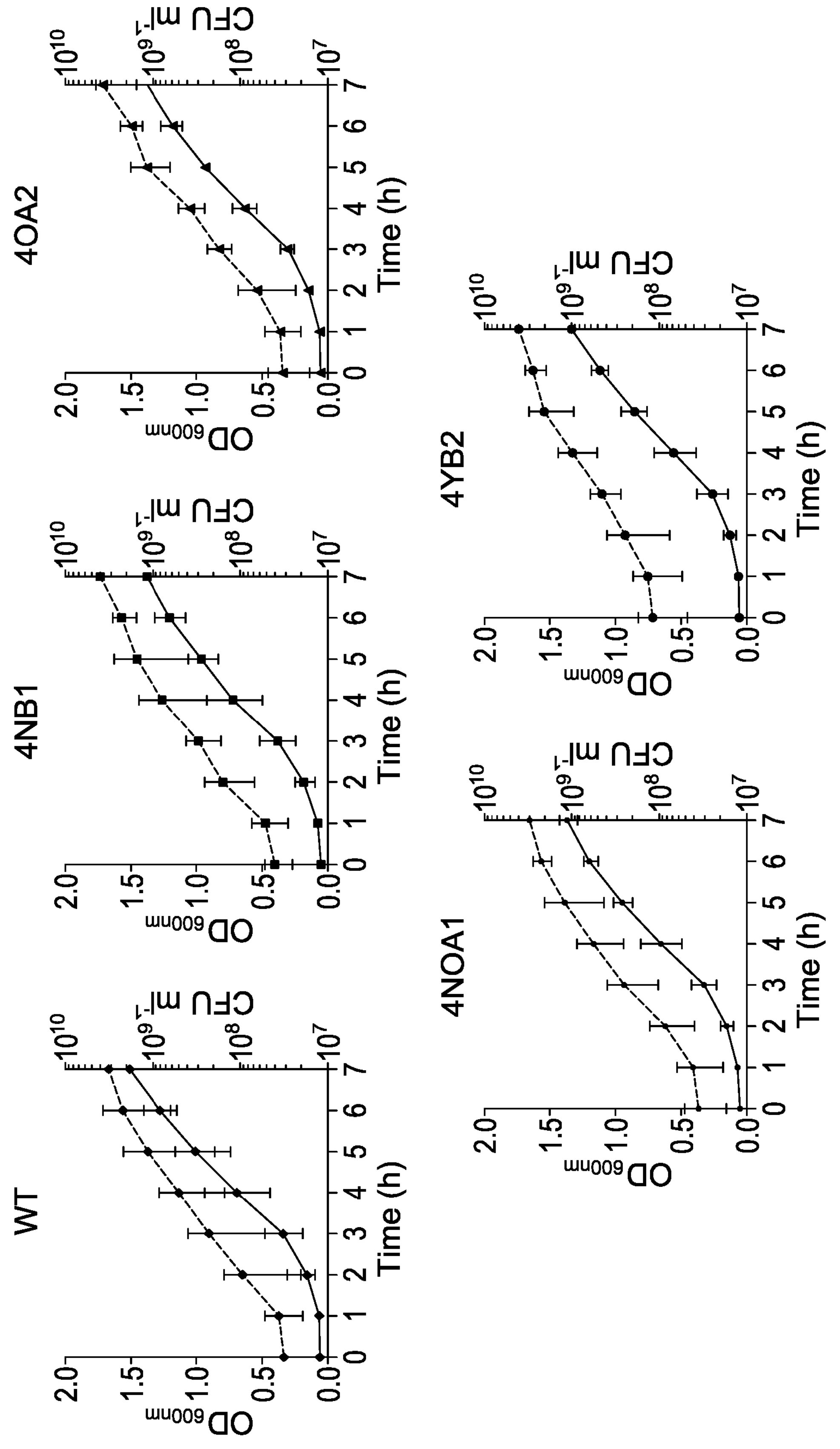

FIG. 39: Expression of NadA, Opc or a combination of both antigens in recombinant *N. lactamica* has no appreciable effect on growth rates in TSB FIGS. 40A and 40B: NadA-expressing strains of *N. lactamica* have increased adherence to HEP-2 cells (FIG. 40A), whilst Opc-expressing strains of *N. lactamica* are internalized by HEP-2 cells in significantly larger numbers (FIG. 40B).

FIGS. 41A and 41B: The NadA-expressing strain of *N. lactamica,* 4NB1, is recovered in significantly higher numbers from within human nasopharyngeal tissue explants than is the wild type FIG. 42: Recombinant strains of *N. lactamica* expressing meningococcal adhesin proteins have similar sensitivity profiles to front-line antibiotics as the wild type FIG. 43: Recombinant strains of *N. lactamica* expressing meningococcal adhesin proteins are competent for uptake of exogenous DNA and can be transformed with efficiencies similar to the wild type FIG. 44: Wild type and recombinant strains of *N. lactamica* are completely refractory to transformation by chromosomal DNA derived from *N. meningitidis*

Figure 45:
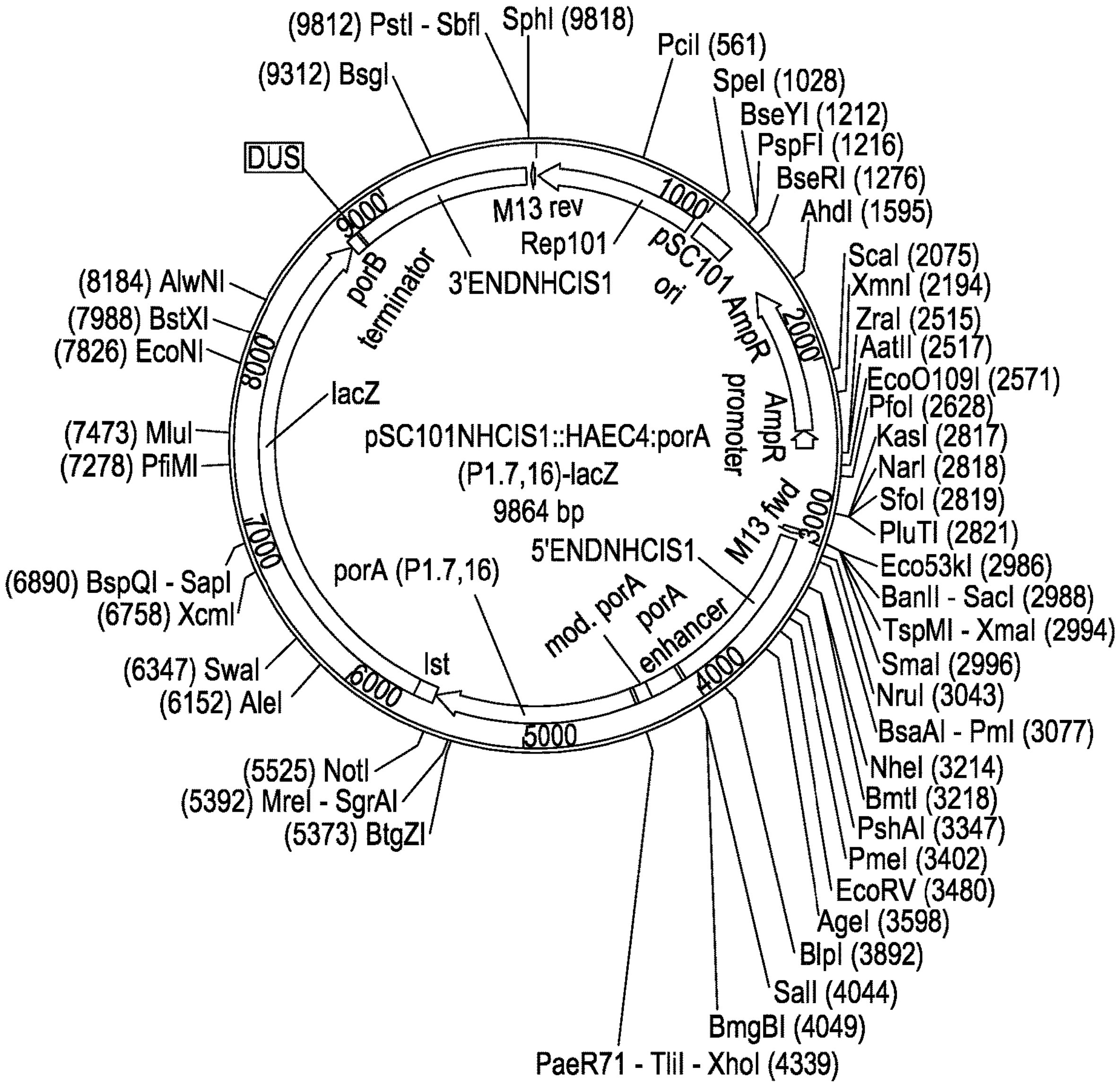

FIG. 45: Plasmid map of pSC101NHCIS1::HAEC4:porA (P1.7,16)-lacZ

Figure 46:
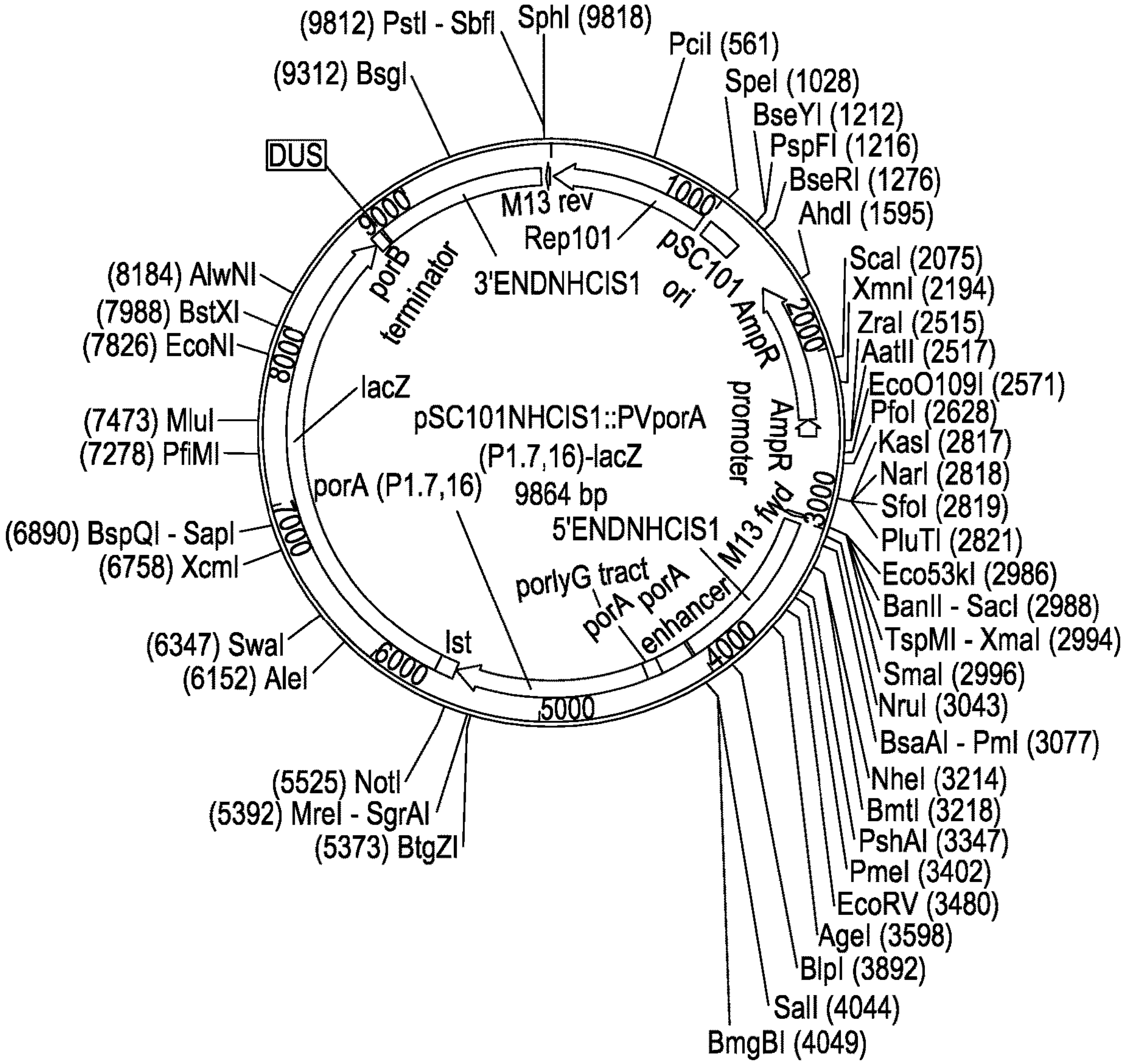

FIG. 46: Plasmid map of pSC101NHCIS1::PVporA(P1.7, 16)-lacZ

FIGS. 47A-47C: Recombinant Nlac strains express Porin A (P1.7, 16) at the cell surface and generate PorA-containing OMV FIGS. 48A and 48B: Immunisation with OMV from recombinant, PorA-expressing Nlac generates anti-meningococcal SBA FIG. 49: Immunisation with OMV from recombinant, NadA-expressing Nlac generates anti-meningococcal SBA Trials of experimental human nasopharyngeal inoculation with wild type *Neisseria lactamica* strain Y92-1009 have shown that successful colonisation of volunteers by the bacterium can lead to persistent carriage of the organism for up to six months, and that inoculation with the live bacterium also broadens the range of humoral immune responses directed against a narrow panel of *Neisseria meningitidis* isolates. Colonisation of the nasopharynx by *Neisseria lactamica* is completely benign. Therefore, the ability to modify the outer membrane components of *Neisseria lactamica* to include proteins not present in the wild type organism would be extremely beneficial, as it would allow the use of these modified strains as either a means of generating novel OMV that contain antigens from biotic sources other than *Neisseria lactamica*, or as a safe means of delivering antigen to the nasopharyngeal mucosa for prolonged periods as an alternative means of vaccination.

The most likely cause of the lack of methods to manipulate the genetics of *Neisseria lactamica* is the battery of restriction enzymes encoded in the genome of *Neisseria lactamica*, most notably the 4-cutter restriction enzyme, NlaIII, which cuts dsDNA at the short palindromic sequence 'CATG'. By random chance and in the absence of negative selection pressure, this sequence motif occurs with high frequency in a given stretch of nucleotides, meaning that uptake of DNA containing one or more of these sequences results in the intracellular degradation of the material before homologous recombination can take place and integrate the exogenous DNA into the *Neisseria lactamica* chromosome. This invention describes a process to circumvent the barriers to transformation of *Neisseria lactamica* and allow targeted genetic modification of this organism to be performed for the first time. The invention allows stable integration of DNA constructs into loci of the *Neisseria lactamica* chromosome, with utility for both deletion of existing genes (i.e. targeted mutagenesis) or insertion of genes from other biotic sources. This procedure differs from normal methods used to transform *Neisseria* in its use of hypermethylated PCR products as the donor material, whereby all the deoxycytosine residues of the nucleotide product have been replaced with methyl-deoxycytosine. Methylation of restriction sites can inhibit the DNA cleavage action of restriction endonucleases, which prevents degradation of the product following uptake and therefore provides sufficient time for homologous recombination to take place and the construct to become integrated into the chromosomal locus of choice. The restriction enzyme NlaIII is inhibited in this way (see FIG. 7), and the use of hypermethylated PCR products to transform *Neisseria lactamica* is demonstrably more efficient than using non-methylated, 'normal' PCR products (see FIG. 6).

A number of cloning vectors have been developed in accordance with the invention. These cloning vectors are based upon the standard cloning vector pUC19, but come in two varieties dependent upon the application. For most routine manipulations and cloning strategies, plasmids containing the pMB1 origin of replication (ori), which maintains a relatively high number of plasmids per cell, can be used. pMB1 is the original ori for pUC19, and all plasmids described in accordance with this invention that contain pMB1 are described as pUC19 derivatives (e.g. pUC19ΔnlaIII::CLOVER-aphA3). In instances where a gene produces a product toxic to *E. coli* (the organism used for the maintenance and amplification of the plasmids), or where high-level expression of a gene is deleterious, a variant plasmid backbone has been developed in which the pMB1 ori has been replaced with the minimally required replication region of pSC101 (repA/ori). Whilst the rest of the plasmid backbone, including the selection marker, remains unchanged from pUC19, these plasmids are maintained at a much lower copy number per cell (i.e. five). The reduction in copy number may therefore prove permissive for cloning of deleterious sequences with high fidelity. All plasmids that contain the repA/ori region of pSC101 are described as pSC101 derivatives (i.e. pSC101NHCIS1::HAEC4:opcA-lacZ).

The majority of cloning vectors developed in accordance with this invention contain large regions of homology to the *Neisseria lactamica* chromosome, with added restriction sites for ease of cloning. The regions of homology are designated the *Neisseria* Heterologous Construct Insertion Sites (NHCIS) and are located in areas of relative gene paucity in the chromosome of the vaccine strain of *Neisseria lactamica*, Y92-1009. The purpose of these plasmids is to streamline the process of inserting DNA coding for heterologous antigen(s) into the Y92-1009 chromosome, specifically into loci where there will be minimal disruption of other genes that are perhaps essential or beneficial to the biological fitness of the bacterium. Using these vectors we have also developed derivatives that contain a novel means of screening for successful transformation of *Neisseria lactamica*, whereby the regions of homology flank Heterologous Antigen Expression Constructs (HAEC), each of which consists of two *Neisseria lactamica* promoter sequences surrounded by a number of unique restriction sites for streamlined manipulation and directional cloning of desired sequences for downstream introduction into the Y92-1009 genome. At the current time there are 4 such constructs, designated HAEC1 through HAEC4, named in the order in which they were created. HAEC1 contains the lst promoter followed (3') by the porB promoter, and this is reversed in HAEC2. HAEC3 contains a hybrid porA/porB promoter, wherein the homopolymeric tract of 'G' nucleotides that renders the wild type porA gene phase variable has been replaced with sequence derived from the wild type, non-phase variable porB promoter of *N. lactamica*. This promoter is preceded by 250 bp of transcriptional enhancer sequence, derived from the wild type porA gene of *N. meningitidis*. The porA/porB hybrid promoter is followed (3') by a second hybrid promoter, wherein the 17 bp that separate the −10 and −35 boxes of the RNA Polymerase binding site of the wild type porB gene have been replaced with 17 bp of sequence derived from the lst promoter. The rest of the promoter is identical to that of the wild type, *N. lactamica* porB gene (FIG. 25). HAEC4 contains an identical porA/porB hybrid promoter to HAEC3, but which is preceded by only 200 bp of porA-derived enhancer sequence. This length of enhancer sequence has been demonstrated to be more potent than the 250 bp version (see FIG. 22). In HAEC4, the lst promoter follows (3') the highly transcriptionally active hybrid promoter (FIG. 26). In each plasmid designed to transform *N. lactamica* in a way suitable for use in human challenge, the second promoter sequence of each HAEC drives a copy of the *Neisseria lactamica* β-galactosidase (lacZ) gene, which we have used as a means of screening for successful transformation of a ΔlacZ mutant derivative of Y92-1009. To construct the ΔlacZ mutant, the procedure described in Protocol A was utilised to completely remove the coding sequence of the lacZ gene—thus minimising the potential for off-target recombination of NHCIS-targeted constructs. Taken together, the ΔlacZ Y92-1009 derivative and the NHCIS (X)::HAEC(Y):(Z)-lacZ vector system constitute a useful tool for generating the recombinant strains of *Neisseria lactamica* described above in a way free from the use of antibiotic resistance cassettes, which would otherwise preclude their use in human challenge studies.

In some examples a ΔlacZ mutant derivative of *N. lactamica* Y92-1009 is further genetically manipulated. This strain was created using the transformation protocol detailed in Protocol A. The strain has had all of the coding sequence for the wild type lacZ gene removed from the chromosome to avoid non-specific recombination events with the Nlac lacZ-containing Cassettes and concomitant mis-targeting of the Cassette to loci other than that intended. This strain provides the background for insertion of genes coding for heterologous antigens without need for antibiotic resistance markers, a preferred state for potential human challenge with recombinant *Neisseria lactamica*.

When referring to the use of restriction sites for restriction/ligation cloning of sequences into various constructs, the same restriction site must be absent from the oligonucleotide sequence being cloned.

PROTOCOL A: Transformation Protocol for *Neisseria lactamica:*

1. Inoculate TSB with multiple colonies of the recipient strain of *Neisseria lactamica* (hereafter, the Culture). This could be a recognised laboratory strain such as Y92-1009, a mutant derivative thereof, or wild type or mutant strains of *N. lactamica* isolated from volunteers.
2. Incubate the Culture at 37° C., 5% $CO_2$ with shaking until an $OD_{600nm}$ is reached of 0.3.
3. Dilute the Culture ×100 in fresh TSB.
4. Spot 10 μl aliquots of the ×100 dilution of the Culture onto Tryptone Soy Broth +0.2% yeast extract agar plates (hereafter, TSB agar) and allow to dry in a Microbiological Safety Cabinet.
5. Replace the lids and transfer the plate(s) (right side up) to a $CO_2$ incubator set to 30° C., 5% $CO_2$. Incubate for 6 h.
6. Onto the surface of the now-visible *N. lactamica* colonies, pipette 10 μl of Tris HCl buffer containing an appropriate amount of Donor material and allow to dry in a Microbiological Safety Cabinet.
7. Transfer the plate(s) to the incubator at 30° C., 5% $CO_2$ and incubate for 9-10 h.

PROTOCOL A.1: Alternative transformation protocol for *Neisseria lactamica:*

1. Grow the recipient strain of *N. lactamica* on suitable (i.e. growth sustaining) agar plates overnight at 37° C., 5% $CO_2$. This could be a recognised laboratory strain such as Y92-1009, a mutant derivative thereof, or wild type or mutant strains of *N. lactamica* isolated from volunteers.
2. Using a sterile microbiological loop, transfer a multitude of colonies to fresh, sterile TSB medium supplemented with 10 mM $Mg^{2+}$ ions (solutions of either $MgSO_4$ or $MgCl_2$ are suitable). Continue this process until the $OD_{600m}$ of the suspension is greater than or equal to 0.3.
3. Transfer aliquots of the concentrated bacterial suspension to fresh, sterile microcentrifuge tubes and adjust the $OD_{600m}$ to 0.3 using fresh, sterile TSB medium supplemented with 10 mM $Mg^{2+}$
4. Prepare the Donor material in sterile PBS. The Donor material could be genomic DNA, a PCR or hypermethylated PCR product, or an artificially synthesized nucleic acid.
5. Add the Donor material to the microcentrifuge tubes, mix by vortexing or pipetting and incubate the tubes at 37° C., 5% $CO_2$ for 3 h.

Continue with Protocol B for constructs using 3-galactosidase activity as the means of identifying transformed bacteria; alternatively, plate the suspensions on an appropriately selective agar medium prior to overnight incubation.

PROTOCOL B: Screening for transformed *Neisseria lactamica* containing (3-galactosidase as part of the genetic construct:

8. Harvest each patch of putatively-transformed *N. lactamica* into 1 ml of fresh, sterile TSB.
9. Perform a 10× serial dilution of the bacterial suspension in TSB: i.e. ×10, $\times 10^2$ and $\times 10^3$.
10. Further dilute the $\times 10^3$ suspension ×5 (i.e. 100 μl of $10^3$ bacterial suspension in to 400 μl TSB).
11. On 5 separate TSB agar plates supplemented with 20 ng/ml 5-bromo-4-chloro-3-indolyl-beta-D-galacto-pyranoside (hereafter X-GAL), spread 100 μl of the $5\times 10^{-3}$ bacterial suspension and allow to dry in a Microbiological Safety Cabinet.
12. Incubate overnight at 37° C., 5% $CO_2$.
13. Isolate each BLUE colony into 1 ml TSB and culture at 37° C., 5% $CO_2$ for production of stocks and isolation of DNA.

Plasmid Map of pUC19ΔnlaIII::CLOVER-aphA3.

With reference to FIG. 1, the pUC19ΔnlaIII::CLOVER-aphA3 Construct is a pUC19-derived plasmid designed to introduce codon-optimised CLOVER and aphA3, under the control of the promoter from the α-2,3-Sialyltransferase gene (lst), into the ORF of the restriction enzyme, NlaIII (nlaIII, NLY_28620). The Cassette, which has been cloned into the HincII restriction site of pUC19 via Gibson Assembly (NEB), consists of sequence amplified from the region of the *N. lactamica* chromosome containing the nlaIII gene, including most of the nlaIII coding sequence, into which has been cloned versions of the CLOVER and aphA3 genes that are codon-optimised for expression in *Neisseria lactamica*. Expression of these genes is controlled by a modified lst promoter, into the 5' untranslated region (hereafter, 5' UTR) of which was introduced an XhoI restriction site to simplify downstream manipulation of the Cassette. The CLOVER and aphA3 genes are tandemly expressed from this promoter, and are separated by (in 5' to 3' order), a NotI restriction site (to facilitate substitution of the CLOVER gene for any other nucleotide sequence), a DUS (to enhance uptake of the Cassette by *N. lactamica* as part of PROTOCOL A), and a modified Ribosome Binding Site (hereafter, RBS) (to ensure translation of mRNA coding aphA3) (see FIG. 2). Immediately 3' of aphA3, the chromosomal sequence has been modified to introduce an XbaI restriction site. This site enables XbaI-digestion of the Construct to release the Cassette, for use as Donor material in PROTOCOL A. The sequence derived from the *N. lactamica* nlaIII-containing chromosomal region also contains an inv. AT-DUS, 5' of the start codon of the nlaIII gene. The plasmid map is presented showing all relevant features, including the insertionally-inactivated ORF for nlaIII, and detailing the location of unique restriction sites with recognition sequences 6 nucleotides or greater.

Nucleotide Sequence of Tandemly-Expressed, *N. lactamica*-Codon-Optimised CLOVER and aphA3 Genes.

With reference to FIG. 2, the sequences of these genes have been codon-optimised for expression in *N. lactamica*. The activity of NlaIII is a significant barrier to successful transformation of *N. lactamica* (see FIG. 6). This piece of the Cassette could be controlled from any *N. lactamica*-compatible promoter sequence and be flanked by a contiguous nucleotide sequence from theoretically any locus in the *N. lactamica* chromosome.

Confocal Microscopy of Wild Type and CLOVER-Expressing Strains of *Neisseria lactamica* Y91-1009.

Figure 3:
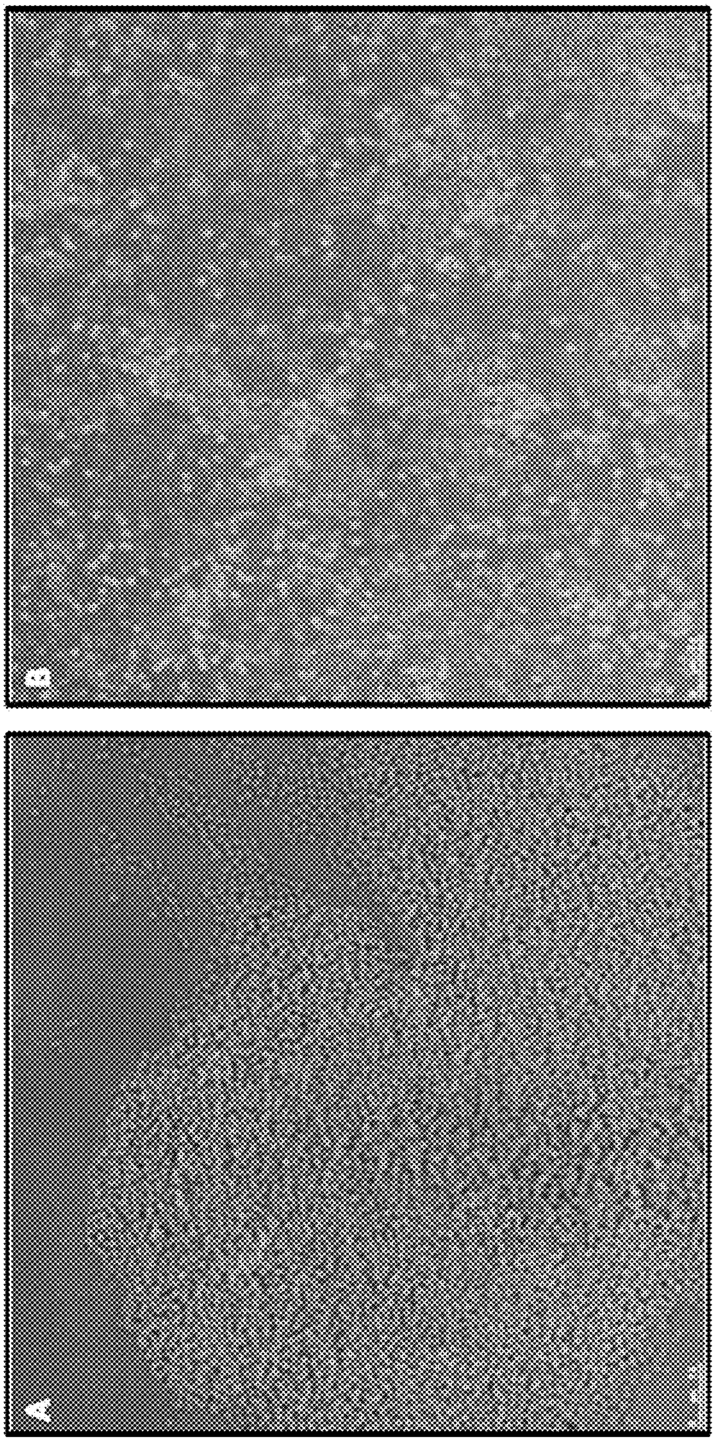

With reference to FIG. 3, wild type *N. lactamica* Y92-1009 was transformed with donor material derived by hypermethylated PCR from pUC19ΔnlaII::CLOVER-aphA3 (FIG. 1), as described in PROTOCOL A. Transformants, which were selected for on the basis of resistance to kanamycin (50 μg/ml in TSB agar plates), were isolated and cultured. Chromosomal integration of the donor material into the nlaIII locus was determined by PCR (data not shown). Stationary phase (overnight) colonies of both wild type Y92-1009 (A) and a transformed, putatively CLOVER-expressing derivative thereof (B), were dispersed into sterile PBS, spread across the surface of a microscope slide and allowed to air dry in a Class II microbiological safety cabinet. Bacteria were visualised under the confocal microscope using light at a wavelength of 988 nm and the images digitally captured. It is important to note that whilst the overall level of fluorescence is low, there is green fluorescence of the CLOVER-transformed bacteria, which is not evident in the wild type, parental strain. This is the first demonstration of significant eukaryotic gene expression in *N. lactamica*. Furthermore, this is the first demonstration of heterologous protein expression in this species of bacterium.

Plasmid Map of pUC19 ΔnlaIII::aphA3.

With reference to FIG. 4, the pUC19ΔnlaIII::aphA3 Construct is a derivative of pUC19ΔnlaIII::CLOVER-aphA3, wherein the aphA3 gene has been placed under direct transcriptional control of the lst promoter, and that which remains of the nlaIII coding sequence has been further truncated. The sequence derived from the *N. lactamica* nlaIII-containing chromosomal region also contains an inv. AT-DUS, 5' of the start codon of the nlaIII gene. The plasmid map is presented showing all relevant features, including the insertionally-inactivated ORF for nlaIII, and detailing the location of unique restriction sites with recognition sequences 6 nucleotides or greater.

Transformation Efficiency of Wild Type *Neisseria lactamica* Using (Hypermethylated) PCR Products Amplified from pUC19ΔnlaIII:aphA3.

With reference to FIG. 5, XbaI-digested pUC19ΔnlaIII::aphA3 was used as a template to amplify the ΔnlaIII::aphA3 Cassette using both traditional (Non-methylated) and 'Hypermethylated' PCR. Traditional PCR uses an equimolar mixture of the four, unmodified deoxyribonucleotides; whereas 'hypermethylated' PCR uses a nucleotide mixture that substitutes 5-methyl-dCTP instead of unmodified dCTP and results in a PCR product in which every C residue is methylated. The primers used in the reaction produced products of identical sequence with 1200 bp of 'flanking' DNA on either side of the aphA3 gene. The transformation was carried out according to Protocol A, using a total of 1000 ng of each PCR product (=0.46 pmol). The number of transformants was considered to be equal to the number of kanamycin-resistant colonies that grew overnight on selective agar plates (TSB+0.2% yeast extract supplemented with 50 μg/ml kanamycin). Indeed, PCR analysis of the nlaIII chromosomal locus from 50 individual, kanamycin resistant colonies derived from transformation with either construct showed that the aphA3 gene had been accurately targeted. The graph shows that transformation into the nlaIII locus is significantly higher through the use of hypermethylated PCR product as compared to an identical, unmodified PCR product. However, it is important to note that the ΔnlaII::aphA3 Cassette is free of 'CATG' sites, the recognition and cleavage site of the NlaIII restriction enzyme.

Transformation efficiency of wild type *Neisseria lactamica* using (hypermethylated) PCR products amplified from pUC19A nlaIII::CLOVER-aphA3 and derivatives thereof, wherein site-directed mutagenesis has been used to remove 'CATG' sequences from the CLOVER coding sequence.

With reference to FIG. 6, the coding sequence of the *Neisseria lactamica*-codon optimised CLOVER gene contains two 'CATG' sequences, which is the recognition and cleavage site for the NlaIII restriction enzyme. As a four-cutter restriction enzyme, the frequency of this sequence in exogenous genetic material is likely to be high, and we hypothesise that the restriction activity of NlaIII is one of the main components of the observed resistance of *Neisseria lactamica* to genetic manipulation. To investigate this, a series of plasmids were generated in which one or both of the two 'CATG' sequences had been removed from the CLOVER gene, using the Q5 Site-directed mutagenesis kit (NEB). The remainder of the construct contained no CATG sequences. These plasmids were used as templates for traditional (i.e. Non-methylated) or 'hypermethylated' PCR. Identical primers were used for both types of PCR, producing PCR products with 600 bp of sequence flanking either side of the CLOVER-aphA3 cassette. Transformation of wild type *Neisseria lactamica* was carried out as described in Protocol A, using 634 ng (=0.46 pmol) of each PCR or hmPCR product. The number of transformants was considered to be equal to the number of kanamycin-resistant colonies that grew overnight on selective agar plates (TSB+0.2% yeast extract supplemented with 50 μg/ml kanamycin), adjusted for dilution and plating volume. Where the transformation efficiency was below the limits of detection, the appropriate data points were calculated as if the transformation derived a single transformant. The graph shows that the transformation efficiency of wild type *Neisseria lactamica* is significantly effected by the presence of 'CATG' sequences, wherein the introduction of a single 'CATG' sequence into an otherwise CATG-free construct reduces the transformation efficiency by an average of 33 fold. The graph also shows that the use of hypermethylated PCR products enhances the transformation efficiency of wild type *Neisseria lactamica*, in keeping with the data presented in FIG. 4. Where two 'CATG' sequences are present in the transformation construct, use of hypermethylated PCR product is approximately 4000 times more efficient at transforming wild type *Neisseria lactamica* than using an equivalent, Non-methylated PCR product. Importantly, there are no differences in the transformation efficiencies measured using any of the hypermethylated PCR products, which implies complete blocking of all restriction endonuclease recognition and cleavage sites. Hypermethylation is also likely to block the restriction function of other endonuclease enzymes in *Neisseria lactamica*, as transforming bacteria with a hypermethylated PCR product derived from the CATG-free template was on average 22 times more efficient than using a Non-methylated PCR product.

Hypermethylation of PCR Product Blocks Restriction Activity of NlaIII.

With reference to FIG. 7, the series of pUC19ΔnlaII::CLOVER-aphA3 plasmids, each with a different number of 'CATG' motifs within the CLOVER coding sequence, were used as templates in both normal (i.e. Non-methylated) and hypermethylated PCR. Amplification of the ΔnlaIII::CLOVER-aphA3 Cassettes was followed by in vitro digestion of 1 μg of each with recombinant NlaIII (NEB) in Cutsmart buffer. Two hundred nanograms of each digested product was then loaded onto a 0.7% agarose gel and electrophoresis was carried out to separate any products. An inverted gel image was captured from the UV transilluminator using a digital camera. Whilst each hypermethylated PCR product (Hm) ran at a slightly increased molecular weight cf. its non-methylated equivalent (N), the former was completely protected from NlaIII enzymatic digest.

Effect of the Length of the Flanking Region and Amount of DNA Used to Transform Wild Type *Neisseria lactamica* Using PROTOCOL A.

With reference to FIG. 8, to investigate the effect of the size of the regions of homology to the *N. lactamica* chromosome on transformation efficiency (A), a series of hypermethylated PCR products of different lengths were derived from XbaI-digested pUC19ΔnlaIII::aphA3 plasmid. In each product the aphA3 gene and its promoter were identical, whilst the length of the nlaIII chromosomal regions surrounding this sequence was varied. The flanking lengths used in this experiment (i.e. the length of the DNA sequence on each side of the aphA3 gene) were: 75 bp, 150 bp, 300 bp, 600 bp and 1200 bp. As shown in FIGS. 6 and 7, the fact that the PCR products were hypermethylated ruled out the presence of 'CATG' sequences in shorter products as a confounding factor, as it is likely that all restriction endonuclease recognition and cleavage sites were blocked by the inclusion of mdCTP. Transformation of wild type *Neisseria lactamica* was carried out according to Protocol A, using 0.46 pmol of each hypermethylated PCR product. The number of transformants was considered to be equal to the number of kanamycin-resistant colonies that grew overnight on selective agar plates (TSB+0.2% yeast extract supplemented with 50 μg/ml kanamycin), adjusted for dilution and plating volume. Graph A shows that with increasing length of the Cassette flanking sequence, there is an increase in the transformation efficiency of *Neisseria lactamica* into the nlaIII locus. However, the presence of longer flanking sequences results in increased inter-experimental variation in transformation efficiency.

To investigate the effect of the amount of donor DNA on the transformation efficiency of *Neisseria lactamica* (B), increasing amounts of hypermethylated PCR product with 600 bp of flanking sequence were used as described in Protocol A. This PCR product was used because there is inherently less inter-experimental variability then when using a product that contains 1200 bp of flanking sequence, implying a better signal-to-noise ratio in the event the effect was a subtle one. Wild type *Neisseria lactamica* were transformed using 0.06, 0.26, 0.46, 0.66, 0.86 and 1.06 pmol of hypermethylated PCR product. The number of transformants was considered to be equal to the number of kanamycin-resistant colonies that grew overnight on selective agar plates (TSB+0.2% yeast extract supplemented with 50 μg/ml kanamycin), adjusted for dilution and plating volume. Graph B shows that there is a potentially bi-phasic peak in transformation efficiency, although the mechanism for this remains even theoretically unclear. The only significant difference in transformation efficiency is between the transformations carried out using 0.26 and 0.46 pmol of DNA, where the lower amount of DNA yields the most transformants. However, this is most probably a statistical anomaly that we predict will disappear with repetition of the experiment.

Effect of the neisserial DNA Uptake Sequence (DUS) on the transformation efficiency of *Neisseria lactamica* using PROTOCOL A.

With reference to FIG. 9, the non-palindromic repeat sequence 5'-GCCGTCTGAA-3' (SEQ ID NO: 1), or close derivatives/relatives thereof, occurs with high frequency in the chromosomes of many *Neisseria* species. Previous studies have demonstrated that bacterial uptake of DNA molecules containing these sequences is enhanced, hypothetically through a charge interaction with a positively charged region of ComP, a pilus-associated protein. The effect of the standard DNA Uptake Sequence (hereafter, DUS) on transformation efficiency is further enhanced by the presence of 'AT' nucleotides at the 5' end. The AT-variant of the DUS (hereafter, AT-DUS) is the 'dialect' of DUS repeated at the highest frequency in the wild type *Neisseria lactamica* chromosome. The nlaIII chromosomal region included in pUC19ΔnlaII::aphA3 contains an inverted AT-DUS sequence in its 5' end. As a result, the primer pairs used to generate the PCR products containing 300 bp, 150 bp and 75 bp of flanking nlaIII chromosomal sequence (see FIG. 6) each contain only one copy of the DUS (that which was deliberately included after the aphA3 coding sequence), as compared to the PCR products containing 600 bp and 1200 bp of flanking nlaIII sequence, which contain two. To investigate the role of an additional AT-DUS on the transformation efficiency of wild type *Neisseria lactamica*, two versions of each PCR product were amplified from XbaI-digested pUC19ΔnlaII:aphA3, using alternative 5' primers: one primer in each set contained a canonical, inverted AT-DUS at the 5' terminus (DUS, black circles), whilst the alternate version contained a scrambled DUS (S-DUS, red squares). The S-DUS contains the same proportions of the same nucleotides as the DUS, but in a configuration designed to ensure no similarity to the various dialects of DUS. Transformation of wild type *Neisseria lactamica* was carried out as described in Protocol A, using 0.46 pmol of each PCR or hmPCR product. The number of transformants was considered to be equal to the number of kanamycin-resistant colonies that grew overnight on selective agar plates (TSB+0.2% yeast extract supplemented with 50 μg/ml kanamycin), adjusted for dilution and plating volume. The graph shows that inclusion of a second DUS in the PCR products used to transform *Neisseria lactamica* increases the transformation efficiency, and that this effect is more enhanced (to the point of becoming statistically significant) with increasing flanking sequence length.

Chromosomal Schematic and Nucleotide Sequence of NHCIS1 (*N. lactamica* Y92-1009).

With reference to FIG. 10, the schematic shows the chromosomal locus of NHCIS1 and its surrounding genes, which are shaded (greyscale) on the basis of GC nucleotide pair content (modified and reproduced from: http://www.xbase.ac.uk/genome/*neisseria*-lactamica-y92-1009/CACL01000001/NLY_27080;/viewer). The nucleotide sequences of the NHCIS1 regions are as detailed on the plasmid map for pUC19NHCIS1::HAEC1:(Z)-lacZ (FIG. 14) (i.e. 5'ENDNHCIS1 and 3'ENDNHCIS1).

Chromosomal Schematic and Nucleotide Sequence of NHCIS2 (*N. lactamica* Y92-1009).

With reference to FIG. 11, the schematic shows the chromosomal locus of NHCIS2 and its surrounding genes, which are shaded (greyscale) on the basis of GC nucleotide pair content (modified and reproduced from: http://www.xbase.ac.uk/genome/*neisseria*-lactamica-y92-1009/CACL01000018/NLY_36160;/viewer). The sequences of the NHCIS2 regions as detailed on the plasmid map for pUC19NHCIS2::HAEC1:(Z)-lacZ (FIG. 16) (i.e. 5'ENDNHCIS2 and 3'ENDNHCIS2). The italicised text represent nucleotides comprising part of the coding sequence for NLY_36160. The 5' NHCIS2 sequence contains an AT-DUS and an inv-AT-DUS, which are highlighted in bold text.

Annotated Nucleotide Sequence of HAEC1.

With reference to FIG. 12, the sequence consists of the *N. lactamica* lst promoter, preceded by a DUS and a SalI restriction site (to facilitate cloning and replacement of the lst promoter sequence), separated from the *N. lactamica* porB promoter sequence by an XhoI restriction site, an interchangeable LINKER sequence and a NotI restriction site. It is important to note that either LINKER sequence can be any given nucleotide sequence (represented as poly-N). By including an XhoI restriction site immediately 5' of the START codon and a NotI restriction site immediately 3' of the STOP codon of any given coding sequence (e.g. through the use of extended primer sequences that incorporate these sites), that sequence can be directionally cloned, IN-FRAME into the Construct for expression from the lst promoter. The featured NdeI restriction site can be used in conjunction with the HindIII restriction site present immediately 5' of the porB terminator sequence to clone any given coding sequence into the Construct. By including an NdeI restriction site immediately 5' of the START codon and a HindIII restriction site immediately 3' of the STOP codon of any given coding sequence (e.g. through the use of extended primer sequences that incorporate these sites), that sequence can be directionally cloned, IN-FRAME into the Construct for expression from the porB promoter. Immediately after the HindIII restriction site, there is a transcriptional terminator sequence, derived from downstream of the *N. lactamica* porB gene. This is immediately followed by an AT-DUS. In the context of heterologous antigen expression in recombinant *Neisseria lactamica*, HAEC1 is flanked on either side by sequences homologous to the *N. lactamica* chromosome (e.g. NHCIS1).

Annotated Nucleotide Sequence of HAEC2.

With reference to FIG. 13, the sequence consists of the *N. lactamica* porB promoter, preceded by a DUS and a SalI restriction site (to facilitate cloning and replacement of the lst promoter sequence), separated from the *N. lactamica* lst promoter sequence by an XhoI restriction site, an interchangeable LINKER sequence and a NotI restriction site. It is important to note that either LINKER sequence can be any given nucleotide sequence (represented as poly-N). By including an XhoI restriction site immediately 5' of the START codon and a NotI restriction site immediately 3' of the STOP codon of any given coding sequence (e.g. through the use of extended primer sequences that incorporate these sites), that sequence can be directionally cloned, IN-FRAME into the Construct for expression from the porB promoter. The featured NdeI restriction site can be used in conjunction with the HindIII restriction site present immediately 5' of the porB terminator sequence to clone any given coding sequence into the Construct. By including an NdeI restriction site immediately 5' of the START codon and a HindIII restriction site immediately 3' of the STOP codon of any given coding sequence (e.g. through the use of extended primer sequences that incorporate these sites), that sequence can be directionally cloned, IN-FRAME into the Construct for expression from the lst promoter. Immediately after the HindIII restriction site, there is a transcriptional terminator sequence, derived from downstream of the *N. lactamica* porB gene. This is immediately followed by an AT-DUS. In the context of heterologous antigen expression in recombinant *Neisseria lactamica*, HAEC2 is flanked on either side by sequences homologous to the *N. lactamica* chromosome (e.g. NHCIS1).

Plasmid Map of pUC19NHCIS1::HAEC1:(Z)-lacZ.

With reference to FIG. 14, the pUC19NHCIS1::HAEC1:(Z)-lacZ plasmid consists of a Cassette, comprised of the intergenic chromosomal sequence between NLY_27080 and NLY_27100 of *N. lactamica* (i.e. NHCIS1, see FIG. 10), disrupted by HAEC1:(Z)-lacZ (where Z represents any given coding sequence) (FIG. 12); cloned into pUC19 between two XbaI restriction sites. In one aspect of the invention, the *N. lactamica* lacZ gene is included as a screening marker, to enable identification of successfully transformed *N. lactamica* on the basis of BLUE/WHITE colony formation on plates containing 5-bromo-4-chloro-3-indolyl-β-D-galactopyranoside (X-Gal). This is deemed essential to the production of strains of *N. lactamica* for potential inoculation into human volunteers. Immediately 3' of the lacZ gene the Construct includes the terminator sequence from the *N. lactamica* porB gene, to ensure there is no translation of downstream, cistronic transcripts. Immediately 5' to the porB terminator sequence there is a unique HindIII restriction site, to facilitate removal of the lacZ gene from the Construct and its substitution with potentially any other oligonucleotide sequence. In other aspects of the invention, the Construct can be manipulated to introduce either one or two of potentially any given oligonucleotide sequence into the chromosome of *N. lactamica* at the NHCIS1 locus, although it is anticipated that one of the two sequences encodes a marker gene to enable screening or selecting for successfully transformed *N. lactamica*. The marker gene could plausibly encode proteins conferring antibiotic resistance, but it is preferable to avoid the use of such markers for producing strains intended for human challenge. The plasmid map is presented showing all relevant features and detailing the location of unique restriction sites with recognition sequences 6 nucleotides or greater.

Plasmid Map of pUC19NHCIS1::HAEC2:(Z)-lacZ.

With reference to FIG. 15, the pUC19NHCIS1::HAEC2:(Z)-lacZ Construct contains many elements identical to pUC19NHCIS1::HAEC1:(Z)-lacZ; except that HAEC1 (FIG. 12) has been replaced by HAEC2 (FIG. 13). The functional difference of this change is that the expression of any gene of interest cloned correctly into this plasmid will be driven by the *N. lactamica* porB promoter, whilst the expression of lacZ is driven by the *N. lactamica* lst promoter. The plasmid map is presented showing all relevant features and detailing the location of unique restriction sites with recognition sequences 6 nucleotides or greater.

Plasmid Map of pNHCIS2::HAEC1:(Z)-lacZ.

With reference to FIG. 16, the pNHCIS2::HAEC1:(Z)-lacZ plasmid consists of a Cassette, comprised of the intergenic chromosomal sequence between NLY_36160 and NLY_36180 of *N. lactamica* (i.e. NHCIS2, see FIG. 11), disrupted by HAEC1:(Z)-lacZ (where Z represents any given coding sequence) (FIG. 12); cloned into a truncated version of pUC19 between two XbaI restriction sites. The plasmid map is presented showing all relevant features and detailing the location of unique restriction sites with recognition sequences 6 nucleotides or greater.

Specific Activity of lacZ, Expressed from Different NHCIS Loci.

With reference to FIG. 17, a ΔlacZ mutant derivative of *N. lactamica* Y92-1009 was transformed with Cassettes derived from either pUC19NHCIS1::HAEC1:(Z)-lacZ or pNHCIS2::HAEC1:(Z)-lacZ according to the procedure detailed in PROTOCOL A. Chromosomal integration of HAEC1:(Z)-lacZ into either NHCIS1 (Strain NHCIS1) or NHCIS2 (Strain NHCIS2) was confirmed by PCR of the respective locus (data not shown) and functionality of the lacZ gene was confirmed by growth of the strains as BLUE colonies on Tryptone Soy Broth+0.2% yeast extract agar plates (hereafter, TSB agar), supplemented with X-Gal (20 ng $ml^{-1}$). Wild type Y92-1009, the ΔlacZ mutant derivative thereof and Strains NHCIS1/2 were cultured in Tryptone Soy Broth, supplemented with 0.2% yeast extract (hereafter, TSB) at 37° C., 5% $CO_2$ and 320 rpm, until reaching mid-log phase ($OD_{600nm}$=0.3). Bacteria were pelleted by centrifugation, washed once in sterile PBS then resuspended into 200 µl of Bacterial Lysis Buffer (BLB) before being lysed through sonication. The supernatant was diluted 5× with BLB, and 5, 2 and 1 µl aliquots were assayed for B-galactosidase activity using the chromogenic substrate ONPG. The activities in each of these aliquots were averaged to provide a value for each sample in each experiment. The protein concentration of each supernatant was measured using the DC Protein Assay Reagent (Bio Rad) and these values were used to normalise the measured β-galactosidase activities (yielding Specific Activity). Values shown are the mean of three independent experiments. Error bars represent the standard error of the mean. Where no error bars are visible, they fall within the line at the top of the column.

These data show that gene expression, driven by identical promoter sequences, is different when the same gene construct is chromosomally integrated into different loci. Assuming that β-galactosidase specific activity is proportional to the amount of β-galactosidase enzyme present, which is itself proportional to the level of transcriptional activity from the porB promoter sequence; the graph shows a significantly higher β-galactosidase activity, indicative of increased levels of gene transcription, were measured in Strain NHCIS2 than in Strain NHCIS1. In both instances expression of the lacZ gene is being controlled by the porB promoter. In the wild type and ΔlacZ strains, β-galactosidase expression is being controlled by its native, inducible lac promoter, except that the coding sequence for β-galactosidase is missing in the ΔlacZ strain, eliminating almost all of β-galactosidase activity. This graph shows that the choice of locus for chromosomal integration of genes coding for heterologous antigen is important. Based on these data; if a high level of protein expression is desired, then the gene coding for the heterologous antigen could be targeted to NHCIS2; conversely, genes coding for either potentially toxic products, or proteins that have a detrimental, concentration-dependent effect on the host organism should be targeted to NHCIS1, where the overall level of gene activity is lower.

Plasmid Map of pUC19NHCIS1::HAEC2:porAplusprom-lacZ

With reference to FIG. 18, the pUC19NHCIS1::HAEC2:porAplusprom-lacZ plasmid is a derivative of pUC19NHCIS1::HAEC2:(Z)-lacZ (FIG. 15), whereby the porA gene sequence, derived from *Neisseria meningitidis* strain H44/76, has been cloned, together with the native porA promoter and 107 bp of upstream chromosomal sequence, in between the SalI and NotI restriction sites of pUC19NHCIS1::HAEC2:(Z)-lacZ. Note that the plasmid map is based upon the ideal sequence for this plasmid, wherein the homopolymeric ‘G’ tract, which separates the −10 and −35 boxes of the native porA promoter contains 11 contiguous guanosine nucleotide residues. The plasmid map is presented showing all relevant features and detailing the location of unique restriction sites with recognition sequences 6 nucleotides or greater.

Expression of PorA in Recombinant *N. lactamica* has No Appreciable Effect on Growth Rate in TSB.

With reference to FIG. 19, the ΔlacZ mutant derivative of *N. lactamica* Y92-1009 was transformed with donor material derived by hypermethylated PCR from pUC19NHCIS1::HAEC2:porAplusprom-lacZ (Clone #7), as described in PROTOCOL A. Individual transformants, screened for on the basis of BLUE/WHITE colony formation on X-gal-containing TSB agar plates, were isolated. Chromosomal integration of the HAEC2:porAplusprom-lacZ cassette into the NHCIS1 locus was demonstrated through PCR (data not shown). Following DNA sequencing of the porA coding sequence in this locus, Strain A (hereafter: 2Pp7.A) was determined to contain genetic material with 100% identity to the porA gene.

Overnight cultures of wild type *N. meningitidis* strain, H44/76 (grown in Mueller Hinton Broth: MHB), the ΔlacZ mutant derivative of *N. lactamica* strain, Y92-1009 and the recombinant *N. lactamica* strain, 2Pp7.A (both grown in TSB+0.2% yeast extract), were washed once in PBS then resuspended into Bacterial Lysis Buffer (hereafter; BLB) supplemented with 100 µg/ml lysozyme, protease inhibitor cocktail and 1 mM PMSF. Suspensions were incubated at 30° C. for 30 minutes before the bacteria were lysed via sonication on ice (3×15 second bursts). Sonicated lysates were supplemented with 2 µl of a 5× dilution of rDNase and adjusted to a final [$Mg^{2+}$] of 2 mM before a further 30 minute incubation at 30° C. Bacterial membrane fractions were collected by centrifugation at 17,000 g for 30 minutes at 4° C., then resolubilised for 10 minutes at 95° C. into 1×LDS reducing sample buffer (Life Technologies). Insoluble material was removed by centrifugation at 17,000 g for 10 minutes at 4° C., following which the protein concentration of the solubilised membrane fraction was measured using the RC DC Protein Assay kit from Bio Rad.

A total of 50 μg of protein was loaded into each well of a 4-12% polyacrylamide gel and proteins were separated by electrophoresis. The proteins were then transferred to a methanol-activated PVDF membrane and the membrane was blocked using 5% milk-TBS for 1 h. The membrane was interrogated with a 1:1000 dilution of SM300 (anti-PorA P 1,7.16 monoclonal antibody) in 5% milk-TBS and an anti-mouse IgG-HRP conjugate (1:10,000 dilution in 5% milk-TBS). Washed membranes were exposed to ECL reagents, and bands were visualised on photographic film.

The Western blot (left) of *Neisseria* membrane fractions shows that the recombinant strain of *N. lactamica,* 2Pp7.A produces a membrane-associated protein that is recognised by the SM300 MAb, similar to but in much less abundance than the meningococcal strain known to express the cognate PorA protein, H44/76. The absence of a similar band in the membrane fraction derived from the ΔlacZ mutant derivative of *N. lactamica* Y92-1009 suggests that this band is the PorA protein. This is, to the best of our knowledge, the first example of meningococcal gene expression in *N. lactamica*. The comparative growth curve (right) of different *N. lactamica* strains in TSB medium supplemented with 0.2% yeast extract shows that the expression of PorA by 2Pp7.A is not detrimental to the aerobic growth of the bacterium.

It is important to note that the relatively low levels of PorA expression in strain 2Pp7.A (as compared to wild type *N. menigitidis* strain H44/76), are attributable to the phase-variable nature of the endogenous porA promoter. Sequencing of the porA promoter region from the chromosome of 2Pp7.A revealed that the homopolymeric 'G' tract that separates the −10 and −35 boxes (RNA Polymerase binding sites) in this promoter was only 10 nucleotides long. Previous work has shown that when replicating this promoter, slipped strand mispairing mutagenesis can lead to variation in the number of 'G' residues in this tract, resulting in a heterologous bacterial population. Whilst a tract length of 10 nucleotides is permissive for gene expression in *N. meningitidis*, the overall levels of gene expression are lower than from porA promoters that contain a tract length of 11 nucleotides (the optimum length). Future iterations of recombinant *N. lactamica* strains expressing PorA will need to either contain non phase variable promoters or have the optimum number of 'G' residues in the homopolymeric tract.

PorA is Surface-Expressed in Recombinant *N. lactamica* Strain 2Pp7.a

With reference to FIG. 20, both wild type *N. lactamica* strain Y92-1009 and its recombinant derivative, the PorA (P1.7,16) expressing strain, 2Pp7.A, were cultured to mid-log phase ($OD_{600nm}$=0.4) in TSB supplemented with 0.2% yeast extract. Aliquots of each culture containing $1\times10^7$ cfu were transferred to fresh microcentrifuge tubes and washed twice in PBS containing 5% foetal calf serum (hereafter, Wash Buffer). Washed bacteria were resuspended into 100 μl of Wash Buffer, supplemented with a 1:100 dilution of SM300 MAb and incubated at 4° C. for 30 minutes. The primary Mab was removed by washing twice with 1 ml of Wash Buffer, and the bacteria were resuspended into 100 μl of Wash Buffer containing a 1:100 dilution of anti-mouse IgG-AlexaFluor488. The secondary antibody was allowed to bind over the course of 30 minutes at 4° C., before the bacteria were again washed twice in Wash Buffer. After labelling, the bacteria were resuspended into 100 μl formalin and were fixed for 10 minutes at room temperature. Once formalin had been removed and the labelled, fixed bacteria washed twice more in Wash Buffer, they were resuspended into 200 μl of Wash Buffer and transferred to FACS tubes for quantitative analysis of AlexaFluor488 fluorescence by Flow Cytometry.

The graph shows that the Mean fluorescence intensity of the sample composed of the recombinant strain of *N. lactamica* (2Pp7.A; BLUE plot), is greater than the Mean fluorescence intensity of the sample composed of wild type *N. lactamica* (BLACK plot). This indicates surface expression of the target for SM300, which is most plausibly the (P1.7, 16) PorA protein. Together with the data from FIG. 19, these data show that the gene for the meningococcal-derived antigen porA has been successfully introduced into the chromosome of *N. lactamica* strain Y92-1009, that the PorA protein is associated with the membrane of the bacterium, and that the PorA protein is expressed on the surface of recombinant strain 2Pp7.A.

Promoter Constructs for Investigating Transcriptional Enhancement by Sequence Associated with the *N. meningitidis* porA Gene With reference to FIG. 21, in previous work conducted on the expression of the porA gene in *N. meningitidis*, it was remarked upon that the sequence immediately 5' of the −35 box of the porA promoter bore resemblance to transcriptional enhancer elements, originally characterised in *E. coli*. These sequences are characterised by multiple poly-'A' and/or poly-'T' nucleotide tracts, which confers on those molecules an ability to physically bend. It has been shown that such DNA bending brings distal DNA sequence elements into close proximity, such that proteins bound to these sequence elements are brought together to interact and potentially to form complexes. To investigate the role of a putative porA enhancer sequence on gene expression, a series of plasmids were developed in which the *N. lactamica* lacZ gene was placed under the transcriptional control of the lst promoter and targeted to NHCIS1 (FIG. 10). Other plasmids in this series were otherwise identical, but also included incrementally larger sequences derived from immediately upstream of the −35 box from the porA promoter in *N. meningitidis* strain MC58. The length of the putative enhancer sequence preceding and abutted to the lst promoter ranged from 50 bp to 400 bp (GREY text). In the diagram, each promoter and enhancer sequence shows restriction sites as black text against a boxed, grey background, the −10 and −35 RNA Polymerase binding sites as white text against a black background and the lst 5' UTR as lower case letters, the 17 bp separating the −10 and −35 boxes of the lst promoter are underlined. The half site shown, CAT, is from the NdeI restriction site immediately preceding the lacZ coding sequence. The second half of this site is the ATG START codon of the lacZ gene.

With the 'naked' (i.e. unenhanced) lst promoter providing a basal level of lacZ gene activity in the NHCIS1 locus, it was hypothesised that any enhancement to gene expression mediated through the upstream, putative enhancer sequences would lead to increased lacZ gene expression, higher amounts of β-galactosidase per bacterium and therefore increased levels of β-galactosidase Specific Activity.

Transcriptional Enhancement of the Lst Promoter by Sequence Cloned from Upstream of the porA Gene from *Neisseria meningitidis* Strain MC58.

With reference to FIG. 22, the series of plasmids containing the *N. lactamica* lacZ gene under transcriptional control of the lst promoter and incrementally larger, putative enhancer sequences derived from chromosomal sequence immediately 5' to the −35 box of the porA gene of *N. meningitidis* strain MC58, were used as PCR templates for the generation of donor genetic material with which to transform the ΔlacZ mutant derivative of *N. lactamica*. Transformation was carried out using hypermethylated PCR product as described in PROTOCOL A. Individual transformants, screened for on the basis of BLUE/WHITE colony formation on X-gal-containing TSB agar plates, were isolated. Chromosomal integration of the lst(X)::lacZ cassettes into the NHCIS1 locus was demonstrated through PCR (data not shown). Following DNA sequencing of the lacZ promoter sequences in this locus, individual clones containing constructs with identical sequences were pooled.

Recombinant *N. lactamica* strains containing the lst promoter-driven lacZ gene, were cultured in TSB at 37° C., 5% $CO_2$ and 320 rpm, until reaching mid-log phase ($OD_{600nm}$=0.3). Bacteria were pelleted by centrifugation, washed once in sterile PBS then resuspended into 200 μl of BLB supplemented with protease inhibitor cocktail, before being lysed through sonication (3×15 seconds pulses) on ice. Immediately after the last round of sonication, lysates were supplemented to a final concentration of 1 mM PMSF. Cell debris was removed by centrifugation at 17,000 g for 10 minutes ands the supernatant transferred to a fresh microcentrifuge tube. The supernatant was diluted 5× with BLB, and 5, 2 and 1 μl aliquots were assayed for (β-galactosidase activity using the chromogenic substrate ONPG. The activities in each of these aliquots were averaged to provide a value for each sample in each experiment. The protein concentration of each supernatant was measured using the DC Protein Assay Reagent (Bio Rad) and these values were used to normalise the measured β-galactosidase activities (yielding Specific Activity). Values shown are the mean of three independent experiments. Error bars represent the standard error of the mean. Where no error bars are visible, they fall within the line at the top of the column.

These data show that the sequence immediately upstream of the RNA Polymerase binding site of the meningococcal porA gene acts as a transcriptional enhancer. The native lst promoter provides a baseline level of β-galactosidase activity when lacZ is expressed from this promoter at the NHCIS1 locus, but the Specific Activity of 3-galactosidase is significantly increased when the upstream sequence of nucleotides is at least 150 bp long and optimal at 200 bp. Further increases to the length of the enhancer sequence disrupt its function in the NHCIS1 context and leads to a reduced Specific Activity in these samples (i.e. at 250 and 400 bp).

Promoter Construct Designed to Investigate the Mechanism of porA Transcriptional Enhancement With reference to FIG. 23, to investigate whether DNA bending is responsible for the enhancement of gene expression observed in FIG. 22, site-directed mutagenesis using the Q5 site-directed mutagenesis kit (NEB) was employed to introduce 5 additional nucleotides into the junction between the enhancer sequence (GREY text) and the −35 box of the lst(200):lacZ promoter. The additional five residues, along with the ultimate ‘A’ residue of the enhancer region (shown as white text), constitute a novel restriction site for NsiI in this construct (shown as black text in grey box: “ATGCAT”). The resulting construct was termed NHCIS1::lst(200+5):lacZ. The presence of an additional 5 nucleotides at the junction of the enhancer and promoter sequences has the effect of turning the enhancer region through half a helix relative to the promoter, given there are 10-11 nucleotide residues per turn of the DNA helix. This hypothetically reverses the directionality of the DNA bending, such that the DNA still bends, but in the opposite direction to the original construct. The consequence of this is that any distal sequence elements and their associated proteins, which would normally be brought into close association with RNA Polymerase and act to enhance open complex formation, would instead be brought into close association with the non-coding strand of the DNA, on the opposite ‘face’ of the DNA to RNA Polymerase. It was hypothesised that, if the porA enhancer sequence functions through a DNA bending phenomenon, then there will be a significantly lower level of β-galatosidase Specific Activity in *N. lactamica* transformed with the lst(200+5):lacZ construct, as compared to *N. lactamica* transformed with lst(200):lacZ. In the diagram, restriction sites are shown as black text against a boxed, grey background, the −10 and −35 RNA Polymerase binding sites are shown as white text against a black background and the lst 5' UTR as lower case letters, with the 17 bp separating the −10 and −35 boxes of the lst promoter underlined. The half site shown, CAT, is from the NdeI restriction site immediately preceding the lacZ coding sequence. The second half of this site is the ATG START codon of the lacZ gene.

DNA Bending is at Least Partially Responsible for the Transcriptional Enhancement Activity of the Sequence Upstream of the *N. meningitidis* porA Gene.

With reference to FIG. 24, the ΔlacZ mutant derivative of *N. lactamica* strain Y92-1009 and the recombinant *N. lactamica* strains lst:lacZ, lst(200):lacZ and lst(200+5):lacZ, were cultured in TSB at 37° C., 5% $CO_2$ and 320 rpm, until reaching mid-log phase ($OD_{600nm}$=0.3). Bacteria were pelleted by centrifugation, washed once in sterile PBS then resuspended into 200 μl of BLB supplemented with protease inhibitor cocktail, before being lysed through sonication (3×15 seconds pulses) on ice. Immediately after the last round of sonication, lysates were supplemented to a final concentration of 1 mM PMSF. Cell debris was removed by centrifugation at 17,000 g for 10 minutes and the supernatant transferred to a fresh microcentrifuge tube. The supernatant was diluted 5× with BLB, and 5, 2 and 1 μl aliquots were assayed for 3-galactosidase activity using the chromogenic substrate ONPG. The activities in each of these aliquots were averaged to provide a value for each sample in each experiment. The protein concentration of each supernatant was measured using the DC Protein Assay Reagent (Bio Rad) and these values were used to normalise the measured 3-galactosidase activities (yielding Specific Activity). Values shown are the mean of three independent experiments. Error bars represent the standard error of the mean. Where no error bars are visible, they fall within the line at the top of the column.

These data show that the addition of 5 extra nucleotides at the junction of the 200 nucleotide-long porA transcriptional enhancer and the −35 box of the lst promoter reduces by approximately 50% the Specific Activity of β-galactosidase measured in bacterial lysates. The graph shows that the addition of the enhancer sequence to the 5' end of the lst promoter results in a large increase in β-galactosidase Specific Activity, as compared to bacteria expressing lacZ from the ‘naked’ (i.e. unenhanced) lst promoter. Despite being otherwise identical to the lst(200):lacZ construct, the presence of 5 extra nucleotides in the lst(200+5):lacZ construct significantly reduces the Specific Activity of β-galactosidase, indicating less transcriptional activity from this promoter construct.

Annotated Nucleotide Sequence of HAEC3.

With reference to FIG. 25, this Cassette has been designed to enable non-phase variable, high level gene expression of heterologous antigen. The sequence consists of a modified *N. meningitidis* porA promoter, wherein the phase variable, 17 bp tract that separates the −10 and −35 boxes in the wild type porA promoter has been replaced with 17 bp of sequence identical to that which separates the −10 and −35 boxes of the *N. lactamica* porB promoter. The −35 box of the modified porA promoter is preceded by 250 bp of the porA-derived transcriptional enhancer sequence (FIG. 22), and most distally a SalI restriction site, to facilitate cloning and replacement of the promoter sequence (when used in conjunction with the XhoI restriction site). The modified, optimally-enhanced porA promoter is separated from the 3', modified *N. lactamica* porB promoter sequence by an XhoI restriction site, an interchangeable LINKER sequence and a NotI restriction site. It is important to note that either LINKER sequence can be any given nucleotide sequence (represented as poly-N). It is also important to note that the 17 bp sequence separating the −10 and −35 boxes of the RNA Polymerase binding site in this porB promoter have been replaced by 17 bp of sequence derived from the lst promoter. This is to avoid recombination between identical sequences within the Cassette that might otherwise lead to loss of the gene coding for heterologous antigen. By including an XhoI restriction site immediately 5' of the START codon and a NotI restriction site immediately 3' of the STOP codon of any given coding sequence (e.g. through the use of extended primer sequences that incorporate these sites), that sequence can be directionally cloned, IN-FRAME into the Construct for expression from the modified, optimally-enhanced porA promoter. The featured NdeI restriction site can be used in conjunction with the HindIII restriction site present immediately 5' of the porB terminator sequence to clone any given coding sequence into the Construct. By including an NdeI restriction site immediately 5' of the START codon and a HindIII restriction site immediately 3' of the STOP codon of any given coding sequence (e.g. through the use of extended primer sequences that incorporate these sites), that sequence can be directionally cloned, IN-FRAME into the Construct for expression from the lst promoter. Immediately after the HindIII restriction site, there is a transcriptional terminator sequence, derived from downstream of the *N. lactamica* porB gene. This is immediately followed by an AT-DUS. In the context of heterologous antigen expression in recombinant *Neisseria lactamica*, HAEC3 is flanked on either side by sequences homologous to the *N. lactamica* chromosome (e.g. NHCIS1).

Annotated Nucleotide Sequence of HAEC4.

With reference to FIG. 26, this Cassette has been designed to enable non-phase variable, high level gene expression of heterologous antigen. The sequence consists of a modified *N. meningitidis* porA promoter, wherein the phase variable, 17 bp tract that separates the −10 and −35 boxes in the wild type porA promoter has been replaced with 17 bp of sequence identical to that which separates the −10 and −35 boxes of the *N. lactamica* porB promoter. The −35 box of the modified porA promoter is preceded by 200 bp of the porA-derived transcriptional enhancer sequence (FIG. 22), and most distally a SalI restriction site, to facilitate cloning and replacement of the promoter sequence (when used in conjunction with the XhoI restriction site). The modified, optimally-enhanced porA promoter is separated from the 3′ *N. lactamica* lst promoter sequence by an XhoI restriction site, an interchangeable LINKER sequence and a NotI restriction site. It is important to note that either LINKER sequence can be any given nucleotide sequence (represented as poly-N). By including an XhoI restriction site immediately 5' of the START codon and a NotI restriction site immediately 3' of the STOP codon of any given coding sequence (e.g. through the use of extended primer sequences that incorporate these sites), that sequence can be directionally cloned, IN-FRAME into the Construct for expression from the modified, optimally-enhanced porA promoter. The featured NdeI restriction site can be used in conjunction with the HindIII restriction site present immediately 5' of the porB terminator sequence to clone any given coding sequence into the Construct. By including an NdeI restriction site immediately 5' of the START codon and a HindIII restriction site immediately 3' of the STOP codon of any given coding sequence (e.g. through the use of extended primer sequences that incorporate these sites), that sequence can be directionally cloned, IN-FRAME into the Construct for expression from the lst promoter. Immediately after the HindIII restriction site, there is a transcriptional terminator sequence, derived from downstream of the *N. lactamica* porB gene. This is immediately followed by an AT-DUS. In the context of heterologous antigen expression in recombinant *Neisseria lactamica*, HAEC4 is flanked on either side by sequences homologous to the *N. lactamica* chromosome (e.g. NHCIS1).

Plasmid Map of pUC19NHCIS1::HAEC4:nadA-lacZ

With reference to FIG. 27, the pUC19NHCIS1::HAEC4:nadA-lacZ plasmid is a derivative of pUC19NHCIS1::HAEC2:porAplusprom-lacZ (Clone #7) (FIG. 18), wherein the majority of the plasmid architecture is identical to pUC19NHCIS1::HAEC2:porAplusprom-lacZ; but where the wild type, non-optimally enhanced porA promoter and the porA coding sequence have been replaced by the optimally enhanced, modified porA/porB hybrid promoter and a *N. lactamica* codon-optimised version of the nadA gene. The nadA gene codes for the membrane associated adhesin, *Neisseria* Adhesin A, one of the four immunogenic components of the Bexsero anti-meningococcal serogroup B vaccine. The hybrid promoter and the nadA coding sequence were synthesised as a gBLOCK gene fragment (Integrated DNA Technologies) and cloned into the SalI-NotI double-digested plasmid vector using Gibson Assembly (NEB). The plasmid map is presented showing all relevant features and detailing the location of unique restriction sites with recognition sequences 6 nucleotides or greater.

Plasmid Map of pUC19NHCIS1::HAEC4:(Z)-lacZ

With reference to FIG. 28, the pUC19NHCIS1::HAEC4:(Z)-lacZ plasmid is a derivative of pUC19NHCIS1::HAEC4:nadA-lacZ, wherein the nadA coding sequence has been replaced by a 14 bp LINKER sequence. To create this plasmid, the nadA coding sequence was excised from pUC19NHCIS1::HAEC4:nadA-acZ using PCR and the plasmid re-circularised using the KLD enzyme mix from the Q5 site-directed mutagenesis kit (NEB). The plasmid map is presented showing all relevant features and detailing the location of unique restriction sites with recognition sequences 6 nucleotides or greater.

NadA-Expressing *N. lactamica* have Increased Adherence to HEP-2 Cells.

With reference to FIG. 29, the pUC19NHCIS1::HAEC4:nadA-lacZ and pUC19NHCIS1::HAEC4:(Z)-lacZ plasmids were used as templates for hypermethylated PCR. Hypermethylated donor genetic material was used to transform the ΔlacZ mutant derivative of *N. lactamica* strain Y92-1009 as described in PROTOCOL A. Individual transformants, screened for on the basis of BLUE/WHITE colony formation on X-gal-containing TSB agar plates, were isolated. Chromosomal integration of either the HAEC4:(Z)-lacZ or HAEC4:nadA-lacZ cassettes into the NHCIS1 locus was demonstrated through PCR (data not shown). Following DNA sequencing of this locus, NadA-expressing *N. lactamica* strain B1 (hereafter: 4NB1) was determined to contain genetic material with 100% identity to the nadA gene, the modified porA/porB hybrid promoter and porA enhancer sequence. NB: Transformation with the HAEC4:(Z)-lacZ cassette provides a procedural control and a transformed derivative (hereafter: 4YB2) that contains identical elements to 4NB1, but without the nadA coding sequence.

Two days prior to infection, HEP-2 cells were seeded into 24 well plates at a density of $2\times10^5$ cells/well. HEP-2 cells were cultured in Dulbecco's Modified Eagle's medium (DMEM) supplemented with 10% Foetal Calf Serum (FCS) at 37° C., 5% $CO_2$. On the morning of infection, duplicate wells of cells were treated with trypsin/EDTA and the average number of cells per well was measured by counting using a haemocytometer. Wild type *N. lactamica* strain Y92-1009, the NadA-expressing strain 4NB1 and the control strain 4YB2 were cultured in TSB at 37° C., 5% $CO_2$ and 320 rpm, until reaching mid-log phase ($OD_{600nm}$=0.3). Aliquots of each culture were isolated, pelleted by centrifugation and then resuspended in fresh DMEM+FCS. The final concentration of bacteria was adjusted so that 500 μl of DMEM contained sufficient bacteria to infect cells at MOI=100. At t=ZERO, HEP-2 cells were washed twice in sterile PBS, then infected at MOI=100 with the relevant bacterial strain. Plates were transferred to the incubator and cultured at 37° C., 5% $CO_2$ until the appropriate time point. At t=2 h, 4 h and 6 h the plates were removed from the incubator, supernatants were carefully aspirated and each well washed 5× with excess, sterile PBS. The final two washes were accompanied by complete aspiration of liquid from the well. A 250 μl aliquot of a 2% saponin solution in PBS was added to each well and the plates were again incubated for 15 minutes at 37° C., 5% $CO_2$. To fully disrupt the HEP-2 monolayers and disperse adherent/internalised bacteria, 750 μl of sterile PBS was added to each well and the cells were mechanically agitated through pipetting. The diluted lysate was serially diluted 10-fold in PBS, and the number of viable bacteria determined by plating onto Columbia Blood Agar (CBA) plates. The viability of each lysate was normalised to the estimated number of HEP-2 cells per well.

The graph shows the number of 'HEP-2 adherent' bacteria of each different strain recovered from infected wells at 2 h, 4 h and 6 h. At all time points there is a trend for the transformed strain, that which putatively expresses the NadA adhesin (4NB1), to bind more readily to HEP-2 cells than either the wild type strain or the transformation control strain (4YB2). Over time, this difference becomes more pronounced, but is similarly more variable. Whether this simple difference in adherence will reflect a higher propensity of this strain to colonise the human nasopharynx has yet to be determined.

Plasmid Map of pSC101NHCIS1::HAEC4:opcA-lacZ

With reference to FIG. 30, each of the pUC-derived plasmids used in this series has a large copy number (50-300 copies per bacterial cell). Whilst this simplifies the harvest of these plasmids, the high copy number may also result in toxicity—especially if the plasmid codes for a genetic system designed to express high levels of a particular product. The metabolic burden to *E. coli* transformed with these plasmids perhaps renders them non-viable, meaning that the only plasmids recovered during transformation are those with mutations in either the coding sequence or the promoter region. One potential solution to the problem of gene dose-mediated toxicity is to change the plasmid's origin of replication. By substituting the pUC origin of replication (modified pMB1) for the minimally-required region for propagation of plasmid pSC101 (repA/ori), the derivative plasmids will have a copy number of only 5 in daughter cells. It is hypothesised that the propensity for mutated plasmids to be selected for will be lower in the pSC101-based plasmids than the pUC19-based ones, increasing the frequency with which high fidelity plasmids containing the correct sequence for the gene of interest are recovered.

The pSC101NHCIS1::HAEC4:opcA-lacZ plasmid contains a *N. lactamica* codon-optimised version of the opcA gene under the control of the optimally-enhanced, modified porA/porB hybrid promoter. The plasmid is designed for use as a template in hypermethylated PCR, so as to generate donor genetic material suitable for the transformation of *N. lactamica* according to PROTOCOL A. The opcA and lacZ genes are targeted to NHCIS1. The plasmid map is presented showing all relevant features and detailing the location of unique restriction sites with recognition sequences 6 nucleotides or greater.

Plasmid Map of pUC19ΔNhba::HAEC1:(Z)-lacZ

With reference to FIG. 31, the pUC19Δnhba::HAEC1:(Z)-lacZ Construct comprises many features identical to those of pUC19NHCIS1::HAEC1:(Z)-lacZ (FIG. 14), but where the sequences homologous to the NHCIS1 locus are replaced by sequences homologous to the *N. lactamica* nhba gene (alternatively, gna2132 OR NLY_32180). The genome of *N. lactamica* strain 020-06 contains the gene: NLA_20270, which codes for the putative lipoprotein GNA2132, otherwise known as the *Neisseria* Heparin Binding Antigen (NHBA). NHBA is one of the four immunogenic components of the 4CMenB (Bexsero) vaccine. The genome of *N. lactamica* strain Y92-1009 contains the NLY_32180 open reading frame, which has an 87.5% similarity with NLA_20270 at the nucleotide sequence level, and codes for a protein with the characteristic, arginine-rich region of NHBA. Therefore NLY_32180 likely codes for the Y92-1009 homologue of NHBA.

The pUC19Δnhba::HAEC1:(Z)-lacZ Construct was designed as the first step in of a two-step strategy to truncate the coding sequence (and therefore effectively delete) the NHBA homologue from the ΔlacZ derivative of Y92-1009, without the need for a screening/selection marker being present in the final strain. Initially, ΔlacZ *N. lactamica* were transformed with the Δnhba::HAEC1:(Z)-lacZ Cassette according to PROTOCOL A, which disrupted the nhba gene with a functional copy of the *N. lactamica* lacZ gene. Successful transformants were screened for on medium containing X-Gal in accordance with PROTOCOL B, and grew as blue colonies. Successful transformants were verified by PCR of the nhba locus and had the genotype: ΔlacZ Δnhba::HAEC1:(Z)-lacZ. One of these strains provided the background for the second transformation event, which used the Δnhba Cassette, amplified from pUC19Δnhba (FIG. 32), to remove the lacZ coding sequence and replace the nhba gene with a truncated version of itself (Δnhba). The plasmid map is presented showing all relevant features and detailing the location of unique restriction sites with recognition sequences 6 nucleotides or greater.

Plasmid Map of pUC19ΔNhba

With reference to FIG. 32, the pUC19Δnhba Construct comprises a truncated copy of the *N. lactamica* nhba gene cloned into a modified, truncated version of pUC19. The pUC19Δnhba Construct was designed as the second step in a two-step strategy to truncate the coding sequence (and therefore effectively delete) the NHBA homologue from the ΔlacZ derivative of Y92-1009, without the need for a screening/selection marker being present in the final strain. The Δnhba Cassette was amplified from this plasmid and transformed into ΔlacZ Δnhba::HAEC1:(Z)-lacZ *N.*

*lactamica* according to PROTOCOL A. Successful transformants were screened for on medium containing X-Gal in accordance with PROTOCOL B, and grew as white colonies. Successful transformants were verified by PCR of the nhba locus and had the genotype: ΔlacZ Δnhba. These strains will provide the background for subsequent transformation events, wherein components of the 4CMenB (Bexsero) vaccine will be expressed in *N. lactamica* in a way suitable for future use of those strains in human challenge. The plasmid map is presented showing all relevant features and detailing the location of unique restriction sites with recognition sequences 6 nucleotides or greater.

Repeated Transformation of *N. lactamica* does NOT Select for a More Transformable Phenotype.

With reference to FIG. 33, a justified cause for concern in using genetically modified *N. lactamica* in a human challenge model is whether recombinant derivatives are more readily transformable than their parent cells. A higher propensity to become transformed by genetic material from the nasopharyngeal milieu means an increased risk of recombinant *N. lactamica* taking up and integrating into its genome the means to synthesise extracellular capsule, which could transition the organism from harmless commensal to potential pathogen. If the process of transforming *N. lactamica* also unintentionally selects for an enhanced inherent transformability, then the serial transformation of strains is likely to result in increased transformation efficiency under experimental conditions.

In creating a Δnhba mutant in *N. lactamica*, bacteria were serially transformed a total of three times. The first transformation removed the coding sequence for β-galactosidase (lacZ) from the wild type organism (to produce ΔlacZ). The ΔlacZ strain provided the background for the knock-out of the nhba gene, which was achieved using a two-step approach. The first step was the introduction of the HAEC1:(Z)-lacZ cassette) into the nhba chromosomal locus (to produce ΔlacZ Δnhba::HAEC1:(Z)-lacZ). The HAEC1 cassette was subsequently removed from sequence-verified transformants, along with a large section of the nhba coding sequence (to produce ΔlacZ Δnhba). Each of the above steps was dependent upon BLUE/WHITE colony formation on X-gal-supplemented TSB agar plates.

Each of the above strains was experimentally transformed with 0.46 pmol of hypermethylated PCR product, amplified from pUC19ΔnlaII:aphA3 (FIG. 4). The number of transformants was considered to be equal to the number of kanamycin-resistant colonies that grew overnight on selective agar plates (TSB+0.2% yeast extract supplemented with 50 μg/ml kanamycin), adjusted for dilution and plating volume. The graph shows that there are no significant INCREASES in the transformation efficiencies of any of the serially-transformed strains, which suggests that we are not inadvertently selecting for an inherently more transformable phenotype.

OMV Production from *Neisseria meningitidis* and *Neisseria lactamica*

Note: *Neisseria meningitidis* is a BSL-2 organism that is spread via creation of aerosols and droplets. Infection rate among laboratory workers is very low, estimated to be 13/100,000, but is approximately 10-fold higher than the general population. Mortality among infected workers is approximately 50%. Historical cases of laboratory-acquired infection are traceable to manipulation of the organism on the open bench by clinical microbiologists. Therefore, all manipulations of the live organism, including sub-culturing of colonies from plates, must only be performed within a class II containment hood.

Effect of the Amount of Donor Material Used to Transform Wild Type *Neisseria lactamica*: Supplemental.

With reference to FIG. 34, wild type *N. lactamica* strain Y92-1009 was transformed with a broad range of dilutions of a hypermethylated PCR construct amplified from pUC19ΔnlaII:aphA3, (ΔnlaII:aphA3(600)) according to Protocol A. The number of transformants was considered to be equal to the number of kanamycin resistant colonies evident after overnight growth on selective media (TSB agar supplemented with 50 μg/ml kanamycin), corrected for dilution factor and plating volume. The total number of viable bacteria was determined by tenfold serial dilution of each suspension of putatively transformed *N. lactamica*. This graph shows a strong relationship between the amount of donor material and the frequency of transformation of wild type *N. lactamica*. The relationship appears to be linear over the dilution range (0.05 pmol-0.000005 pmol), but appears to approach saturation when transforming using 0.5 pmol of donor material. This is consistent with FIG. 8 (B), wherein small changes in the amount of available donor material when provided in relatively large quantities (0.06 pmol-1 pmol) do not appear to appreciably impact the frequency of Nlac transformation. Points represent the Mean±SEM of six biological replicates.

Plasmid Map of pSC101::ΔlacZ:opcA

With reference to FIG. 35, the vector component of this plasmid, comprising the origin of replication (repA/ori) from pSC101 and the ampicillin resistance gene and M13 primer binding sites of pUC19, is identical to that of pSC101NHCIS1::HAEC4:opc-lacZ (FIG. 30). The pSC101::ΔlacZ:opcA plasmid contains an *N. lactamica* codon-optimized version of the opcA gene (eg. NMB1053) under the control of the optimally enhanced, modified porA/porB hybrid promoter and flanked on either side by sequences derived from the 5' and 3' ends of the Nlac lacZ gene. The purpose of the ΔlacZ:opcA construct is to introduce the opcA gene into the coding sequence of the lacZ gene, which was itself introduced into the NHCIS1 locus along with the nadA gene (using the NHCIS1::HAEC4:nadA-lacZ construct—FIG. 27). Transformation of *N. lactamica* strain 4NB1 with this construct generated the strain ΔlacZ NHCIS1::HAEC4:nadA-ΔlacZ:opcA, which contained chromosomal sequences with 100% identity to both the porA(P1.7,16) and opcA genes and grew as WHITE colonies on X-gal-containing TSB agar plates. The plasmid map is presented showing all relevant features and unique restriction sites.

Plasmid Map of pSC101::ΔlacZ-Synth.lacZ-3'ENDNHCIS1

With reference to FIG. 36, the vector component of this plasmid, comprising the origin of replication (repA/ori) from pSC101 and the ampicillin resistance gene and M13 primer binding sites of pUC19, is identical to that of pSC101NHCIS1::HAEC4:opc-lacZ (FIG. 30). The pSC101::ΔlacZ-synth.lacZ-3'ENDNHCIS1 plasmid contains a synthetic version of the lacZ gene (synth.lacZ), in which the coding sequence has been adjusted to maximize its diversity from the endogenous Nlac version of the lacZ gene at the nucleotide sequence level, whilst maintaining the fidelity of the amino acid sequence of β-galactosidase (see FIG. 37). The synth.lacZ gene is flanked at its 5' end by nucleotide sequence identical to the 3' end of the endogenous Nlac version of the lacZ gene, and at its 3' end by nucleotide sequence identical to the 3' end of NHCIS1. The purpose of the ΔlacZ-synth.lacZ-3'ENDNHCIS1 construct is to introduce a functional copy of the lacZ gene back into the chromosome of Nlac strain ΔlacZ NHCIS1::HAEC4:nadA-ΔlacZ:opcA, so that all strains in the NadA/Opc mutant panel retain β-galactosidase activity. Transformation of *N. lactamica* strain ΔlacZ NHCIS1::HAEC4:nadA-ΔlacZ:opcA with this construct generated the strain, ΔlacZ NHCIS1::HAEC4:nadA-ΔlacZ:opcA-lacZ (hereafter, 4NOA1), which contained chromosomal sequences with 100% identity to both the porA(P1.7,16) and opcA coding sequences, and grew as BLUE colonies on X-gal-containing TSB agar plates. The plasmid map is presented showing all relevant features and unique restriction sites.

Coding Sequence of Synth.lacZ

With reference to FIG. 37, this coding sequence has been designed to maximize diversity from the nucleotide sequence of the endogenous Nlac version of lacZ, whilst maintaining the fidelity of the amino acid sequence of β-galactosidase (CAI: 0.687). These adjustments were necessary in order to minimize the likelihood of the synthetic lacZ gene undergoing homologous recombination with the remaining lacZ fragments left in the NHCIS1 locus of Nlac strain ΔlacZ NHCIS1::HAEC4:nadA-ΔlacZ:opcA, which would have most probably resulted in the excision of the opcA gene from the chromosome. Where nucleotides have been manually substituted in order to increase nucleotide sequence diversity, they are in lower case.

Expression of NadA and Opc Outer Membrane Proteins on the Surface of Recombinant Strains of *N. lactamica*

With reference to FIG. 38, wild type *N. lactamica* strain Y92-1009 and its recombinant derivatives, the putatively NadA-expressing strain, 4NB1 and the putatively Opc-expressing strain, 4OA2, were cultured to mid-log phase ($OD_{600nm}$=0.4) in TSB supplemented with 0.2% yeast extract. Aliquots of each culture containing $2\times10^7$ CFU were transferred to fresh microcentrifuge tubes and washed twice in Wash Buffer. Washed bacteria were resuspended into 100 μl of Wash Buffer, supplemented with either a 1:200 dilution of anti-NadA monoclonal antibody, 6E3 (WT and 4NB1) or a 1:50 dilution of anti-Opc monoclonal antibody, 279/5c (WT and 4OA2) and incubated at 4° C. for 30 minutes. The primary mAbs were removed by washing twice with 1 ml of Wash Buffer, and the bacteria were resuspended into 100 μl of Wash Buffer containing a 1:100 dilution of anti-mouse IgG-AlexaFluor488 (1.5 mg/ml). The secondary antibody was allowed to bind over the course of 30 minutes at 4° C., before the bacteria were again washed twice in Wash Buffer. After labelling, the bacteria were resuspended into 100 μl formalin and were fixed for 10 minutes at room temperature. Once formalin had been removed and the labelled, fixed bacteria washed twice more in Wash Buffer, they were resuspended into 200 μl of Wash Buffer and transferred to FACS tubes for quantitative analysis of AlexaFluor488 fluorescence by Flow Cytometry.

The graphs in this figure show that, in both instances, the Mean fluorescence intensity of the samples composed of the recombinant strains of *N. lactamica* (either 4NB1, GREEN plot or 4OA2, BLUE plot), are greater than the Mean fluorescence intensity of the samples composed of wild type *N. lactamica* (RED plots). This indicates surface expression of the targets for 6E3 and 279/5c mAbs, which are most plausibly the NadA and Opc outer membrane proteins, respectively. Combined with the binding and internalisation data collected from analysis of the interaction of these recombinant Nlac strains with HEP-2 cells (FIG. 40) and (in the case of 4NB1) human nasopharyngeal tissue explants (FIG. 41), these graphs suggest the NadA and Opc outer membrane proteins are functionally expressed on the surface of recombinant Nlac strains 4NB1 and 4OA2, respectively.

Expression of NadA, Opc or a Combination of Both Antigens in Recombinant *N. lactamica* has No Appreciable Effect on Growth Rates in TSB With reference to FIG. 39, it is plausible that expression of one or more outer membrane protein(s) in additional to the usual complement of Nlac proteins, might constitute a metabolic burden for recombinant strains of *N. lactamica*. A significant metabolic burden might manifest as impairment in the growth characteristics of the strains as compared to wild type. To investigate this, wild type *N. lactamica* strain Y92-1009 and the mutant derivatives thereof, 4NB1, 4OA2, 4NOA1 and 4YB2 were cultured in TSB and the $OD_{600nm}$ and viability of each culture was measured hourly. Area Under Curve analyses of these data show that there are no significant differences between the growth rates or viability of these strains, suggesting that expression of additional outer membrane protein(s) do(es) not constitute a significant metabolic burden in rich medium. Points represent Mean±SD of four biological replicates, where no bars are visible, they fall within the points.

Figure 40:
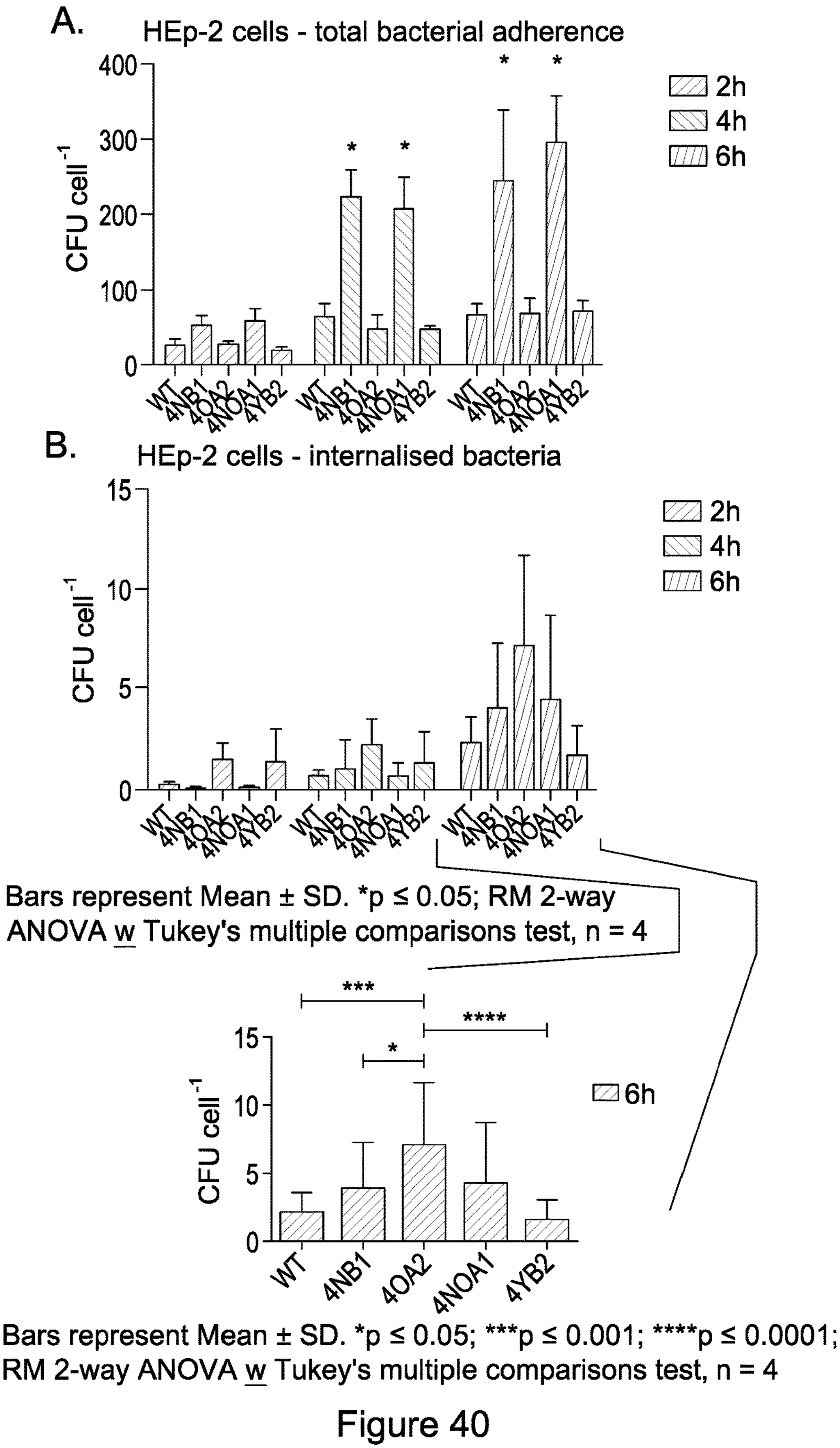

NadA-Expressing Strains of *N. lactamica* have Increased Adherence to HEP-2 Cells, Whilst Opc-Expressing Strains of *N. lactamica* are Internalized by HEP-2 Cells in Significantly Larger Numbers With reference to FIG. 40, wild type *N. lactamica* strain Y92-1009 and the recombinant, (meningococcal adhesin-expressing) derivatives thereof: 4NB1, 4OA2, 4NOA1 and 4YB2 were grown to mid-log phase, washed, resuspended into Dulbecco's modified Eagles medium (DMEM) supplemented with 10% foetal bovine serum (FBS) and used to infect duplicate confluent monolayers of HEP-2 epithelial cells at a multiplicity of infection (MOI) of 100 (i.e. 100 bacteria per HEP-2 cell). Infected cells were incubated at 37° C., 5% CO2 and samples were processed every 2 h for a total of 6 h. Thirty minutes prior to each sampling, the infected supernatant was removed from one of each pair of duplicates and the HEP-2 cells were gently washed with sterile PBS. Pre-warmed (37° C.) DMEM+10% FBS, supplemented with 100 μg/ml gentamicin and g/ml penicillin G was then added to each aspirated well and the plates returned to the incubator, with the intention of killing all bacteria adherent to the surface of the cells. At the appropriate time points, all media was aspirated from the HEP-2 cells, which were subsequently washed 5 times with an excess of sterile PBS. Following aspiration of the final wash, 250 μl of a 2% saponin solution in PBS was added to each well and, after 15 minutes incubation at 37° C. and repeated pipetting to break up the HEP-2 monolayers, was supplemented with 750 μl of sterile PBS (yielding all HEP-2 associated bacteria, or all HEP-2 internalised bacteria from a given well in a total volume of 1 ml). These suspensions were serially diluted in sterile PBS and the number of viable CFU enumerated on CBA agar. Viable counts were normalized to the number of HEP-2 cells present in each well. These data show that: (A). By 4 h of infection (light gray bars), Nlac strains expressing the meningococcal adhesin NadA on their surface (4NB1 and 4NOA1) associate in significantly higher numbers with HEP-2 cells than do any of the other strains examined. The wild type parental strain (WT), the Opc-expressing strain (4OA2) and the transformation procedure-control strain (4YB2) all associate in similar numbers with HEP-2 cells at every time point studied, but in consistently lower numbers when compared to both 4NB1 and 4NOA1. For all strains, these data suggest that the binding capacity of the HEP-2 cells becomes saturated at or before 4 h of infection, but that a significantly larger population of the NadA-expressing strains can associate with this cell line. This likely indicates the existence of an as-yet unidentified receptor for NadA binding on the HEP-2 cell surface, which is not bound by the surface armamentarium of wild type Nlac. *p≤0.05, RM 2-way ANOVA with Tukey's Multiple Comparisons test, n=4. (B). By 6 h of infection (dark gray bars, also shown in isolation in blow-out below main graph), the Nlac strain expressing the meningococcal adhesin Opc on its surface (4OA2) becomes internalized by HEP-2 cells in significantly higher numbers than every other strain examined except for 4NOA1. Although 4NOA1 also expresses Opc along with NadA, the internalization of this strain by HEP-2 cells is not significantly different from that of any other strain examined. Whether the presence of NadA in addition to Opc somehow interferes with the internalization process is not yet clear, although the relative expression levels of each adhesin on the surface of these bacteria, as compared to strains expressing one or the other protein, have not yet been determined. Bars represent Mean±SD; *p≤0.05, *p≤0.001 and **p≤0.0001, RM 2-way ANOVA with Tukey's Multiple Comparisons test, n=4.

Figure 41:
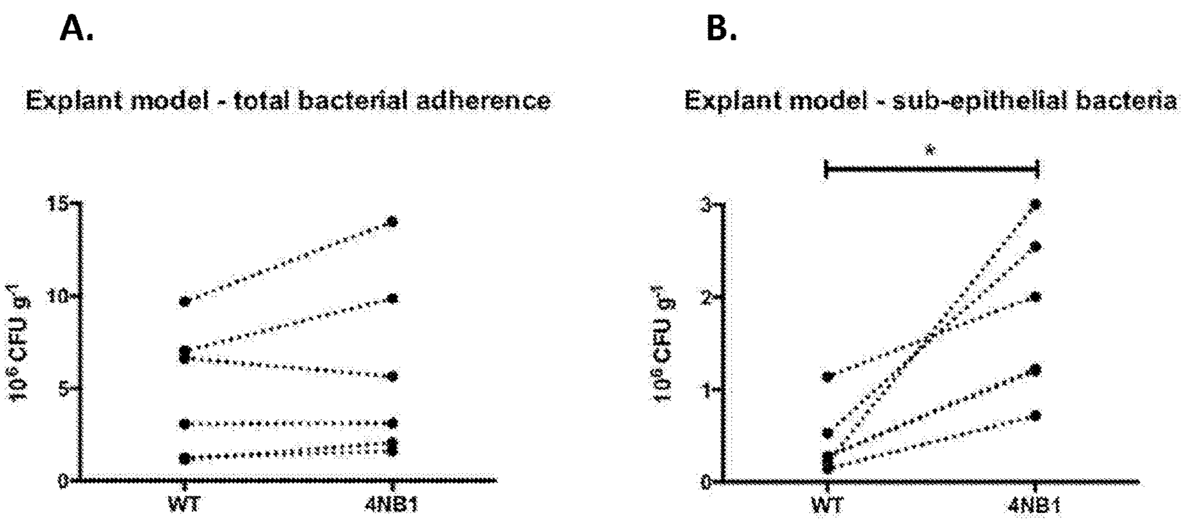

The NadA-Expressing Strain of *N. lactamica,* 4NB1, is Recovered in Significantly Higher Numbers from within Human Nasopharyngeal Tissue Explants than is the Wild Type With reference to FIG. 41, wild type *N. lactamica* strain Y92-1009 and the recombinant, NadA-expressing derivative thereof, 4NB1 were grown to mid-log phase, washed, resuspended in sterile PBS and used to infect the epithelium of agarose-mounted, transwell-suspended nasopharyngeal tissue explants derived from human turbinets from consenting donors. Each strain was used to infect four replicate explants. Explants were incubated at 37° C., 5% CO2 for 24 h, after which they were carefully removed from the agarose, weighed and processed. Duplicate explants were washed either three times in sterile PBS by vortexing (30 seconds per wash) or were vortexed for 30 seconds in a 0.2% solution of sodium taurocholate (bile salts) in PBS, followed by an additional 2 washes in sterile PBS. The wash in bile salts effectively sterilizes the surface of the explant, isolating the population of viable bacteria that have penetrated the epithelium (i.e. 'sub-epithelial bacteria'). Each explant was subsequently disrupted into 1 ml of a sterile 2% saponin solution in PBS, using a high-pressure, one-shot tissue disruptor. The resultant cell suspension was incubated for 15 minutes at 37° C., 5% CO2 to release any intracellular bacteria. An aliquot of each saponised lysate was serially diluted and plated on CBA agar to enumerate viable bacteria (CFU/ml). Viable counts were normalized to the weight of each explant (g). Points on each graph represent the average of values derived from duplicate explants. Paired Explants (derived from the same donor but infected with different bacterial strains) are joined by dotted lines. Although there is no significant difference between the total number of wild type or 4NB1 bacteria associated with the explants (i.e. surface-bound and those within the body of the explant), a significantly larger number of CFU were recovered from inside explants infected with strain 4NB1 than with wild type Nlac (*p=0.0313, Wilcoxon matched pairs signed rank test, n=5). These data suggest that although surface expression of meningococcal NadA by *N. lactamica* does not significantly enhance the ability of the strain to bind to the epithelial surface of nasopharyngeal explants compared to wild type, a significantly larger number of 4NB1 bacteria are able to penetrate the epithelium. Whether these sub-epithelial bacteria are intracellular or not remains to be elucidated; however, given the existence of sub-epithelial *Neisseria* microcolonies in tonsillar crypts (Sim et al, 2000 Research Letters| Volume 356, Issue 9242, P1653-1654), we hypothesize that an increased propensity to cross the nasopharyngeal epithelium ex vivo may impact upon the colonisation dynamics of this recombinant strain in human challenge. Penetration of the mucosal epithelium could plausibly mean the bacteria are protected from elements of the innate immune system operating at the mucosal service, effectively sheltering the strain from killing and promoting its persistence in a given human host. However, we must be mindful that the sub-epithelial location of these bacteria might preclude their recovery by swabbing of the nasopharynx, leading to false negative results in terms of an individual's colonization status.

Recombinant Strains of *N. lactamica* Expressing Meningococcal Adhesin Proteins have Similar Sensitivity Profiles to Front-Line Antibiotics as the Wild Type With reference to FIG. 42, and in the context of potentially using these strains in experimental human challenge, it is important to determine whether the process of creating recombinant strains of *N. lactamica* has decreased their sensitivity to clinically relevant antibiotics. Although the expectation is that these strains pose no threat to human health, the ability to kill these bacteria using front-line antibiotics should it become necessary needs to be assessed. Wild type *N. lactamica* strain Y92-1009 and recombinant Nlac strains 4NB1, 4OA2, 4NOA1 and 4YB2 were cultured in TSB to mid log phase. Sterile cotton swabs were saturated with these suspensions, which were then used to inoculate the surface of TSB agar plates supplemented with 5% horse blood in such a way as to generate a confluent lawn of bacteria after overnight growth. Onto the surface of each inoculated plate, an E-test strip was placed containing one of rifampicin, ciprofloxacin or ceftriaxone across a range of concentrations. The minimum inhibitory concentration (MIC) of each antibiotic was determined to be the concentration at which the bacterial lawn failed to develop following overnight growth, characterized by an area of clearance surrounding the E-test strip (Table 1). With reference to Table 2, which details the MIC and antibiotic 'sensitivity' levels of the pathogenic species of *Neisseria* to each of these antimicrobials, it is evident that each strain remains "sensitive" to these antibiotics. These data demonstrate that the process of generating our recombinant strains of *N. lactamica* has not significantly altered the susceptibility profile of these bacteria to the antimicrobial agents used to treat infections of the pathogenic *Neisseria* species.

Figure 43:
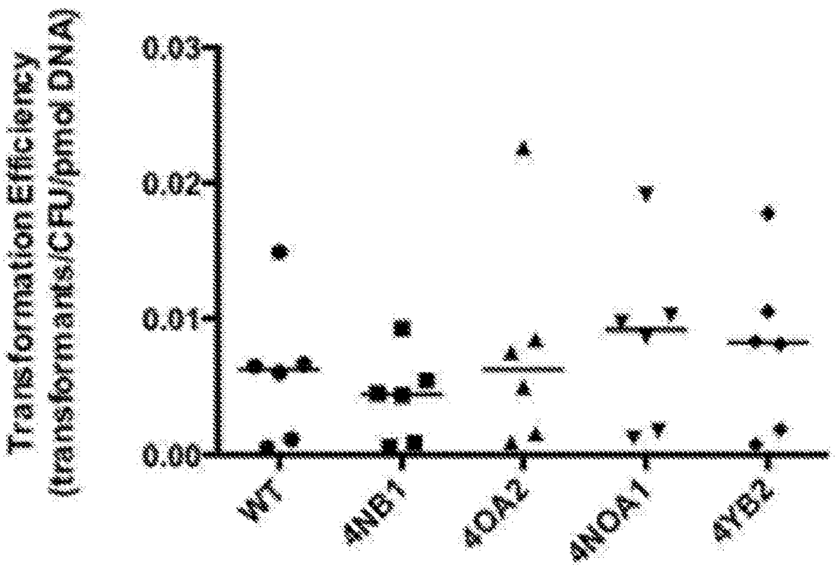

Recombinant Strains of *N. lactamica* Expressing Meningococcal Adhesin Proteins are Competent for Uptake of Exogenous DNA and can be Transformed with Efficiencies Similar to the Wild Type In reference to FIG. 43, wild type *N. lactamica* strain Y92-1009 and recombinant Nlac strains 4NB1, 4OA2, 4NOA1 and 4YB2 were transformed with 0.5 pmol of hypermethylated PCR construct: ΔnlaII:aphA3(600), as described in Protocol A. The number of transformants was considered to be equal to the number of kanamycin-resistant colonies that grew overnight on selective agar plates (TSB+0.2% yeast extract supplemented with 50 μg/ml kanamycin), adjusted for dilution factor and plating volume. This experiment was performed to determine whether serial transformation of *N. lactamica* had inadvertently selected for a "more transformable" phenotype compared to the WT strain. This is important, as our argument that recombinant Nlac is safe for use in human challenge experiments is predicated on the fact that they are no more likely to assimilate genetic information from the environment than the parental strain.

An increased propensity to take up exogenous DNA could plausibly translate into an increased likelihood to assimilate capsule synthesis genes from the nasopharyngeal milieu, with the potential to transform commensal strains into facultative pathogens. Strains 4NB1, 4OA2 and 4YB2 have each undergone two transformations from the wild type background, whereas strain 4NOA1 has been transformed a total of four times. These data show no significant differences in the transformation efficiency between any of the strains investigated and is consistent with the data presented in FIG. 33. This implies that isolation of serially-transformed bacteria does not also select for an inherently 'more transformable' phenotype.

Wild Type and Recombinant Strains of *N. lactamica* are Completely Refractory to Transformation by Chromosomal DNA Derived from *N. meningitidis*

Figure 44:
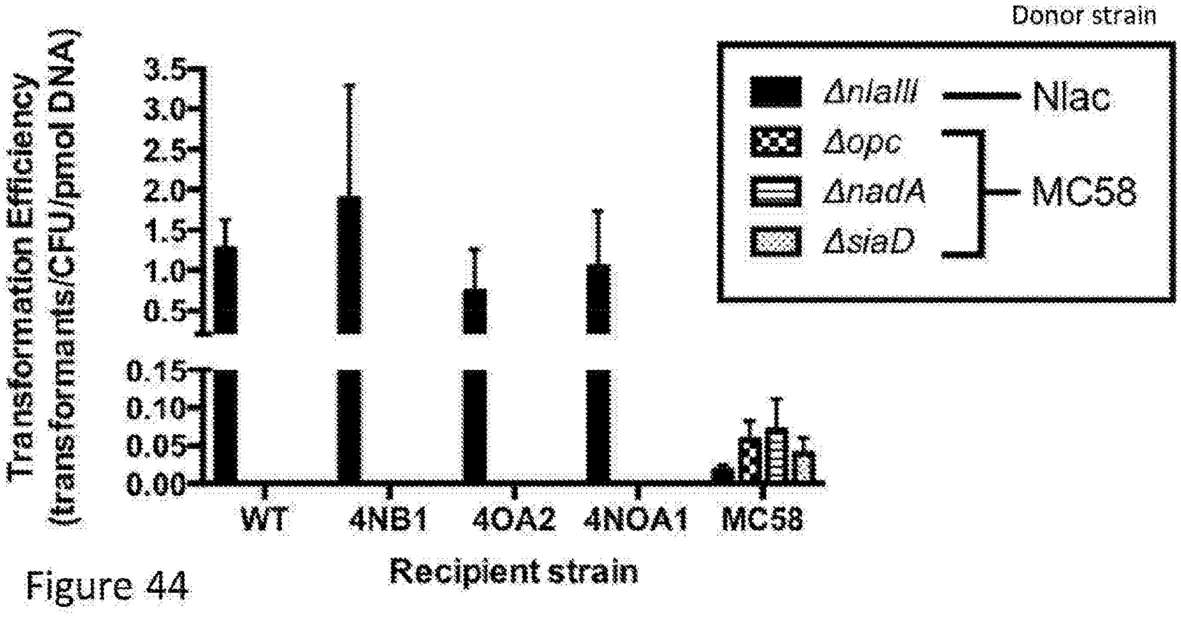

In reference to FIG. 44, the wild type meningococcal strain MC58, along with the wild type *N. lactamica* strain Y92-1009 and the recombinant derivatives thereof, 4NB1, 4OA2 and 4NOA1, were exposed to $1\times10^{-4}$ pmol of chromosomal DNA isolated from four mutant strains of *Neisseria*, as described in Protocol A. 1. Chromosomal DNA was isolated from the Nlac mutant derivative of Y92-1009 containing an insertionally-inactivated copy of the nlaIII gene (ΔnlaIII) and mutant derivatives of MC58 containing insertionally-inactivated copies of the opc, nadA and siaD genes, (Δopc, ΔnadA and ΔsiaD, respectively). All insertionally-inactivated meningococcal genes contained the full coding sequence of the appropriate gene, disrupted by identical copies of the kanamycin resistance gene, aphA3, transcriptionally controlled by the Nlac lst gene promoter. The same antibiotic resistance-conferring marker was used to disrupt the nlaIII coding sequence. The number of transformants was considered to be equal to the number of kanamycin-resistant colonies that grew overnight on selective agar plates (Columbia agar supplemented with horse blood and saturated then allowed to dry with 3 ml of a 2 μg/ml kanamycin solution), adjusted for dilution factor and plating volume.

This experiment was designed to determine the propensity of (recombinant) Nlac strains to take up and become transformed with chromosomal DNA from a meningococcal donor, which is the most plausible source of capsule synthesis genes these strains might encounter in the nasopharyngeal milieu. As such, all the strains were exposed to chromosomal DNA derived from MC58 ΔsiaD. Because Nlac does not express capsule, and instead contains the capsule null locus (cnl) in a position homologous to the capsule synthesis locus in Nmen, the incorporation of the insertionally-inactivated siaD gene into the Nlac chromosome would represent a de novo, untargeted recombination event and could theoretically occur at any locus. This is also true for all the recombinant Nlac strains. However, each of the recombinant strains contains at least one additional region of similarity to the meningococcal chromosome not present in the WT strain, i.e. the opc and nadA genes incorporated into NHCIS1. Both coding sequences for the Nlac versions of opc and nadA are approximately 80% similar to the appropriate MC58 homologue, which could plausibly facilitate homologous recombination of meningococcal DNA into the Nlac genome. As such, strains 4NB1 and 4OA2 were exposed to DNA derived from MC58 ΔnadA and MC58 Δopc, respectively, whilst strain 4NOA1 was exposed to DNA derived from both of these sources. Because we hypothesize that exogenous, non-Nlac derived chromosomal DNA taken up into *N. lactamica* will be degraded by potent restriction endonuclease activities (specifically, NlaIII), it was important to demonstrate that each of the Nlac strains in this experiment were actually competent for DNA uptake and homologous recombination. As such, each Nlac strain was also exposed to chromosomal DNA isolated from Y92-1009 ΔnlaIII, which reproducibly transformed wild type Nlac with high efficiency in preliminary experiments. As a demonstration that the isolated, meningococcal chromosomal DNA was capable of transforming a competent and compatible recipient, wild type MC58 bacteria were exposed to chromosomal DNA from all mutant sources. These data demonstrate that each strain of Nlac is highly competent for DNA uptake and homologous recombination when transformed with chromosomal DNA from a compatible source (ΔnlaIII, black bars). Interestingly, ΔnlaIII chromosomal DNA was also capable of transforming wild type MC58 with low efficiency, in what is presumably a de novo, untargeted recombination event due to the absence of an nlaIII coding sequence in the MC58 genome. This observation is in keeping with data that demonstrates horizontal gene transfer from Nlac into the pathogenic *Neisseria* in vivo. Each pool of chromosomal DNA derived from the MC58 mutant strains was capable of transforming wild type MC58 with low efficiency, as compared to the analogous back-cross into Nlac. However, each strain of Nlac was completely refractory to transformation with meningococcal DNA isolated from any mutant source (Δopc, checked bars; ΔnadA, striped bars or ΔsiaD, dotted bars), with absolutely no recovery of kanamycin-resistant colonies across biological replicates (n=6). Bars denote Mean±SD.

Plasmid Map of pSC101NHCIS1::HAEC4:porA(P1.7,16)-lacZ

With reference to FIG. 45, the pSC101NHCIS1::HAEC4:porA(P1.7,16)-lacZ plasmid is a derivative of pSC101NHCIS1::HAEC4:opcA-lacZ (FIG. 30), wherein the majority of the plasmid architecture is identical to pSC101NHCIS1::HAEC4:opcA-lacZ; but where the opcA coding sequence has been replaced by an Nlac codon-optimized version of the gene coding for Porin A (P1.7,16) (porA(P1.7,16)). Important to note is the fact that the nucleotide sequence of porA (P1.7,16) has been adjusted to remove the homopolyadenosine tract present at the 5' end of the wild type porA gene, so as to reduce the likelihood of porA(P1.7,16) expression being downregulated through phase variation. Transformation of strain ΔlacZ with hypermethylated NHCIS1::HAEC4:porA(p1.7,16)-lacZ construct gave rise to strain ΔlacZ NHCIS1::HAEC4:porA(p1.7,16)-lacZ (hereafter, 4PA1), which contained chromosomal sequences with 100% identity to the porA(P1.7,16) gene and grew as BLUE colonies on TSB agar plates supplemented with X-gal. The plasmid map is presented showing all relevant features and detailing the location of unique restriction sites.

Plasmid Map of pSC101NHCIS1::PVporA(P1.7,16)-lacZ

With reference to FIG. 46, the pSC101NHCIS1::PVporA(P1.7,16)-lacZ plasmid is a derivative of pSC101NHCIS1::HAEC4:opcA-lacZ (FIG. 30), wherein the majority of the plasmid architecture is identical to pSC101NHCIS1::HAEC4:opcA-lacZ; but where the porA/porB hybrid promoter and the opcA coding sequence have been replaced with the native porA promoter and porA(P1.7,16) coding sequence, amplified from the chromosome of wild type meningococcal strain H44/76. It is important to note that, unlike pUC19NHCIS1::HAEC2:porAplusprom-lacZ (FIG. 18), in which there was significant truncation of the porA transcriptional enhancer sequence (FIGS. 21 & 22), the pSC101NHCIS1::PVporA(P1.7,16)-lacZ plasmid contains the optimum length of 200 bp of enhancer sequence upstream of the porA promoter. Note that the plasmid map is based upon the ideal sequence for this plasmid, wherein the homopolymeric 'G' tract, which separates the −10 and −35 boxes of the native porA promoter contains 11 contiguous guanosine nucleotide residues. The plasmid map is presented showing all relevant features and detailing the location of unique restriction sites.

Figure 47:
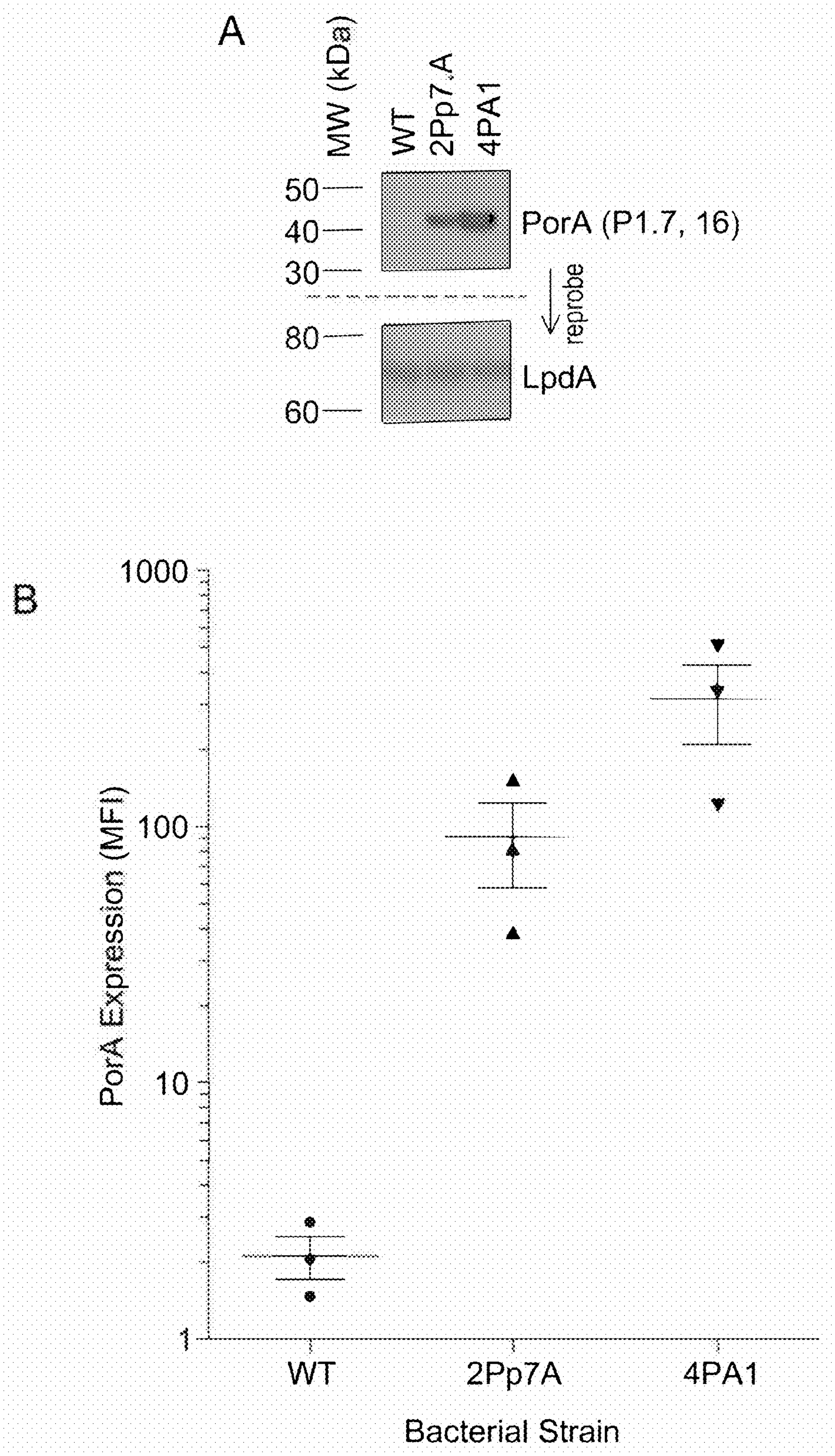
Figure 47:
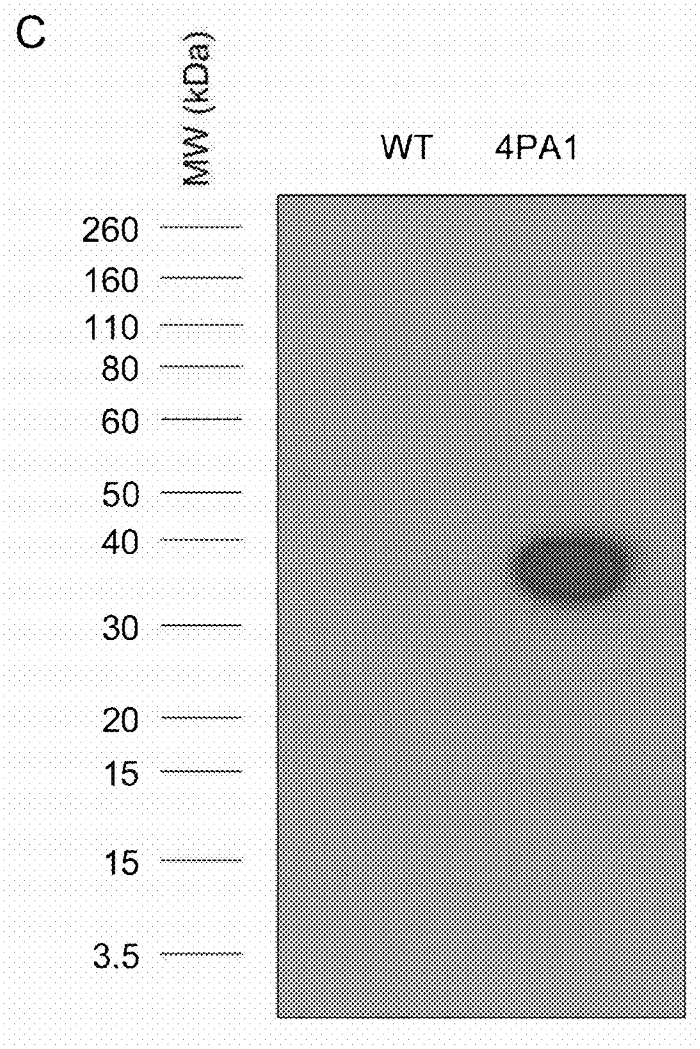

Recombinant Nlac Strains Express Porin a (P1.7, 16) at the Cell Surface and Generate PorA-Containing OMV In reference to FIG. 47, wild type *N. lactamica* strain Y92-1009 and the (putatively) PorA-expressing strains 2Pp7.A and 4PA1 were assessed for Porin A expression by western blot and flow cytometry (A and B, respectively). Outer membrane vesicles of the wild type and 4PA1 strains were analysed for PorA content by western blotting (C) prior to their use to immunize mice (see FIG. 48).

(A) Wild type (WT) Nlac and strains 2Pp7.A and 4PA1 were grown to mid-log phase and lysed with sonication. Equal amounts (50 rig) of each crude membrane preparation were separated by SDS-PAGE and transferred to activated PVDF. Expression of PorA in the membrane was detected by interrogation with anti-P1.7, 16 mAb, SM300. PVDF was subsequently stripped and reprobed with antibody directed against the constitutively-expressed membrane protein LpdA.

(B) WT Nlac and strains 2Pp7.A and 4PA1 were grown to mid-log phase and $2\times10^7$ whole cells were labelled with anti-meningococcal serosubtype P1.7 mAb (NIBSC) and a goat-derived, anti-murine IgG-Alexafluor488 conjugate. After labelling, the bacteria were fixed in formalin prior to analysis on a FACSCalibur flow cytometer. Graph shows the Median Fluorescence Intensity of three independent bacterial cultures, lines denote Mean MFI. These data are consistent with that presented in FIG. 20, which showed a low level of PorA expression on the cell surface of strain 2Pp7.A. The addition of approximately 100 bp to the 5' end of the porA enhancer sequence (FIGS. 21 & 22) and the substitution of the native homopolymeric G tract present in the wild type porA promoter for 17 bp derived from the non-phase variable porB promoter, have resulted in an increased level of PorA expression in strain 4PA1.

(C) WT Nlac and strain 4PA1 were grown overnight in modified Catlin medium (MC.7) to produce OMV, which was harvested with deoxycholate-extraction. Five micrograms (5 rig) of each OMV preparation were analysed for PorA by western blotting with anti-P1.7,16 mAb, SM300.

Immunisation with OMV from Recombinant Nlac Generates Anti-Meningococcal SBA

Figure 48:
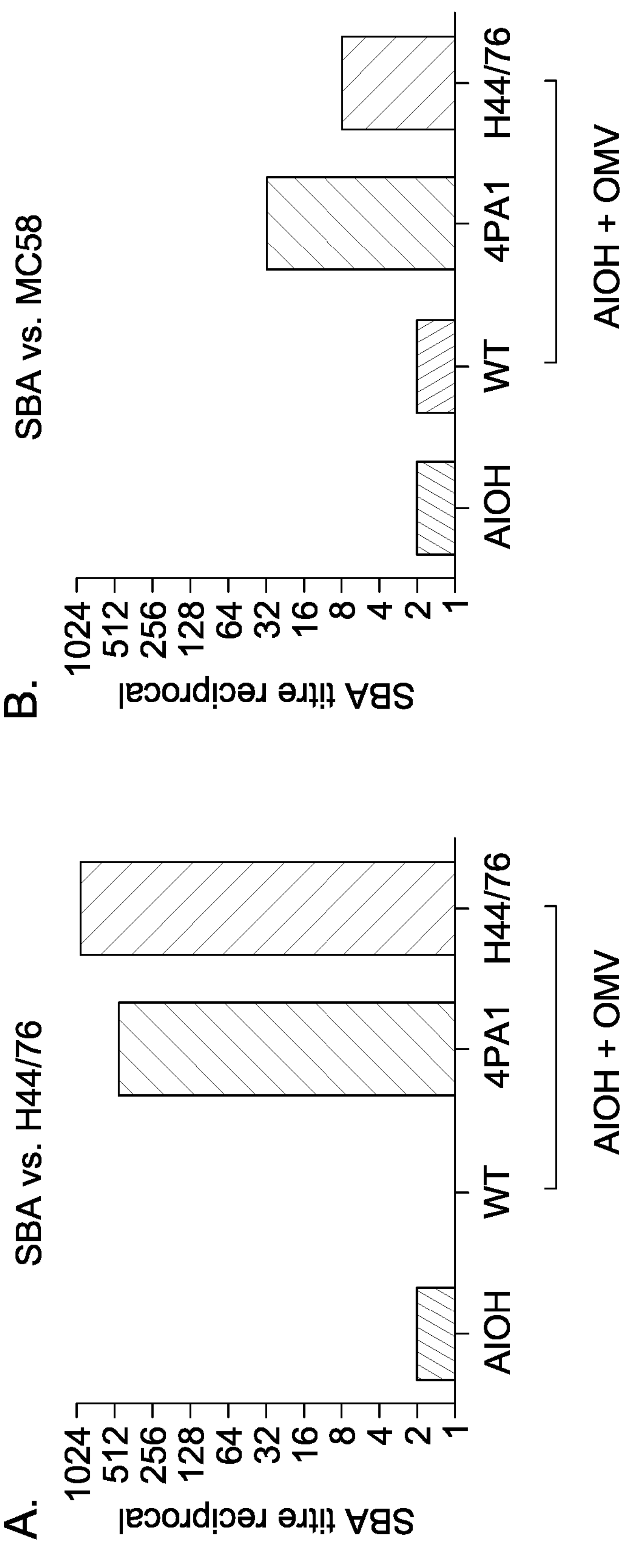

In reference to FIG. 48, mice were immunised i/p using a standard prime/boost strategy. Mice were injected with either Alum alone (AlOH) or Alum combined with deoxycholate-extracted OMV derived from one of: wild type Nlac (WT), the PorA-expressing recombinant Nlac strain 4PA1 (4PA1) or wild type serogroup B meningococcal strain H44/76 (H44/76). NB: H44/76 expresses the cognate PorA serosubtype, P1.7, 16. Sera from 5 immunised mice per group were pooled and doubling dilutions were assessed for SBA against (A) H44/76 and (B) MC58 (which expresses PorA serosubtype P1.7, 16-2). The maximum dilution of sera tested was 1:1024. OMV derived from strain 4PA1 elicited strong SBA against H44/76. Serum from these mice was more potent against strain MC58 than mice immunised with OMV from H44/76, suggesting Nlac OMV could provide broader anti-meningococcal adjuvant properties than Nmen-derived OMV.

Figure 49:
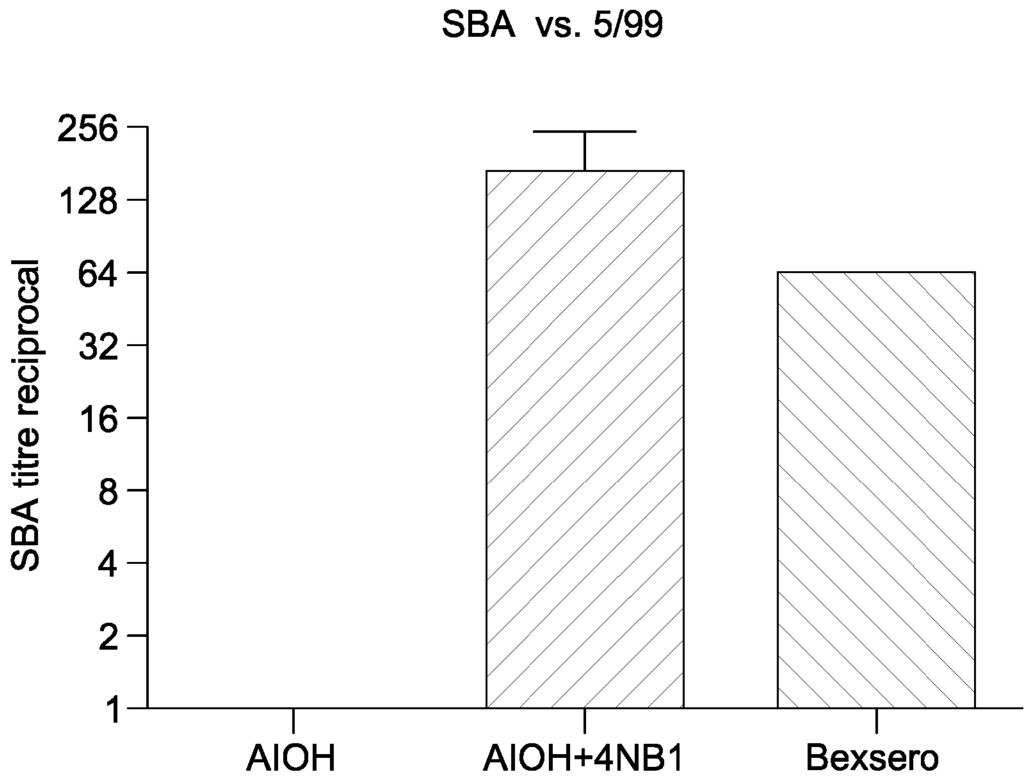

In reference to FIG. 49, mice were immunised i/p using a standard prime/boost strategy. Mice were injected with either Alum alone (AlOH) or Alum combined with deoxycholate-extracted OMV derived from the NadA-expressing recombinant Nlac strain 4NB1 (4NB1+AlOH). Sera from 5 immunised mice per group were pooled and doubling dilutions were assessed for SBA against *Neisseria meningitidis* strain 5/99 (a reference strain that expresses NadA to high levels). OMV derived from strain 4NB1 elicited strong SBA against 5/99 (SBA titre reciprocal: 170.67±74). Serum from these mice was more potent against strain 5/99 than antisera from humans immunised with the 4CMenB (Bexsero) anti-meningococcal vaccine (SBA titre reciprocal: 64±0). Bars represent Mean SBA titre reciprocal±SD. n≥2.

Materials 50 ml bio-reaction tubes (50 ml tubes with 0.22 μm filter cap) (GPE Scientific) 250 ml shaker flask, baffled with vented cap (Fisherbrand, pack of 12, Cat no 11735253): These flasks are fully autoclavable, including cap.

Glass homogeniser and plunger (VWR: Vessel=5 ml capacity, cat no. 432-0201. Plunger=5 ml, cat no. 432-0207.

*Ultracentrifuge bottles for rotor 55.2 Ti fixed-angle rotor: Polycarbonate bottle×6 with cap assembly, 26.3 ml 25×89 mm. Beckman Coulter, Cat no. 355618.

Yeast extract powder (500 g, Fisher Scientific, Cat no. 10108202)

Agar Plates

Tryptone Soya Broth Media Powder (500 g, Fisher Scientific, Cat No. 10198002)

Add 15 g of powder to 500 ml of water. Supplement with 0.2% (Ig) yeast extract. Sterilise by autoclaving at 121° C. for 15 minutes to make broth.

To make agar, add 7.5 g of bacteriological agar to the above mix prior to autoclaving. Then swirl to mix agar and allow to cool until the bottle can comfortably be held in the palm of the bare hand.

Agar Bacteriological (Agar No. 1) (500 g, Fisher Scientific, Cat No. 10351303)

Pour into petri dishes within a class II containment hood. Leave half uncovered to cool before replacing lids to avoid build up of condensation.

Media

Modified Catlin Medium (MC.7)

Dissolve the following components in distilled water for a final volume of 1000 ml and 500 ml respectively. pH will be approximately 7.

| | 1000 ml | 500 ml |
|---|---|---|
| NaCl | 5.8 g | 2.9 g |
| $K_2HPO_4$ | 4 g | 2 g |
| $NH_4Cl$ | 1 g | 0.5 g |
| $K_2SO_4$ | 1 g | 0.5 g |
| D-(+)-glucose | 10 g | 5 g |
| $MgCl_2$•$6H_2O$ | 0.4 g | 0.2 g |
| $CaCl_2$•$2H_2O$ | 0.03 g | 0.015 g |
| Yeast extract | 0.8 g | 0.4 g |
| HEPES | 5.96 g | 2.98 g |
| EDDA | 0.005 g | 0.0025 g |

Dissolve the following reagents in distilled water and filter sterilise using a 0.2 m syringe filter.

| | | |
|---|---|---|
| L-glutamic acid | 2 × 1.95 g | 1.95 g |

Weigh 1.95 g into 21 ml 1M HCl. Warm to 60° C. and add 6 M HCl dropwise until it dissolves. Bring pH back to 7 using 6 M NaOH. Top up to 50 ml with distilled water and filter sterilise. Make up 2×50 ml tube for 1000 ml of medium.

| | | |
|---|---|---|
| L-Cysteine•HCl | 0.1 g | 0.05 g |

For 500 ml make up to 25 ml with water and filter sterilise. For 100 ml make up to 50 ml Add the above to the autoclaved medium within a class II containment hood to keep medium sterile.

After autoclaving, the medium is yellow and may contain a large white precipitate that will not dissolve. In the event of precipitate formation, ensure thorough resuspension of the precipitate before use.

Buffers

Buffer 1

0.1M Tris-HCl pH 8.6

10 mM EDTA 0.5% (W/V) Deoxycholic acid sodium salt

Buffer 2

50 mM Tris-HCl pH 8.6

2 mM EDTA 1.2% Deoxycholic acid sodium salt

20% sucrose (W/V)

After addition of EDTA to above buffers, heat to 60° C. in a water batch to encourage it to dissolve. If it does not fully dissolve, add 1 M NaOH whilst stirring until a solution is obtained. Then add remaining reagents.

Buffer 3

0.2M glycine buffer

3% sucrose

Filter sterilise buffers.

Protocol (Work within a Class II Containment Hood Until Step 20) for Use with Either MHB, MC.6 or MC.7 Media Note: All materials that come in direct contact with live *Neisseria meningitidis* must either be decontaminated overnight in 2% Virkon, or sealed prior to disposal via the clinical waste stream or by autoclaving. Keep a sealable plastic bag inside the hood for disposal of gloves. After use, seal the bag, place inside a clinical waste bag and dispose of the clinical waste at the end of the experiment by taping up the neck of the bag and placing inside a large yellow clinical waste bin. At the end of the experiment disinfect surfaces such as the centrifuge control panel, door handles and pipettes with 70% ethanol.

1. At the end of the day, thaw a stock of *N. lactamica* or *N. meningitidis*. Remove 200 μl using a sterile pipette tip and plate onto the centre of a TSB+0.2% yeast extract agar plate.
2. Using a sterile cell spreader, place the spreader on the centre of the plate and rotate the centre of spreader so that the inoculum is spread evenly over the surface.
3. Replace the lid and place in a 37° C. 5% $CO_2$ incubator for 20 minutes with the lid facing up to allow the inoculum to soak into the agar. Also prepare a streak plate to assess purity of culture.
4. Turn plate upside down so that the lid is facing down and culture overnight.
5. At the end of the next day there should be a bacterial lawn covering the plate. Assess streak plate to ensure there is a mono-culture of *N. lactamica*, with no obvious contaminants.
6. Add 3 ml of MC.7 medium to the edge of the bacterial lawn and use a sterile spreader to very gently scrape over the surface of the lawn to liberate the adhered bacteria into the medium. Caution: Aerosol formation.
7. Using a Pasteur pipette, transfer the bacterial suspension from the surface of the plate into a 50 ml tube containing a 0.2 μm filter fitted into the cap (Bio-reaction tube).
8. Top the tube up to 30 ml with medium.
9. Incubate at 37° C. in a 5% $CO_2$ shaking incubator at 350 RPM overnight.
10. Use 2 ml of the culture from step 9 to inoculate 150 ml of medium in a 250 ml baffled, vented flask. Use the remainder of the culture to prepare fresh glycerol stocks if required. Caution: Aerosol formation.
11. Incubate for 8 hours. Divide this culture into two other bottles, giving a total of 3 bottles containing 150 ml in each. Culture overnight until an $OD_{600nm}$ of at least 2.0 has been reached.
12. Pour the contents of the bottle into 50 ml tubes. Caution: Aerosol formation. Spray the outside of the tubes with 70% ethanol to decontaminate any spillages and spray your gloves to do the same. Dispose of gloves, wash hands and put on a fresh pair of gloves.
13. Place tubes in a water bath set to 56° C. and heat kill the bacteria by incubating for 45 minutes. 30 minutes is sufficient, but it will take 10 minutes for the suspension to reach temperature.
14. Centrifuge heat-killed bacteria at 4,500×g for 1 hour at 20° C. to pellet.
15. Pour off supernatant. Pellet may be stored at −20° C.
16. Measure wet mass of cell pellet and Resuspend in buffer 1 using a buffer:biomass ratio of 5:1 (V/W).
17. Homogenise pellet using a glass homogeniser. Sterilise the glass homogeniser by filling with 70% ethanol. Leave for 5 minutes and then rinse with sterile water.
18. Centrifuge suspension at 20,000×g for 30 minutes at 4° C. Sterilise the ultracentrifuge tubes by filling with 70% ethanol for 5 minutes. Spray caps with 70% ethanol. Then rinse tubes and caps with sterile water. Do not autoclave the ultracentrifuge tubes and do not expose to pure ethanol.
19. Retain supernatant and resuspend pellet in buffer 1 (a third of the volume used in step 5).
20. Repeat steps 17 and 18.
21. Retain supernatant and combine with that from step 19.
22. Ultracentrifuge suspension at 100,000×g for 2 hours at 4° C.
23. Resuspend pellet in 2.5 ml of buffer 2 by flicking and vortexing.
24. Ultracentrifuge suspension at 100,000×g for 2 hours at 4° C.
25. Resuspend pellet in 2 ml of buffer 3 and transfer to a sterile universal.
26. Homogenise dOMV suspension by adding 6 sterile glass beads to the suspension and vortexing for approximately 10 minutes.
27. Measure protein concentration of homogenised OMV.
28. Assess OMVs by SDS-PAGE followed by coomassie blue staining or silver staining.
29. Store OMV frozen at −20° C. or −80° C.

Plasmid Vector Sequences

The following vectors are encompassed by the invention herein and their sequences are provided in the sequence listing as part of the description.

pUC19ΔnlaIII:CLOVER-aphA3 (SEQ ID NO: 21)

pUC19ΔnlaIII:aphA3 (SEQ ID NO: 22)

pUC19NHCIS1::HAEC1:(Z)-lacZ (SEQ ID NO: 23)

pUC19NHCIS1::HAEC2:(Z)-lacZ (SEQ ID NO: 24)
pUC19NHCIS2::HAEC1:(Z)-lacZ (SEQ ID NO: 25)
pUC19NHCIS1::HAEC2:porAplusprom-lacZ (SEQ ID NO: 26)
pUC19NHCIS1::HAEC4:nadA-lacZ (SEQ ID NO: 27)
pUC19NHCIS1::HAEC4:(Z)-lacZ (SEQ ID NO: 28)
pSC101NHCIS1::HAEC4:opcA-lacZ (SEQ ID NO: 29)
pUC19Δnhba::HAEC1:(Z)-lacZ (SEQ ID NO: 30)
pUC19Δnhba (SEQ ID NO: 31)
pSC101ΔlacZ:opcA (SEQ ID NO: 32)
pSC101ΔlacZ-synth.lacZ-3'NHCIS1 (SEQ ID NO: 33)
pSC101NHCIS1::HAEC4:porA(P1.7,16)-lacZ (SEQ ID NO: 34)
pSC101NHCIS1::PVporA(P1.7,16)-lacZ (SEQ ID NO: 35)

The invention claimed is:

1. A modified *Neisseria lactamica*, wherein the modified *Neisseria lactamica* is transformed with recombinant DNA encoding a heterologous protein, and wherein the modified *Neisseria lactamica* is modified by wild-type lacZ gene knockout or removal of wild-type lacZ gene sequence.

2. The modified *Neisseria lactamica* according to claim 1, wherein the heterologous protein is a *Neisseria meningitidis* protein.

3. The modified *Neisseria lactamica* according to claim 1, wherein the heterologous protein is a eukaryote protein, viral protein, or non-*Neisseria* prokaryote protein.

4. The modified *Neisseria lactamica* according to claim 1, wherein:

the heterologous protein comprises meningococcal adhesin NadA, or a functional homologue thereof having at least 70% sequence identity to meningococcal adhesin NadA; and/or the heterologous protein comprises *N. meningitidis* PorA, or a functional homologue thereof having at least 70% sequence identity to *N. meningitidis* PorA.

5. The modified *Neisseria lactamica* according to claim 1, wherein the recombinant DNA is:

inserted into the chromosome of *Neisseria lactamica* to provide the modified *Neisseria lactamica*; and/or inserted into an intergenic chromosomal sequence; and/or inserted into NHCIS1 or NHCIS2, or an equivalent thereof in other *Neisseria lactamica* strains.

6. The modified *Neisseria lactamica* according to claim 5, wherein the intergenic chromosomal sequence is:

between genes NLY_27080 and NLY_27100 of *Neisseria lactamica* strain Y92-1009, or an equivalent loci thereof in other *Neisseria lactamica* strains; or between genes NLY_36160 and NLY_36180 of *Neisseria lactamica* strain Y92-1009, or an equivalent loci thereof in other *Neisseria lactamica* strains.

7. The modified *Neisseria lactamica* according to claim 1, wherein the recombinant DNA encoding the heterologous protein is at least 600 bp in length.

8. The modified *Neisseria lactamica* according to claim 1, wherein:

the modified *Neisseria lactamica* is a β-galactosidase (lacZ) deficient mutant; and/or the modified *Neisseria lactamica* does not comprise a functional or non-functional wild-type lacZ gene.

9. The modified *Neisseria lactamica* according to claim 1, wherein the recombinant DNA encodes a promoter to promote expression of the heterologous protein.

10. The modified *Neisseria lactamica* according to claim 9, wherein:

the recombinant DNA further encodes a selection marker and encodes a further promoter that promotes expression of the selection marker.

11. The modified *Neisseria lactamica* according to claim 1, wherein the modified *Neisseria lactamica* does not comprise wild type lacZ gene sequence.

12. A method of prophylactic treatment for pathogenic infection of a subject comprising nasopharyngeal inoculation of the modified *Neisseria lactamica*, according to claim 1, wherein the heterologous protein is an antigen from the pathogen.

13. The method of prophylactic treatment according to claim 12, wherein the pathogenic infection is meningococcal infection and the heterologous protein is a meningococcal antigen.

14. The method according to claim 12, wherein the modified *Neisseria lactamica* is provided in a suspension comprising between $2\times10^2$ per ml and $2\times10^8$ per ml of the modified *Neisseria lactamica.*

15. The method according to claim 14, wherein the suspension of modified *Neisseria lactamica* comprises a pharmaceutically acceptable carrier.

* * * * *